(12) United States Patent
Kong et al.

(10) Patent No.: US 9,051,248 B2
(45) Date of Patent: Jun. 9, 2015

(54) METHODS, COMPOUNDS, AND COMPOSITIONS FOR DELIVERING 1,3-PROPANEDISULFONIC ACID

(75) Inventors: Xianqi Kong, Dollard-des-Ormeaux (CA); Nigel Levens, Beaconsfield (CA); Abderrahim Bouzide, Mississauga (CA); Stephane Ciblat, Montreal (FR); Richard Frenette, Laval (CA); Johanne Renaud, Laval (CA)

(73) Assignee: BHI Limited Partnership, Laval (CA)

( * ) Notice: Subject to any disclaimer, the term of this patent is extended or adjusted under 35 U.S.C. 154(b) by 467 days.

(21) Appl. No.: 13/389,606

(22) PCT Filed: Aug. 6, 2010

(86) PCT No.: PCT/CA2010/001229
§ 371 (c)(1),
(2), (4) Date: Apr. 20, 2012

(87) PCT Pub. No.: WO2011/017800
PCT Pub. Date: Feb. 17, 2011

(65) Prior Publication Data
US 2012/0208850 A1    Aug. 16, 2012

Related U.S. Application Data

(60) Provisional application No. 61/232,597, filed on Aug. 10, 2009.

(51) Int. Cl.
| | |
|---|---|
| C07C 309/65 | (2006.01) |
| C07D 319/06 | (2006.01) |
| A61K 31/366 | (2006.01) |
| A61K 31/365 | (2006.01) |
| A61K 31/255 | (2006.01) |
| C07D 309/22 | (2006.01) |
| A61K 31/351 | (2006.01) |
| C07C 309/05 | (2006.01) |
| C07C 311/06 | (2006.01) |
| C07C 311/51 | (2006.01) |
| C07D 213/64 | (2006.01) |
| C07D 213/65 | (2006.01) |
| C07D 231/12 | (2006.01) |
| C07D 307/33 | (2006.01) |
| C07D 307/58 | (2006.01) |
| C07D 307/77 | (2006.01) |
| C07D 327/10 | (2006.01) |
| C07F 9/09 | (2006.01) |
| C07F 9/40 | (2006.01) |

(52) U.S. Cl.
CPC .......... *C07C 309/65* (2013.01); *C07D 319/06* (2013.01); *A61K 31/366* (2013.01); *A61K 31/365* (2013.01); *A61K 31/255* (2013.01); *C07D 309/22* (2013.01); *A61K 31/351* (2013.01); *C07C 309/05* (2013.01); *C07C 311/06* (2013.01); *C07C 311/51* (2013.01); *C07C 2101/04* (2013.01); *C07C 2101/14* (2013.01); *C07D 213/64* (2013.01); *C07D 213/65* (2013.01); *C07D 231/12* (2013.01); *C07D 307/33* (2013.01); *C07D 307/58* (2013.01); *C07D 307/77* (2013.01); *C07D 327/10* (2013.01); *C07F 9/091* (2013.01); *C07F 9/4006* (2013.01)

(58) Field of Classification Search
CPC . A61K 31/366; A61K 31/351; A61K 31/365; A61K 31/255; C07C 309/65; C07D 319/06; C07D 309/22; C07D 307/58; C07D 307/33
See application file for complete search history.

(56) References Cited

U.S. PATENT DOCUMENTS

| | | | |
|---|---|---|---|
| 4,001,201 A | 1/1977 | Kyburz | |
| 5,716,756 A * | 2/1998 | Pawlowski et al. | 430/270.1 |
| 5,728,506 A | 3/1998 | Kometani | |
| 6,562,836 B1 | 5/2003 | Szarek et al. | |
| 6,670,399 B2 | 12/2003 | Green et al. | |
| 7,393,875 B2 | 7/2008 | Szarek et al. | |
| 7,786,174 B2 | 8/2010 | Szarek et al. | |
| 7,858,289 B2 | 12/2010 | Yamashita | |
| 7,994,218 B2 | 8/2011 | Jandeleit et al. | |
| 2004/0248876 A1 | 12/2004 | Szarek et al. | |
| 2008/0227767 A1 | 9/2008 | Szarek et al. | |
| 2008/0262088 A1 | 10/2008 | Hauck et al. | |

(Continued)

FOREIGN PATENT DOCUMENTS

| | | |
|---|---|---|
| CA | 1008848 C | 4/1977 |
| DE | 119 040 | 4/1976 |

(Continued)

OTHER PUBLICATIONS

McElvain t al. J. Am. Chem. Soc. 1945, 67, 1578-1581.*

(Continued)

*Primary Examiner* — Joseph Kosack
*Assistant Examiner* — Matthew Coughlin
(74) *Attorney, Agent, or Firm* — McCarter & English, LLP; Danielle L. Herritt; Emily Dertz

(57) ABSTRACT

The invention relates to methods, compounds, and compositions for delivering 1,3-propanedisulfonic acid (1,3PDS) in a subject, preferably a human subject. The invention encompasses compounds that will yield or generate 1,3PDS, either in vitro or in vivo. The invention also relates to sulfonate ester prodrugs of 1,3PDS as well as Gemini dimmers and oligomers of 1,3PDS for the prevention or treatment of associated diseases and conditions.

21 Claims, No Drawings

(56) References Cited

U.S. PATENT DOCUMENTS

| | | | |
|---|---|---|---|
| 2009/0069419 A1 | 3/2009 | Jandeleit et al. | |
| 2009/0076147 A1 | 3/2009 | Jandeleit et al. | |
| 2009/0082440 A1 | 3/2009 | Jandeleit et al. | |
| 2009/0082464 A1 | 3/2009 | Jandeleit et al. | |
| 2009/0099253 A1 | 4/2009 | Li et al. | |

FOREIGN PATENT DOCUMENTS

| | | | |
|---|---|---|---|
| DE | 198 23 722 A1 | | 12/1999 |
| DE | 19823722 A1 | * | 12/1999 |
| GB | 1537461 A | | 12/1978 |
| JP | 2006162735 A | | 6/2006 |
| WO | 94/22437 A2 | | 10/1994 |
| WO | 96/28187 A1 | | 9/1996 |
| WO | 00/71101 A2 | | 11/2000 |
| WO | 2004/113275 A2 | | 12/2004 |
| WO | 2004/113391 A2 | | 12/2004 |
| WO | 2007/004072 A2 | | 1/2007 |
| WO | 2007/125385 A2 | | 11/2007 |
| WO | 2008/078176 A1 | | 7/2008 |

OTHER PUBLICATIONS

Clutterbuck et al. J. Chem. Soc. 1922, 121, 120-128.*
CAS Registry Entry for Registry No. 150374-57-5, which entered STN on Oct. 1, 1993.*
CAS Registry Entry for Registry No. 100976-92-9, which entered STN on Mar. 22, 1986.*
CAS Registry Entry for Registry No. 61660-42-2, which entered STN on Nov. 16, 1984.*
Johnston, T., "Synthesis of Potential Anticancer Agents. XXI. Nitrosated Sulfonamides Related to Myleran," J. Org. Chem., Mar. 1960, vol. 25, pp. 399-402; Cited in International Search Report of corresponding PCT/CA2010/001229 on Nov. 10, 2010.
Ogura, F., et al., "Dimethyl and Diethyl 2-Oxo-1,3-propanedisulfonates as Practical Alkylating Reagents," Bull. Chem. Soc. Jap., Apr. 1983, vol. 56, pp. 1257-1258; Cited in International Search Report of corresponding PCT/CA2010/001229 on Nov. 10, 2010.
Strepikheev, A., et al. "Linear polymers containing sulfamido groups in the methylene chains," STN CAPlus Accession No. 1955:23821*Registry 100976-92-9*,Cited in International Search Report of corresponding PCT/CA2010/001229 on Nov. 10, 2010.
Geiseler, G., et al., "1,3-Propanedisulfonic acid anhyderide. II. The vibrational spectrum of the anhydride and of some derivatives of the disulfonic acid," STN CAPlus Accession No. 1959:16698 *Registry 4720-58-5 & 119276-67-4*; Cited in International Search Report of corresponding PCT/CA2010/001229 on Nov. 10, 2010.
Levchenko, E., et al., "N-Arylsulfonyliminothionyl chlorides," STN CAPlus Accession No. 1961:143836 *Registry 101864-25-9 & 102592-13-2*; Cited in International Search Report of corresponding PCT/CA2010/001229 on Nov. 10, 2010.
Esayan, G., et al., "Transformations of disulfonyl chlorides. I. Interaction of alkandisulfonyl chlorides with phenois and aromatic amines containing halide and nitro groups," STN CAPlus Accession No. 1964:461454 *Registry 92550-38-4, 93734-21-5, & 857193-27-2*; Cited in International Search Report of corresponding PCT/CA2010/001229 on Nov. 10, 2010.
Esayan, G., et al., "Transformations of disulfonyl chlorides. II. Synthesis of 4 methyl-7-coumaryl and 8-quinolyl esters of some disulfonic acids," STN CAPlus Accession No. 1965:498169 *Registry 4053-54-7 & 4053-58-1*; Cited in International Search Report of corresponding PCT/CA2010/001229 on Nov. 10, 2010.
Organesyan, E., et al., "Reactions of disulfonyl chlorides. VI. Reactions of beta alkanedisulfonyl chlorides with dimedone," STN CAPlus Accession No. 1976:16828 *Registry 57630-54-3*; Cited in International Search Report of corresponding PCT/CA2010/001229 on Nov. 10, 2010.
Gichner, T. et al, "The Mutagenic Activity of Beta-Hydroxyethyl Methanesulfonate, Beta-Methoxyethyl Methanesulfonate and Diethyl 1,3-Propanedisulfonate," Hereditas, 1968, vol. 59, No. 2-3, pp. 253-262.
Lichtenberger, J., et al., "No. 34.—Sur les di-esters sulfoniques," Bull. Soc. Chim. 1961, pp. 363-369, France.
International Search Report, issued on Nov. 10, 2010, in corresponding PCT/CA2010/001229.
Adamczyk, M. et al., Bioluminescence & Chemiluminescence: Perspectives for the $21^{st}$ Century: Proc. of the $10^{th}$ Int. Symp. On Biolum. & Chemilum., pp. 37-40.
English Translation of Geiseler, G. et al., Chemische Berichte, 1958, vol. 91, No. 7, pp. 1512-1515.
English Translation of Mariani, A. et al., "Radiomimetic effects of monofunctional and bifunctional alkylating compounds in triticum monococcum (2X) and triticum durium (4x)," 1965, Atti, Associazione Genetica Italiana, vol. 10, pp. 136-149.
Geiseler, G. et al., Chemische Berichte, 1958, vol. 91, No. 7, pp. 1512-1515.
Mariani, A. et al., "Radiomimetic effects of monofunctional and bifunctional alkylating compounds in triticum monococcum (2X) and triticum durium (4x)," 1965, Atti, Associazione Genetica Italiana, vol. 10, pp. 136-149.

* cited by examiner

METHODS, COMPOUNDS, AND COMPOSITIONS FOR DELIVERING 1,3-PROPANEDISULFONIC ACID

This application is the national stage application of International Application Serial No. PCT/CA2010/001229, filed Aug. 6, 2010, which claims the benefit of U.S. Application Ser. No. 61/232,597 filed Aug. 10, 2009.

FIELD OF THE INVENTION

The invention relates to methods, compounds and compositions for delivering 1,3-propanedisulfonic acid (1,3PDS) in a subject, preferably a human subject. The invention encompasses compounds that will yield or generate 1,3PDS, either in vitro or in vivo. Preferred compounds include sulfonate ester prodrugs of 1,3PDS for use, including but not limited to, the prevention and treatment of metabolic, renal and pancreatic diseases and disorders, including AA amyloidosis, diabetic nephropathy, diabetes and metabolic syndrome.

BACKGROUND OF THE INVENTION 1,3-Propanedisulfonic acid (1,3PDS, eprodisate, Kiacta™) is an investigational new drug for the treatment of AA amyloidosis (or secondary (AA) amyloidosis), which is a manifestation of a number of diseases that provoke a sustained acute phase response. Such diseases include chronic inflammatory disorders, chronic local or systemic microbial infections, and malignant neoplasms. The most common form of AA amyloidosis is seen as the result of long-standing inflammatory conditions. For example, patients with Rheumatoid Arthritis or Familial Mediterranean Fever (a genetic disease) can develop AA amyloidosis.

1,3PDS has also exhibited potential activity for the treatment of renal disorders such as diabetic nephropathy and reduction of triglyceride serum levels, such as for the treatment of dyslipidemia and vascular or cardiovascular diseases (patent application published on Oct. 11, 2007 as US 2007/0238788 and PCT application published as WO 2007/125385, incorporated herein by reference in their entirety). It has also been found to exhibit beneficial properties in vivo against features of metabolic syndrome and diabetes, such as insulin and glucose levels as well as for preserving pancreatic islets of Langherans (patent application published on Oct. 23, 2008 as US 2008/0262088 and PCT application published as WO 2008/078176, incorporated herein by reference in their entirety).

Generally, when used as a therapeutic, expected dosage of 1,3PDS to be used may range from about 800 mg to about 3200 mg per day, separated in multiple doses throughout the day.

SUMMARY OF THE INVENTION

The invention includes methods, compounds and compositions for delivering in a subject, preferably a human subject, 1,3-propanedisulfonic acid, or salts thereof. 1,3-Propanedisulfonic acid (referred to herein as 1,3PDS) has the following structure:

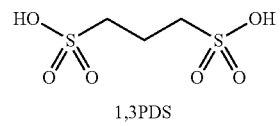

1,3PDS

According to one aspect, the present invention relates to compounds or compositions that will yield or generate 1,3PDS after being administered to a subject. In one embodiment, the compound that will yield 1,3PDS is a sulfonate ester prodrug of 1,3PDS. In another embodiment, the compound that will yield 1,3PDS is a neopentyl sulfonate ester or a neopentyl-derived sulfonate ester of 1,3PDS. In another embodiment, the compound that will yield 1,3PDS is a monosulfonate ester prodrug of 1,3PDS. In another embodiment, the compound is a disulfonate ester prodrug of 1,3PDS. In another embodiment, the compound that will yield or generate 1,3PDS is an oligomer or gemini dimer of 1,3PDS which comprises at least one sulfonate ester of 1,3PDS. In another embodiment, the compound that will yield or generate 1,3PDS is an oligomer or gemini dimer of 1,3PDS which comprises a neopentyl or neopentyl-derived sulfonate ester of 1,3PDS. In certain embodiments, the sulfonate ester prodrugs of 1,3PDS that are capable of yielding or generating, either in vitro or in vivo 1,3PDS have one of the general or specific formulae or structures disclosed herein.

More particularly, the invention relates to compounds of any one of Formulae I, II, II-A, III and III-A, IV and V, as well as any embodiments and examples described in section II of the description, such as Formulae (B) to (F) and embodiments thereof, as well as their pharmaceutically acceptable salts and solvates. The invention also encompasses the compounds exemplified herein, for example, Compounds A1-A73, Compounds B1-B87, Compounds C1-C3, Compounds D1-D8, Compounds G1-G4, Compounds N1-N18, and Compound P1, as well as their pharmaceutically acceptable salt and solvates where applicable.

The invention also further relates to a method or process for preparing the compounds of the invention. The invention, for example, relates to a method for the preparation of a compound of Formula II-A as herein described, comprising the steps of: a) preparing a disulfonyl chloride of the formula: $ClO_2S$—$(CH_2)_3$—$SO_2Cl$; b) reacting the disulfonyl chloride of step (a) with a compound of the formula PGOH, wherein PG is a protecting group to produce a monosulfonyl chloride of the formula: $PGO_3S$—$(CH_2)_3$—$SO_2Cl$; c) reacting the monosulfonyl chloride of step (b) with an alcohol of the formula $R^4OH$, wherein $R^4$ is as herein described to produce a monoprotected compound of the formula: $PGO_3S$—$(CH_2)_3$—$SO_3OR^4$; and d) cleaving the protecting group from the monoprotected compound of step c) to produce a compound of Formula II-A. In one embodiment, step (a) comprises reacting a the disodium salt of 1,3PDS with phosphorus pentachloride. In one embodiment, the PGOH compound of step (b) is phenol and step (d) comprises reacting the monoprotected compound with a source of palladium and a source of hydrogen gas, for example palladium hydroxide $(Pd(OH)_2)$, an acid and hydrogen gas, for example palladium hydroxide, acetic acid and hydrogen gas. In another embodiment, steps (b) and (c) further comprise addition of a base, for example an organic base, for example pyridine.

The present invention also relates to pharmaceutical compositions comprising a compound of the present invention, optionally together with a pharmaceutically acceptable carrier.

The invention also relates to the use of the compounds of the invention for the treatment of pancreatic and/or renal and/or metabolic and/or vascular diseases and disorders. The invention further relates to the use of the compounds of the invention in the treatment of amyloid A amyloidosis (AA amyloidosis). The invention further relates to the use of the compounds of the invention in the treatment or prevention of renal impairment in patients with AA amyloidosis. The invention also relates to the use of the compounds of the invention in the treatment of renal disorders, such as diabetic nephropathy. The invention further relates to the use of the compounds of the invention in delaying the onset or the need for dialysis in renally impaired patients, e.g. in patients with AA amyloidosis or diabetic nephropathy. The invention further relates to the use of the compounds of the invention in the treatment of dyslipidemia, hyperlipidemia, and for reducing serum triglyceride levels. The invention further relates to the use of the compounds of the invention in the treatment of metabolic syndrome and/or diabetes.

In another aspect, the invention relates to the use of the compounds of the invention for increasing insulin levels circulating in blood in response to food, decreasing resistance to insulin and/or increasing insulin sensitivity in selected tissues (e.g. fat, muscle and liver), increasing insulin secretion by pancreatic cells, increasing beta-cells and/or islets of Langerhans neogenesis and/or regeneration of islets of Langerhans or preventing their destruction by apoptosis, preventing apoptosis in beta-cells, and stabilizing, restoring, and/or improving pancreatic function, and more particularly stabilizing, restoring, and/or improving beta-cells size, growth and/or function.

In another aspect, this invention relates to a method for the prevention or treatment of hyperglycemia, a disease directly related to an undesirably high glycemia or undesirably low circulating levels of insulin and/or low insulin secretion by pancreatic cells and/or restoring its target organ sensitivity to its action on glucose disposal, to a method of reducing serum glucose levels, preferably the disease is diabetes, e.g. type 1 and/or type 2. The invention further includes a method for stabilizing renal function or delaying progression of a renal disorder.

The invention also provides methods for the treatment or prevention of the aforementioned diseases comprising administration of a therapeutically effective amount of a compound of the invention or a composition comprising the same, to a subject, preferably a human subject in need thereof.

The present invention further relates to a method for increasing the therapeutic effectiveness of 1,3PDS comprising administering to a subject, preferably a human subject, an effective amount of a prodrug of the present invention.

The present invention also provides processes for converting compounds of the invention to 1,3PDS. The conversion and/or generation of 1,3PDS involve contacting any of the compounds of the invention with, for example, blood, plasma, organs and/or cells. The conversion can occur in vitro or in vivo. The conversion may also occur in the presence of enzymes capable of cleaving the prodrug bonds, including sulfonate ester bonds and amide bonds, such as peptidases, or other enzymes appropriate for other structures herein, including those found in the blood, plasma and/or organs.

In certain embodiments, a pharmaceutical composition, formulation, or dosage form of the present invention is capable of maintaining a therapeutically effective concentration of 1,3PDS in the plasma or blood of a patient for a time period of at least about 1 hour, for at least 2 hours, for at least 3 hours, 4 hours, for at least about 8 hours, for a period of at least about 12 hours, at least about 16 hours, at least about 20 hours, and in certain embodiments for at least about 24 hours after the pharmaceutical composition, formulation, or dosage form comprising a corresponding compound according to the invention and a pharmaceutically acceptable vehicle is orally administered to the patient. In certain embodiments, a pharmaceutical composition, formulation, or dosage form of the present invention is capable of improving the $T_{max}$ of 1,3PDS by at least 2 fold, or by at least 3, 4, 5, 6, 7, 8, 9 or 10 fold or more. In certain embodiments, a pharmaceutical composition, formulation, or dosage form of the present invention is capable of improving the bioavailability (% F) of 1,3PDS by at least 1.2 fold, or by at least 1.5, 1.8, 2, 2.5, 3, 4, 5, 6 fold or more. In certain embodiments, a pharmaceutical composition, formulation, or dosage form of the present invention is capable of improving the AUC of 1,3PDS by at least 1.2 fold, or by at least 1.5, 1.8, 2, 2.5, 3, 4, 5, 6 fold or more.

Additional objects, advantages and features of the present invention will become more apparent upon reading of the following non-restrictive description of preferred embodiments which are exemplary and should not be interpreted as limiting the scope of the invention.

DETAILED DESCRIPTION

I. Definitions

All technical and scientific terms used herein have the same meaning as commonly understood by one ordinary skilled in the art to which the invention pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

It should be noted that, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For greater certainty, other examples of abbreviations include 1,3PDS (1,3-propanedisulfonic acid), MeOH (methanol), EtOH (ethanol), $Et_2O$ (diethyl ether), $CH_2Cl_2$ (dichloromethane), $CH_2I_2$ (diiodomethane), $CH_3CN$ or MeCN (acetonitrile), $H_2O$ (water), THF (tetrahydrofuran), DMF (N,N-dimethylformamide), HCl (hydrochloric acid), and DBU (1,8-biazabicyclo[5.4.0]undec-7-ene).

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "—" in general represents a bond between two atoms in the chain. Thus $CH_3$—O—$CH_2$—$CH(R_i)$—$CH_3$ represents a 2-substituted-1-methoxypropane compound. In addition, the symbol "—" represents the point of attachment of the substituent to a compound. Thus for example —($C_1$-$C_6$)alkylaryl indicates an arylalkyl group, such as benzyl, attached to the compound through the alkyl moiety. Further, when partial structures of the compounds are illustrated, brackets or equivalents indicate the point of attachment of the partial structure to the rest of the molecule.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

As used herein, the terms "compounds of the present invention", "prodrugs of the present invention" and equivalent expressions refer to compounds mentioned herein as being useful for at least one purpose of the invention, e.g., those encompassed by structural Formulae such as (I), (II), (II-A), (III), (III-A), (IV) and (V) optionally with reference to any of the applicable embodiments of Formulae (B) to (F), and includes specific compounds mentioned herein such as, for example, Compounds A1-A73, B1-B87, C1-C3, D1-D8, G1-G4, N1-N18, and P1, as well as their pharmaceutically acceptable salts and solvates when applicable. Reference to specific salts in the examples is made by the addition of the counterion in brackets (e.g. Compound B51(2TFA) is understood as the bis-trifluoroacetic acid salt of Compound D51). Embodiments herein may exclude one or more of the compounds of the invention. Compounds may be identified either by their chemical structure and/or chemical name. When the chemical structure and chemical name conflict, the chemical structure is determinative of the identity of the compound.

The term compounds of the invention, unless otherwise noted, also encompass all possible enantiomers and stereoisomers of the illustrated compounds including the stereoisomerically pure form (e.g., geometrically pure, enantiomerically pure, or diastereomerically pure) and enantiomeric and stereoisomeric mixtures if applicable. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. Accordingly, the term also encompass all possible tautomeric forms of the illustrated compounds. The term also include isotopically labeled compounds where one or more atoms have an atomic mass different from the atomic mass most abundantly found in nature. Examples of isotopes that may be incorporated into the compounds of the present invention include, but are not limited to, $^2H$ (D), $^3H$ (T), $^{11}C$ $^{13}C$ $^{14}C$, $^{15}N$, $^{18}O$, $^{17}O$, any one of the isotopes of sulfur, etc. Compounds may exist in unsolvated forms as well as solvated forms, including hydrated forms. Certain compounds may exist in multiple crystalline or amorphous forms. In general, all physical forms are equivalent for the uses contemplated herein and are intended to be within the scope of the present invention, and are intended to be included by the term "compounds of the invention" and equivalents.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the biodistribution (e.g., to allow agents which would not typically enter the reactive site of the protease) or the pharmacokinetics for a particular agent. A wide variety of groups have been used to modify compounds to form prodrugs, for example, esters, ethers, phosphates, etc. When the prodrug is administered to a subject, the group is cleaved, enzymatically or non-enzymatically, reductively, oxidatively, or hydrolytically, or otherwise to reveal the active form. Prodrugs are frequently, although not necessarily, pharmacologically inactive until converted to the parent drug.

The term "oligomer" or "gemini dimer" and equivalent expressions refer to a synthetic compound comprising at least two moieties of the same agent or drug coupled together. For background on gemini dimers, see: Hammell D C, Hamad M, Vaddi H K, Crooks P A, Stinchcomb A L, A duplex "Gemini" prodrug of naltrexone for transdermal delivery, *J Control Release*, 2004, 97(2):283-90. In preferred embodiment, the gemini dimers of the invention are made of two linked 1,3PDS molecules that may be converted in vitro or in vivo directly or indirectly to release at least one, preferably two, pharmaceutically active 1,3PDS molecules.

The term "ester" refers to compounds that can be represented by the formula RCOOR (carboxylic ester) or the formula $RSO_3R'$ (sulfonate ester), where the group R can be, for example 1, 3PDS or the 3-sulfopropane part thereof, and the group R' is another organic group. These compounds are usually respectively formed by the reaction between a carboxylic or a sulfonic acid and an alcohol usually with the elimination of water, or by the reaction of an activated form of the carboxylic or sulfonic acid with an alcohol. The term "sulfonate ester" refers to an esterified sulfonic acid, and which are represented, for example, by the compounds of Formulae II and II-A.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, as well as amino acids having nitrogen or oxygen-containing side chains (such as Lys, Orn, or Ser) in which the nitrogen or oxygen atom has been acylated or alkylated. Amino acids may be pure L or D isomers or mixtures of L and D isomers, including racemic mixtures. Amino acid may be α-, or β-, or γ-, or δ-, or ω-amino acid.

The term "natural amino acid" and equivalent expressions refer to L-amino acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), tyrosine (Tyr), β-alanine (β-ALA), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein and are meant to include the same moieties. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), 2-aminopimelic acid (Apm), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-$C_{12}$-Phe), 3,4-difluororphenylalanine (3,4-$F_2$-Phe), 3,5-diiodotyrosine (3,5-$I_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

The term "aliphatic group" includes organic moieties characterized by straight or branched-chains, typically having between 1 and 16 carbon atoms, or having between 1 to 12, 1 to 8, 1 to 5 or 1 to 3 carbon atoms. Aliphatic groups include acyclic alkyl groups, alkenyl groups, and alkynyl groups.

As used herein, the term "acyclic" refers to an organic moiety without ring system.

As used herein, the term "alkyl" refers to saturated hydrocarbons having from one to sixteen carbon atoms, including linear or branched alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. The term "$C_1$-$C_n$alkyl" refers to an alkyl group having from 1 to the indicated "n" number of carbon atoms.

As used herein, the term "alkenyl" refers to unsaturated hydrocarbons having from two to sixteen carbon atoms, including linear or branched alkenyl groups, and comprising between one and six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, and the like. The term alkenyl includes both unsubstituted alkenyl groups and substituted alkenyl groups. The term "$C_2$-$C_n$alkenyl" refers to an alkenyl group having from 2 to the indicated "n" number of carbon atoms.

As used herein, the term "alkynyl" refers to unsaturated hydrocarbons having from two to twelve carbon atoms, including linear or branched alkynyl groups, and comprising between one to six carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl" refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal or less than 6 carbon atoms.

The terms "cycloalkyl", "alicyclic", "carbocyclic" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo [4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

The term "heterocycloalkyl" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members, where one or more (up to six) ring members are substituted or unsubstituted heteroatoms (e.g. N, O, S, P) or groups containing such heteroatoms (e.g. $NH$, $NR_x$ ($R_x$ is alkyl, acyl, aryl, heteroaryl or cycloalkyl), $PO_2$, $SO$, $SO_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl" refers to a heterocycloalkyl group having from 3 to the indicated "n" number of atoms (carbon or heteroatom or group) in the ring structure, including at least one hetero group or atom as defined above. Unless the number of carbons is otherwise specified, "lower heterocycloalkyl" groups as herein used, have at least 3 and equal or less than 8 ring members in their ring structure.

The terms "aryl" and "aryl ring" refer to aromatic groups having 4n+2 π(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl" refers to an aryl group having from 6 to the indicated "n" number of carbons in the ring structure.

The terms "heteroaryl" and "heteroaryl ring" refer to aromatic groups having 4n+2 π(pi) electrons, wherein n is an integer from 1 to 3, in a conjugated monocyclic or polycyclic system (fused or not) and having five to fourteen ring members, including one to six substituted or unsubstituted heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g. via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, 3H-indolyl, indolinyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_6$-$C_n$heteroaryl refers to an heteroaryl group having from 5 to the indicated "n" number of atoms (carbon or heteroatom or group) in the ring structure, including at least one hetero group or atom as defined above.

The terms "heterocycle" or "heterocyclic" or "heterocyclyl" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula $-NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term "aminocarbonyl" includes compounds or moieties which contain a nitrogen atom bound to the carbon of a carbonyl or a thiocarbonyl group. The term acylamino refers to an amino group directly attached to an acyl group as defined herein.

The term "nitro" means $-NO_2$; the terms "halo" and "halogen" refer to bromine, chlorine, fluorine or iodine substituents; the term "thiol", "thio", or "mercapto" means SH; and the term "hydroxyl" or "hydroxy" means $-OH$. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as halogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_n$alkyl, $C_1$-$C_n$alkenyl, $C_1$-$C_n$alkynyl, wherein n is an integer from 2 to 10; e.g. acetyl, a cycloalkyl group (e.g. $C_3$-$C_8$cycloalkyl), a heterocyclic group (e.g. $C_3$-$C_8$heterocycloalkyl and $C_5$-$C_6$heteroaryl), an aromatic group (e.g. $C_6$aryl, e.g., benzoyl), and the like. Acyl groups may be unsubstituted or substituted acyl groups (e.g. salicyloyl).

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, hemihydrates, ethanolates, hemiethanolates, n-propanolates, iso-propanolates, 1-butanolates, 2-butanolate, and solvates of other physiologically acceptable solvents, such as the Clas 3 solvents described in the International Conference on Harmonization (ICH), Guide for Industry, Q3C Impurities: Residual Solvents (1997). The compounds of the invention include each solvate and mixtures thereof.

A "pharmaceutically acceptable salt" of a compound and equivalent expressions, means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron, vanadium and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from the parent agent that contains a basic or acidic moiety, by conventional chemical methods. Generally, such salts are prepared by reacting the free acid or base forms of these agents with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

"AUC" is the area under a curve representing the concentration of a compound in a biological sample of a subject as a function of time following administration of the compound to the subject. Examples of biological samples include biological fluids such as plasma and blood, or organ homogenates such as brain or liver homogenates. The AUC can be determined by measuring the concentration of a compound in a biological sample such as the plasma, blood or brain homogenate using methods such as liquid chromatography-tandem mass spectrometry (LC/MS/MS), at various time intervals, and calculating the area under the concentration-versus-time curve. Suitable methods for calculating the AUC from a drug concentration-versus-time curve are well known in the art. As relevant to the disclosure here, an AUC for 1,3PDS can be determined by measuring the concentration of 1,3PDS in the plasma, blood or brain homogenate of a subject following oral administration of a compound of the invention to the subject. Unless noted otherwise herein; AUC means $AUC_{O-\infty}$.

"Bioavailability" refers to the rate and amount of a drug that reaches the systemic circulation of a subject following administration of the drug or prodrug thereof to the patient and can be determined by evaluating, for example, the plasma or blood concentration-versus-time profile for the drug. Parameters useful in characterizing a plasma or blood concentration-versus-time curve include the area under the curve (AUC), the time to peak concentration ($T_{max}$), and the maximum drug concentration ($C_{max}$). Bioavailability is often expressed as F (%) referring to the ratio in percentage of the AUC of the compound for a specific mode of administration (e.g. orally) over AUC of the compound after an IV administration. "$C_{max}$" is the maximum concentration of a drug in the biological sample of a subject following administration of a dose of the drug or prodrug to the subject. "$T_{max}$" is the time to the maximum concentration ($C_{max}$) of a drug in the biological sample of a subject following administration of a dose of the drug or prodrug to the subject.

"Bioequivalence" refers to equivalence of the rate and extent of absorption of a drug after administration of equal doses of the drug or prodrug to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the size, age, and general health of the subject; the specific disease involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances.

As used herein the term "therapeutic bio-distribution of 1,3PDS" refers to one or more pharmacokinetic parameters of 1,3PDS which affect 1,3PDS therapeutic activity. Examples of such pharmacokinetic (PK) parameters include but are not limited to: bioavailability of 1,3PDS, AUC of 1,3PDS, $C_{max}$ of 1,3PDS, $T_{max}$ of 1,3PDS, bio-absorption of 1,3PDS, bio-distribution of 1,3PDS etc.

As used herein the terms "increased (or like terms, e.g., increasing, increase in, etc.) therapeutic effectiveness of 1,3PDS" and "enhanced (or like terms, e.g., enhancing, enhancement, etc.) therapeutic effectiveness of 1,3PDS" refer to an increased effectiveness of 1,3PDS as measured, e.g., by one or more parameters listed under "therapeutic bio-distribution of 1,3PDS" above, e.g., by 5%, 10%, 20%, 30%, 40%, 50%, 60%, 70%, 80%, 90%, 95%, 99%, 125%, etc., or even more, e.g., 2, or 4 fold, or even more when administered to a subject, e.g., animal or human, which increase is with respect to the same equivalent molar dose of 1,3PDS administered orally in water solution.

The term "reduction of side effects of 1,3PDS" refers to decreasing the amount of or severity of one or more side effects of 1,3PDS by, e.g., 5%, 10%, 20%, 30%, 40%, 50%, 60%, 70%, 80%, 90%, 95%, 99%, or 99.9%, or even 100%, which decrease is with respect to the amount of or severity of a side effect of 1,3PDS that is exhibited when the same equivalent molar dose of free or disodium salt of 1,3PDS is administered orally.

The term "reduction of effective dosage of 1,3PDS" refers to decreasing the molar amount of 1,3PDS in the prodrug necessary to be administered to achieve the same or equivalent result as achieved by administering free 1,3PDS (e.g. to achieve equivalent parameters such as one of AUC, $C_{max}$, $T_{max}$, % F, an the like). The decrease is for example administration of 5%, 10%, 20%, 30%, 40%, 50%, 60%, 70%, or 80%, of the dose of 1,3PDS (molar equivalent) in order to achieve the same or equivalent blood levels as compared to administration of free 1,3PDS, or to reach equivalent efficacy.

More generally, the terms lessening etc., increasing etc., refer in context herein to the percentage changes, e.g., by 5%, 10%, 20%, 30%, 40%, 50%, 60%, 70%, 80%, 90%, 95%, 99%, 125%, etc., or even more, e.g., 2, or 4 fold, or even more.

When referring to "1,3PDS" being produced (e.g., released from a formulation or prodrug), all forms of 1,3PDS are included, e.g., solvates thereof, ionically dissociated forms thereof, charged forms thereof, etc.

"Pharmaceutically acceptable" and equivalent expressions refer to salts, drugs, medicaments, inert ingredients, carrier, vehicle, fillers, etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutical composition" refers to at least one compound and at least one pharmaceutically acceptable vehicle, with which the compound is administered to a subject.

"Pharmaceutically acceptable vehicle" and equivalent expressions refer to a diluent, adjuvant, excipient, or carrier with which a compound is administered.

Reference will now be made in detail to certain embodiments of compounds and methods. The disclosed embodiments are not intended to be limiting of the invention.

II. Compounds of the Invention

The present invention relates to methods, compounds and compositions for delivering in a subject, preferably a human subject, 1,3-propanedisulfonic acid, or salts thereof, also referred herein as 1,3PDS. The invention encompasses compounds that will yield or generate 1,3PDS, either in vitro or in vivo.

Accordingly, the invention relates to compounds of Formula I:

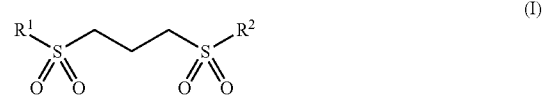

(I)

wherein,
R$^1$ is selected from OR$^3$, —NHC(O)R$^5$, —NHC(NH)NHR$^5$, and —NH(C$_5$-C$_{10}$heteroaryl);

$R^2$ is selected from $OR^4$, —$NHC(O)R^5$, —$NHC(NH)NHR^5$, and —$NH(C_5$-$C_{10}$heteroaryl), or $R^1$ is a covalent bond and $R^2$ is selected from O, $OC_1$-$C_3$alkylO, NH, $NC(O)R^5$, $NC(NH)NHR^5$, and $N(C_5$-$C_{10}$heteroaryl) when $R^1$ and $R^2$ are taken together with their adjacent atoms to form a heterocycle;

$R^3$ is selected from hydrogen and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

$R^4$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl; and $R^5$ is selected from hydrogen and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

or a pharmaceutically acceptable salt or solvate thereof.

The invention pertains to both salt forms and free acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein as free acids or bases.

To avoid any confusion, in this section the exemplary compounds of the invention are all shown in their free (i.e. free acid or base) form. Reference to specific salts in the examples is made by the addition of the counterion in brackets. For example, Compound A29(Na) or Compound A29(sodium salt) is the sodium salt of Compound A29, and Compound B51(2TFA) is understood as the bis(trifluoroacetic acid) salt of Compound B51.

The sulfonate ester moiety, any other pharmacokinetic modulating moiety of the prodrugs, their precursors, as well as combinations thereof, may be cleaved prior to absorption by the gastrointestinal tract (e.g., within the stomach or intestinal lumen) and/or after absorption by the gastrointestinal tract (e.g., in intestinal tissue, blood, liver, or other suitable tissue of a mammal). In certain embodiments, 1,3PDS remains covalently attached to the pharmacokinetic modulating moiety during transit across the intestinal mucosal barrier. In certain embodiments, pharmacokinetic modulating moieties according to the invention are essentially not metabolized to the corresponding 1,3PDS within cells of the intestine or liver (e.g. enterocytes, hepatocytes), but generates the parent 1,3PDS molecule once within the systemic circulation. These prodrugs may be absorbed into the systemic circulation either by active transport, passive diffusion, or by a combination of both active and passive processes.

The pharmacokinetic modulating moiety of certain of the compounds according to the invention may be cleaved either chemically and/or enzymatically. One or more enzymes present in the stomach, intestinal lumen, intestinal tissue, blood, liver, or any other suitable tissue or organ of a mammal may enzymatically cleave release 1,3PDS. The pharmacokinetic moiety may also be cleaved indirectly by the cleavage of a moiety located, for example, 5 to 7 atoms away from the sulfonate ester, the cleavage of said moiety triggering internal cyclization, or other internal reaction, to liberate the desired free drug. The cleavable moiety will generally comprise a bond which is known to be so cleavable such as but not limited to, a peptide, amide, ester, sulfide, disulfide, carboxamate, urea, —N—O—, etc. bond, and others as demonstrated for example in the structures disclosed herein, all of which are in general applicable as linkages in compounds in general. Actual cleavability of the linker can be assessed in vitro and/or in vivo by using hydrolytic-, enzymatic- (e.g. peptidase, esterase) or metabolic-based tests and assays well known in the art. International PCT application WO 91/14434, WO 96/18609, published applications US 2005/0096317, and US 2006/0046967, and Yan L. et al, (2004), *J. Med. Chem.*, 47, 1031-43, are all incorporated herein by reference in their entirety since they describe a variety of linkers that may be useful according to the present invention.

Although theory of operation is discussed herein, for specific compound structures, including all generic structural formulas and specific names and formulas of compounds, the invention is not limited by any such theories unless specifically stated otherwise. Thus, all uses of all novel compounds are encompassed by the invention, irrespective of mechanism or theory of operation.

A. The sulfonate ester prodrugs:

The invention also relates to a compound of the Formula II:

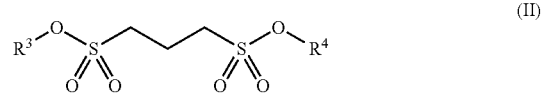

(II)

wherein, $R^3$ is selected from hydrogen and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl; and $R^4$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

or a pharmaceutically acceptable salt or solvate thereof.

The invention also relates to compounds of Formula II, wherein at least one of $R^3$ or $R^4$ is a pharmacokinetic modulating moiety. Examples of suitable pharmacokinetic modulating moieties include sulfonate esters, neopentyl sulfonate esters, aryl sulfonate ester, and nitro-substituted aryl sulfonate esters.

In another aspect, the invention relates to Formula II-A, as well as salts and solvates thereof:

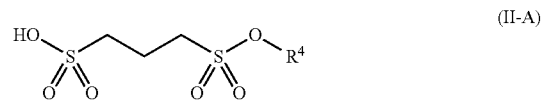

(II-A)

wherein, $R^4$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

or a pharmaceutically acceptable salt or solvate thereof.

The invention also relates to compounds of Formula II or II-A, wherein $R^3$ and/or $R^4$ are each independently selected from the group consisting of: (i) a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl; (ii) a substituted or unsubstituted group selected from $C_1$-$C_{12}$alkyl, $C_2$-$C_{12}$alkenyl, $C_6$-$C_{15}$aryl, and $C_3$-$C_{15}$heteroaryl; (iii) a substituted or unsubstituted group selected from $C_3$-$C_8$alkyl, $C_6$-$C_{10}$aryl, and $C_5$-$C_{10}$heteroaryl; (iv) a substituted or unsubstituted $C_1$-$C_{12}$alkyl group; (v) a substituted $C_3$-$C_8$alkyl group; (vi) a branched $C_3$-$C_8$alkyl group; (vii) a substituted branched $C_3$-$C_8$alkyl group; (viii) a substituted or unsubstituted neopentyl group; (ix) a substituted neopentyl group; or (x) a group of Formula B:

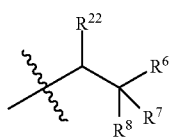
(B)

wherein, $R^6$, $R^7$ and $R^8$ are each independently a substituted or unsubstituted group selected from $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, $C_6$-$C_{10}$aryl, $C_5$-$C_{10}$heteroaryl, C(O)OH, C(O)O$C_1$-$C_6$alkyl, $NH_2$, NHC(O)O$C_1$-$C_6$alkyl, or $R^7$ and $R^8$ are taken together with their adjacent carbon atom to form a group selected from $C_3$-$C_8$cycloalkyl, and $C_3$-$C_8$heterocycloalkyl, or $R^6$, $R^7$ and $R^8$ are taken together with their adjacent carbon atom to form a $C_4$-$C_{10}$cycloalkyl or $C_4$-$C_{10}$heterocycloalkyl fused ring group, or a $C_6$-$C_{10}$aryl, and $C_5$-$C_{10}$heteroaryl; and $R^{22}$ is a hydrogen atom or a group selected from $C_1$-$C_6$alkyl, C(O)OH, or C(O)O$C_1$-$C_6$alkyl.

According to one aspect, at least one of $R^3$ and/or $R^4$ in Formula II or II-A is the group of Formula B, wherein $R^{22}$ is $C_2$-$C_6$alkyl, wherein $R^{22}$ is a $C_3$-$C_5$alkyl, or wherein $R^{22}$ is a $C_3$-$C_4$alkyl. According to another aspect, at least one of $R^3$ and/or $R^4$ in Formula II or II-A is a group of Formula B' defined as follows:

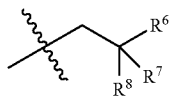
(B')

wherein, $R^6$, $R^7$ and $R^8$ are as previously defined.

More particularly, the invention relates to compounds of Formula II or II-A, wherein $R^3$ and/or $R^4$ are each independently a group of Formula B or B', wherein $R^6$ is —$CH_2CH_2$Nu or —$CH_2$Nu, wherein Nu is a nucleophilic group, which is a functional group having a reactive pair of electrons and having the ability of forming a chemical bond by donating electrons. For example, the nucleophilic group is selected from the group consisting of carboxylates, sulfonates, substituted or unsubstituted amines, alcohols (hydroxyl), thiols, sulfides, hydroxylamines, and imines. In another embodiment, the nucleophilic group is selected from the group consisting of substituted or unsubstituted amines, and alcohols (hydroxyl), preferably an unsubstituted amine ($NH_2$). The invention also further relates to compounds of Formula II or II-A, wherein $R^4$ is a group of Formula B or B', wherein $R^6$ is —$CH_2CH_2NH_2$, and $R^7$ and $R^8$ are each independently a substituted or unsubstituted group selected from $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, $C_6$-$C_{10}$aryl, and $C_5$-$C_{10}$heteroaryl, or $R^7$ and $R^8$ are taken together with their adjacent carbon atom to form a group selected from $C_3$-$C_8$cycloalkyl and $C_3$-$C_8$heterocycloalkyl. Also, $R^4$ may be a group of Formula B or B' wherein $R^6$ is —$CH_2CH_2NH(aa)_{1-3}$, wherein aa is independently in each occurrence, the residue of a C-coupled amino acid, and $R^7$ and $R^8$ are each independently a substituted or unsubstituted group selected from $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, $C_6$-$C_{10}$aryl, and $C_5$-$C_{10}$heteroaryl, or $R^7$ and $R^8$ are taken together with their adjacent carbon atom to form a group selected from $C_3$-$C_8$cycloalkyl and $C_3$-$C_8$heterocycloalkyl. In a further aspect, $R^4$ is a group of Formula B or B' wherein $R^6$ is —$CH_2CH_2NH_2$, and $R^7$ and $R^8$ are each independently a $C_1$-$C_6$alkyl, or $R^7$ and $R^8$ are taken together with their adjacent carbon atom to form a $C_3$-$C_8$cycloalkyl, preferably $R^7$ and $R^8$ are each a methyl group. In yet another aspect, $R^4$ is a group of Formula B or B' wherein $R^6$ is —$CH_2CH_2$NH(aa), wherein aa is the residue of a C-coupled amino acid, and $R^7$ and $R^8$ are each independently a $C_1$-$C_6$alkyl, or $R^7$ and $R^8$ are taken together with their adjacent carbon atom to form a $C_3$-$C_8$cycloalkyl, preferably $R^7$ and $R^8$ are each a methyl group. In a further aspect, $R^7$ and $R^8$ are taken together with their adjacent carbon atom to form a $C_3$-$C_8$heterocycloalkyl, or $R^7$ and $R^8$ are taken together with their adjacent carbon atom to form a lactone (e.g. a furanone). In yet a further aspect, $R^6$ is a methyl group and $R^7$ and $R^8$ are taken together with their adjacent carbon atom to form a $C_3$-$C_8$heterocycloalkyl, or $R^7$ and $R^8$ are taken together with their adjacent carbon atom to form a lactone (e.g. a furanone).

The invention also relates to compounds of Formula II or II-A, wherein $R^3$ and/or $R^4$ are each independently a group of Formula B or B', wherein $R^6$ is a group of Formula C:

(C)

wherein, $R^9$ is, separately in each occurrence, selected from hydrogen, hydroxyl, halogen, cyano, trifluoromethyl, nitro, and a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl, C(O)OH, C(O)O$R^{11}$, O$R^{11}$, OC(O)$R^{11}$, OC(O)O$R^{11}$, NHC(O)$R^{11}$, $NH_2$, NH$R^{11}$, and N($R^{11}$)$_2$;

X is selected from the group consisting of OH, $NH_2$, $NO_2$, CN, SH, C(O)OH, C(O)O$R^{12}$, OC(O)O$R^{12}$, NHC(O)O$R^{12}$, SC(O)O$R^{12}$, P(O)(OH)$_2$, P(O)(O$R^{12}$)$_2$, P(O)(O$R^{12}$)(OH), OC(O)$R^{13}$, OC(O)NH$R^{13}$, SC(O)$R^{13}$, C(O)$R^{14}$, and NH$R^{15}$;

n is an integer selected from 0, 1, 2 and 3;

$R^{11}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl and benzyl;

$R^{12}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl, benzyl, $CH_2R^{16}$, and CH($C_1$-$C_6$alkyl)$R^{16}$;

$R^{13}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl, and benzyl;

$R^{14}$ is the residue of a natural or unnatural N-coupled amino acid having an protected or unprotected carboxyl end;

$R^{15}$ is the residue of a natural or unnatural C-coupled amino acid having an protected or unprotected amino end; and $R^{16}$ is selected from the group consisting of OC(O)$C_1$-$C_6$alkyl and OC(O)O$C_1$-$C_6$alkyl.

The invention also relates to compounds of Formula II or II-A, wherein $R^3$ and/or $R^4$ are each independently a group of Formula B or B', wherein $R^6$ is a group of Formula C, wherein $R^9$ is selected from hydrogen, hydroxyl, $C_1$-$C_6$alkyl, $OR^{11}$, $OC(O)R^{11}$, and $OC(O)OR^{11}$, and all other groups are as previously defined. In one example, $R^9$ is selected from hydrogen, hydroxyl, $C_1$-$C_6$alkyl, $OR^{11}$, $OC(O)R^{11}$, and $OC(O)OR^{11}$. In another example, $R^9$ is selected from hydrogen, hydroxyl, $C_1$-$C_6$alkyl, $OR^{11}$, $OC(O)R^{11}$, and $OC(O)OR^{11}$. In another example, $R^9$ is selected from hydroxyl, $OR^{11}$, $OC(O)R^{11}$, and $OC(O)OR^{11}$. According to a further example, $R^9$ is hydroxyl and all other groups are as previously defined. In yet another example, $R^9$ is selected from $C(O)OH$ and $C(O)OR^{11}$.

Another example of compounds of the invention are compounds of Formula II or II-A, wherein at least one of $R^3$ and $R^4$ is a group of Formula B or B', wherein $R^6$ is a group of Formula C, wherein X is selected from OH, $NH_2$, and SH. In another example, X is selected from $C(O)OH$, $C(O)OR^{12}$, and $C(O)R^{14}$. In another example, X is selected from $OC(O)OR^{12}$, $OC(O)R^{13}$, and $OC(O)NHR^{13}$. In another example, X is selected from $SC(O)R^{13}$ and, $SC(O)OR^{12}$. In another example, X is selected from $NHC(O)OR^{12}$ and $NHR^{15}$. In another example, X is selected from OH, $OC(O)OR^{12}$, $OC(O)R^{13}$, and $OC(O)NHR^{13}$. In a further example, X is selected from SH, $SC(O)R^{13}$ and, $SC(O)OR^{12}$. In yet another example, X is selected from $NH_2$, $NHC(O)OR^{12}$ and $NHR^{15}$.

The invention also relates to compounds of Formula II or II-A, wherein $R^3$ and/or $R^4$ are each independently a group of Formula B or B', wherein $R^6$ is a group of Formula C, wherein X is $C(O)OR^{12}$ and all other groups are as previously defined. As an example, X is $C(O)OR^{12}$, and $R^{12}$ is selected from $C_1$-$C_6$alkyl, $C_6$aryl, benzyl, $CH_2R^{16}$, and $CH(C_1$-$C_6$alkyl)$R^{16}$. As another example, X is $C(O)OR^{12}$, and $R^{12}$ is selected from $C_1$-$C_6$alkyl, $CH_2R^{16}$, and $CH(C_1$-$C_6$alkyl)$R^{16}$ and all other groups are as previously defined. According to another example, X is $C(O)OR^{12}$, $R^9$ is selected from hydrogen, hydroxyl, $C_1$-$C_6$alkyl, $OR^{11}$, $OC(O)R^{11}$, and $OC(O)OR^{11}$, and all other groups are as previously defined. In a further example, X is $C(O)OR^{12}$, $R^9$ is selected from hydrogen, hydroxyl, $C_1$-$C_6$alkyl, $OR^{11}$, $OC(O)R^{11}$, and $OC(O)OR^{11}$, and $R^{12}$ is selected from $C_1$-$C_6$alkyl, $C_6$aryl, benzyl, $CH_2R^{16}$, and $CH(C_1$-$C_6$alkyl)$R^{16}$. In yet another example, X is $C(O)OR^{12}$, $R^9$ is selected from hydrogen, hydroxyl, $C_1$-$C_6$alkyl, $OR^{11}$, $OC(O)R^{11}$, and $OC(O)OR^{11}$, and $R^{12}$ is selected from $C_1$-$C_6$alkyl, $CH_2R^{16}$, and $CH(C_1$-$C_6$alkyl)$R^{16}$. In one aspect, when X is $C(O)OR^{12}$, then n is an integer selected from 1 or 2, preferably n is 1.

The invention also relates to compounds of Formula II or II-A, wherein $R^3$ and/or $R^4$ are each independently a group of Formula B or B', wherein $R^6$ is a group of Formula C and wherein X is $NHC(O)OR^{12}$ and all other groups are as previously defined. As an example, X is $NHC(O)OR^{12}$, and $R^{12}$ is selected from $C_1$-$C_6$alkyl, $C_6$aryl, benzyl, $CH_2R^{16}$, and $CH(C_1$-$C_6$alkyl)$R^{16}$. In another example, X is $NHC(O)OR^{12}$, and $R^{12}$ is selected from $C_1$-$C_6$alkyl, $CH_2R^{16}$, and $CH(C_1$-$C_6$alkyl)$R^{16}$. According to another example, X is $NHC(O)OR^{12}$, and $R^9$ is selected from hydrogen, hydroxyl, $C_1$-$C_6$alkyl, $OR^{11}$, $OC(O)R^{11}$, and $OC(O)OR^{11}$, and all other groups are as previously defined. In another example, X is $NHC(O)OR^{12}$, $R^9$ is selected from hydrogen, hydroxyl, $C_1$-$C_6$alkyl, $OR^{11}$, $OC(O)R^{11}$, and $OC(O)OR^{11}$, and $R^{12}$ is selected from $C_1$-$C_6$alkyl, $C_6$aryl, benzyl, $CH_2R^{16}$, and $CH(C_1$-$C_6$alkyl)$R^{16}$. In a further example, X is $NHC(O)OR^{12}$, $R^9$ is selected from hydrogen, hydroxyl, $C_1$-$C_6$alkyl, $OR^{11}$, $OC(O)R^{11}$, and $OC(O)OR^{11}$, and $R^{12}$ is selected from $C_1$-$C_6$alkyl, $CH_2R^{16}$, and $CH(C_1$-$C_6$alkyl)$R^{16}$. The invention also relates to compounds of Formula II or II-A, wherein $R^3$ and/or $R^4$ are each independently a group of Formula B or B', wherein $R^6$ is a group of Formula C and wherein n is 2, X is $NHC(O)OR^{12}$, and all other groups are as previously defined. As an example, n is 2, X is $NHC(O)OR^{12}$, and $R^{12}$ is selected from $C_1$-$C_6$alkyl, $C_6$aryl, benzyl, $CH_2R^{16}$, and $CH(C_1$-$C_6$alkyl)$R^{16}$. In another example, n is 2, X is $NHC(O)OR^{12}$, and $R^{12}$ is selected from $C_1$-$C_6$alkyl, $CH_2R^{16}$, and $CH(C_1$-$C_6$alkyl)$R^{16}$. In another example, n is 2, X is $NHC(O)OR^{12}$, $R^{12}$ is selected from $C_1$-$C_6$alkyl, $CH_2R^{16}$, and $CH(C_1$-$C_6$alkyl)$R^{16}$ and $R^9$ in at least one occurrence, is selected from hydroxyl, $C_1$-$C_6$alkyl, $OR^{11}$, $OC(O)R^{11}$, and $OC(O)OR^{11}$. In a further example, n is 2, X is $NHC(O)OR^{12}$, $R^{12}$ is selected from $C_1$-$C_6$alkyl, $CH_2R^{16}$, and $CH(C_1$-$C_6$alkyl)$R^{16}$ and $R^9$ in at least one occurrence, is selected from $C(O)OH$ and $C(O)OR^{11}$. In one aspect, when X is $NHC(O)OR^{12}$, then n is an integer selected from 1 or 2, preferably n is 2.

The invention also relates to compounds of Formula II or II-A, wherein $R^3$ and/or $R^4$ are each independently a group of Formula B or B', wherein $R^6$ is a group of Formula C and wherein X is $OC(O)R^{13}$ and all other groups are as previously defined. For example, X is $OC(O)R^{13}$, and $R^{13}$ is selected from $C_1$-$C_6$alkyl, $C_6$aryl, and benzyl. In another example, X is $OC(O)R^{13}$, and $R^{13}$ is $C_1$-$C_6$alkyl. In another example, X is $OC(O)R^{13}$, and $R^{13}$ is $C_6$aryl. According to another example, X is $OC(O)R^{13}$, and $R^9$ is selected from hydrogen, hydroxyl, $C_1$-$C_6$alkyl, $OR^{11}$, $OC(O)R^{11}$, and $OC(O)OR^{11}$. In another example, X is $OC(O)R^{13}$, $R^9$ is selected from hydrogen, hydroxyl, $C_1$-$C_6$alkyl, $OR^{11}$, $OC(O)R^{11}$, and $OC(O)OR^{11}$, and $R^{13}$ is selected from $C_1$-$C_6$alkyl, $C_6$aryl, and benzyl. In another example, X is $OC(O)R^{13}$, $R^9$ is selected from hydrogen, hydroxyl, $C_1$-$C_6$alkyl, $OR^{11}$, $OC(O)R^{11}$, and $OC(O)OR^{11}$, and $R^{13}$ is $C_1$-$C_6$alkyl. In yet another aspect, X is $OC(O)R^{13}$, $R^9$ is selected from hydrogen, hydroxyl, $C_1$-$C_6$alkyl, $OR^{11}$, $OC(O)R^{11}$, and $OC(O)OR^{11}$, and $R^{13}$ is $C_6$aryl, and all other groups are as previously defined. The invention also relates to compounds of Formula II or II-A, wherein $R^3$ and/or $R^4$ are each independently a group of Formula B or B', wherein $R^6$ is a group of Formula C and wherein n is 2, X is $OC(O)R^{13}$, and all other groups are as previously defined. As an example, n is 2, X is $OC(O)R^{13}$, and $R^9$ in at least one occurrence, is selected from hydroxyl, $C_1$-$C_6$alkyl, $OR^{11}$, $OC(O)R^{11}$, and $OC(O)OR^{11}$. In a further example, n is 2, X is $OC(O)R^{13}$, and $R^9$ in at least one occurrence, is selected from $C(O)OH$ and $C(O)OR^{11}$. In one aspect, when X is $OC(O)R^{13}$, then n is an integer selected from 1 or 2, preferably n is 2.

The invention also relates to compounds of Formula II or II-A, wherein $R^3$ and/or $R^4$ are each independently a group of Formula B or B', wherein $R^6$ is a group of Formula C and wherein X is SH, $SC(O)R^{13}$ or $SC(O)OR^{12}$ and all other groups are as previously defined. In one aspect, when X is SH, $SC(O)R^{13}$ or $SC(O)OR^{12}$, then n is an integer selected from 1 or 2, preferably n is 2. In another example, n is 2, X is SH, $SC(O)R^{13}$ or $SC(O)OR^{12}$, and all other groups are as previously defined. As another example, n is 2, X is SH, $SC(O)R^{13}$ or $SC(O)OR^{12}$, and $R^9$ in at least one occurrence, is selected from hydroxyl, $C_1$-$C_6$alkyl, $OR^{11}$, $OC(O)R^{11}$, and $OC(O)OR^{11}$. In a further example, n is 2, X is SH, $SC(O)R^{13}$ or $SC(O)OR^{12}$, and $R^9$ in at least one occurrence, is selected from $C(O)OH$ and $C(O)OR^{11}$.

The invention also relates to compounds of Formula II or II-A, wherein $R^3$ and/or $R^4$ are each independently a group of Formula B or B', wherein $R^6$ is a group of Formula C and wherein X is $NHR^{15}$ and all other groups are as previously defined. For example, X is $NHR^{16}$, and $R^{15}$ is the residue of a natural C-coupled amino acid. In another example, X is NHR$^{16}$, and R$^{15}$ is the residue of a natural C-coupled hydrophobic amino acid, such as an aliphatic hydrophobic amino acid (e.g. alanine, isoleucine, leucine, valine and the like), an aromatic hydrophobic amino acid (e.g. phenylalanine, tryptophan, tyrosine and the like) or a polar hydrophobic amino acid (e.g. cystein, methionine and the like). In another example, X is NHR$^{15}$, and R$^{15}$ is the residue of a natural C-coupled hydrophilic amino acid (e.g. arginine, lysine, asparagine, histidine, proline, aspartic acid, glutamic acid and the like). In another example, X is NHR$^{15}$, and R$^{15}$ is the residue of a natural C-coupled neutral polar amino acid (e.g. asparagine, cystein, glutamine, methionine, serine, threonine and the like). In another example, X is NHR$^{15}$, and R$^{15}$ is the residue of a natural C-coupled acidic amino acid (e.g. aspartic acid, glutamic acid and the like). In yet another example, X is NHR$^{15}$, and R$^{15}$ is the residue of a natural C-coupled basic amino acid (e.g. arginine, histidine, lysine and the like). According to another example, X is NHR$^{15}$, and R$^9$ is selected from hydrogen, hydroxyl, C$_1$-C$_6$alkyl, OR$^{11}$, OC(O)R$^{11}$, and OC(O)OR$^{11}$. In another example, X is NHR$^{15}$, R$^9$ is selected from hydrogen, hydroxyl, C$_1$-C$_6$alkyl, OR$^{11}$, OC(O)R$^{11}$, and OC(O)OR$^{11}$, and R$^{15}$ is the residue of a natural C-coupled amino acid. In a further example, X is NHR$^{15}$, R$^9$ is selected from hydrogen, hydroxyl, C$_1$-C$_6$alkyl, OR$^{11}$, OC(O)R$^{11}$, and OC(O)OR$^{11}$, and R$^{15}$ is the residue of a natural C-coupled lipophilic amino acid. In yet another example, X is NHR$^{15}$, R$^9$ is selected from hydrogen, hydroxyl, C$_1$-C$_6$alkyl, OR$^{11}$, OC(O)R$^{11}$, and OC(O)OR$^{11}$, and R$^{15}$ is the residue of a natural C-coupled hydrophilic amino acid. The invention also relates to compounds of Formula II or II-A, wherein R$^3$ and/or R$^4$ are each independently a group of Formula B, wherein R$^6$ is a group of Formula C and wherein n is 2, X is NHR$^{15}$, and all other groups are as previously defined. As an example, n is 2, X is NHR$^{15}$, and R$^9$ in at least one occurrence, is selected from hydroxyl, C$_1$-C$_6$alkyl, OR$^{11}$, OC(O)R$^{11}$, and OC(O)OR$^{11}$. In a further example, n is 2, X is NHR$^{15}$, and R$^9$ in at least one occurrence, is selected from C(O)OH and C(O)OR$^{11}$. In one aspect, when X is NHR$^{15}$, then n is an integer selected from 1 or 2, preferably n is 2.

Furthermore, the compounds of the invention are encompassed by Formula II or II-A, wherein R$^3$ and/or R$^4$ are each independently a group of Formula B or B' and wherein R$^6$ is a group of Formula C, and all other groups are as previously defined. In one example, R$^6$ is a group of Formula C, and R$^7$ and R$^8$ are each independently a substituted or unsubstituted group selected from C$_1$-C$_6$alkyl, C$_2$-C$_6$alkenyl, C$_2$-C$_6$alkynyl, C$_3$-C$_6$cycloalkyl, C$_3$-C$_6$heterocycloalkyl, C$_6$-C$_{10}$aryl, and C$_5$-C$_{10}$heteroaryl, or R$^7$ and R$^8$ are taken together with their adjacent carbon atom to form a group selected from C$_3$-C$_8$cycloalkyl and C$_3$-C$_8$heterocycloalkyl. In another example, R$^6$ is a group of Formula C, and R$^7$ and R$^8$ are each independently a C$_1$-C$_6$alkyl, or R$^7$ and R$^8$ are taken together with their adjacent carbon atom to form a C$_3$-C$_8$cycloalkyl, preferably R$^7$ and R$^8$ are each a methyl group.

The invention also relates to compounds of Formula II or II-A, wherein R$^3$ and/or R$^4$ are each independently a substituted or unsubstituted C$_6$-C$_{10}$aryl or C$_5$-C$_{10}$heteroaryl. For example, R$^3$ and/or R$^4$ are each independently a substituted C$_6$-C$_{10}$aryl or C$_5$-C$_{10}$heteroaryl. In another example, R$^3$ and/or R$^4$ are each independently a substituted or unsubstituted C$_6$aryl or C$_5$-C$_6$heteroaryl. In a further example, R$^3$ and/or R$^4$ are each independently a group of Formula D:

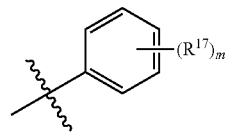

wherein,

R$^{17}$ in each occurrence is each independently a hydrogen atom or a substituted or unsubstituted group selected from C$_1$-C$_6$alkyl, C$_2$-C$_6$alkenyl, C$_2$-C$_6$alkynyl, C$_3$-C$_6$cycloalkyl, C$_3$-C$_6$heterocycloalkyl, C$_6$-C$_{10}$aryl, C$_5$-C$_{10}$heteroaryl, an electron-withdrawing group or a substituent selected from the group consisting of amino, amido, hydroxyl, alkoxy, acyloxy, alkoxycarbonyloxy, and the like; and m is an integer from 1 to 5.

For example, in Formula II or II-A, where R$^3$ and/or R$^4$ are each independently a group of Formula D, then R$^{17}$ is, in at least one occurrence, an electron-withdrawing group, which is a group having the ability to attract valence electrons from neighboring atoms. In another embodiment, R$^{17}$ is an electron-withdrawing group selected from nitro, acyl (ketone), carboxylate (acid), alkoxycarbonyl (ester), alkylaminocarbonyl (amide), formyl (aldehyde), sulfonyl, trifluoromethyl, halogeno (chloro, fluoro, iodo and bromo), and cyano groups. In another example, R$^{17}$ is selected from nitro, acyl (ketone), carboxylate, trifluoromethyl, and halogeno groups (chloro, fluoro, iodo and bromo). In another example, m is an integer selected from 1 to 3, preferably 1 or 2, preferably 1.

The following structures are examples of monosulfonate ester prodrugs of the invention and are illustrative of the invention only and they should not be construed as further limiting:

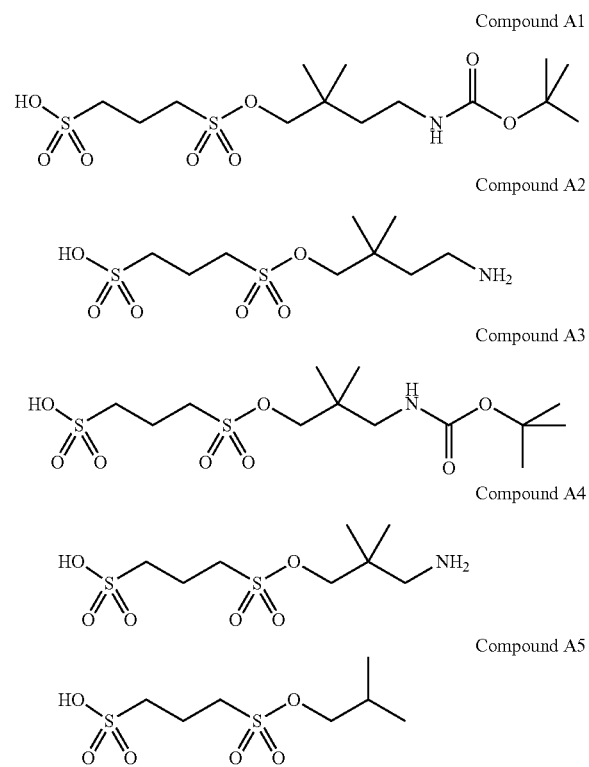

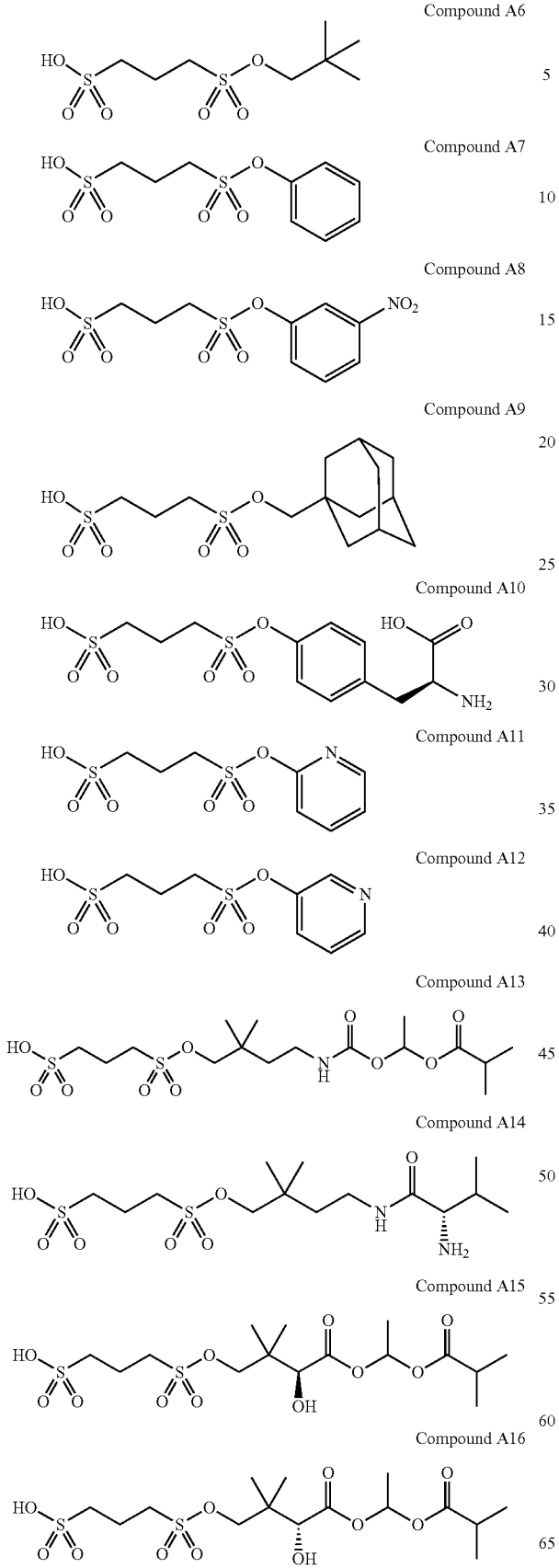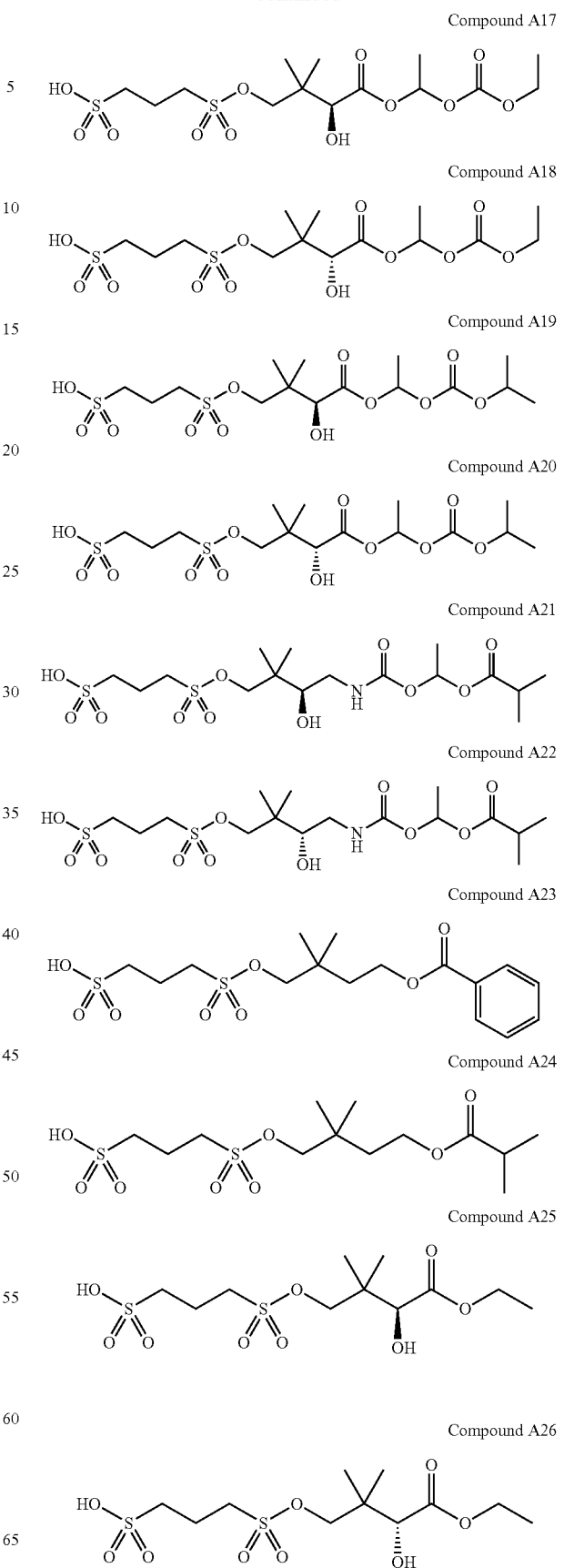

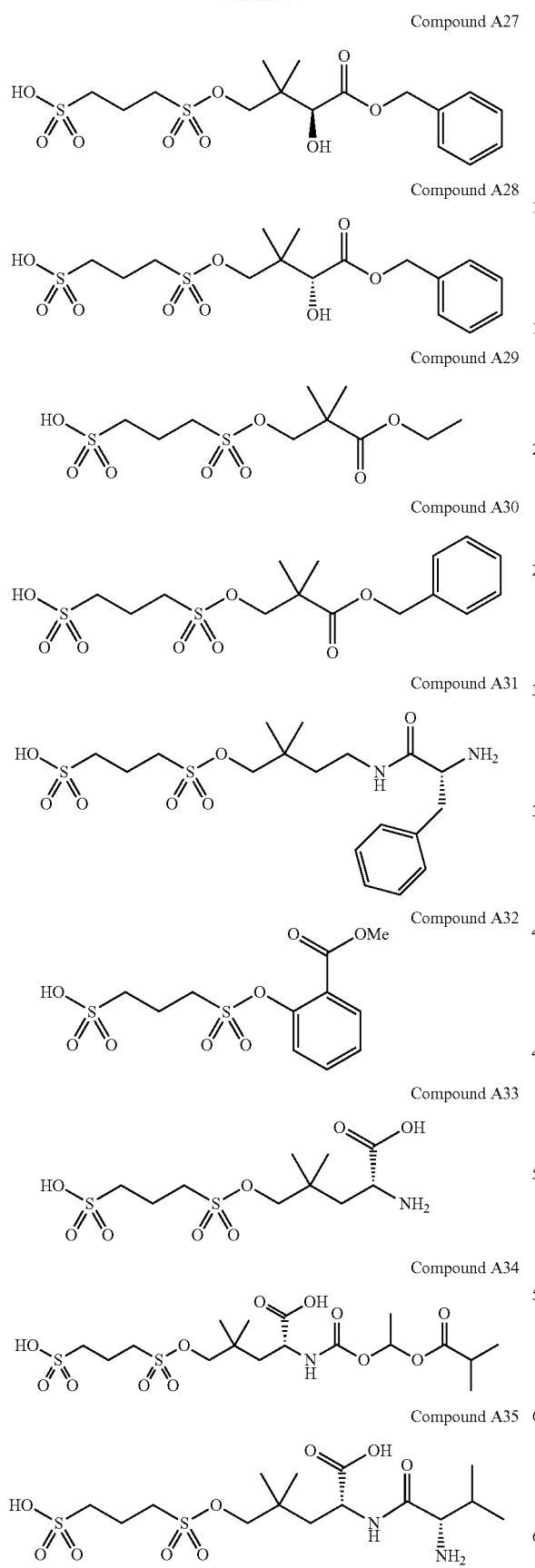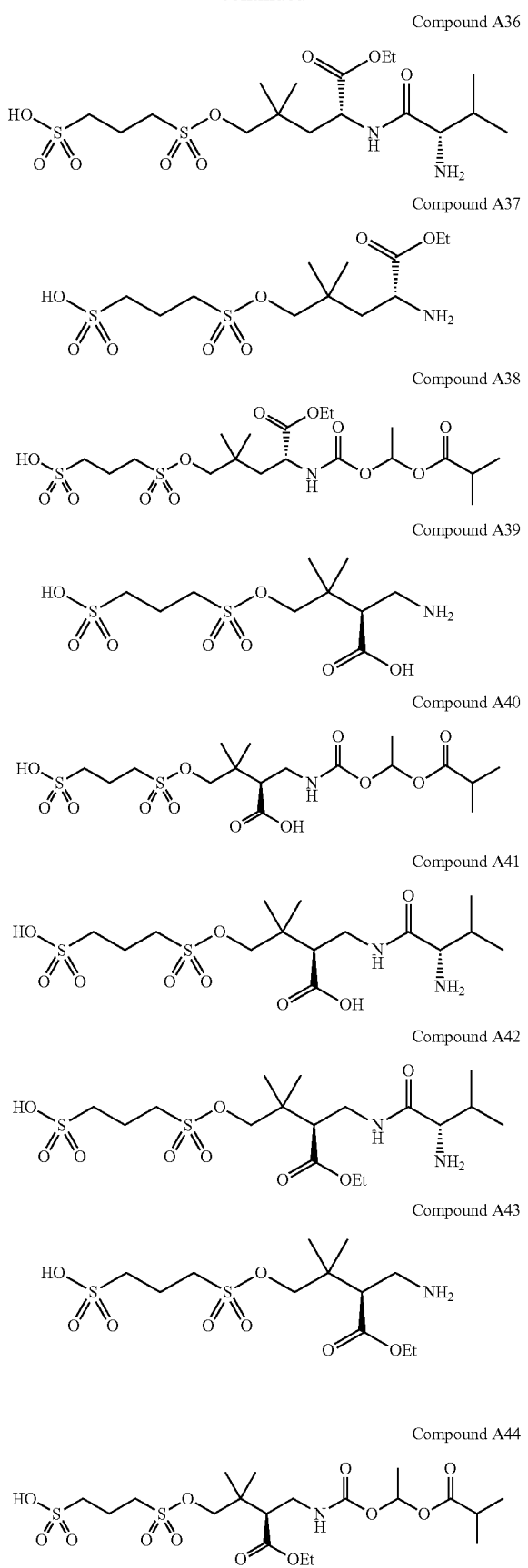

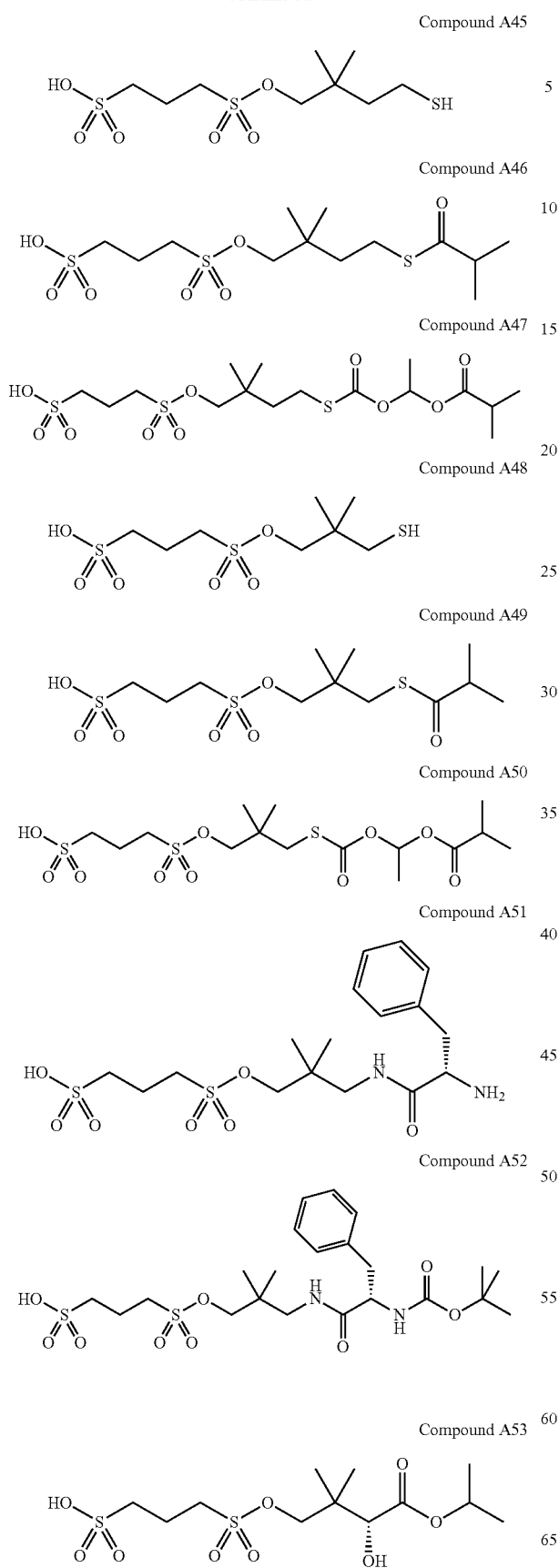
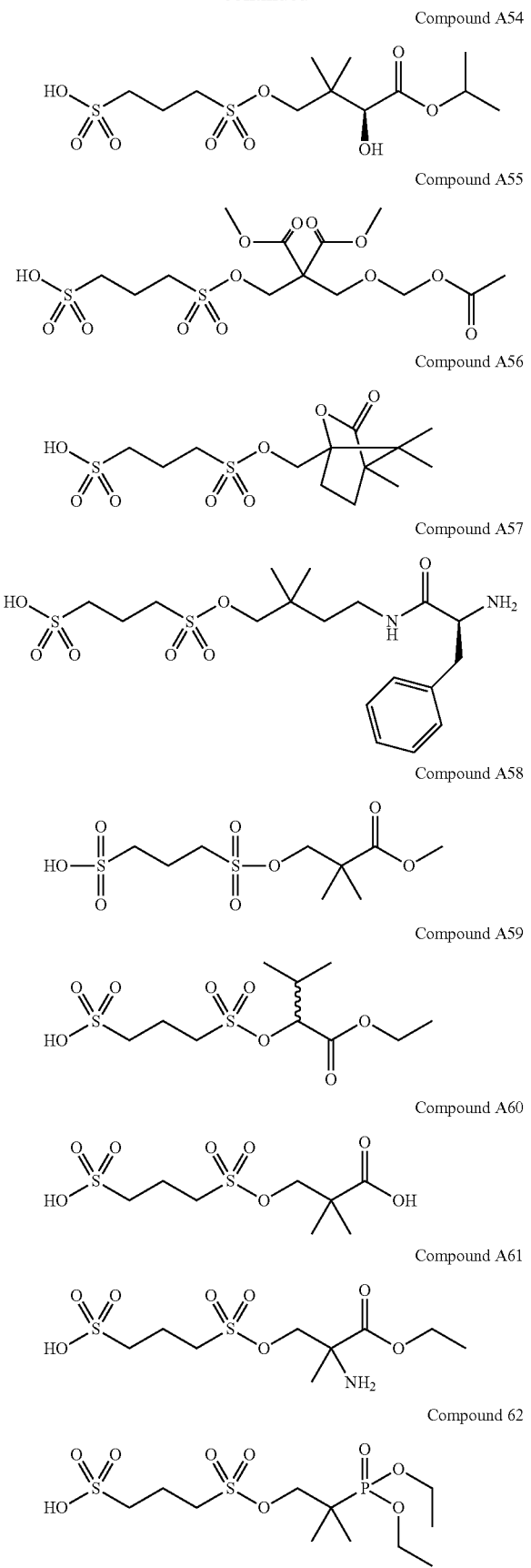

Compound A63

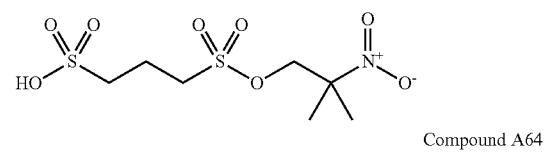

Compound A64

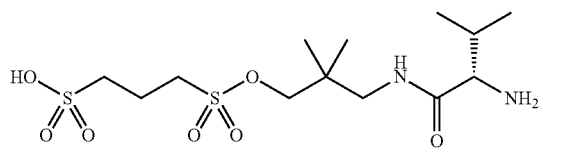

Compound A65

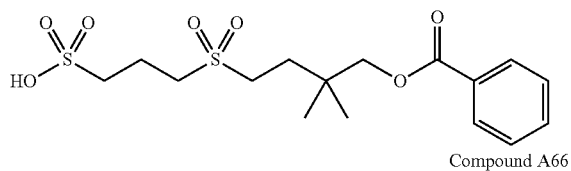

Compound A66

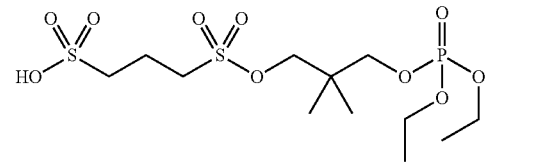

Compound A67

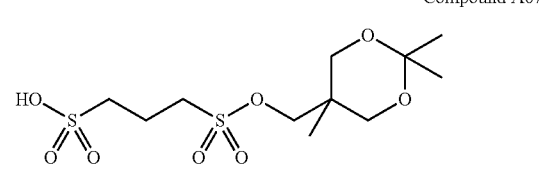

Compound A68

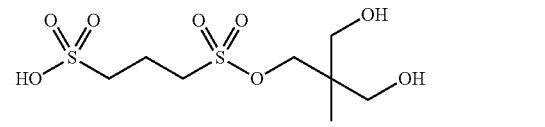

Compound A69

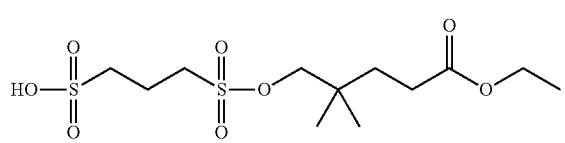

Compound A70

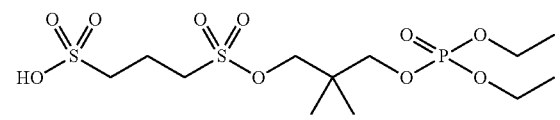

Compound A71

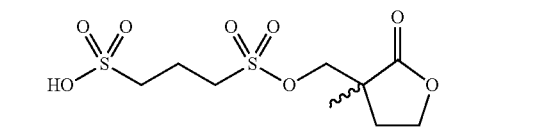

Compound A72

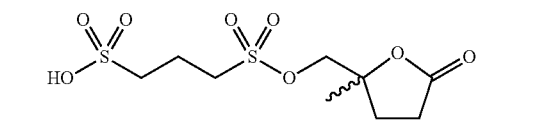

Compound A73

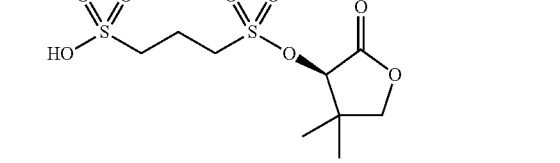

or a pharmaceutically acceptable salt or solvate of any one of Compounds A1 to A73.

The following structures are examples of disulfonate ester prodrugs of the invention and are illustrative of the invention only and they should not be construed as further limiting:

Compound B1

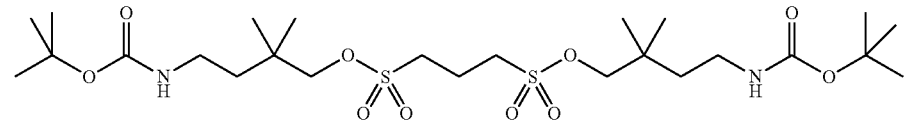

Compound B2

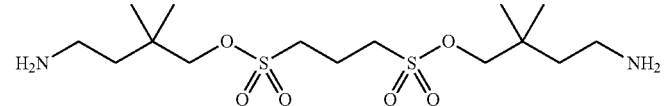

Compound B3

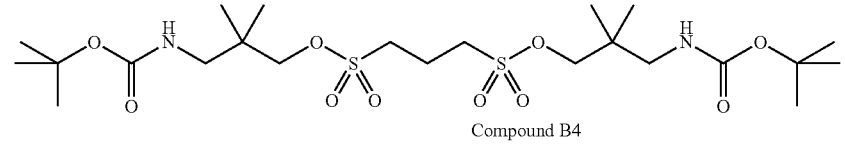

Compound B4

Compound B5

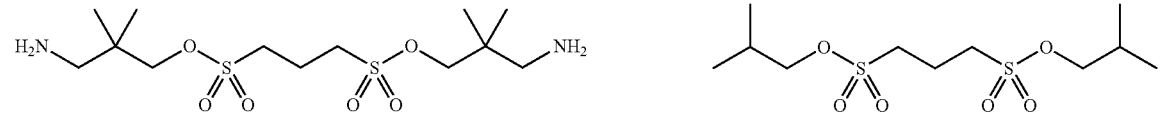

-continued
Compound B6
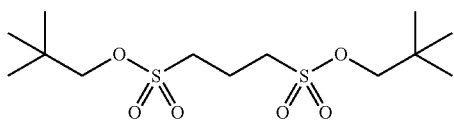
Compound B7
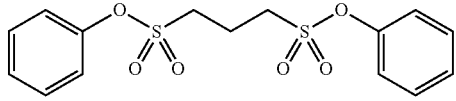
Compound B8
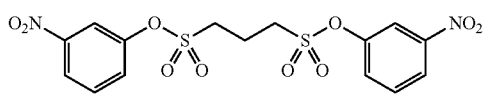
Compound B9
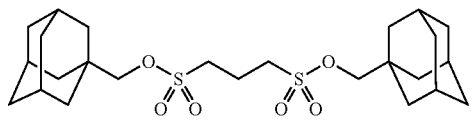
Compound B10
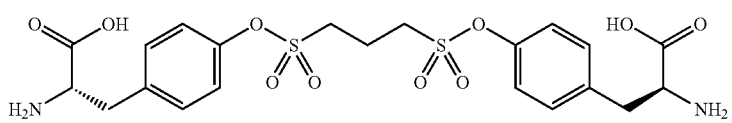
Compound B11
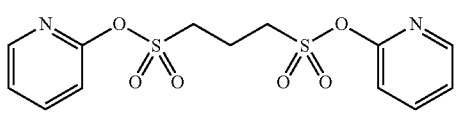
Compound B12
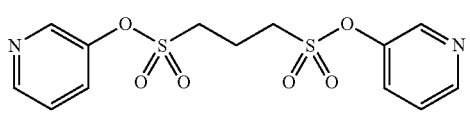
Compound B13
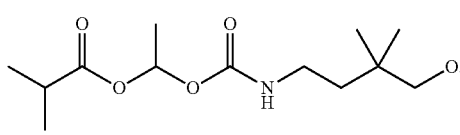
Compound B14
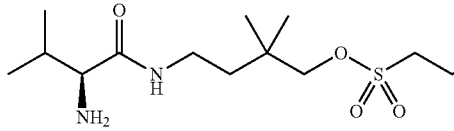
Compound B15
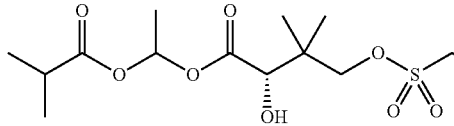
Compound B16
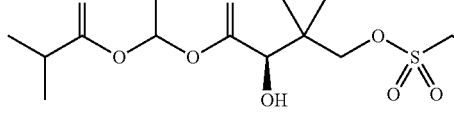
Compound B17
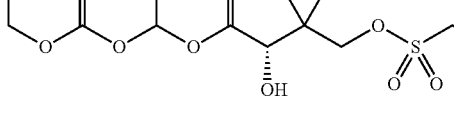
Compound B18
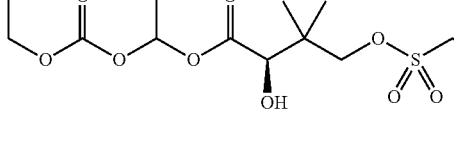
Compound B19
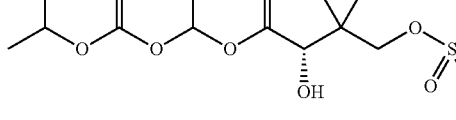

Compound B20
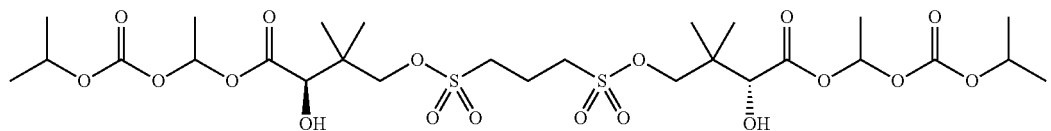
Compound B21
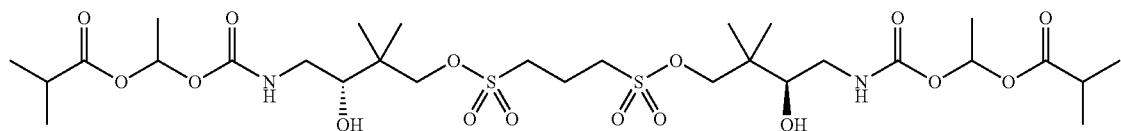
Compound B22
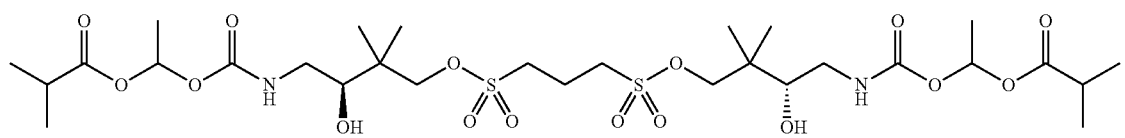
Compound B23
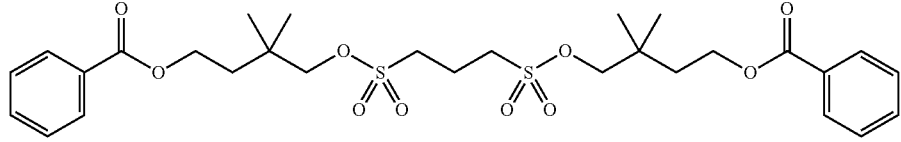
Compound B24
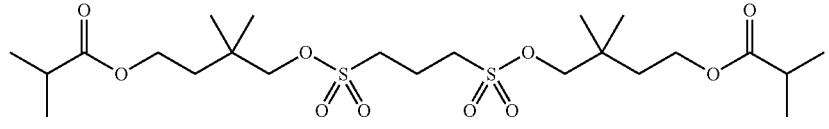
Compound B25
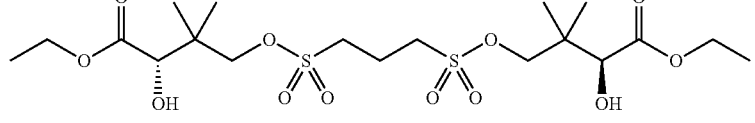
Compound B26
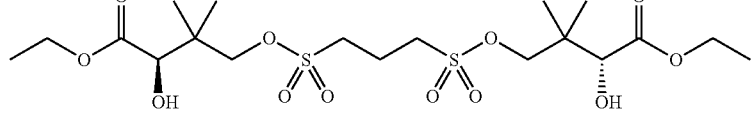
Compound B27
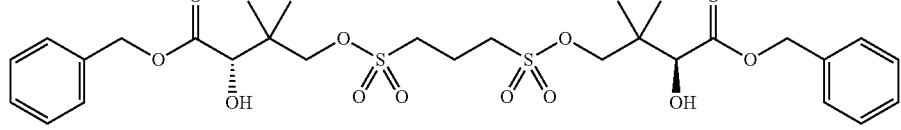
Compound B28
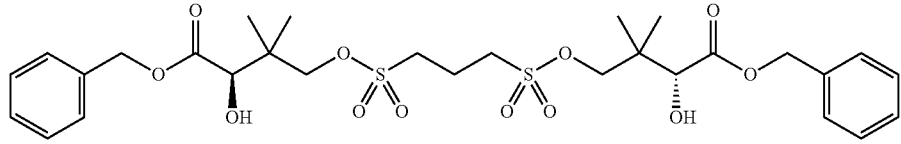
Compound B29
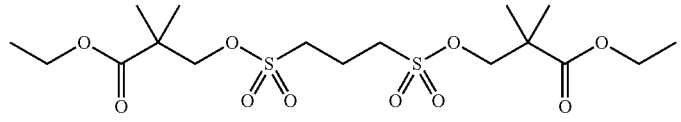

Compound B30
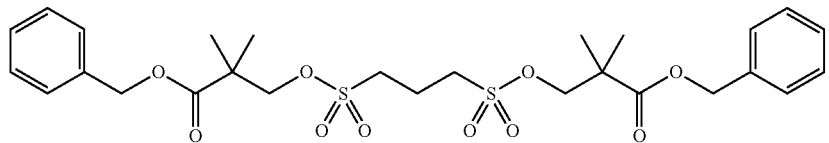
Compound B31
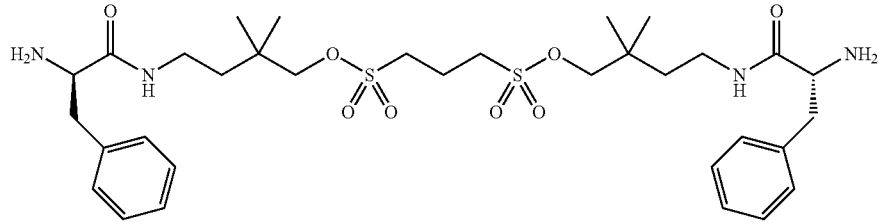
Compound B32
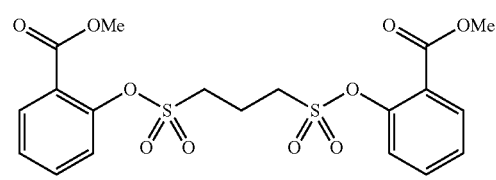
Compound B33
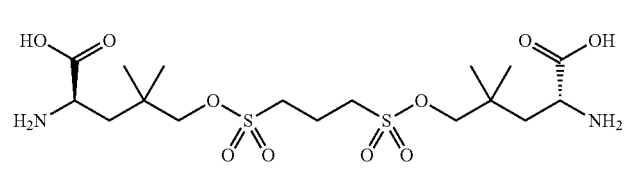
Compound B34
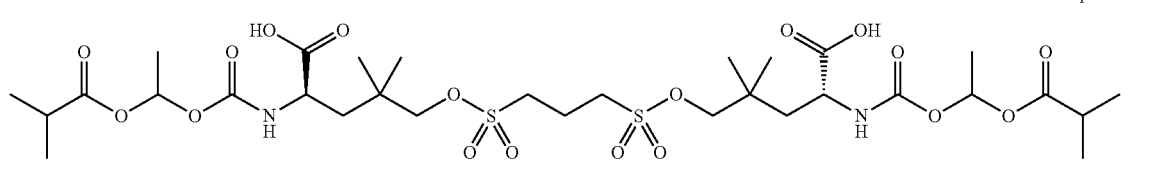
Compound B35
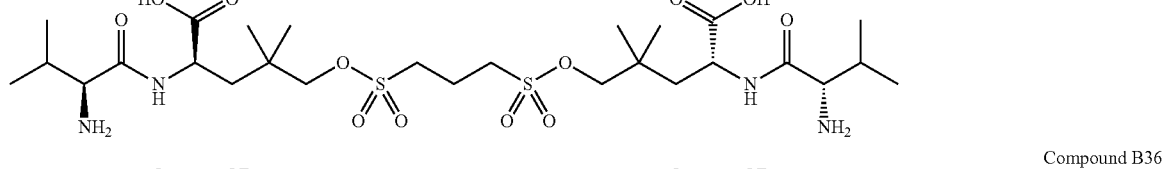
Compound B36
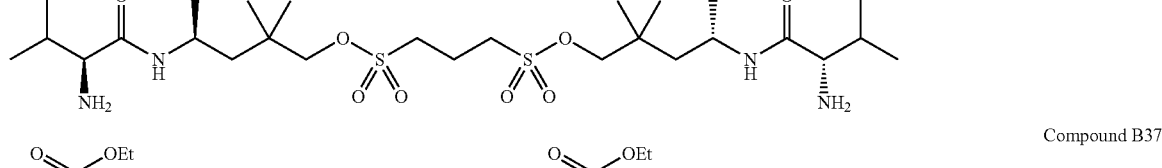
Compound B37
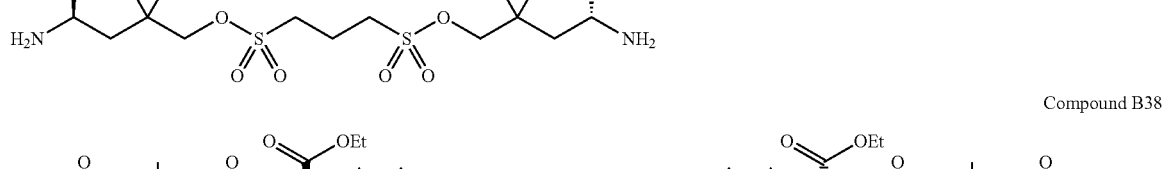
Compound B38
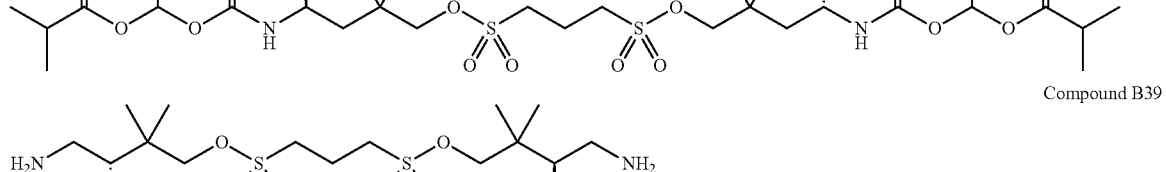
Compound B39
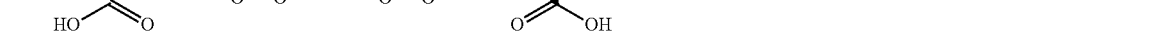

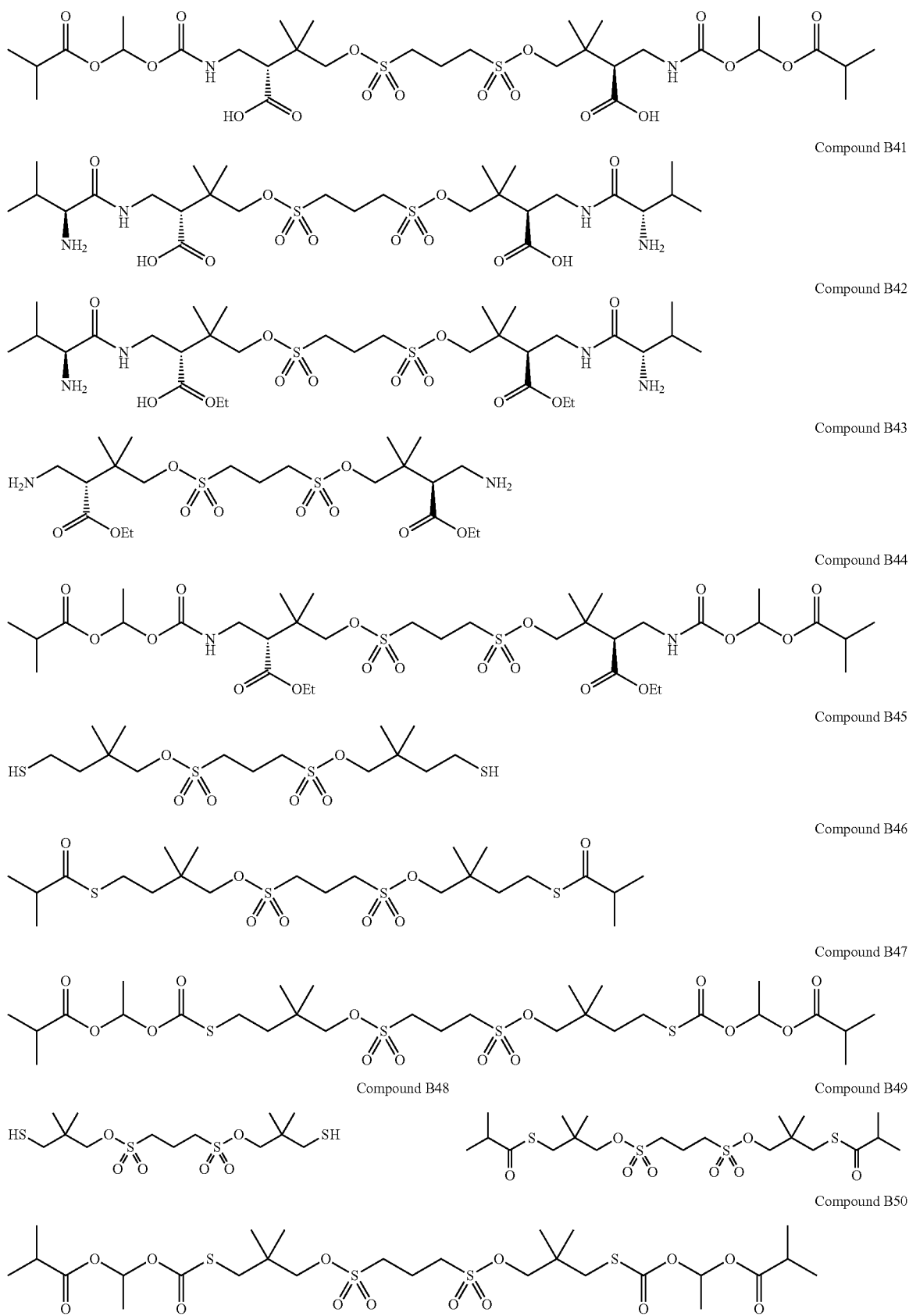

Compound B51
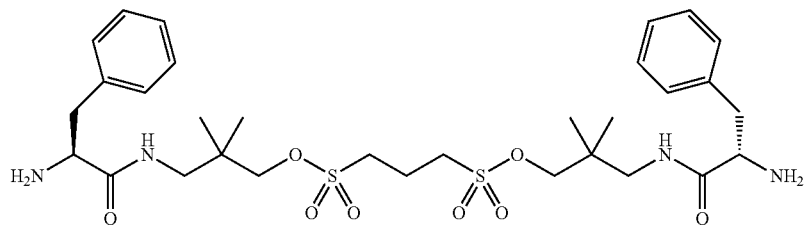
Compound B52
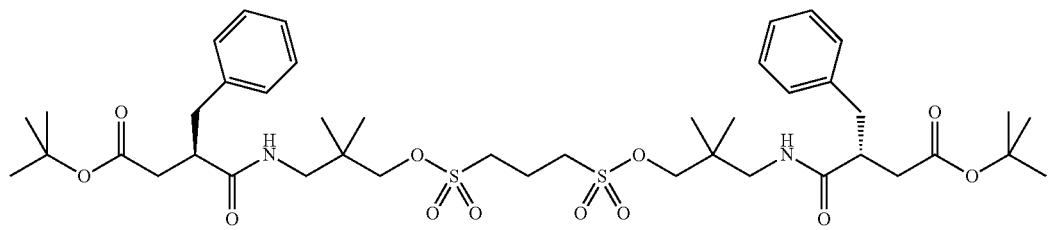
Compound B53
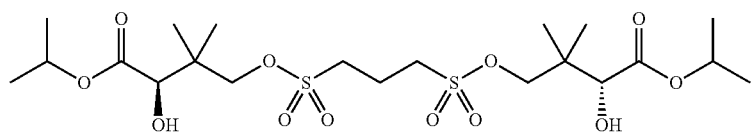
Compound B54
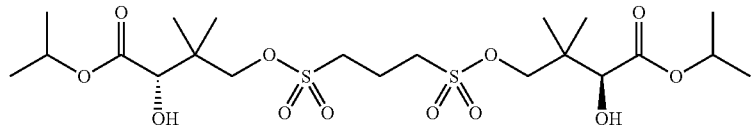
Compound B55
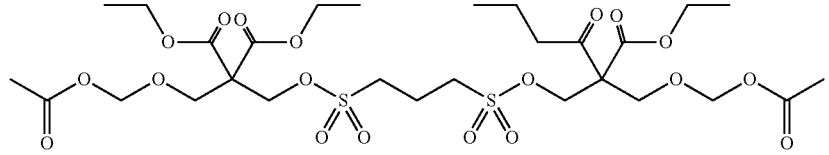
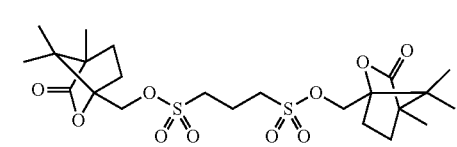
Compound B56
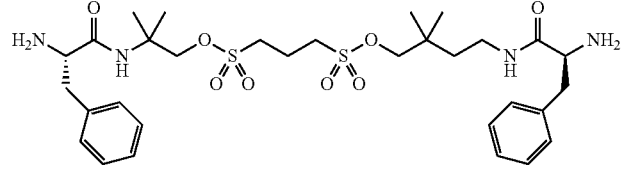
Compound B57
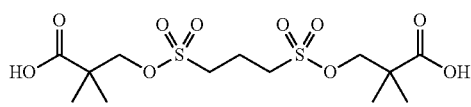
Compound B58
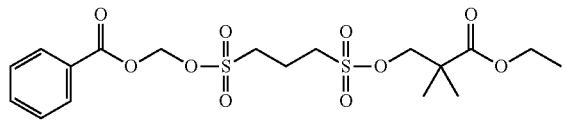
Compound B59
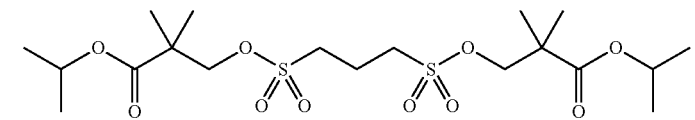
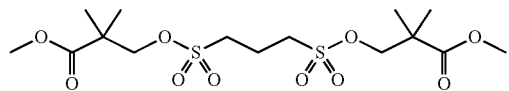
Compound B60
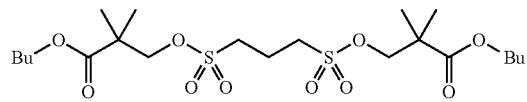
Compound B61
Compound B62

-continued
Compound B63
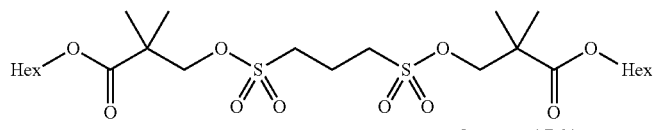
| Compound B64 | Compound B65 |
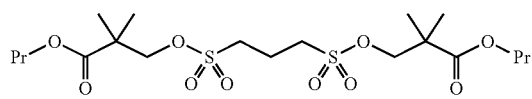 
Compound B66
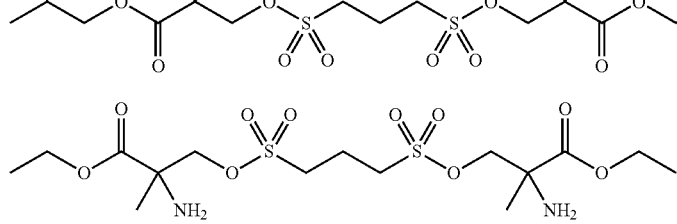
| Compound B67 |
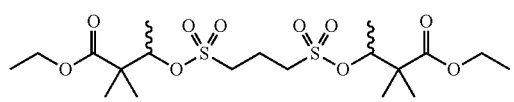
(dl-HCl salt)
| Compound B68 | Compound B69 |
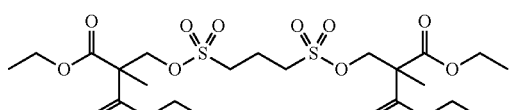
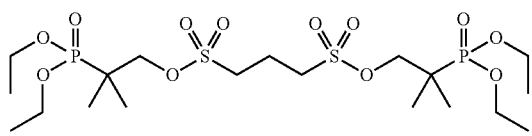 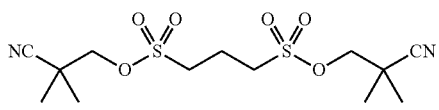
| Compound B70 | Compound B71 |
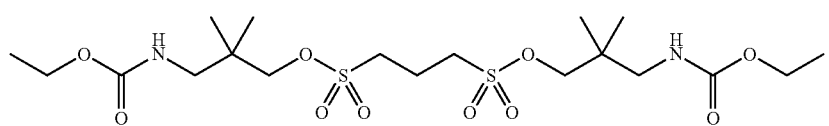
Compound B72
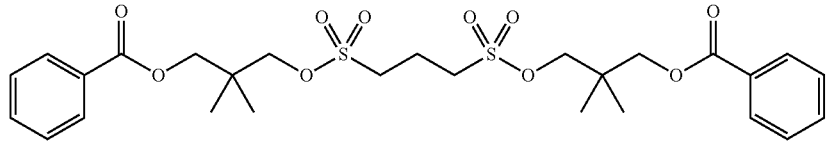
Compound B73
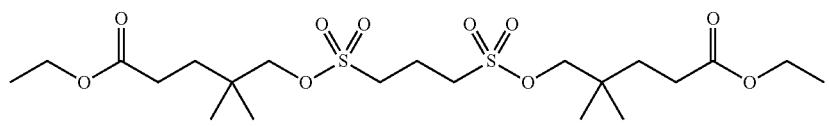
Compound B74
Compound B75
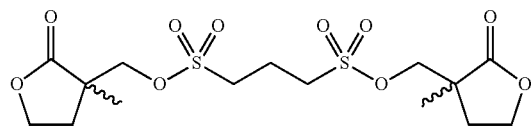
| Compound B76 | Compound B77 |
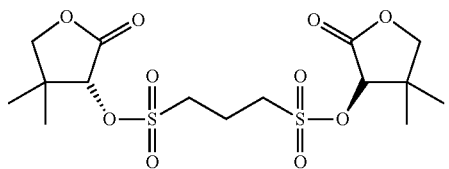

-continued

Compound B78
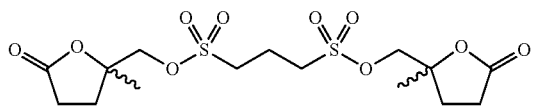

Compound B79
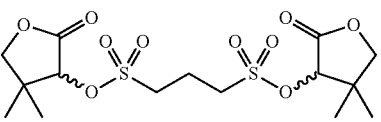

Compound B80
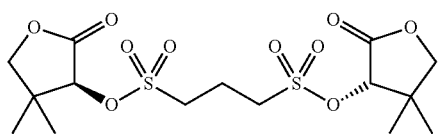

Compound B81
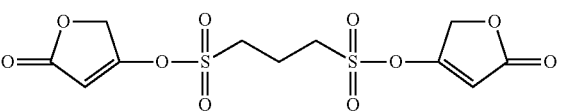

Compound B82
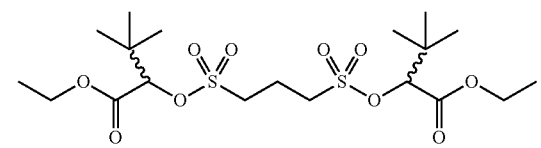

Compound B83
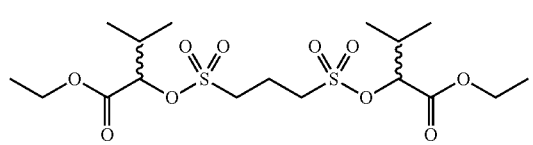

Compound B84
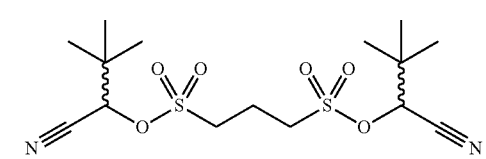

Compound B85
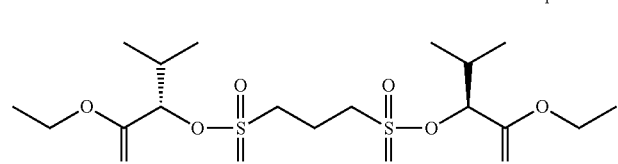

Compound B86
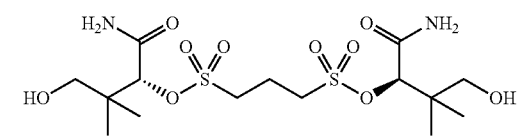

Compound B87
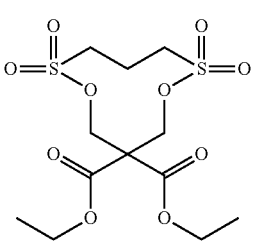

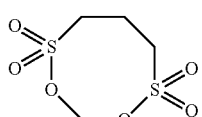

or a pharmaceutically acceptable salt or solvate of any one of Compounds B1-B87.

In another example, the compound is a compound of Formula I, wherein $R^1$ is a covalent bond, and $R^2$ is an oxygen atom, then $R^1$ and $R^2$ taken together with their adjacent atoms form the 6-membered heterocyclic ring Compound C1.

Compound C1
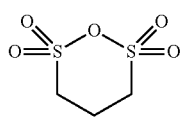

In yet another example, the compound is a compound of Formula I, wherein $R^1$ is a covalent bond, and $R^2$ is a substituted or unsubstituted $OC_1$-$C_3$alkylO group, and $R^1$ and $R^2$ taken together with their adjacent atoms form an 8 to 10-membered heterocyclic ring. In one embodiment, the compound is Compound C2.

Compound C2
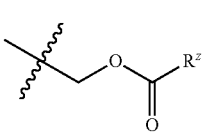

In another embodiment, the compound is Compound C3.

Compound C3

The invention also further relates to a compound of Formula II, wherein at least one of $R^3$ or $R^4$ is a group of Formula E:

(E)

wherein, $R^z$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, $OC_1$-$C_{12}$alkyl, $OC_2$-$C_{12}$alkenyl, $OC_2$-

$C_{12}$alkynyl, $OC_3$-$C_{15}$cycloalkyl, $OC_3$-$OC_{15}$heterocycloalkyl, $OC_6$-$C_{15}$aryl, and $OC_5$-$C_{15}$heteroaryl.

According to one aspect, the compound of the invention is a compound of Formula II, and one of $R^3$ or $R^4$ is a group of Formula E. In an embodiment of this aspect, $R^4$ is Formula E, wherein $R^z$ is a group selected from $OC_1$-$C_6$alkyl, $C_1$-$C_6$alkyl, $C_3$-$C_7$cycloalkyl, or $C_6$aryl, and $R^3$ is H. In another embodiment, $R^4$ is Formula E, wherein $R^z$ is a group selected from $OC_1$-$C_6$alkyl, $C_1$-$C_6$alkyl, $C_3$-$C_7$cycloalkyl, or $C_6$aryl, and $R^3$ is a group of Formula B. In another embodiment, $R^4$ is Formula E, wherein $R^z$ is a group selected from $OC_1$-$C_6$alkyl, $C_1$-$C_6$alkyl, $C_3$-$C_7$cycloalkyl, or $C_6$aryl, and $R^3$ is a group of Formula B, wherein $R^6$ is a group of Formula C. In another embodiment, $R^4$ is Formula E, wherein $R^z$ is a group selected from $OC_1$-$C_6$alkyl, $C_1$-$C_6$alkyl, $C_3$-$C_7$cycloalkyl, or $C_6$aryl, and $R^3$ is a group of Formula B, wherein $R^6$ is a group of Formula C, and wherein X is C(O)OR$^{12}$. In another embodiment, $R^4$ is Formula E, wherein $R^z$ is a $C_1$-$C_6$alkyl, and $R^3$ is H. In another embodiment, $R^4$ is Formula E, wherein $R^z$ is a $C_1$-$C_6$alkyl, and $R^3$ is a group of Formula B. In another embodiment, $R^4$ is Formula E, wherein $R^z$ is a $C_1$-$C_6$alkyl, and $R^3$ is a group of Formula B, wherein $R^6$ is a group of Formula C. In another embodiment, $R^4$ is Formula E, wherein $R^z$ is a $C_1$-$C_6$alkyl, and $R^3$ is a group of Formula B, wherein $R^6$ is a group of Formula C, and wherein X is C(O)OR$^{12}$. In another embodiment, $R^4$ is Formula E, wherein $R^z$ is a $C_2$-$C_5$alkyl, and $R^3$ is H. In another embodiment, $R^4$ is Formula E, wherein $R^z$ is a $C_2$-$C_5$alkyl, and $R^3$ is a group of Formula B. In another embodiment, $R^4$ is Formula E, wherein $R^z$ is a $C_2$-$C_5$alkyl, and $R^3$ is a group of Formula B, wherein $R^6$ is a group of Formula C. In another embodiment, $R^4$ is Formula E, wherein $R^z$ is a $C_2$-$C_5$alkyl, and $R^3$ is a group of Formula B, wherein $R^6$ is a group of Formula C, and wherein X is C(O)OR$^{12}$. In another embodiment, $R^4$ is Formula E, wherein $R^z$ is a $C_3$-$C_7$cycloalkyl, and $R^3$ is H. In another embodiment, $R^4$ is Formula E, wherein $R^z$ is a $C_3$-$C_7$cycloalkyl, and $R^3$ is a group of Formula B. In another embodiment, $R^4$ is Formula E, wherein $R^z$ is a $C_3$-$C_7$cycloalkyl, and $R^3$ is a group of Formula B, wherein $R^6$ is a group of Formula C. In another embodiment, $R^4$ is Formula E, wherein $R^z$ is a $C_3$-$C_7$cycloalkyl, and $R^3$ is a group of Formula B, wherein $R^6$ is a group of Formula C, and wherein X is C(O)OR$^{12}$. In another embodiment, $R^4$ is Formula E, wherein $R^z$ is a $C_5$-$C_6$cycloalkyl, and $R^3$ is H. In another embodiment, $R^4$ is Formula E, wherein $R^z$ is a $C_5$-$C_6$cycloalkyl, and $R^3$ is a group of Formula B. In another embodiment, $R^4$ is Formula E, wherein $R^z$ is a $C_5$-$C_6$cycloalkyl, and $R^3$ is a group of Formula B, wherein $R^6$ is a group of Formula C. In another embodiment, $R^4$ is Formula E, wherein $R^z$ is a $C_5$-$C_6$cycloalkyl, and $R^3$ is a group of Formula B, wherein $R^6$ is a group of Formula C, and wherein X is C(O)OR$^{12}$. In another embodiment, $R^4$ is Formula E, wherein $R^z$ is a $C_6$aryl, and $R^3$ is H. In further another embodiment, $R^4$ is Formula E, wherein $R^z$ is a $C_6$aryl, and $R^3$ is a group of Formula B. In yet another embodiment, $R^4$ is Formula E, wherein $R^z$ is a $C_6$aryl, and $R^3$ is a group of Formula B, wherein $R^6$ is a group of Formula C. In a further embodiment, $R^4$ is Formula E, wherein $R^z$ is a $C_6$aryl, and $R^3$ is a group of Formula B, wherein $R^6$ is a group of Formula C, and wherein X is C(O)OR$^{12}$.

In another aspect, the compound of the invention is a compound of Formula II, and $R^3$ and $R^4$ are each independently a group of Formula E. In one embodiment of this aspect, $R^z$ in each of $R^3$ and $R^4$ is independently a group selected from $C_1$-$C_6$alkyl, $C_3$-$C_7$cycloalkyl, or $C_6$aryl. In another embodiment, $R^z$ in the group $R^3$ is a group selected from $OC_1$-$C_6$alkyl, $C_1$-$C_6$alkyl, $C_3$-$C_7$cycloalkyl, or $C_6$aryl, and $R^z$ in the group $R^4$ is $C_1$-$C_6$alkyl. In another embodiment, $R^z$ in the group $R^3$ is a group selected from $OC_1$-$C_6$alkyl, $C_1$-$C_6$alkyl, $C_3$-$C_7$cycloalkyl, or $C_6$aryl, and $R^z$ in the group $R^4$ is $C_2$-$C_5$alkyl. In another embodiment, $R^z$ in the group $R^3$ is a group selected from $OC_1$-$C_6$alkyl, $C_1$-$C_6$alkyl, $C_3$-$C_7$cycloalkyl, or $C_6$aryl, and $R^z$ in the group $R^4$ is $C_3$-$C_7$cycloalkyl. In another embodiment, $R^z$ in the group $R^3$ is a group selected from $OC_1$-$C_6$alkyl, $C_1$-$C_6$alkyl, $C_3$-$C_7$cycloalkyl, or $C_6$aryl, and $R^z$ in the group $R^4$ is $C_5$-$C_6$cycloalkyl. In another embodiment, $R^z$ in the group $R^3$ is a group selected from $OC_1$-$C_6$alkyl, $C_1$-$C_6$alkyl, $C_3$-$C_7$cycloalkyl, or $C_6$aryl, and $R^z$ in the group $R^4$ is $C_6$aryl. In another embodiment, $R^z$ in the group $R^3$ is $C_1$-$C_6$alkyl, and $R^z$ in the group $R^4$ is a group selected from $OC_1$-$C_6$alkyl, $C_1$-$C_6$alkyl, $C_3$-$C_7$cycloalkyl, or $C_6$aryl. In another embodiment, $R^z$ in each of $R^3$ and $R^4$ is independently a $C_1$-$C_6$alkyl group. In another embodiment, $R^z$ in the group $R^3$ is $C_1$-$C_6$alkyl, and $R^z$ in the group $R^4$ is $C_2$-$C_5$alkyl. In another embodiment, $R^z$ in the group $R^3$ is $C_1$-$C_6$alkyl, and $R^z$ in the group $R^4$ is $C_3$-$C_7$cycloalkyl. In another embodiment, $R^z$ in the group $R^3$ is $C_1$-$C_6$alkyl, and $R^z$ in the group $R^4$ is $C_5$-$C_6$cycloalkyl. In another embodiment, $R^z$ in the group $R^3$ is $C_1$-$C_6$alkyl, and $R^z$ in the group $R^4$ is $C_6$aryl. In another embodiment, $R^z$ in the group $R^3$ is $C_2$-$C_5$alkyl, and $R^z$ in the group $R^4$ is a group selected from $OC_1$-$C_6$alkyl, $C_1$-$C_6$alkyl, $C_3$-$C_7$cycloalkyl, or $C_6$aryl. In another embodiment, $R^z$ in the group $R^3$ is $C_2$-$C_5$alkyl, and $R^z$ in the group $R^4$ is $C_1$-$C_6$alkyl. In another embodiment, $R^z$ in each of $R^3$ and $R^4$ is independently a $C_2$-$C_5$alkyl group. In another embodiment, $R^z$ in the group $R^3$ is $C_2$-$C_5$alkyl, and $R^z$ in the group $R^4$ is $C_3$-$C_7$cycloalkyl. In another embodiment, $R^z$ in the group $R^3$ is $C_2$-$C_5$alkyl, and $R^z$ in the group $R^4$ is $C_5$-$C_6$cycloalkyl. In another embodiment, $R^z$ in the group $R^3$ is $C_2$-$C_5$alkyl, and $R^z$ in the group $R^4$ is $C_6$aryl. In another embodiment, $R^z$ in the group $R^3$ is $C_3$-$C_7$cycloalkyl, and $R^z$ in the group $R^4$ is a group selected from $OC_1$-$C_6$alkyl, $C_1$-$C_6$alkyl, $C_3$-$C_7$cycloalkyl, or $C_6$aryl. In another embodiment, $R^z$ in the group $R^3$ is $C_3$-$C_7$cycloalkyl, and $R^z$ in the group $R^4$ is $C_1$-$C_6$alkyl. In another embodiment, $R^z$ in the group $R^3$ is $C_3$-$C_7$cycloalkyl, and $R^z$ in the group $R^4$ is $C_2$-$C_5$alkyl. In another embodiment, $R^z$ in each of $R^3$ and $R^4$ is independently a $C_3$-$C_7$cycloalkyl group. In another embodiment, $R^z$ in the group $R^3$ is $C_3$-$C_7$cycloalkyl, and $R^z$ in the group $R^4$ is $C_5$-$C_6$cycloalkyl. In another embodiment, $R^z$ in the group $R^3$ is $C_3$-$C_7$cycloalkyl, and $R^z$ in the group $R^4$ is $C_6$aryl. In another embodiment, $R^z$ in the group $R^3$ is $C_5$-$C_6$cycloalkyl, and $R^z$ in the group $R^4$ is a group selected from $OC_1$-$C_6$alkyl, $C_1$-$C_6$alkyl, $C_3$-$C_7$cycloalkyl, or $C_6$aryl. In another embodiment, $R^z$ in the group $R^3$ is $C_5$-$C_6$cycloalkyl, and $R^z$ in the group $R^4$ is $C_1$-$C_6$alkyl. In another embodiment, $R^z$ in the group $R^3$ is $C_5$-$C_6$cycloalkyl, and $R^z$ in the group $R^4$ is $C_2$-$C_5$alkyl. In another embodiment, $R^z$ in the group $R^3$ is $C_5$-$C_6$cycloalkyl, and $R^z$ in the group $R^4$ is $C_3$-$C_7$cycloalkyl. In another embodiment, $R^z$ in each of $R^3$ and $R^4$ is independently a $C_5$-$C_6$cycloalkyl group. In another embodiment, $R^z$ in the group $R^3$ is $C_5$-$C_6$cycloalkyl, and $R^z$ in the group $R^4$ is $C_6$aryl. In another embodiment, $R^z$ in the group $R^3$ is $C_6$aryl, and $R^z$ in the group $R^4$ is a group selected from $OC_1$-$C_6$alkyl, $C_1$-$C_6$alkyl, $C_3$-$C_7$cycloalkyl, or $C_6$aryl. In another embodiment, $R^z$ in the group $R^3$ is $C_6$aryl, and $R^z$ in the group $R^4$ is $C_1$-$C_6$alkyl. In another embodiment, $R^z$ in the group $R^3$ is $C_6$aryl, and $R^z$ in the group $R^4$ is $C_2$-$C_5$alkyl. In a further embodiment, $R^z$ in the group $R^3$ is $C_6$aryl, and $R^z$ in the group $R^4$ is $C_3$-$C_7$cycloalkyl. In a further embodiment, $R^z$ in the group $R^3$ is $C_6$aryl, and $R^z$ in the group $R^4$ is $C_5$-$C_6$cycloalkyl. In yet another embodiment, $R^z$ in each of $R^3$ and $R^4$ is independently a $C_6$aryl group. In a further embodiment, the compound of the invention is Compound B59, or a pharmaceutically acceptable salt or solvate thereof.

The following structures are examples of sulfonate ester prodrugs of the invention and are illustrative of the invention only and they should not be construed as further limiting:

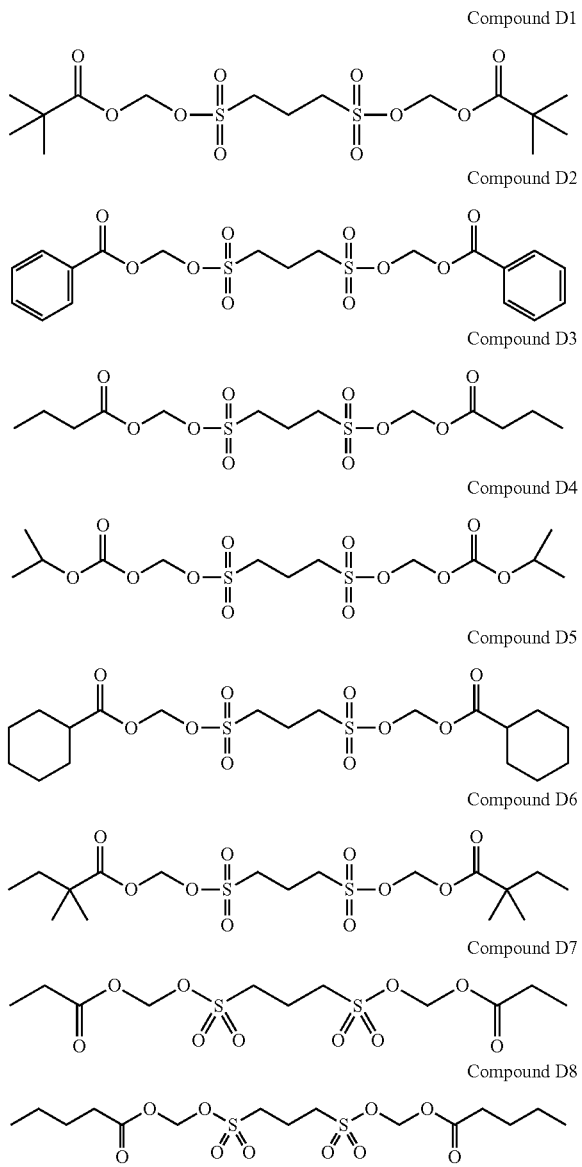

Compound D1
Compound D2
Compound D3
Compound D4
Compound D5
Compound D6
Compound D7
Compound D8

or a pharmaceutically acceptable salt or solvate of any one of Compounds D1 to D8.

In yet another aspect, the invention further relates to a compound of Formula II, wherein at least one of $R^3$ or $R^4$ is a group of Formula F:

(F)

wherein,

W—Y—Z is selected from $C(O)OCH_2$, $OC(O)CH_2$, $CH_2C(O)O$, and $CH_2OC(O)$;

$R^w$, $R^x$, and $R^y$ are each independently selected from a hydrogen atom or a substituted or unsubstituted $C_1$-$C_3$ alkyl group, or $R^w$ and $R^x$ are taken together with their adjacent carbon atoms to form a double bond; and k is an integer selected from 0, 1 and 2.

According to one aspect, the compound of the invention is a compound of Formula II, and one of $R^3$ or $R^4$ is a group of Formula F. In one embodiment of this aspect, $R^w$ is a methyl group. In another embodiment, $R^w$ is a methyl group and each of $R^x$ and $R^y$ are hydrogen atoms. In another embodiment, $R^x$ and $R^y$ are each a methyl group and $R^w$ is a hydrogen. In yet another embodiment, $R^w$ and $R^x$ are taken together with their adjacent carbon atoms to form a double bond. In yet another embodiment, $R^w$ and $R^x$ are taken together with their adjacent carbon atoms to form a double bond, and $R^y$ is a hydrogen.

According to another aspect, the compound of the invention is a compound of Formula II, and $R^3$ and $R^4$ are each independently a group of Formula F. In one embodiment of this aspect, $R^w$ is a methyl group. In another embodiment, $R^w$ is a methyl group and each of $R^x$ and $R^y$ are hydrogen atoms. In another embodiment, $R^x$ and $R^y$ are each a methyl group and $R^w$ is a hydrogen. In yet another embodiment, $R^w$ and $R^x$ are taken together with their adjacent carbon atoms to form a double bond. In yet another embodiment, $R^w$ and $R^x$ are taken together with their adjacent carbon atoms to form a double bond, and $R^y$ is a hydrogen.

The invention further relates to compounds of Formula II, wherein said compound is any one or more of Compounds A71, A72, A73, B76, B77, B78, B79, B80 and B81, or a pharmaceutically acceptable salt or solvate thereof.

B. Oligomers and Gemini Dimers

In further aspects of the invention, the compounds of Formula I may comprise two or more 1,3PDS molecules linked together. Therefore, another aspect of the invention relates to oligomers of 1,3PDS, i.e., a molecule comprising, or consisting essentially of, or consisting of two or more molecules of 1,3PDS linked together through cleavable linkage(s). Thus, the invention relates to a compound of Formula III:

$$A\text{-}(L^x\text{-}A)_p\text{-}L^x\text{-}A \qquad (III)$$

wherein,

A is 1,3-propanedisulfonic acid moiety;

$L^x$ is a cleavable linkage for covalently and dissociably coupling together two 1,3PDS moieties respectively; and p is 0 or an integer selected from 1, 2, 3, 4, or 5;

or a pharmaceutically acceptable salt, ester, or solvate thereof.

Alternatively, the invention relates to a compound of Formula III-A:

$$L^y(A)_m \qquad (III\text{-}A)$$

wherein, m is an integer from 2 to 5;

A is 1,3-propanedisulfonic acid moiety; and

L' is a multivalent carrier moiety for covalently and dissociably coupling from two to five A moieties, at either sulfonic acid end of A;

or a pharmaceutically acceptable salt, ester, or solvate thereof.

The free sulfonic acid group at each end may or may not be further esterified with a $R^3$ or $R^4$ group as described herein. Those skilled in the art will be capable to select proper linkers and linkage site and test the resulting product for efficacy and for capability of cleavage under various chemical and/or biological conditions.

The following structures are examples of prodrugs of the invention containing more than one 1,3PDS moiety and are illustrative of the invention only and they should not be construed as further limiting.

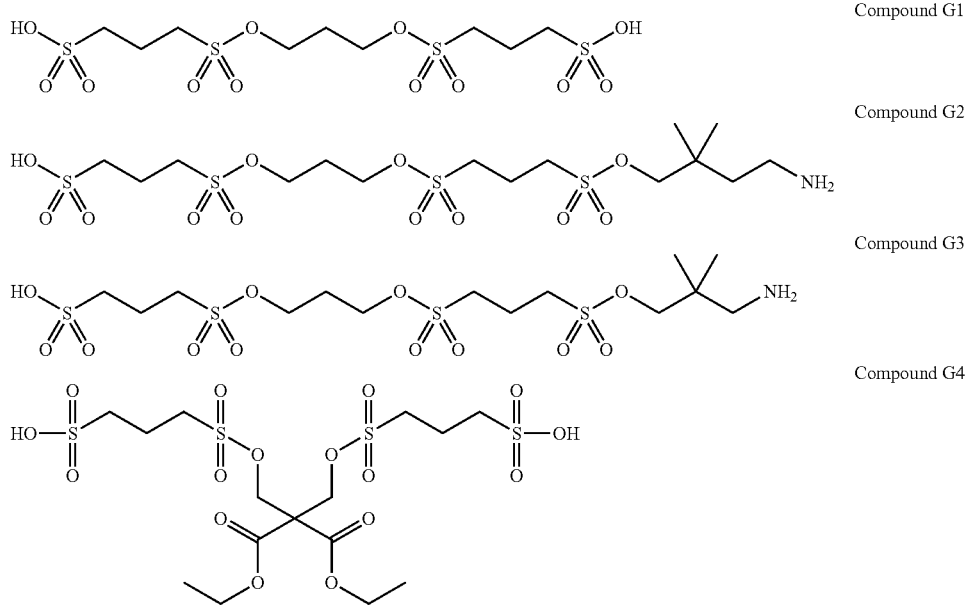

Compound G1

Compound G2

Compound G3

Compound G4 or a pharmaceutically acceptable salt or solvate of any one of Compounds G1 to G4.

C. Non-Ester Prodrugs

In one aspect, the invention relates to compounds of Formula IV:

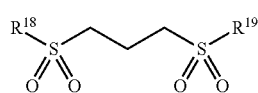

(IV)

wherein, $R^{18}$ is selected from $OR^3$, $NH_2$, —NHC(O)$R^5$, —NHC(NH)NH$R^5$, —NH($C_5$-$C_{10}$heteroaryl), —N$R^{20}R^{21}$, $R^{14}$, and —NH$R^{15}$;

$R^{19}$ is selected from $NH_2$, —NHC(O)$R^5$, —NHC(NH)NH$R^5$, —NH($C_5$-$C_{10}$heteroaryl), —N$R^{20}R^{21}$, $R^{14}$, and —NH$R^{15}$;

$R^3$, $R^5$, $R^{14}$, and $R^{15}$ are as previously defined; and $R^{20}$ and $R^{21}$ are taken together with their adjacent nitrogen atom to form a mono or bicyclic heteroaryl having from 5 to 10 ring members;

or a pharmaceutically acceptable salt or solvate thereof.

The invention relates to compounds of Formula IV, wherein $R^{18}$ is OH, or a pharmaceutically acceptable salt thereof. The invention also relates to compounds of Formula IV, wherein $R^{19}$ is —NHC(O)$R^5$. The invention also relates to compounds of Formula IV, wherein $R^{19}$ is —NHC(NH)NH$R^5$. The invention also relates to compounds of Formula IV, wherein $R^{19}$ is —NH($C_5$-$C_{10}$heteroaryl). For example, $R^{19}$ is —NH($C_5$-$C_{10}$heteroaryl), wherein said $C_5$-$C_{10}$heteroaryl is selected from thiazol-2-yl, imidazol-2-yl, 1,3-oxazol-2-yl, 1,3-benzothiazol-2-yl, 1,3-benzoimidazol-2-yl, and 1,3-benzoxazol-2-yl. In another example, $R^{19}$ is —NH($C_5$-$C_{10}$heteroaryl), wherein said $C_5$-$C_{10}$heteroaryl is selected from thiazol-2-yl, imidazol-2-yl, and 1,3-oxazol-2-yl. In a further example, $R^{19}$ is —NH(thiazol-2-yl), and all other groups are as previously defined.

The invention also relates to compounds of Formula IV, wherein said $R^5$ is selected from hydrogen and a substituted or unsubstituted group selected from $C_1$-$C_{12}$alkyl, $C_3$-$C_{15}$cycloalkyl, $C_3$-$C_{15}$heterocycloalkyl, $C_6$-$C_{15}$aryl, and $C_5$-$C_{15}$heteroaryl. As an example, $R^5$ is selected from hydrogen and a substituted or unsubstituted $C_1$-$C_{12}$alkyl. In another example, $R^5$ is hydrogen. In a further example, $R^5$ is a substituted or unsubstituted $C_1$-$C_6$alkyl, and all other groups are previously defined.

The following structures are examples of prodrugs of the invention containing non-sulfonate ester prodrug moiety and are illustrative of the invention only and they should not be construed as further limiting:

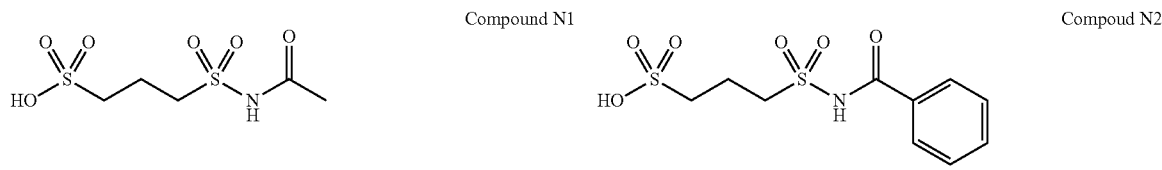

Compound N1

Compoud N2

-continued

Compound N3

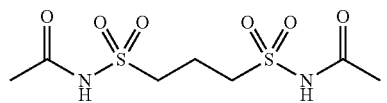

Compound N4

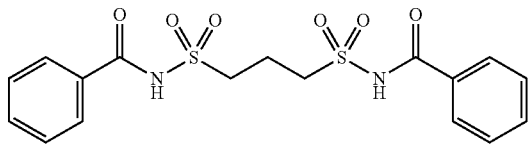

Compound N5

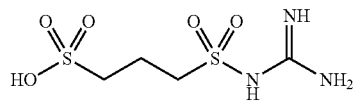

Compound N6

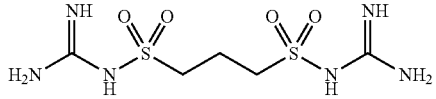

Compound N7

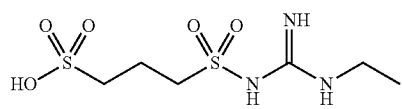

Compound N8

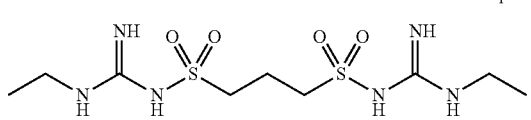

Compound N9

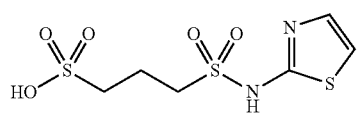

Compound N10

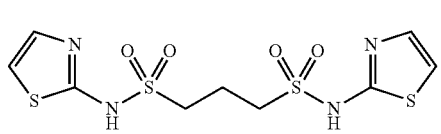

Compound N11

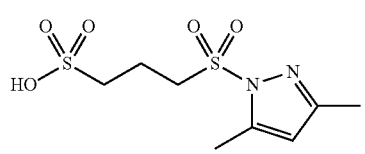

Compound N12

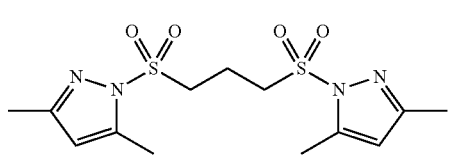

Compound N13

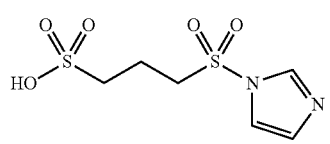

Compound N14

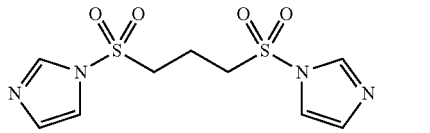

Compound N15

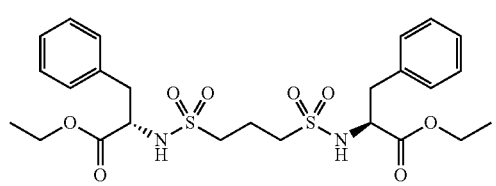

Compound N16

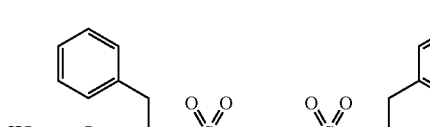

Compound N17

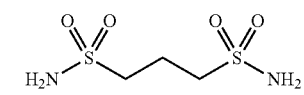

Compound N18

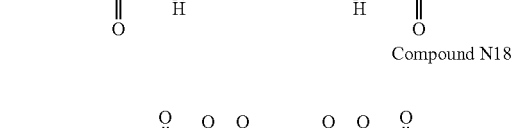

or a pharmaceutically acceptable salt or solvate of any one of Compounds N1 to N18.

D. Precursor Prodrugs

In further aspects of the invention, the compounds of the invention are precursors of 1,3PDS, i.e. Therefore, another aspect of the invention relates to a molecule comprising, or consisting essentially of, or consisting of . . . . Thus, the invention relates to a compound of Formula V:

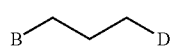

(V)

wherein,

B and D are each independently a precursor of an $SO_3H$ group;

or a pharmaceutically acceptable salt, ester, or solvate thereof.

The invention further relates to compounds of Formula (V), wherein B and D are each independently selected from SH and $SO_2H$.

The following structure is an example of a precursor prodrug of the invention, is illustrative of the invention only and should not be construed as further limiting:

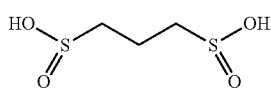

Compound P1 or a pharmaceutically acceptable salt or solvate of Compound P1.

III. Synthesis of the Compounds of the Invention

In general, all compounds of the present invention may be prepared by the methods illustrated in the Examples hereinafter and/or other conventional methods, using readily available and/or conventionally preparable starting materials, reagents and conventional synthesis procedures. In these reactions, it is also possible to make use of variants which are in themselves known, but are not mentioned here. Certain novel and exemplary methods of preparing the inventive compounds are described in the Exemplification section. Such methods are within the scope of this invention. Functional and structural equivalents of the compounds described herein and which have the same general properties, wherein one or more simple variations of substituents are made which do not adversely affect the essential nature or the utility of the compound are also included.

More particularly, the sulfonate ester prodrugs of the present invention may be prepared by the methods illustrated in the Examples section hereinafter.

The compounds of the present invention may be readily prepared in accordance with the synthesis schemes and protocols described herein, as illustrated in the specific procedures provided. However, those skilled in the art will recognize that other synthetic pathways and/or modified synthetic pathways for preparing the compounds of this invention may be used, and that the following is provided merely by way of example, and is not limiting to the present invention. See, e.g., "Comprehensive Organic Transformations" by R. Larock, VCH Publishers (1989), incorporated herein by reference. It will be further recognized that various protecting and deprotecting strategies will be employed that are standard in the art (See, e.g., "Protective Groups in Organic Synthesis" by Greene and Wuts (1991), incorporated herein by reference). Those skilled in the relevant arts will recognize that the selection of any particular protecting group (e.g., amine, hydroxyl, thio, and carboxyl protecting groups) will depend on the stability of the protected moiety with regards to the subsequent reaction conditions and will understand the appropriate selections.

Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Advanced Organic Chemistry: Reactions, Mechanisms, and Structure" by J. March, 4th Edition, John Wiley & sons (1992); T. D. Ocain, et al., *J. Med. Chem.*, 31, 2193-99 (1988); E. M. Gordon, et al., *J. Med. Chem.*, 31, 2199-10 (1988); "Practice of Peptide Synthesis" by M. Bodansky and A. Bodanszky, Springer-Verlag, New York (1984); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992), each incorporated herein by reference.

The synthesis of compounds of the invention is preferably carried out in a solvent. Suitable solvents are liquids at ambient room temperature and pressure or remain in the liquid state under the temperature and pressure conditions used in the reaction. The choice of solvent is within the general skills of the skilled artisan and will depend on the reaction conditions, such, temperature, the nature of the reagents and starting material, solubility and stability of the reagents and starting material, the type of reaction, and the like. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlororbenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); amides (e.g., N,N-dimethylformamide, N,N-dimethylacetamide); nitriles (e.g., acetonitrile); ketones (e.g., acetone); esters (e.g., methyl acetate or ethyl acetate); alcohols (e.g., methanol, ethanol, isopropanol); water and mixtures thereof.

"Activated esters" and equivalent expressions may be represented by the formula COX for carboxylate esters or $SO_2X$ for sulfonate esters, where X is a leaving group, typical examples of which include halogens (e.g. chloride or bromide), N-hydroxysulfosuccinimidyl and N-hydroxysuccinimidyl groups; aryloxy groups substituted with electron-withdrawing groups (e.g., p-nitro, pentafluoro, pentachloro, p-cyano, or p-trifluoromethyl); and carboxylic acids activated by a carbodiimide or other conventional coupling reagents to form an anhydride or mixed anhydride, e.g., —$OCOR^a$ or —$OCNR^aNHR^b$, where $R^a$ and $R^b$ are independently $C_1$-$C_6$ alkyl, $C_5$-$C_8$ alkyl (e.g., cyclohexyl), $C_1$-$C_6$ perfluoroalkyl, or $C_1$-$C_6$ alkoxy groups. An activated ester may be formed in situ or may be an isolable reagent. The ester leaving group may be, for example, sulfosuccinimidyl esters, pentafluorothiophenol esters, sulfotetrafluorophenol, substituted or unsubstituted $C_1$-$C_5$ alkyl (such as methyl, ethyl, propyl, isopropyl, butyl, isobutyl, sec-butyl, tert-butyl, pentyl, or hexyl), or substituted or unsubstituted $C_6$-$C_{14}$ aryl or heterocyclic groups, such as 2-fluoroethyl, 2-chloroethyl, 2-bromoethyl, 2,2-dibromoethyl, 2,2,2-trichloroethyl, 3-fluoropropyl, 4-chlorobutyl, methoxymethyl, 1,1-dimethyl-1-methoxymethyl, ethoxymethyl, N-propoxymethyl, isopropoxymethyl, N-butoxymethyl, tert-butoxymethyl, 1-ethoxyethyl, 1-methyl-1-methoxyethyl, 1-(isopropoxy)ethyl, 3-methoxypropyl-4-methoxybutyl, fluoromethoxymethyl, 2,2,2-trichloroethoxymethyl, bis(2-chloroethoxy)methyl, 3-fluoropropoxymethyl, 4-chlorobutoxyethyl, dibromomethoxyethyl, 2-chloroethoxypropyl, fluoromethoxybutyl, 2-methoxyethoxymethyl, ethoxymethoxyethyl, methoxyethoxypropyl, methoxyethoxybutyl, benzyl, phenethyl, 3-phenylpropyl, 4-phenylbutyl, α-naphthylmethyl, β-naphthylmethyl, diphenylmethyl, triphenylmethyl, α-naphthyldipheylmethyl, 9-anthrylmethyl, 4-methylbenzyl, 2,4,6-trimethylbenzyl, 3,4,5-trim ethylbenzyl, 2-nitrobenzyl, 4-nitrobenzyl, 4-methoxybenzyl, 4-methoxyphenyldiphenylmethyl, 4-chlorobenzyl, 4-bromobenzyl, 4-cyanobenzyl, 4-cyanobenzyldiphenylmethyl, or bis(2-nitrophenyl)methyl groups.

IV. Pharmaceutical Compositions

Preferably, the compounds of the invention are formulated prior to administration into pharmaceutical compositions using techniques and procedures well known in the art. Accordingly, in another embodiment, the present invention relates to pharmaceutical compositions (e.g. solid or semi-solid mixtures, solutions, suspensions or emulsions) comprising effective amounts of one or more compounds according to any of the Formulae herein and a pharmaceutically acceptable vehicle, as well as methods of using and manufacturing such pharmaceutical compositions.

The pharmaceutical compositions are formulated for suitable administration (orally, parenterally, (IV, IM, depo-IM, SC, and depo-SC), sublingually, intranasally (inhalation), intrathecally, topically, or rectally). Suitable pharmaceutical vehicles include, without limitation, any non-immunogenic pharmaceutical carrier or diluent suitable for oral, parenteral, nasal, mucosal, transdermal, topical, intrathecal, rectal, intravascular (IV), intraarterial (IA), intramuscular (IM), and subcutaneous (SC) administration routes, such as phosphate buffer saline (PBS). Also, the present invention includes such compounds which have been lyophilized and which may be reconstituted to form pharmaceutically acceptable formulations for administration, as by intravenous, intramuscular, or subcutaneous injection. Administration may also be intradermal or transdermal.

Preferably, the pharmaceutical composition of the invention is suitable for oral administration. The formulations may conveniently be presented in unit dosage form and may be prepared by any methods well known in the art of pharmacy. In general, the formulations are prepared by uniformly and intimately bringing into association a compound of the present invention with a pharmaceutically acceptable vehicle (e.g. an inert diluent or an assimilable edible, liquid or finely divided solid (or both), carrier) and, optionally, one or more accessory ingredients and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and the like, each containing a predetermined amount of a compound of the present invention as an active ingredient. A compound of the present invention may also be administered as a bolus, electuary or paste, or incorporated directly into the subject's diet. Moreover, the compounds can be orally formulated to (a) provide for instant or rapid drug release (i.e., have no coating on them); (b) be coated, e.g., to provide for sustained drug release over time; or (c) be enterically coated for better gastrointestinal tolerability or protection from degradation in the stomach.

In solid dosage forms of the invention for oral administration the active ingredient is typically mixed with one or more pharmaceutically acceptable carriers or non-active pharmaceutical ingredients, such as sodium citrate or dicalcium phosphate, or any of the following: fillers or extenders (e.g. starches, lactose, sucrose, glucose, mannitol, or silicic acid); binders (e.g. carboxymethylcellulose, alginates, gelatin, polyvinyl pyrrolidone, sucrose or acacia); humectants (e.g. glycerol); disintegrating agents (e.g. agar-agar, calcium carbonate, potato or tapioca starch, alginic acid, certain silicates, and sodium carbonate); solution retarding agents (e.g., as paraffin); absorption accelerators (e.g. quaternary ammonium compounds); wetting agents (e.g., cetyl alcohol and glycerol monostearate); absorbents (e.g., kaolin and bentonite clay); lubricants (e.g. talc, calcium stearate, magnesium stearate, solid polyethylene glycols, sodium lauryl sulfate, and mixtures thereof); and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants.

Pharmaceutical compositions suitable for injectable use include sterile aqueous solutions (where water soluble) or dispersions, and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof. Solvent or dispersion medium suitable for injectable use are, for example, water, ethanol, polyols (for example, glycerol, propylene glycol, and liquid polyethylene glycol, and the like), suitable mixtures thereof, and vegetable oils. Proper fluidity is maintained, for example, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Pharmaceutical formulations are also provided which are suitable for administration as an aerosol, by inhalation. These formulations comprise a solution or suspension of the desired compound of any Formula herein or a plurality of solid particles of such compound(s). As a liquid, the formulation will comprise, for example, a water-soluble compound of the invention, or a salt thereof, in a carrier which comprises water. A surfactant may be present which lowers the surface tension of the formulation sufficiently to result in the formation of droplets within the desired size range when subjected to nebulization. On the other hand, solid particles can be obtained by processing the solid form of a compound, or a salt thereof, in any appropriate manner known in the art, such as by micronization. The liquid droplets or solid particles should have a particle size in the range of about 0.5 to about 5 microns. The size of the solid particles or droplets will be, for example, from about 1 to about 2 microns. The desired formulation may be placed in a small chamber and nebulized. Nebulization may be accomplished by compressed air or by ultrasonic energy to form a plurality of liquid droplets or solid particles comprising the agents or salts. In this respect, commercial nebulizers are available to achieve this purpose.

The compositions of this invention can also be administered topically to a subject, e.g., by the direct lying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included. The compound(s) of the invention may also be administered parenterally, intraperitoneally, intraspinally, or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

To administer the compound(s) of the invention by other than parenteral administration, it may be useful to coat the compound(s) with, or co-administer the compound(s) with a material to prevent its inactivation. For example, the compound(s) of the invention may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutical compositions according to the invention may also be coated by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Dosage forms provide the compound in a pharmaceutical composition of the invention for in vivo administration to a subject, e.g. a human patient. It is understood that appropriate doses depend upon a number of factors within the knowledge of the ordinarily skilled physician, veterinarian, or researcher (e.g. see Wells et al. eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), incorporated herein by reference). The dose(s) of the compound(s) of the invention will vary, for example, depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined using the assays described herein or known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in the composition of the present invention. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include single or multiple doses of about 5 to about 1000 mg, about 25 to about 800 mg, about 25 to about 400 mg, about 50 to about 200 mg, or about 50, about 100, about 150 mg, about 200 mg, about 250 mg, about 300 mg, about 400 mg, or about 500 mg, and, preferably, daily or twice daily, or lower or higher amounts. Further exemplary doses include daily doses in a human of about 50 mg to about 4000 mg, about 100 mg to about 3500 mg, about 100 mg to about 2500 mg, about 100 mg to about 1200 mg, about 100 mg to about 800 mg, about 400 mg to about 2500 mg, about 400 mg to about 1200 mg, about 400 mg to about 800 mg, about 800 mg to about 4000 mg, about 800 mg to about 3500 mg, about 800 mg to about 2500 mg, about 800 mg to about 1200 mg, about 1200 mg to about 4000 mg, about 1200 mg to about 3200 mg, about 1200 mg to about 2500 mg, administered as a single daily dose or divided in multiple doses throughout the day. Examples of dosages of 1,3PDS (e.g. herein using molar equivalence or less of the prodrug) are described in PCT published applications WO 2007/004072, WO 2007/125385 and WO 2008/078176, incorporated herein by reference in their entirety for all purposes.

It is generally advantageous to formulate parenteral compositions in dosage unit form for ease of administration and uniformity of dosage. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical vehicle. The specification for the dosage unit forms of the invention may vary and are dictated by and directly dependent on (a) the unique characteristics of the therapeutic agent and the particular therapeutic effect to be achieved, and (b) the limitations inherent in the art of compounding such a therapeutic agent for the prevention of treatment of the disease or disorder.

Administration of the compounds and compositions of the present invention to a subject to be treated can be carried out using known procedures, at dosages and for periods of time effective to achieved the desired purpose. Dosage regimens can be adjusted to provide the optimum therapeutic response. For example, several divided doses may be administered daily or the dose may be proportionally reduced as indicated by the exigencies of the therapeutic situation. Preferably, the compound(s) of the invention is administered at a therapeutically effective dosage sufficient to reduce the disease's or disorder's symptoms in a subject, preferably a human subject.

The compound(s) of the invention may be packaged as part of a kit or a pharmaceutical package, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

V. Methods of Uses of the Compounds

Another aspect of the invention pertains to a method for treating a disease or disorder in a subject by administering an effective amount of a prodrug of the present invention. The term "subject" includes living organisms with a disease or disorder treatable by 1,3PDS, or which are susceptible to such a disease or disorder, e.g. amyloid A amyloidosis, renal disorders, diabetic nephropathy, hyperglycemia, dyslipidemia, diabetes mellitus (e.g. type 1 or type 2), diabetes with features of metabolic syndrome, metabolic syndrome, any underlying or resulting disease or symptom of any the foregoing, or any combination thereof. Examples of subjects include humans, monkeys, cows, rabbits, sheep, goats, pigs, dogs, cats, rats, mice, and transgenic species thereof. The term "subject" preferably includes animals susceptible to states characterized by amyloidosis and/or metabolic diseases, e.g. mammals, e.g. primates, e.g. humans. The animal can also be an animal model for a disorder, e.g., an AA amyloidosis mouse model, or an obese or diabetic mouse or rat model.

In certain embodiments of the invention, the human subject is in need of treatment by the methods of the invention, and is selected for treatment based on this need. A subject in need of treatment is art-recognized, and includes subjects that have been identified as having any of the foregoing disease or disorder, has a symptom of such a disease or disorder, or is at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

For example, the human subject may be a human over 20 year sold, over 30 years old, human over 40 years old, a human over 50 years old, a human over 60 years old, a human over 70 years old, a human over 80 years old. The subject may be a female human, including a postmenopausal female human, who may be on hormone (estrogen) replacement therapy. The subject may also be a male human. In another embodiment, the subject is under 40 years old.

In one aspect, the subject has a disease that provokes a sustained acute phase response. For example, such diseases include chronic inflammatory disorders (e.g. long standing inflammation), chronic local or systemic microbial infections, and malignant neoplasms. For example, such a disease includes Rheumatoid Arthritis or Familial Mediterranean Fever (a genetic disease).

In another aspect, the subject has amyloid A amyloidosis, with or without renal impairment. For example, the subject has amyloid A amyloidosis with renal, which may vary from mild, moderate and severe impairment.

In another aspect, the subject's rate of creatinine clearance is lower than about 80 mL/min, lower than about 30 mL/min (severe), from about 30 to about 80 mL/min (moderate), or greater than about 80 mL/min (mild to none).

In some aspects, the subject may have symptoms of a metabolic disease or condition, such as diabetes (e.g. type II diabetes), metabolic syndrome, obesity, etc. In another embodiment, the subject may have symptoms of type II diabetes and be overweight. For example, the subject has a body mass index (BMI) of 25 or more, a BMI between 25 and 30, or a BMI of 30 or more. The Body Mass Index, or BMI is a measure of a person's weight taking into account their height. It is given by the formula: BMI equals a person's weight (mass) in kilograms divided by the square of the person's height in meters. In some aspects, the subject is diabetic and requires administration of exogenous insulin. In one aspect, the subject is diabetic and does not require exogenous insulin, and the treatment with the compound of the invention allows delaying the requirement for treating the diabetic patient with insulin.

"Preventing" or "prevention" is intended to refer at least the reduction of likelihood or the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" or "preventing" is also used to describe the administration of a compound or composition of the invention to a subject who is at risk of (or susceptible to) such a disease or condition. Patients amenable to treatment for prevention of the disease or condition include individuals at risk of the disease or condition but not showing symptoms, as well as patients presently showing symptoms. Predisposing factors identified or proposed in the scientific literature include, among others, genetic factors, environmental factors, chronic inflammation and other conditions (such as ones predisposing to AA amyloidosis), sedentary lifestyle, eating habits, and metabolic disorders predisposing a subject to a disease or disorder as described herein. Prevention also includes delaying onset of certain endpoint, for example, delaying the need for dialysis in renally impaired patients, or the need for insulin in diabetes patients.

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; improving a subject's physical or mental well-being, reducing symptoms experienced by the patient; and, in some situations additionally improving at least one parameter of a renal disorder (creatinine clearance, proteinuria, etc) or metabolic disorder (e.g. glucose tolerance, insulin secretion, reducing serum triglycerides levels, etc). The treatment or amelioration of symptoms can be based on objective or subjective parameters; including the results of a physical examination or the subject's evaluation of symptoms, or of a test known in the art (e.g. glucose level, etc). The treatment or amelioration of symptoms also includes delaying the onset of dialysis, i.e. the necessity for dialysis.

As used herein the term "therapeutically effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the size, age, and general health of the subject; the specific disease(s) involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances.

Improvement in condition is present within the context of the present invention if there is a measurable difference between the performances of subjects treated using the methods of the invention as compared to members of a placebo group, historical control, or between subsequent tests given to the same subject.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

In certain embodiments, the compounds and composition according to the invention can be used in combination therapy with at least one other therapeutic or a nutraceutical agent. The compounds of the invention when administered in association with at least one other agent(s), can act additively or, in certain embodiments, synergistically.

The compounds of the invention can be administered prior, subsequent to or concomitantly with the other agent. The compositions of the present invention can be administered with the other therapeutic agent as part of the same pharmaceutical composition as, or in a different composition from, that containing the compounds of the present invention. The at least one other agent can be effective for treating the same or different disease, disorder, or condition. Preferably, the other agent is suitable for the treatment of symptoms of a metabolic disorder, e.g. diabetes, diabetes with features of metabolic syndrome, metabolic syndrome, and the like.

Methods of the present invention include administration of one or more compounds or pharmaceutical compositions of the present invention and one or more other therapeutic agents provided that the combined administration does not inhibit the therapeutic efficacy of the one or more compounds of the present invention and/or does not produce adverse combination effects.

In some aspects, the combination therapy comprises alternating between administering a composition of the present invention and a composition comprising another therapeutic agent, e.g., to minimize adverse side effects associated with a particular drug. When a compound of the present invention is administered concurrently with another therapeutic agent that potentially can produce adverse side effects including, but not limited to, toxicity, the therapeutic agent can advantageously be administered at a dose that falls below the threshold at which the adverse side effect is elicited. A pharmaceutical composition can also further comprise substances to enhance, modulate and/or control release, bioavailability, therapeutic efficacy, therapeutic potency, stability, and the like.

The compounds or pharmaceutical compositions of the present invention include, or can be administered to a patient together with, another therapeutic drug that may be available over-the-counter or by prescription. Therapeutic drugs as well as nutraceuticals useful in a combination with a therapeutic compound of the present invention are known to the skilled artisan. Preferred therapeutic drugs to be used with the compounds or pharmaceutical compositions of the present invention are therapeutic drugs useful in the prevention or treatment of, but not limited to, chronic inflammation, nephropathy, or diabetes and other metabolism disorders, or any disease, disorder or symptom associated with any of the conditions disclosed herein.

Preferred therapeutic drugs to be used with the 1,3PDS prodrugs and dimers and oligomers of the present invention are therapeutic drugs useful in the prevention or treatment of renal disorders as well as diabetes and associated symptoms and syndromes. PCT patent application WO 2008/078176 (incorporated herein by reference) provide a long but non-exhaustive list of "therapeutic drugs" that can be useful, in combination, according to the invention.

VI. Standard Methods for Testing the Compounds of the Invention

The compounds according to the invention can be further analyzed, tested or validated using a variety of in vitro assays, or in vivo assays to confirm their safety and bioavailabity, their capability to deliver 1,3PDS, etc. The following are illustrative of the type of biological assays that can be conducted to assess the instant compounds.

i) Determination of Enzymatic Cleavage of Prodrugs In Vitro

For orally administered prodrugs, it is generally desirable that the prodrug remains mostly intact (i.e., uncleaved or not converted to the parent drug) while in the gastrointestinal tract and be cleaved (i.e., to release the parent drug) while in the systemic circulation. A useful level of stability can at least in part be determined by the mechanism and kinetics of absorption of the prodrug by the gastrointestinal tract. A useful level of lability can at least in part be determined by the pharmacokinetics of the prodrug and parent drug in the systemic circulation. In general, prodrugs that are more stable in a Caco-2 S9 and/or pancreatin assay and are more labile in rat plasma, human plasma, rat liver S9, and/or human liver S9 preparation can be useful as an orally administered prodrug. The results of tests, for determining the enzymatic cleavage of prodrugs in vitro can be used to select prodrugs for in vivo testing.

ii) Bioavailability of Prodrugs In Vivo

Prodrugs that provide, following administered to a patient or a subject, a certain level of bioavailability of the corresponding parent drug can be useful as therapeutic agents. Bioavailability of the compounds of the invention and of released 1,3PDS can be measured in vivo (humans and/or laboratory animals) using methods well known in the art.

iii) Toxicity

A variety of different parameters can be monitored to assess toxicity. Examples of such parameters include, but are not limited to, cell proliferation, monitoring activation of cellular pathways for toxicological responses by gene or protein expression analysis, DNA fragmentation, changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis, including cGMP formation and NO formation.

Toxicity and therapeutic efficacy of the compound(s) and composition(s) of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While agents that exhibit toxic side effects may be used, care should be taken to design a delivery system that targets such agents to the site of affected tissue in order to minimize potential damage to unaffected cells and, thereby, reduce side effects.

iv) Gastrointestinal Absorption

The compounds or drugs according to the invention can be further analyzed, tested or validated for their ability to be absorbed by the gut and/or intestine if so desired.

Intestinal permeability and transport of a drug candidate may be estimated using a variety of in vitro, in situ, as well as in vivo models (Balimane et al. (2000) J Pharmacol Toxicol Methods 44:385-401; Hidalgo I. (2001) Curr Top Med Chem 1:385-401, Hillgreen K, Kato A and Borchardt R. (1995) 15:83-109, each incorporated herein by reference).

For instance, parallel artificial membrane permeability (PAMPA) assay and cell-based systems such as Caco-2 and Mardin-Darby canine kidney (MDCK) cells are the most frequently used in vitro models. The PAMPA model consists of a hydrophobic filter material coated with a mixture of lecithin/phospholipids dissolved in an inert organic solvent creating an artificial lipid membrane barrier that mimics the intestinal epithelium. Caco-2 cells, a human colon adenocarcinoma, undergo spontaneous enterocytic differentiation in culture and become polarized cells with well-established tight junctions, resembling intestinal epithelium in humans. Caco-2 cell model has been the most popular and the most extensively characterized cell-based model in examining the permeability of drugs in both the pharmaceutical industries and academia. Alternatively, MDCK cells which also develop tight junctions and form monolayers of polarized cells are used.

An in situ study such as an intestinal perfusion could also be performed to assess drug absorption. Isolated intestinal segments comprise the absorptive cells and the underlying muscle layers. As it is commonly used, this technique only allows sampling from the mucosal side; drug disappearance is assumed to be equal to drug absorption. Typically, a whole animal absorption study (pharmacokinetic study) will be performed in parallel with the in vitro and/or in situ studies to assess intestinal permeability. In general, drug absorption in animals is believed to be a good predictor of absorption in humans.

v) Gastrointestinal Toxicity

The compounds or drugs according to the invention can be further analyzed, tested or validated for gastrointestinal (GI) toxicity. Gastrointestinal toxicity of a compound in vivo can be reliably established through the implementation of a standard battery of general toxicological assessments. Generally, regulatory test guidelines from the EU, OECD, ICH, FDA and JMOHW are used as reference material for the preparation of study protocols for such assessments. In North America, the toxicological assessments will generally be carried out in compliance with the United States Food and Drug Administration Title 21 Code of Federal Regulations Part 58, Good Laboratory Practice for Non-clinical studies issued on Dec. 22, 1978, Federal Register plus subsequent amendments.

Within the context of such a non-clinical assessment of the toxicity of a particular compound, GI toxicity may specifically be assessed through the monitoring of body weight gain, the gross examination of materials emitted by the test subject (specifically vomitus and feces) and the monitoring of food/water consumption (appetence). Furthermore, upon termination of a non-clinical toxicological assessment, the retention and processing of GI tract tissues from the test subject(s) to the slide stage, followed by histopathological examination of said tissues by a trained pathologist, is a useful tool, complementary to the aforementioned "in-life" observations.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary syntheses of certain representative compounds of the invention.

Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The present invention also relates to novel compounds and the synthesis thereof. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques. In some cases, the compounds may be commercially available. Accordingly, the following examples are presented to illustrate how some sulfonate ester prodrugs according to the invention may be prepared.

Commercial material is generally available from known sources, for example, Sigma-Aldrich, Bachem, Lancaster, Alfa Aesar, etc.

Example 1

General Synthetic Protocol for the Synthesis of Mono and Disulfonate Esters

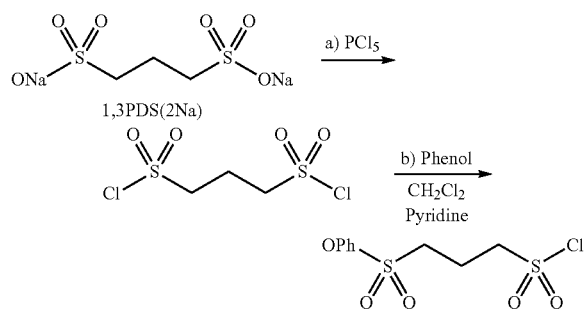

a) 1,3-propanedisulfonyl dichloride 1,3-Propanedisulfonic acid disodium salt (1,3PDS(2Na)), 74 g, 0.29 mol) was well grounded and dried at 110° C. for 15 h. PCl$_5$ (72 g, 0.62 mol) was added and the two solids were stirred until they melt. The reaction mixture was stirred for 2 h then cooled to room temperature. The resulting material was added with caution to ice (200 g), followed by addition of ethyl acetate (200 mL). The mixture was stirred until a clear two phases was obtained. The organic layer was separated, washed with hydrochloric acid (1 M), and concentrated under reduced pressure to produce an amorphous brownish solid. Recrystallization in ether allowed the isolation of 1,3-propanedisulfonyl dichloride (62 g) as a white solid: $^1$H NMR (CDCl$_3$, 500 MHz) δ in ppm 2.78 (q, J=7.0 Hz, 2H), 3.95 (t, J=7.0 Hz, 4H).

Alternate Protocol:

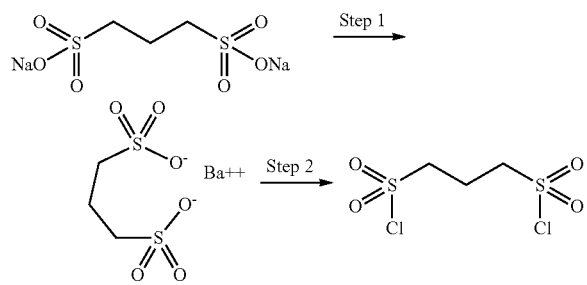

Step 1: To a solution of 1,3-propanedisulfonic acid disodium salt (23.5 g, 94.7 mmol) in water (30 mL) was added a hot solution of BaCl$_2$.H$_2$O in H$_2$O (20 mL). A white precipitate was formed. The suspension was heated at ~80° C. for 2 h then cooled to room temperature and allowed to settle by standing. The white solid was collected by filtration and dried under high vacuum at 120° C. for 15 h to afford barium 1,3-propanedisulfonate (20 g, 62%): $^1$H NMR (CDCl$_3$, 500 MHz) δ 2.04 (m, 2H), 2.92 (t, J=7.0 Hz, 4H).

Step 2: The fine powder of barium 1,3-propanedisulfonate (15 g, 44.17 mmol) was mixed with phosphorus pentachloride (PCl$_5$) and heated at 110° C. for 5 h. (the mixture melted completely after 1-h heating). The reaction mixture was cooled to room temperature, and then quenched with ice/water (150 mL) and ethyl acetate. The organic layer was isolated, washed with water, dried over sodium sulfate, and concentrated to dryness, affording 1,3-propanedisulfonyl dichloride (6 g): $^1$H NMR (CDCl$_3$, 500 MHz) δ 2.78 (q, J=7.0 Hz, 2H), 3.95 (t, J=7.0 Hz, 4H).

b) 3-phenoxysulfonyl-1-propanesulfonyl chloride

To a cold (0° C.) solution of 1,3-propanedisulfonyl dichloride from Step (a) (4.8 g, 20 mmol) in dichloromethane (30 mL) was added dropwise a solution of phenol (1.88 g, 20 mmol) in dichloromethane/pyridine (20 mL:5 mL). The reaction mixture was stirred for 3 h while it was gradually warmed to room temperature. Aqueous HCl (1M) was added to the reaction mixture. The organic layer was separated, dried over magnesium sulfate, filtered and concentrated. The residual material was purified by silica gel chromatography using hexanes/ethyl acetate (70:30) as eluent to isolate 3-phenoxysylfonyl-1-propanesulfonyl chloride (7.2 g): $^1$H NMR (500 MHz, CDCl$_3$) δ in ppm 2.71 (quint, J=7.0 Hz, 2H), 3.52 (t, J=7.0 Hz, 2H), 3.95 (t, J=7.0 Hz, 2H), 7.26-7.45 (m, 5H).

c) 1,3-propanedisulfonic acid monoesters

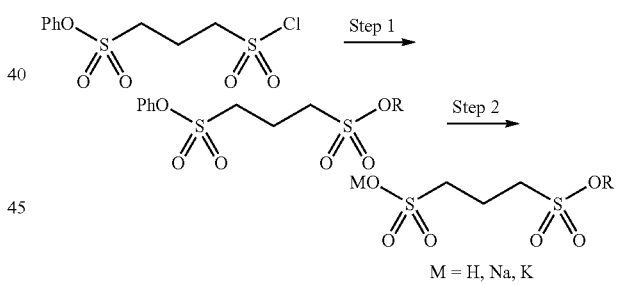

M = H, Na, K (R is R$^4$ as previously described)

Step 1: Esterification: To a cold (0° C.) solution of 3-phenoxysylfonyl-1-propanesulfonyl chloride from Step (b) (5.97 g, 20 mmol, see (b)) in CH$_2$Cl$_2$ (30 mL) is added dropwise a solution of the corresponding alcohol (22 mmol) in CH$_2$Cl$_2$/pyridine (20 mL/5 mL). The reaction mixture is stirred for 3-15 h while it is gradually warmed to room temperature. Aqueous hydrochloric acid (1M) is added to the reaction mixture. The organic layer is separated, dried over magnesium sulfate and concentrated. The residual material is purified by silica gel chromatography using hexanes/ethyl acetate as eluent to isolate the corresponding intermediate 1,3-propanesulfonic acid alkyl phenyl ester.

Step 2: Deprotection: To a solution of the intermediate 1,3-propanesulfonic acid alkyl phenyl ester from Step 1 (2 mmol) in MeOH (50 mL) is added acetic acid (5 mL) followed by addition of Pd(OH)$_2$ (200 mg) in water (5 mL). The reaction mixture is stirred under hydrogen (1 atm., balloon)

for 2-3 h (or until complete consumption of starting material). The suspension is filtered, and the filtrate is concentrated to dryness. To the residual material is added an aqueous solution of sodium carbonate (1M, 2 mL); and the resulting mixture is stirred for 30 min and then concentrated. The residue is purified by silica gel chromatography using dichloromethane/methanol (90:10 to 80:20) as eluent to give the corresponding 1,3-propanedisulfonic acid monoester.

d) 1,3-propanedisulfonic acid monoesters (Alternate Protocol)

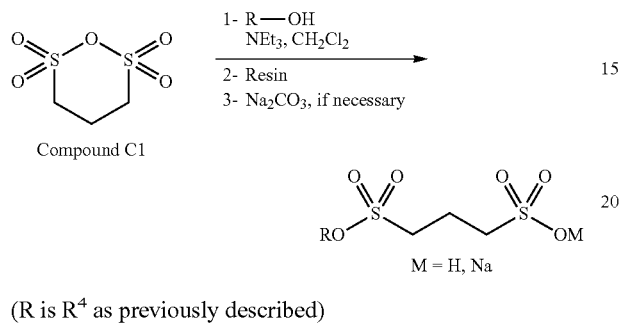

Compound C1

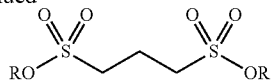

M = H, Na (R is R$^4$ as previously described)

Compound C1 (Example 13) (5.0 mmol) and triethylamine (20.0 mmol) are added to a stirred solution of selected alcohol (5.25 mmol) in dichloromethane (15 mL). The resulting mixture is stirred for 24 h at room temperature and the reaction mixture concentrated in vacuo. The residue is diluted with water and passed through a column of strongly acid cation exchange resin (Dowex™ Marathon™ C, 30-40 mesh, 30 g). Elution with water permitted to isolate the monosulfonic acid prior to silica gel chromatography. The corresponding sodium salt can also be obtained after treatment of the monosulfonic acid in methanol with aqueous 1N sodium carbonate (10.0 mmol) for 15 min. at room temperature. The mixture is then concentrated to dryness and subjected to silica gel chromatography using a mixture of dichloromethane and methanol as eluent to isolate the corresponding 1,3-propanedisulfonic acid monoester. The final product can also be lyophilized as its final solid form.

e) 1,3-propanedisulfonic acid diesters

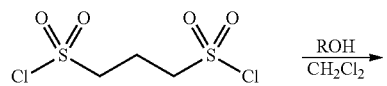

(R is R$^3$ in one occurrence and R$^4$ in another and are as previously described)

To a cold (0° C.) solution of 1,3-propanedisulfonyl dichloride from Step (a) (4.8 g, 20 mmol) in dichloromethane (30 mL) is added dropwise a solution of a corresponding alcohol (44 mmol) in dichloromethane/pyridine (20 mL:5 mL). The reaction mixture is stirred for 3-15 h while it is gradually warmed to room temperature. Aqueous hydrochloric acid (1 M) is added to the reaction mixture. The organic layer is separated, dried over magnesium sulfate and concentrated. The residual material is purified by silica gel column using hexanes/ethyl acetate as eluent to isolate the corresponding 1,3-propanedisulfonic acid diester.

Example 2

Preparation of Compounds B1 and B2(bis(trifluoroacetate) salt)

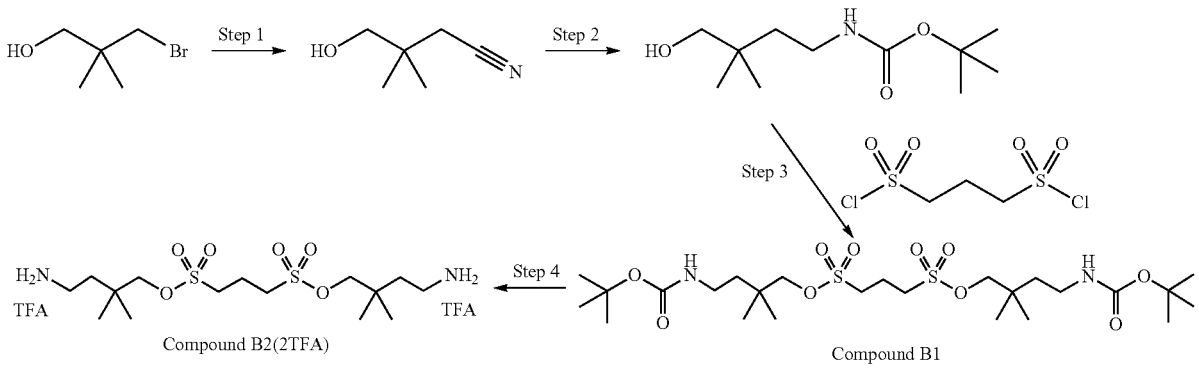

Step 1: To a stirred solution of commercial 3-bromo-2,2-dimethylpropanol (3.5 g, 21 mmol) in dimethylsulfoxide (50 mL) was added well grounded potassium cyanide (3.8 g, 58 mmol). The reaction mixture was stirred at 100° C. for 15 h, then cooled to room temperature and diluted with 1M hydrochloric acid. The mixture was extracted with ethyl acetate and the extracts were washed with 1M hydrochloric acid, dried over sodium sulfate and evaporated to an oily residue. The residual material was purified by column chromatography (silica gel, hexanes/ethyl acetate 70:30 then 50:50) to afford 3.2 g of 4-hydroxy-3,3-dimethylbutanenitrile. $^1$H NMR (CDCl$_3$, 500 MHz) δ (ppm) 1.01 (s, 6H), 2.00 (m, 1H), 2.31 (s, 2H), 3.36 (d, J=3.0 Hz, 2H); $^{13}$C NMR (CDCl$_3$, 125 MHz) δ (ppm) 23.89, 27.10, 35.46, 70.0, 118.83.

Step 2: Water-wet Raney-nickel (1 g) was added to a stirred solution of 4-hydroxy-3,3-dimethylbutanenitrile from Step 1 (3.0 g, 26.51 mmol) in ethanol (100 mL). To this suspension was added ammonium hydroxide (30% in water, 10 mL). The reaction mixture was stirred under atmospheric pressure of hydrogen for 2 days, and then filtered. The filtrate was concentrated; and the resulting residue was dissolved in dichloromethane (60 mL) followed by addition of di(tert-butyl) dicarbonate (6.3 g, 29 mmol). The reaction mixture was stirred at room temperature for 2 h and then concentrated under reduced pressure. The residual material was purified by silica gel column chromatography (hexanes/ethyl actetate 80:20 then 70:30) to isolate 4-t-butoxycarbonylamino-2,2-dimethyl-1-butanol (3.8 g, 66%). $^1$H NMR (CDCl$_3$, 500 MHz) δ (ppm) 1.90 (s, 6H), 1.43 (s, 9H), 1.46 (m, 2H), 2.10 (bs, 1H), 3.13 (m, 2H), 3.35 (d, J=6.0 Hz, 2H), 4.65 (bs, 1H).

Step 3: To a stirred solution of 4-t-butoxycarbonylamino-2,2-dimethyl-1-butanol from Step 2 (0.43 g, 2 mmol) in pyridine (10 mL) was added 1,3-propanedisulfonyl dichloride (Example 1 (a)) (812 mg, 4 mmol). The reaction mixture was stirred at room temperature for 2 h, diluted with toluene, and concentrated under reduced pressure. The residual material was diluted with ethyl acetate. The resulting solution was washed with water, dried over sodium sulfate and concentrated. The residual material was purified by column chromatography (silica gel, hexane/ethyl acetate 70:30 then 60:40), providing Compound B1 (1.1 g, 96% yield) as a white solid. $^1$H NMR (CDCl$_3$, 500 MHz) δ (ppm) 1.00 (s, 12H), 1.44 (s, 18H), 1.52 (m, 4H), 2.43 (quint, J=7.2 Hz, 2H), 3.15 (m, 4H), 3.36 (t, J=7.0 Hz, 4H), 3.93 (s, 4H), 4.58 (bs, 2H); $^{13}$C NMR (CDCl$_3$, 125 MHz) δ (ppm) 18.71, 24.10, 28.65, 33.97, 36.51, 38.61, 47.95, 77.70, 79.51, 156.08; ES-MS 601 (M−1).

Step 4: Trifluoroacetic acid (1 mL) was added to a stirred solution of Compound B1 from Step 3 (0.22 g, 0.36 mmol) in CH$_2$Cl$_2$ (6 mL). The reaction mixture was stirred at room temperature for 2 h then concentrated under reduced pressure to afford Compound B2 (bis(trifluoroacetate) salt) in quantitative yield as a colorless waxy solid. $^1$H NMR (D$_2$O, 500 MHz) δ (ppm) 0.88 (s, 12H), 1.55 (m, 4H), 2.25 (quint, J=7.0 Hz, 2H), 2.91 (m, 4H), 3.47 (t, J=7.2 Hz, 4H), 3.95 (s, 4H); $^{13}$C NMR (D$_2$O, 125 MHz) δ (ppm) 18.00, 22.65, 33.22, 35.29, 35.73, 47.17, 78.162; ES-MS 403 (M+1).

Example 3

Preparation of Compounds A1 (Potassium Salt) and A2

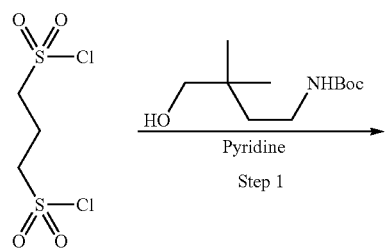

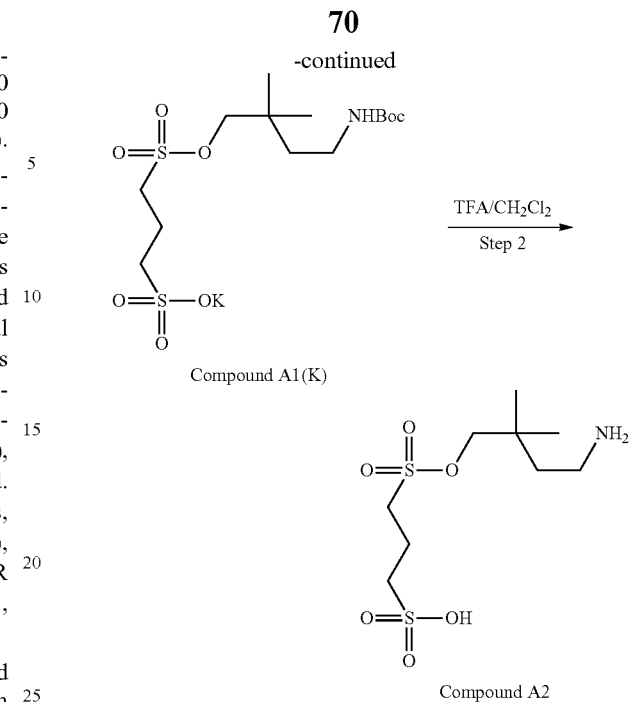

Compound A1(K)

Compound A2

Step 1: To a stirred solution of 4-t-butoxycarbonylamino-2,2-dimethyl-1-butanol (Example 2, Step 2) (0.43 g, 2 mmol) in pyridine/CH$_2$Cl$_2$ (10 mL:10 mL) was added 1,3-propanedisulfonyl dichloride (Example 1 (a)) (407 mg, 2 mmol), followed by addition of 1M aqueous potassium carbonate (5 mL). The reaction mixture was vigorously stirred for 30 min then concentrated under reduced pressure. The residual material was purified by silica gel chromatography (dichloromethane/methanol 90:10 then 80:20) to isolate Compound A1(potassium salt) (0.42 g, 49% yield) as a white solid. $^1$H NMR (D$_2$O, 500 MHz) δ (ppm) 0.86 (s, 6H), 1.29 (s, 9H), 1.38 (m, 2H), 2.14 (m, 2H), 2.93 (t, J=7.0 Hz, 2H), 2.98 (m, 2H), 3.43 (t, J=7.0 Hz, 2H), 3.92 (s, 2H); $^{13}$C NMR (D$_2$O, 125 MHz) δ (ppm) 19.10, 23.08, 27.91, 33.33, 36.13, 37.53, 47.84, 48.78, 78.98, 81.06, 158.28; ES-MS 402 (M−1−K).

Step 2: Trifluoroacetic acid (1 mL) was added to a stirred solution of Compound A1(K) from Step 1 (0.20 g, 0.47 mmol) in dichloromethane (6 mL). The reaction mixture was stirred at room temperature for 2 h then concentrated under reduced pressure. The residual material was suspended in ethanol/diethyl ether; and the resulting suspension was filtered. The solid material was washed with ether then dried to obtain Compound A2 (0.12 g, 88% yield) as a white solid. $^1$H NMR (D$_2$O, 500 MHz) δ (ppm) 0.88 (s, 6H), 1.57 (m, 2H), 2.14 (quint, J=7.0 Hz, 2H), 2.90-2.95 (m, 4H), 3.46 (t, J=7.0 Hz, 2H), 4.64 (s, 2H); $^{13}$C NMR (D$_2$O, 125 MHz) δ (ppm) 19.14, 22.72, 33.18, 35.35, 35.81, 47.84, 48.67, 78.24; ES-MS 302 (M−1).

Example 4

Preparation of Compounds B3, B4(bis(trifluoroacetate) salt) and B73

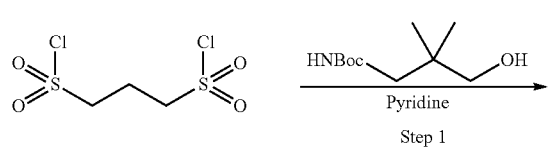

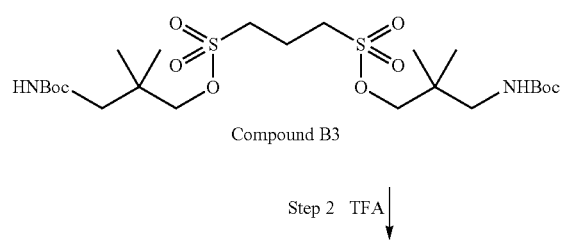

Compound B3

Step 2 TFA

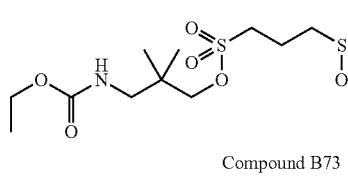 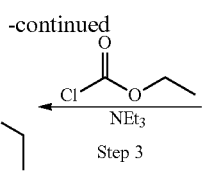 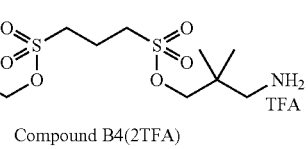

Compound B73

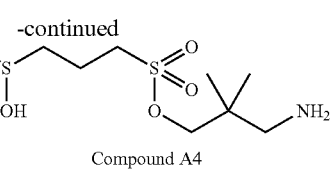

Compound B4(2TFA)

Step 1 and Step 2: Using an amended version of the procedure of Example 2 (Steps 3 and 4) used for the synthesis of Compounds B1 and B2(bis(trifluoroacetate)salt), Compounds B3 (used as an intermediate) and B4(bis(trifluoroacetate)salt) were prepared by replacing 4-(t-butoxycarbonylamino-2,2-dimethyl-1-butanol with commercial 3-(t-butoxycarbonylamino-2,2-dimethyl-1-propanol (Steps 1 and 2). Compound B4(bis(trifluoroacetate)salt) was obtained (0.59 g) as a colorless waxy solid. $^1$H (D$_2$O, 500 MHz) δ in ppm 0.90 (s, 12H), 2.27 (quint, J=7.2 Hz, 2H), 2.88 (s, 4H), 3.48 (t, J=7.2 Hz, 4H), 4.07 (s, 4H); $^{13}$C (D$_2$O, 125 MHz) δ (ppm) 17.90, 20.80, 33.92, 46.22, 47.32, 76.33, 116.00 (q, J=293 Hz, CF$_3$ of TFA), 163.00 (q, J=36 Hz, CO of TFA); ES-MS 373 (M−1−2TFA).

Step 3: To a suspension of Compound B4(bis(trifluoroacetate)salt) from Step 2 (0.671 g, 1.5 mmol) in dichloromethane (40 mL) was added triethylamine (1.3 mL, 9.0 mmol) followed by commercial ethyl chloroformate (0.86 mL, 9.0 mmol). The mixture was stirred for 2 h at room temperature, diluted with 1H HCl and extracted three times with ethyl acetate. The combined organic layers were washed with water, dried over magnesium sulfate, filtered and filtrate evaporated to give a residue. The crude product was purified by silica gel chromatography using hexane/ethyl acetate (50:50) to isolate Compound B73 (0.46 g, 59% yield) as a colorless oil. $^1$H NMR (CDCl$_3$, 500 MHz) δ in ppm 0.975 (s, 2×6H), 1.24 (t, J=7.3 Hz, 2×3H), 2.45 (quint, J=7.0 Hz, 2H), 3.12 (d, J=7.0 Hz, 2×2H), 3.39 (t, J=7.0 Hz, 2×2H), 3.97 (s, 2×2H), 4.10 (q, J=7.3 Hz, 2×2H), 4.96 (bt, 2×NH).

Example 5

Preparation of Compounds A3 (Potassium Salt) and A4

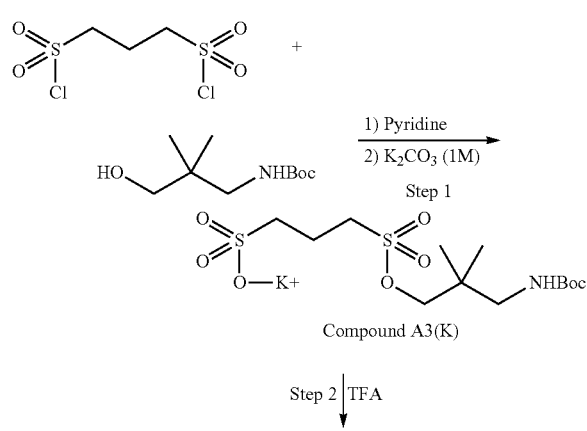

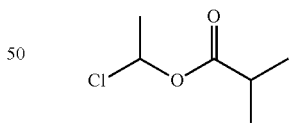

Compound A4

Step 1: Using an amended version of Step 1 of the procedure of Example 3, used for the preparation of Compound A1(potassium salt), Compound A3(potassium salt) was prepared from commercial 3-t-butoxycarbonylamino-2,2-dimethyl-1-propanol and 1,3-propanedisulfonyl dichloride (Example 1 (a)). Compound A3(potassium salt) was obtained (0.19 g) as a white powder. $^1$H NMR (D$_2$O, 500 MHz) δ ppm 0.82 (s, 6H), 1.29 (s, 9H), 2.13 (quint, J=7.2 Hz, 2H), 2.90 (s, 2H), 2.92 (t, J=7.2 Hz, 2H), 3.42 (t, J=7.2 Hz, 2H), 3.93 (s, 2H); $^{13}$C NMR (D$_2$O, 125 MHz) δ 19.04, 21.22, 27.83, 35.73, 46.79, 47.84, 48.76, 76.87, 81.03, 158.50; ES-MS 426 (M−1).

Step 2: Compound A4 was prepared from Compound A3(potassium salt) from Step 2 using an amended version of Step 2 of the procedure of Example 3, used for the preparation of Compound A2. Compound A4 was obtained (0.16 g) as a white solid. $^1$H NMR (D$_2$O, 500 MHz) δ ppm 0.97 (s, 6H), 2.13 (quint, J=7.2 Hz, 2H), 2.89 (s, 2H), 2.95 (t, J=7.2 Hz, 2H), 3.46 (t, J=7.0 Hz, 2H), 4.06 (s, 2H); $^{13}$C NMR (D$_2$O, 125 MHz) δ 19.09, 20.88, 33.90, 46.32, 47.96, 48.66, 76.11; ES-MS 288 (M−1).

Example 6

Preparation of 1-chloroethyl 2-methylpropanoate

To a cold (0° C.) solution of isobutyryl chloride (10 mL, 98 mmol) in CH$_2$Cl$_2$ (250 mL) was added zinc chloride (1.6 g, 9.8 mmol), followed by acetaldehyde (6.5 g, 147 mmol). The reaction mixture was stirred for 4 h at room temperature then concentrated. The crude material was diluted in diethyl ether and water, and the phases obtained were separated. The organic layer was washed with brine, dried over magnesium sulfate, filtered and concentrated in vacuo. The residue was purified by silica gel chromatography using diethyl ether/hexanes (1:10) as eluent to provide 7.0 g of the title compound as a colorless liquid. $^1$H NMR (500 MHz, CDCl$_3$) δ in ppm 1.17-1.20 (m, 6H), 1.79 (d, J 6.0 HHz, 3H), 2.51-2.61 (m, 1H), 6.54 (q, J=6.0 Hz, 1H),

Example 7

Preparation of Compounds A14, A51, A52(Sodium Salt), B14, B51(bis(trifluoroacetate) salt) and B52 a) Compound A51:

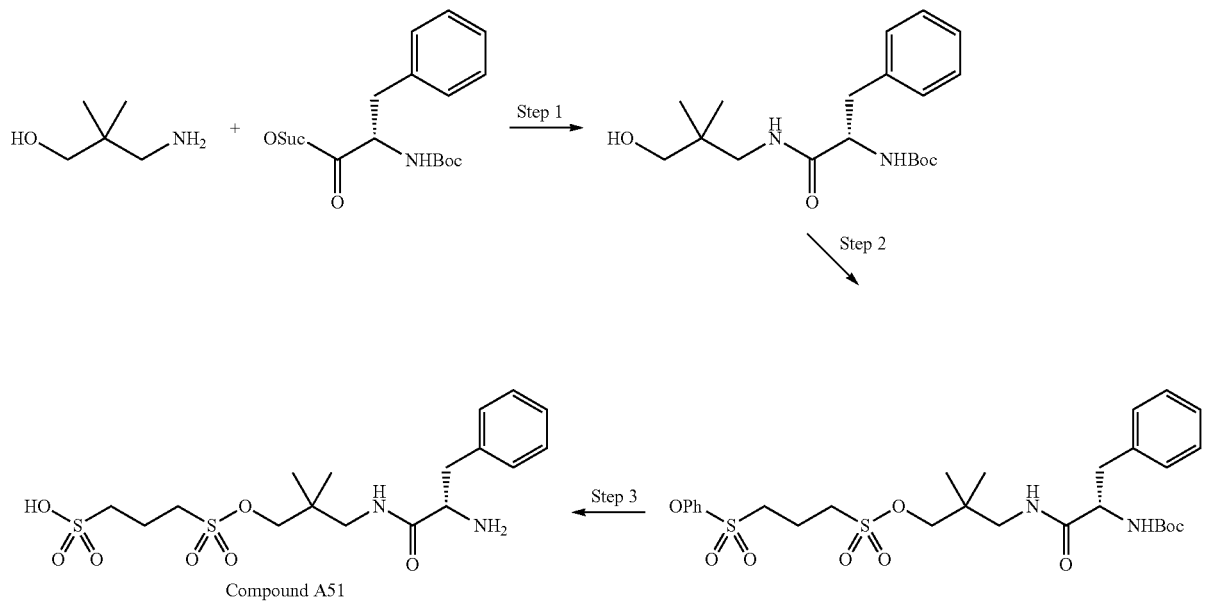

Compound A51

Step 1: To a mixture of commercial 3-amino-2,2-dimethyl-1-propanol (1.33 g, 13 mmol) in tetrahydrofuran (40 mL) and 1 M aqueous potassium carbonate (10 mL) was added a solution of N-Boc-Phe-O-Succinimide (4.60 g, 13 mmol). The reaction mixture was stirred vigorously at room temperature for 2 h. The two phases were separated and the organic layer was concentrated to afford 3-(N-Boc-L-phenylalaninamido)-2,2-dimethylpropanol as a white solid ready for use without further purification.

Step 2: To a stirred solution of 3-(N-Boc-L-phenylalaninamido)-2,2-dimethylpropanol from Step 1 (2 mmol) in a mixture of pyridine/dichloromethane (5 mL:10 mL) was added a solution of phenyl 3-phenoxysulfonyl-1-propanesulfonyl chloride (Example 1 (b)) (2.2 mmol) in dichloromethane (5 mL). The reaction mixture was stirred at room temperature for 15 h, then concentrated and rediluted with ethyl acetate and aqueous hydrochloric acid (1 N). The organic phase was isolated, washed with aqueous hydrochloric acid (1 N) and concentrated. The residual material was purified by silica gel chromatography using hexanes/ethyl acetate (70:30 to 50:50) as eluent to afford 3-phenoxysulfonyl-1-propanesulfonic acid 3-(N-Boc-L-phenylalaninamido)-2,2-dimethylpropyl ester.

Step 3: To a solution of 3-phenoxysulfonyl-1-propanesulfonic acid 3-(N-Boc-L-phenylalaninamido)-2,2-dimethylpropyl ester from Step 2 (1.24 g, 2 mmol) in methanol (50 mL) was added acetic acid (5 mL) followed by addition of Pd(OH)$_2$ (200 mg) in water (5 mL). The reaction mixture was stirred under hydrogen atmosphere (balloon) for 2-3 h (or until complete consumption of starting material). The suspension was filtered, and the filtrate was concentrated to dryness. The resulting crude material was dissolved in dichloromethane (10 mL), followed by addition of trifluoroacetic acid (5 ml). The reaction mixture was stirred for 2 h, concentrated under reduce pressure, and purified by silica gel chromatography using dichloromethane/methanol (90:10) as eluent to yield Compound A51 (800 mg) as a white solid. $^1$H NMR (D$_2$O, 500 MHz) δ in ppm 0.77 (s, 3H), 0.80 (s, 3H), 2.27 (quint, J=7.0 Hz, 2H), 2.95 (d, J=14.0 Hz, 1H), 3.06 (t, J=7.5 Hz, 2H), 3.15 & 3.25 (ABX, J=14.0 & 8.0 Hz, 2H), 3.24 (m, 1H), 3.53 (t, J=7.0 Hz, 2H), 3.97 (AB, J=9.0 Hz, 2H), 4.25 (dd, J=9.0 & 7.0 Hz, 1H), 7.31-7.44 (m, 5H), 8.05 (bt, CONH, not completely exchanged with D$_2$O).

b) Compound A52(sodium salt):

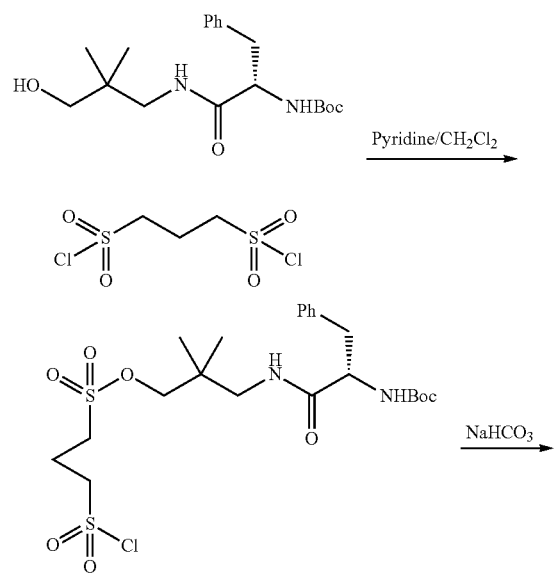

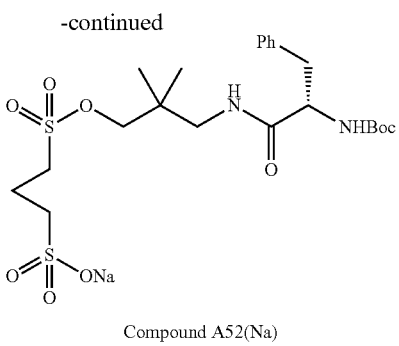

Compound A52(Na)

To a stirred solution of 3-(N-Boc-L-phenylalaninamido)-2,2-dimethylpropanol (Example 7 (a), Step 1) (2.0 g) in a mixture of pyridine (5 mL) and dichloromethane (40 mL) was added 1,3-propanedisulfonyl dichloride (Example 1 (a)) (1.37 g). The reaction mixture was stirred at room temperature for 15 h and concentrated under reduced pressure. The residue was purified by silica gel chromatography using hexanes/ethyl acetate (70:30) as eluant to yield 1.5 g of the monoesterification product. The product was dissolved in tetrahydrofuran (10 mL) to which was added a 1M aqueous solution of sodium bicarbonate (10 mL) and tetrahydrofuran (10 mL). The reaction mixture was stirred for 15 h and concentrated under reduced pressure. The residual material was purified by silica gel chromatography (dichloromethane/methanol 90:10) to isolate Compound A52(sodium salt) (0.63 g) as white solid. $^1$H NMR DMSO-$d_6$ 500 MHz) δ ppm 0.83 (s, 6H), 1.23 (s, minor rotamer, 1.3H) and 1.30 (s, major rotamer, 7.7H), 2.00 (quint, J=7.0 Hz, 2H), 2.55 (t, J=7.0 Hz, 2H), 2.76 (dd, J=14.0 & 10.0 Hz, 1H), 2.90 (dd, J=14.0 & 5.0 Hz, 1H), 3.0 (t, J=7.0 Hz, 2H), 3.48 (t, J=7.5 Hz, 2H), 3.86 (s, 2H), 4.18 (m, 1H), 6.95 (d, J=8.5 Hz, 1H), 7.15-7.30 (m, 5H), 7.88 (t, J=6.5 Hz, 1H).

c) Compounds B51(bis(trifluoroacetate) salt) and B52

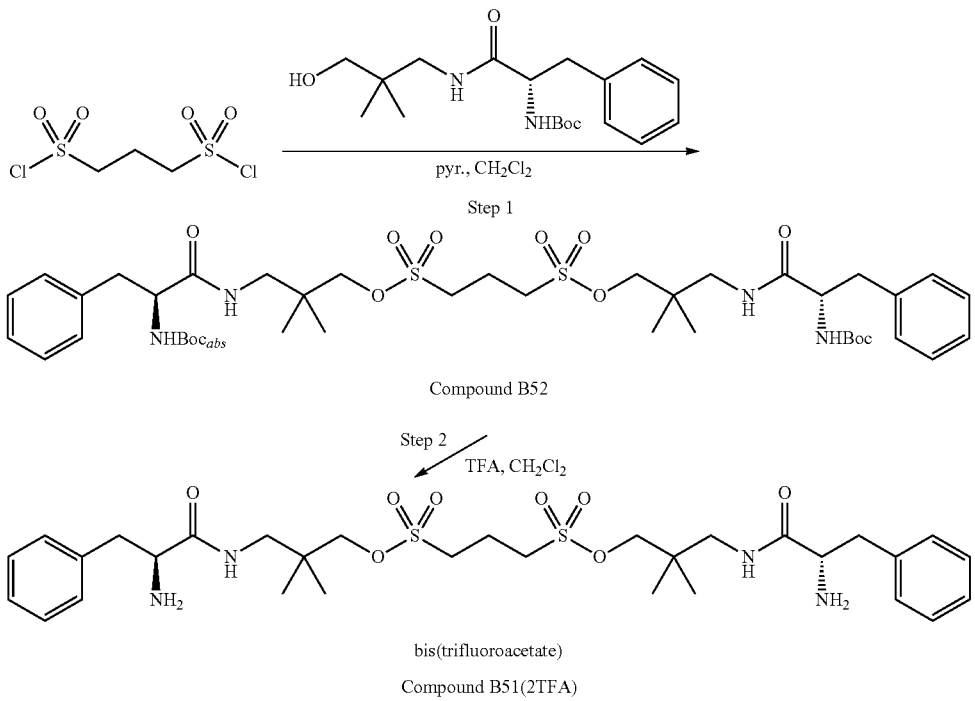

Step 1: To a stirred solution of 3-(N-Boc-L-phenylalaninamido)-2,2-dimethylpropanol (Example 7 (a), Step 1) (3.50 g) in a mixture of pyridine (10 mL) and dichloromethane (50 mL) was added 1,3-propanedisulfonyl dichloride (Example 1 (a)) (1.50 g). The reaction mixture was stirred at room temperature for 15 h then concentrated under reduced pressure. The residue was purified by silica gel chromatography using hexanes/ethyl acetate (70:30) as eluant to afford 3.5 g of Compound B52 which was used for the next step.

Step 2: Compound B52 (3.5 g) from Step 1 was dissolved in dichloromethane (10 mL) to which was added trifluoroacetic acid (5 mL). The reaction mixture was stirred for 2 h and concentrated under reduced pressure to afford Compound B51(bis(trifluoroacetate) salt) (0.5 g) as a white solid. $^1$H NMR (CD$_3$OD, 500 MHz) δ ppm 0.85 (s, 2×3H), 0.90 (s, 2×3H), 2.35 (quint, J=7.0 Hz, 2H), 3.00 & 3.26 (AB, J=14.0 Hz, 2×2H), 3.10 & 3.20 (ABX, J=14.0 & 7.0 Hz, 2×2H), 3.46 (t, J=7.3 Hz, 2×2H), 3.85 (AB, J=9.5 Hz, 2×2H), 4.11 (t, J=7.5 Hz, 2×1H), 7.31-7.42 (m, 2×5H).

d) Compound A14:

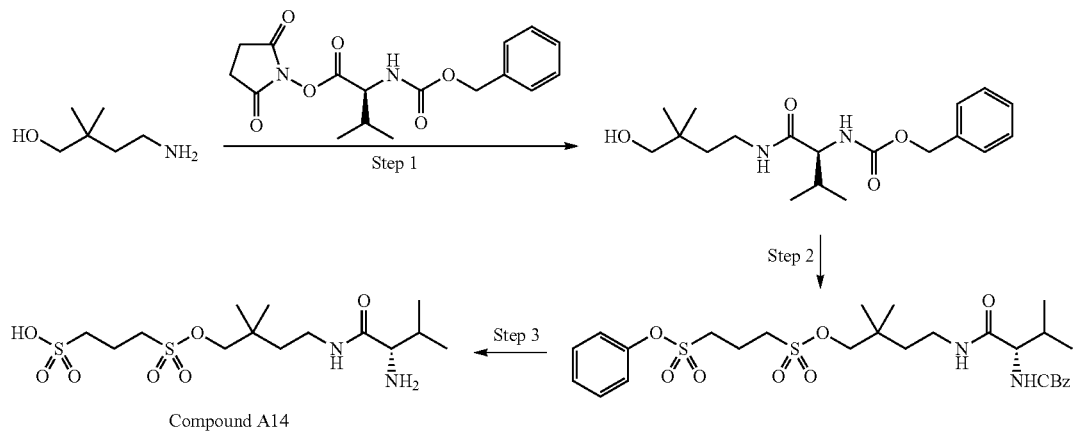

Compound A14

Step 1: Commercial N-Cbz-L-valine-O-succinimide (5.44 g, 16 mmol) was added to a solution of 4-amino-2,2-dimethyl-1-butanol (Example 2, Step 2 prior to the di(tert-butyl) dicarbonate step) (1.06 g, 6.9 mmol) and sodium bicarbonate (1.74 g, 20.7 mmol) in water/tetrahydrofuran 1:1 (200 mL). After 18 h of stirring, the solution was diluted with water (100 mL) and ethyl acetate (200 mL). The organic layer was separated and the aqueous layer was extracted with ethyl acetate (100 mL). The combined organic layers were washed with brine, filtered and concentrated to dryness. The crude material was purified by silica gel chromatography (hexanes/ethyl acetate 80:20 to 0:100 linear gradient) to afford 4-(N-CBz-L-valinamido)-2,2-dimethyl-1-butanol (2.14 g, 6.11 mmol, 88%) as a white solid.

Step 2: Following the procedure shown in Example 1(c)-Step 1, 4-(N-CBz-L-valinamido)-2,2-dimethyl-1-butanol from Step 1 (1 g, 2.86 mmol) is reacted with 3-phenoxysulfonyl-1-propanesulfonyl chloride (Example 1 (b)) (0.94 g, 3.2 mmol) in the presence of pyridine (2.30 mL, 28.6 mmol). Following usual workup, the mixture was purified by silica gel chromatography (hexanes/ethyl acetate 70:30 to 50:50) to afford 3-phenoxysulfonyl-1-propanesulfonic acid 4-(N-CBz-L-valinamido)-2,2-dimethyl-1-butyl ester (1.37 g, 78%) as a pale yellow oil.

Step 3: A solution of 3-phenoxysulfonyl-1-propanesulfonic acid 4-(N-CBz-L-valinamido)-2,2-dimethyl-1-butyl ester from Step 2 (1.37 g, 2.22 mmol) in methanol (100 mL) was degassed with nitrogen gas, followed by addition of Pd/C (10% wet). The mixture was stirred for 24 h under 1 atmosphere of hydrogen. The reaction mixture was filtered through a Celite™ pad. The filtrate was evaporated to dryness. The residual material was purified by silica gel chromatography (ethanol as eluent) to afford Compound A14 (800 mg, 89% yield) as a white solid. $^1$H NMR (D$_2$O, 500 MHz) δ in ppm 1.00 (m, 12H), 1.59 (m, 2H), 1.13 (m, 1H), 2.27 (m, 2H), 3.06 (t, J=7.5 Hz, 2H), 3.26 (m, 1H), 3.34 (m, 1H), 3.57 (t, J=7.5 Hz, 2H), 3.61 (d, J=6.0 Hz, 1H), 4.07 (s, 2H).

e) Compound B14:

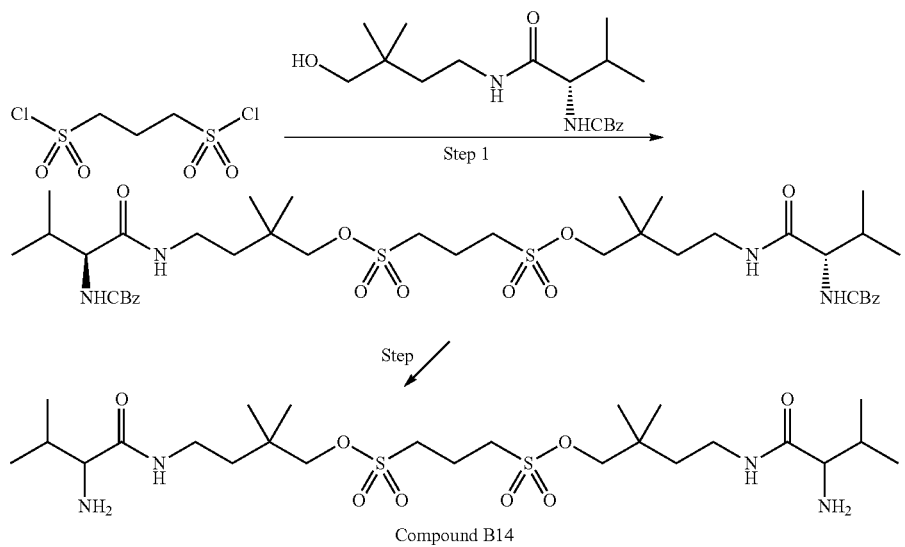

Compound B14

Step 1: Following the general procedure for the synthesis of diprotected sulfonic acids (Example 1(e)): 4-(N-CBz-L-valinamido)-2,2-dimethyl-1-butanol (2.14 g, 6.1 mmol) (Example 7 (d), Step 1) was reacted with 1,3-propanedisulfonyl dichloride (Example 1 (a)) (0.740 g, 3.1 mmol) in dichloromethane (200 mL) in the presence of pyridine (2.5 mL, 30.6 mmol). Solvent was evaporated, and the residual material was purified by silica gel chromatography (hexanes/ethyl acetate 70:30 to 0:100 linear gradient) to afford 1,3-propanedisulfonic acid bis(4-(N-CBz-L-valinamido)-2,2-dimethyl-1-butyl) ester (1.73 g, 75%) as a pale yellow oil.

Step 2: A solution of 1,3-propanedisulfonic acid bis(4-(N-CBz-L-valinamido)-2,2-dimethyl-1-butyl) ester from Step 1 (0.70 g, 0.80 mmol) in EtOH (50 mL) was degassed with nitrogen gas, followed by addition of Pd/C (10% wet). The mixture was stirred for 24 h under hydrogen gas atmosphere (1 atm.). The resulting solution was filtered through a pad of Celite™ and the filtrate was evaporated to dryness. The residual material was purified by reverse phase chromatography (C18, water/methanol (0.01% ammonium hydroxide) 100/0 to 80/20) to afford Compound B14 (0.41 g, 86% yield) as a light yellow oil. $^1$H NMR (DMSO, 500 MHz) δ in ppm 0.77 (d, J=6.5 Hz, 6H), 0.85 (d, J=7.0 Hz, 6H), 0.93 (s, 12H), 1.41 (m, 4H), 1.83 (m, 2H), 2.11 (m, 2H), 2.88 (d, J=5.0 Hz, 2H), 3.10 (m, 4H), 3.51 (t, J=8.0 Hz, 4H), 3.92 (s, 4H), 7.81 (br t, J=5.0 Hz, 2H).

Example 8

Preparation of Compounds A15(Sodium Salt) to A20(Sodium Salt) and Compounds B15 to B20 a) Compound A20(Sodium Salt):

Step 1: To a solution of (3S)-2,2-dimethyl-3-(phenylmethoxy)pent-4-en-1-ol (4.21 g; prepared according to WO2009/033054, incorporated herein by reference) in dichloromethane (40 mL) was added pyridine (7.8 mL), followed by a slow addition of a solution of 3-phenoxysulfonyl-1-propanesulfonyl chloride (Example 1 (b)) (6.87 g) in dichloromethane (15 mL). The dark-colored solution obtained was stirred at room temperature for 18 h. The reaction mixture was diluted with 2N aqueous hydrochloric acid (100 mL) and dichloromethane (100 mL). The aqueous layer was extracted with dichloromethane (2×100 mL). The combined organic layers were successively washed with 1N aqueous hydrochloric acid (100 mL) and brine:water (1:1; 100 mL), dried over magnesium sulfate and filtered. The solvent was evaporated to give a dark oil residue, which was purified by silica gel chromatography using ethyl acetate/hexane (20:80) as eluent to obtain the O1-[(3S)-3-benzyloxy-2,2-dimethyl-pent-4-enyl]O3-phenyl propane-1,3-disulfonate (7.05 g, 76% yield) as a white solid.

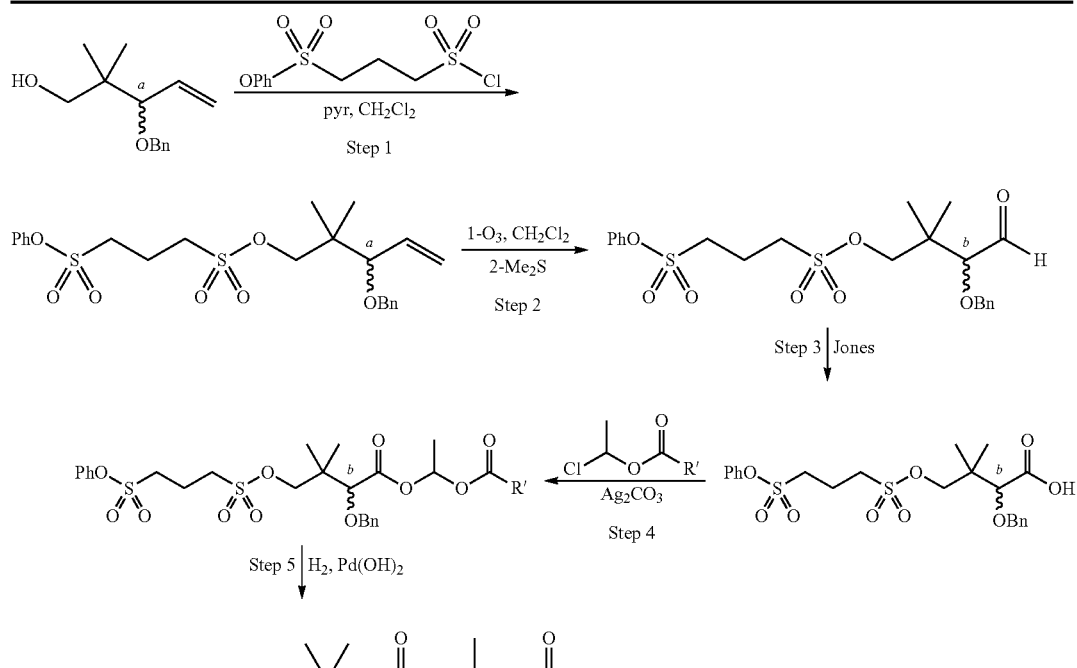

| a | b | R' | Compound |
|---|---|---|---|
| (R) | (S) | i-Pr | A15 |
| (S) | (R) | i-Pr | A16 |
| (R) | (S) | OEt | A17 |
| (S) | (R) | OEt | A18 |
| (R) | (S) | Oi-Pr | A19 |
| (S) | (R) | Oi-Pr | A20 |

Step 2: A solution of the ethenyl intermediate from Step 1 (3.98 g) in dichloromethane (125 mL) was cooled to −78° C. The solution was purged with oxygen followed by a mixture of oxygen and ozone at the same temperature until the solution turned slightly blue. The reaction was followed by thin layer chromatography until disappearance of the starting material. The solution was then purged with oxygen and finally nitrogen to remove residual ozone. Excess dimethylsulfide (3.0 mL) was added to the reaction mixture at −78° C. and stirred, over a period of 1 hour, with gradual warming to room temperature. The solvents were removed under reduced pressure using a rotary evaporator to give the O1-[(3R)-3-benzyloxy-2,2-dimethyl-4-oxo-butyl]O3-phenyl propane-1, 3-disulfonate (4.62, 100% yield) as a colorless oil. The residue was used for next step without further purification.

Step 3: A solution of the aldehyde intermediate from Step 2 (4.62 g, crude) in acetone (60 mL) was cooled to 0° C. At this temperature, a freshly prepared 2.0 M aqueous Jones-Reagent solution (5.0 mL, 10 mmol)) was added slowly to the stirred solution. The reaction mixture quickly turned brown and solid formed. The reaction was stirred at 0° C. for 1 hour. After the starting material was completely consumed, excess isopropanol (3.2 mL) was added at 0° C. to consume excess oxidant and the reaction mixture was stirred for an additional hour. The reaction mixture was diluted with water (80 mL), acidified with 1N aqueous hydrochloric acid (12 mL), transferred to an evaporator and concentrated. The aqueous residue was diluted with ethyl acetate and extracted three times with ethyl acetate. The combined organic extracts were washed with brine, dried over magnesium sulfate, filtered, and the solvents removed under reduced pressure. The crude acid was purified by silica gel chromatography using a mixture of hexane/ethyl acetate/acetic acid (70:30:3) as eluent to afford the (2R)-2-benzyloxy-3,3-dimethyl-4-(3-phenoxysulfonylpropylsulfonyloxy) butanoic acid (3.0 g, 73% yield) as an oil which crystallized on standing at +4° C. to give a white solid.

Step 4: The (R)-carboxylic acid from Step 3 (1.23 g) was dissolved in anhydrous toluene (10 mL) and reacted with commercial 1-chloroethyl isopropylcarbonate (1.15 mL) in the presence of silver carbonate (1.70 g, 6.15 mmol). The reaction mixture was wrapped in aluminium foil and well stirred at 40° C. for over 18 h. The residual solid (silver salts) was filtered using a short plug of Celite™ in a Büchner-funnel and the cake rinsed with toluene.

The solvent was removed under reduced pressure. The crude material was further purified by silica gel chromatography using ethyl acetate/hexane (20:80) as eluent to give 1-isopropoxycarbonyloxyethyl(2R)-2-benzyloxy-3,3-dimethyl-4-(3-phenoxysulfonylpropyl sulfon yloxy)butanoate (0.72 g, 47% yield) as an oil.

Step 5: The (R)-ester from Step 4 (722 mg) was dissolved in a mixture of methanol (24 mL) and water (3 mL). To this mixture was added 20% palladium hydroxide (0.16 g) and the mixture was subjected to hydrogen (one atmosphere, balloon). The mixture was stirred at room temperature for 18 hours. The mixture is filtered through a pad of Celite™ and the cake rinsed with methanol. The filtrate was treated with one equivalent of 1.0N NaOH, stirred at room temperature for 5 minutes, and concentrated under reduced pressure to give the crude product. The crude material was purified by silica gel chromatography using a mixture of dichloromethane/methanol (4:1) as eluent to afford Compound A20(sodium salt) (0.51 g, 91% yield) as a white solid. $^1$H NMR (500 MHz, DMSO) δ in ppm 0.89 (d, J=5.1 Hz, 3H) & 0.95 (d, J=5.1 Hz, 3H), 1.22-1.24 (m, 6H), 1.46 (d, J=5.4 Hz, 3H), 1.96-2.01 (m, 2H), 2.54 (t, J=7.1 Hz, 2H), 3.41-3.52 (m, 2H), 3.87-3.93 (m, 2H), 4.06-4.09 (m, 1H), 4.76-4.82 (m, 1H), 5.84 (d, J=5.6 Hz, 0.5H, OH) & 5.90 (d, J=5.6 Hz, 0.5H, OH), 6.67-6.72 (m, 1H).

b) Compound A18(Sodium Salt):

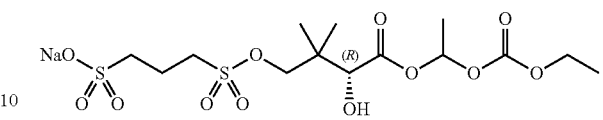

Compound A18(sodium salt) is prepared using the same methodology as described for Compound A20(sodium salt) (Example 8 (a)) by replacing 1-chloroethyl isopropylcarbonate in Step 4 with commercially available 1-chloroethyl ethylcarbonate. Compound A18(sodium salt) was obtained (0.43 g) as a white solid. $^1$H NMR (500 MHz, DMSO) δ in ppm 0.89 (d, J=6.1 Hz, 3H) & 0.94 (d, J=6.1 Hz, 3H), 1.20-1.23 (m, 3H), 1.47 (dd, J=5.6 Hz, 3H), 1.95-2.01 (m, 2H), 2.54 (t, J=7.1 Hz, 2H), 3.41-3.51 (m, 2H), 3.87-3.93 (m, 2H), 4.06-4.08 (m, 1H), 4.13-4.18 (m, 2H), 5.87 (d, J=5.6 Hz, 0.5H, OH) & 5.90 (d, J=5.6 Hz, 0.5H, OH), 6.67-6.72 (m, 1H).

c) Compound A16(Sodium Salt):

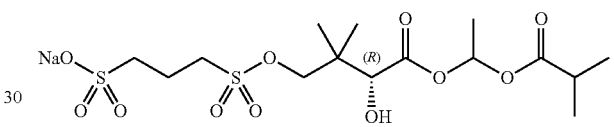

Compound A16(sodium salt) was prepared using the same methodology as described for Compound A20(sodium salt) (Example 8 (a)) by replacing 1-chloroethyl 2-isopropylcarbonate in Step 4 with 1-chloroethyl 2-methylpropanoate (Example 6). Compound A16(sodium salt) was obtained (0.35 g) as a white solid. $^1$H NMR (500 MHz, DMSO) δ in ppm 0.88 (d, J=7.3 Hz, 3H), 0.94 (d, J=2.2 Hz, 3H), 1.07-1.09 (m, 6H), 1.44-1.45 (m, 3H), 1.95-2.01 (m, 2H), 2.50-2.57 (m, 1H+2H, partly underneath DMSO-d$_6$), 3.42-3.52 (m, 2H), 3.87-3.93 (m, 2H), 4.06-4.09 (m, 1H), 5.82 (d, J=5.6 Hz, 0.5H, 0.50H) & 5.87 (, J=5.6 Hz, 0.5H, 0.50H), 6.78-6.82 (m, 1H).

d) Compound A15(Sodium Salt):

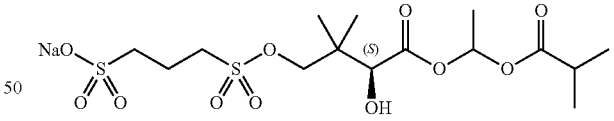

Compound A15(sodium salt) was prepared using the same methodology as described for Compound A16(sodium salt) by replacing in Step 1 starting material (3S)-2,2-dimethyl-3-(phenylmethoxy)pent-4-en-1-ol with (3R)-2,2-dimethyl-3-(phenylmethoxy)pent-4-en-1-ol, which was prepared similarly from the corresponding (S)-pantolactone.

e) Compound A17(Sodium Salt):

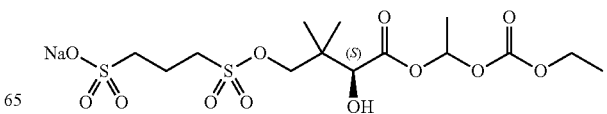

Compound A17(sodium salt) was prepared using the same methodology as described for the sodium salt of Compound A15(sodium salt) by replacing 1-chloroethyl 2-methylpropanoate in Step 4 with commercially available 1-chloroethyl ethylcarbonate.

f) Compound A19(Sodium Salt):

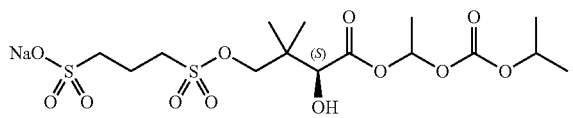

Compound A19(sodium salt) was prepared using the same methodology as described for Compound A15(sodium salt) by replacing 1-chloroethyl 2-methylpropanoate in Step 4 with commercial 1-chloroethyl isopropylcarbonate.

g) Compounds B15 to B20:

Compound B15 to B20 are prepared following an amended version of Example 8(a) to (f) used for the preparation of Compounds A15(sodium salt) to A20(sodium salt), replacing 3-phenoxysulfonyl-1-propanesulfonyl chloride (Example 1(b)) in Step 1 with 1,3-propanedisulfonyl dichloride (Example 1(a)) and adjusting the molar ratio of alcohol/disulfonyl dichloride derivative to (2:1).

Example 9

Preparation of Compounds A26(Sodium Salt) and A53(Sodium Salt)

a) Compound A26(Sodium Salt):

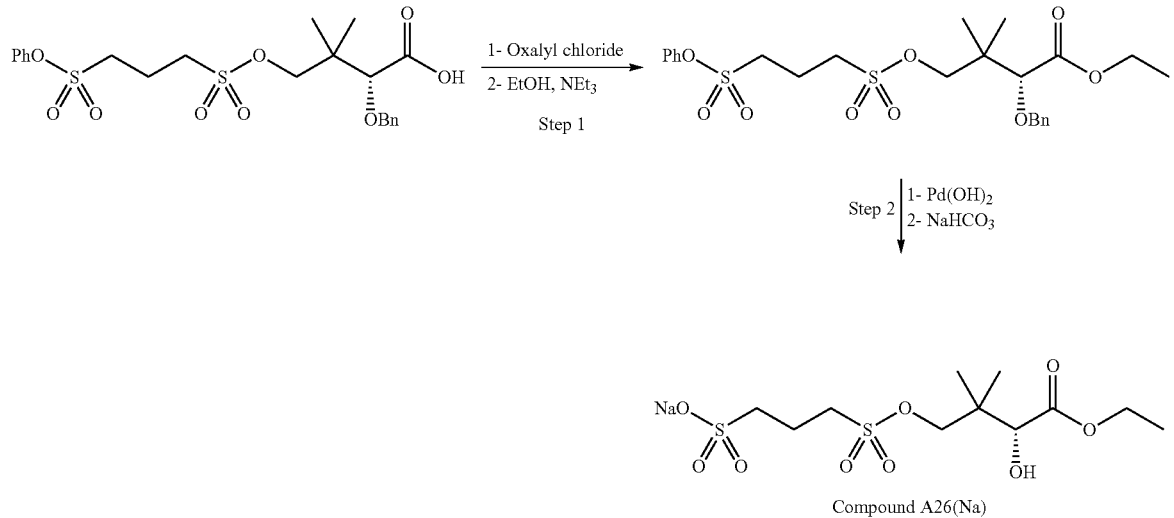

Compound A26(Na)

Step 1: To a stirred 0° C. solution of (2R)-2-benzyloxy-3,3-dimethyl-4-(3-phenoxysulfonylpropylsulfonyloxy)butanoic acid (Example 8(a), Step 3) (0.8 g) in dichloromethane (10 mL), was added oxalyl chloride (0.28 mL) followed by a drop of N,N-dimethylformamide. The reaction mixture was stirred for 1 hour and concentrated in vacuo. The resulting residue was dissolved in dichloromethane (10 mL), to which was added ethanol (2 mL). The reaction mixture was stirred overnight at room temperature. The volatiles were removed, and the residual material was purified by silica gel chromatography (hexanes/ethyl acetate 70:30) to afford ethyl (2R)-2-benzyloxy-3,3-dimethyl-4-(3-phenoxysulfonylpropylsulfonyloxy)butanoate (0.70 g).

Step 2: To a stirred solution of the ethyl ester from Step 1 (0.7 g) in methanol (10 mL) was added acetic acid (2 mL) followed by Pd(OH)$_2$ (0.2 g) in water (2 mL). The reaction mixture was stirred under hydrogen (balloon) for 2-3 hours (or until complete consumption of starting material). The suspension was filtered, and the filtrate was concentrated to dryness. A 1M aqueous sodium bicarbonate solution (2.6 ml) was added and the resulting mixture was stirred for 30 min, and then concentrated. The residual material was purified by silica gel chromatography using dichloromethane/ethanol (80:20) as eluent to yield the Compound A26(sodium salt) (0.4 g) as a white solid. $^1$H NMR (D$_2$O, 500 MHz) δ in ppm 1.05 (s, 6H), 1.31 (t, J=7.0 Hz, 3H), 2.28 (quint, J=7.0 Hz, 2H), 3.07 (t, J=7.0 Hz, 2H), 3.57 (t, J=7.0 Hz, 2H), 4.15 & 4.21 (AB, J=9.3 Hz, 2H), 4.17 (s, 1H), 4.27 (m, 1H).

b) Compound A53(Sodium Salt):

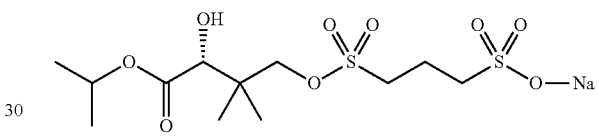

Compound 53(sodium salt) was produced using the same procedure as described for the synthesis of Compound A26 (sodium salt) (Example 9 (a)) by replacing ethanol in Step 1 with isopropanol to give Compound 53(sodium salt) (0.35 g) as a white solid. $^1$H NMR (D$_2$O, 500 MHz) δ in ppm 1.05 (s, 3H), 1.06 (s, 3H), 1.31 (d, J=7.0 Hz, 3H), 1.32 (d, J=7.0 Hz, 3H), 2.29 (quint, J=7.0 Hz, 2H), 3.08 (t, J=7.0 Hz, 2H), 3.59 (t, J=7.0 Hz, 2H), 4.14 (s, 1H), 4.16 & 4.23 (AB, J=9.5 Hz, 2H), 5.11 (hept, J=7.0 Hz, 1H).

Example 10

Preparation of Compounds A13 and B13 a) Compound A13:

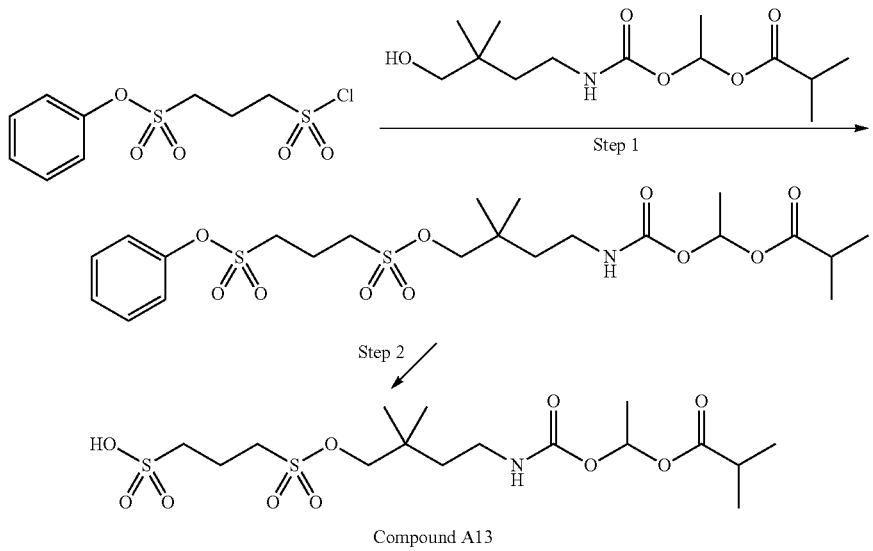

Compound A13

Step 1: Following the general procedure for the synthesis of monoprotected sulfonic acids (Example 1(c), Step 1), 1-(4-hydroxy-2,2-dimethyl-1-butylaminocarbonyloxy)-1-ethyl 2-methylpropanoate (US published application 2005/0222431, incorporated herein by reference) (1.0 g, 3.6 mmol) was reacted with 3-phenoxysulfonyl-1-propanesulfonyl chloride (Example 1(b)) (1.20 g, 4.0 mmol) in the presence of pyridine (2.93 mL, 36.4 mmol). The crude mixture obtained was purified by silica gel chromatography (hexanes/ethyl acetate 70:30 to 50:50) to afford 1-[[3,3-dimethyl-4-(3-phenoxysulfonylpropylsulfonyloxy)butyl]carbamoyloxy]ethyl 2-methylpropanoate (1.65 g, 85% yield) as a pale yellow oil.

Step 2: Following the general procedure for the synthesis of monoprotected sulfonic acids (Example 1(c), Step 2), starting material from Step 1 of Example 10(a) (1.65 g, 3.09 mmol) in methanol (100 mL) was degassed with nitrogen before addition of palladium on charcoal (10% wet). The mixture was stirred for 24 h under hydrogen gas (1 atm.). The mixture was filtered through Celite™ and the filtrate was concentrated under reduced pressure. The residual material was purified by silica gel chromatography (dichloromethane/methanol 100:0 to 60:40) to afford Compound A13 (1.16 g, 82% yield) as a white solid. $^1$H NMR (DMSO, 500 MHz) δ in ppm 0.91 (s, 6H), 1.05 (d, J=2.0 Hz, 3H), 1.07 (d, J=2.5 Hz, 3H), 1.037 (d, J=5 Hz, 3H), 1.41 (t, J=8.0H, 2H), 1.99 (m, 2H), 2.50 (m, 1H), 2.55 (t, J=7.5 Hz, 2H), 3.00 (m, 2H), 3.48 (dd, J=7.5, 9.5 Hz, 2H), 3.86 (s, 2H), 6.65 (q, J=5.5 Hz, 1H), 7.44 (t, J=5.5 Hz, 1H).

b) Compound B13:

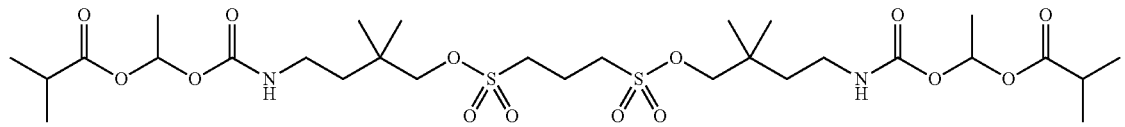 [SMILES: CC(OC(=O)NCCC(C)(C)COS(=O)(=O)CCCS(=O)(=O)OCC(C)(C)CCNC(=O)OC(C)OC(=O)C(C)C)OC(=O)C(C)C]

Following the general procedure for the synthesis of diprotected sulfonic acids (Example 1(e): 1-(4-hydroxy-2,2-dimethyl-1-butylaminocarbonyloxy)-1-ethyl 2-methylpropanoate (US published application 2005/0222431) (2.60 g, 9.45 mmol) was reacted with 1,3-propanedisulfonyl dichloride (Example 1(a)) (1.14 g, 4.73 mmol) in dichloromethane (200 mL) in the presence of pyridine (7.6 mL, 94.5 mmol). After evaporation, the crude product was purified by silica gel chromatography (hexanes/ethyl acetate 80/20 to 50/50) to afford Compound B13 (2.31 g, 68% yield) as a pale yellow oil. $^1$H NMR (CDCl$_3$, 500 MHz) δ in ppm 1.00 (s, 12H), 1.16 (d, J=7.0 Hz, 12H), 1.45 (d, J=5.5 Hz, 6H), 1.55 (t, J=8.0 Hz, 4H), 2.43 (m, 2H), 2.53 (m, 2H), 3.17-3.25 (m, 4H), 3.36 (m, 4H), 3.94 (s, 4H), 4.86 (br d, J=4.5 Hz, 2H), 6.76 (q, J=5.5 Hz, 2H).

Example 11

Preparation of Compounds A29(Sodium Salt), A30(Sodium Salt), B29 and B30 a) Compound A29(Sodium Salt):

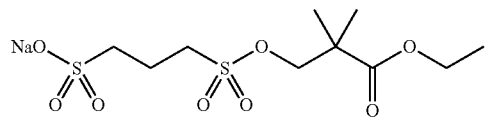

Following the general procedure for the synthesis of monoprotected sulfonic acids (Example 1(d)), commercial ethyl 3-hydroxy-2,2-dimethylpropanoate was reacted with Compound C1(Example 13). Compound A29(sodium salt) was obtained (4.3 g) as a white solid. ¹H NMR (D₂O, 500 MHz) δ in ppm 4.37 (s, 2H), 4.21 (q, J=7.1 Hz, 2H), 3.57 (t, J=7.6 Hz, 2H), 3.06 (t, J=7.6 Hz, 2H), 2.26 (quintet, J=7.6 Hz, 2H), 1.28 (t, overlap with a singlet at 1.275, J=7.1 Hz, 3H), 1.275 (s, 6H).

b) Compound A30(Sodium Salt):

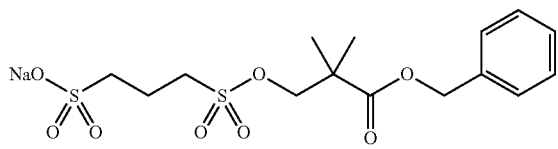

Following the general procedure for the synthesis of mono-protected sulfonic acids (Example 1(d)), commercial benzyl 3-hydroxy-2,2-dimethylpropanoate was reacted with Compound C1(Example 13). Compound A30(sodium salt) was obtained (0.91 g) as white solid. ¹H NMR (D₂O, 500 MHz) δ in ppm 1.28 (s, 6H), 2.12-2.18 (m, 2H), 2.96 (t, J=7.6 Hz, 2H), 3.40 (t, J=7.3 Hz, 2H), 4.35 (s, 2H), 5.23 (s, 2H), 7.42-7.46 (m, 5H).

c) Compound B29:

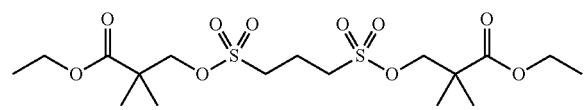 [SMILES: CCOC(=O)C(C)(C)COS(=O)(=O)CCCS(=O)(=O)OCC(C)(C)C(=O)OCC]

Following the general procedure for the synthesis of diprotected sulfonic acids (Example 1(e)), commercial ethyl 3-hydroxy-2,2-dimethylpropanoate was reacted with 1,3-propanedisulfonyl dichloride (Example 1 (a)). Compound B29 was obtained (16.0 g) as a white solid. ¹H NMR (CDCl₃, 500 MHz) δ in ppm 4.23 (s, 4H), 4.17 (q, J=7.1 Hz, 4H), 3.35 (t, J=7.3 Hz, 4H), 2.37 (m, 2H), 1.273 (t, overlap with a singlet at 1.266, 6H) 1.266 (s, 12H).

d) Compound B30:

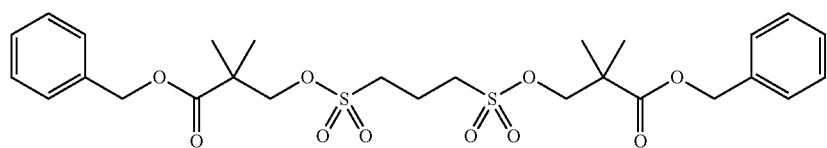 [SMILES: CC(C)(COS(=O)(=O)CCCS(=O)(=O)OCC(C)(C)C(=O)OCc1ccccc1)C(=O)OCc1ccccc1]

Following the general procedure for the synthesis of diprotected sulfonic acids (Example 1(e)), commercial benzyl 3-hydroxy-2,2-dimethylpropanoate was reacted with 1,3-propanedisulfonyl dichloride (Example 1 (a)). Compound B30 was obtained (9.0 g, 78% yield) as a white solid. ¹H NMR (CDCl₃, 500 MHz) δ in ppm 1.29 (s, 12H), 2.21 (quint, J=7.0 Hz, 2H), 3.17 (t, J=7.0 Hz, 4H), 4.22 (s, 4H), 5.15 (s, 4H), 7.33-7.38 (m, 10H); MS positive mode: 602 (M+NH₄⁺); MS negative mode: 643 (M+AcO⁻).

Example 12

Preparation of Compounds A32(Sodium Salt) and B32

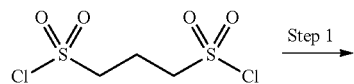

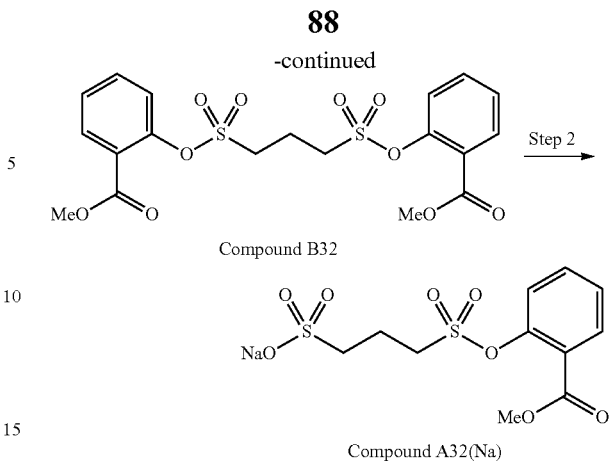

Step 1: Following the general procedure for the synthesis of diprotectedسulfonic acids (Example 1(e)), commercial methyl salicylate was reacted with 1,3-propanedisulfonyl dichloride (Example 1 (a)). Compound B32 was obtained (1.8 g, 74% yield) as an oil. ¹H NMR (CDCl₃, 500 MHz) δ in ppm 2.75 (quint, J=7.0 Hz, 2H), 2.73 (t, J=7.0 Hz, 4H), 3.91 (s, 6H), 7.26-7.45 (m, 4H), 7.58 (t, J=8.0 Hz, 2H), 7.98 (d, J=7.8 Hz, 2H).

Step 2: To a solution of Compound B32 from Step 1 (1.89 g, 4 mmol) in methanol (100 mL) was added acetic acid (10 mL) followed by Pd(OH)₂ (0.3 g) in water (2 mL). The reaction mixture was stirred under hydrogen (1 atm., balloon) for 3 h. The suspension was filtered, and the filtrate was concentrated to dryness. The residual material was dissolved in methanol (10 mL), followed by addition of 1M aqueous sodium carbonate (4 mL). The mixture was stirred for 1 h, concentrated and purified by silica gel chromatography using dichloromethane/methanol (90:10 to 80:20) as eluent to give Compound A32(سodium salt) (0.85 g, 59% yield) as a white solid. ¹H NMR (D₂O, 500 MHz) δ in ppm 2.41 (quint, J=7.0 Hz, 2H), 3.10 (t, J=7.0 Hz, 2H), 3.75 (t, J=7.0 Hz, 2H), 3.94 (s, 3H), 7.45-7.55 (m, 4H), 7.72 (t, J=8.0 Hz, 2H), 7.96 (d, J=7.8 Hz, 2H).

Example 13

Preparation of Compound C1

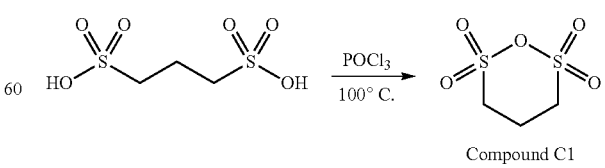

A stirred solution of 1,3-propanedisulfonic acid (30 g) in phosphorus(V) oxychloride (P(O)Cl₃, 100 ml) was heated at 100° C. for 1 h. The reaction mixture was allowed to cool to room temperature and chloroform (300 mL) was added. The resulting solid was filtered and washed with chloroform (2×100 mL). The solid was then added to 1.4 L of a stirring ice/water mixture. The solid was then filtered, washed with water (2×200 mL) and dried under high vacuum to afford Compound C1(23.3 g, 85% yield) as a white solid. $^1$H NMR (D$_2$O, 500 MHz) δ in ppm 2.13 (m, 2H), 3.01 (t, J=7.5 Hz, 4H).

Example 14

Preparation of Compounds A23(Sodium Salt) and B23 a) Starting Material:

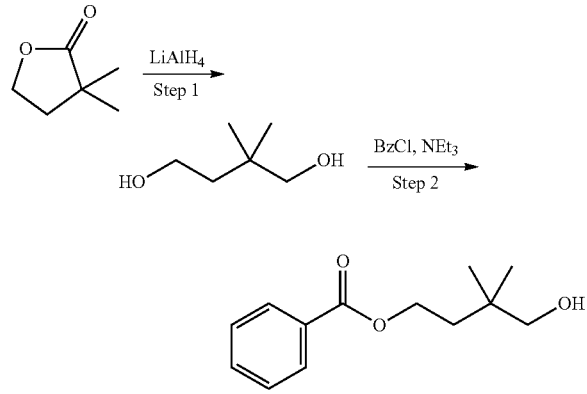

Step 1: A solution of commercial 2,2-dimethylbutyrolactone (5 mL) in tetrahydrofuran (20 mL) was added dropwise to a cooled (−78° C.) solution of 1M lithium aluminum hydride in diethylether (44 mL). After 1 h at −78° C., the mixture was warmed to room temperature and stirred for 15 hours. The reaction was then cooled to 0° C., and ethyl acetate (10 mL) was added followed by careful addition of water (10 mL). The mixture was stirred at room temperature for 1 h. The resulting solution was filtered over a pad of Celite™ and the solid was washed several times with ethyl acetate. After evaporation, the product was purified by silica gel chromatography (hexanes/ethyl acetate 70:30 to 0:100) to afford the desired 2,2-dimethylbutane-1,4-diol (3.18 g, 61% yield) as a colorless oil.

Step 2: Benzoyl chloride (3.13 mL) was added to a cooled (−78° C.) solution of 2,2-dimethylbutane-1,4-diol from Step 1 (3.18 g), triethylamine (7.5 mL) and 4-(dimethylamino) pyridine (0.05 g) in dichloromethane (100 mL). The mixture was then slowly warmed up to room temperature and stirred overnight. The reaction mixture was concentrated in vacuo and the compound was purified by silica gel chromatography (hexanes/ethyl acetate 95:5 to 60:40) to afford 3,3-dimethyl-4-hydroxy-1-butyl benzoate (2.6 g, 44% yield) as a colorless oil.

b) Compound B23:

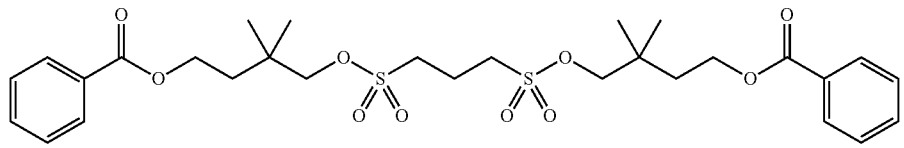 [SMILES: CC(C)(CCOC(=O)c1ccccc1)COS(=O)(=O)CCCS(=O)(=O)OCC(C)(C)CCOC(=O)c1ccccc1]

Following the general procedure for the synthesis of diprotected sulfonic acids (Example 1(e)), 3,3-dimethyl-4-hydroxy-1-butyl benzoate (Example 14 (a), Step 2) was reacted with 1,3-propanedisulfonyl dichloride (Example 1 (a)). Compound B23 was obtained (0.65 g, 54% yield) as a white solid. $^1$H NMR (CDCl$_3$, 500 MHz) δ in ppm 1.08 (s, 12H); 1.83 (t, J=7.0 Hz, 4H); 2.43 (m, 2H); 3.34 (t, J=7.0 Hz, 4H); 4.02 (s, 4H); 4.40 (t, J=7.0 Hz, 4H); 7.44 (t, J=8.0 Hz, 4H); 7.56 (t, J=7.0 Hz, 2H); 8.02 (dd, J=8.0, 1 Hz, 4H).

c) Compound A23(Sodium Salt):

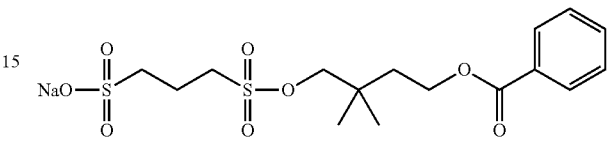

Following the general procedure for the synthesis of monoprotected sulfonic acids (Example 1(d)), 3,3-dimethyl-4-hydroxy-1-butyl benzoate (Example 14 (a), Step 2) was reacted with Compound C1(Example 13). Compound A23(sodium salt) was obtained (16.8 g) as a white solid. $^1$H NMR (DMSO, 500 MHz) δ in ppm 1.01 (s, 6H); 1.75 (t, J=7.0 Hz, 2H); 2.01 (m, 2H); 2.57 (t, J=7.5 Hz, 2H); 3.49 (t, J=7.5 Hz, 2H); 3.97 (s, 2H); 4.36 (t, J=7.0 Hz, 2H); 7.53 (t, J=8.0 Hz, 2H); 7.65 (t, J=7.5 Hz, 1H); 7.97 (d, J=7.0 Hz, 2H).

Example 15

Preparation of Compounds A6(Sodium Salt) and B6

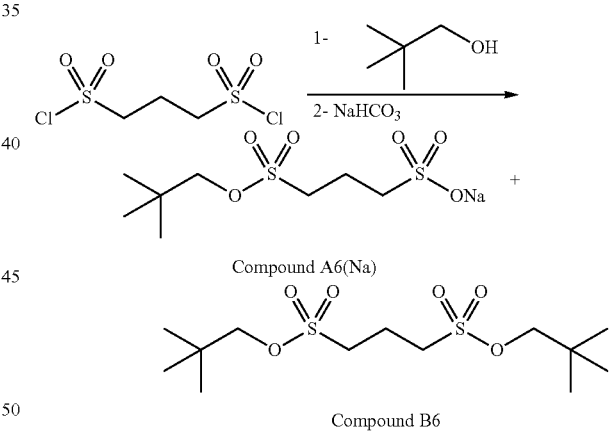

To a stirred solution of neopentyl alcohol (1.75 g) in a mixture of pyridine (10 mL) and dichloromethane (50 mL) was added 1,3-propanedisulfonyl dichloride (Example 1 (a)) (4.82 g). The reaction mixture was stirred at room temperature for 15 hours and concentrated in vacuo. A 1M aqueous solution of sodium bicarbonate (20 mL) was added and the reaction mixture was stirred for 1 h and concentrated under reduced pressure. The residual material was purified by silica gel chromatography using dichloromethane/methanol as an eluant with first, a 98:2 ratio to yield Compound B6, and second, with a 80:20 ratio to yield Compound A6(sodium salt) (0.5 g) as a white solid. $^1$H NMR (D$_2$O, 500 MHz) δ in ppm 0.98 (s, 9H), 2.28 (quint, J=7.5 Hz, 2H), 3.08 (t, J=7.5 Hz, 2H), 3.55 (t, J=7.5 Hz, 2H), 4.02 (s, 2H). Compound B6 (0.47 g) as a white solid, $^1$H NMR (CDCl$_3$, 500 MHz) δ in ppm 3.90 (s, 4H), 3.34 (t, J=7.0 Hz, 4H), 2.43 (q, J=7.0 Hz, 2H), 0.99 (s, 18H).

Example 16

Preparation of Compound A56(Sodium Salt)

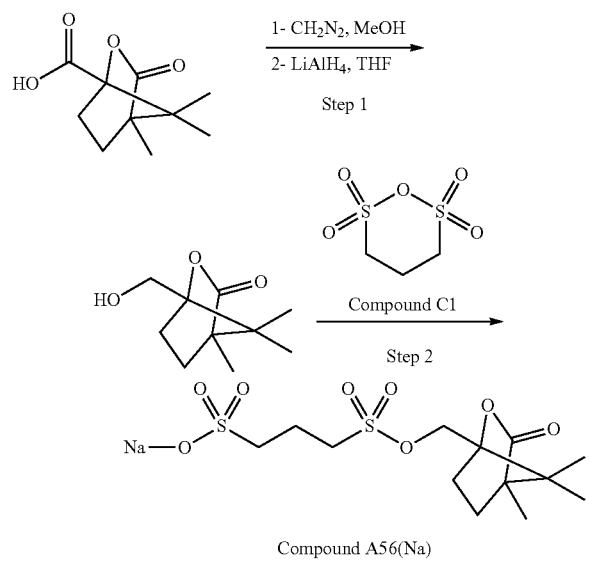

Compound A56(Na)

Step 1: To a 0° C. solution of commercial (S)-camphanic acid (1.98 g) in methanol (50 mL), was added freshly prepared solution of diazomethane in diethyl ether until the yellow coloration persisted. The solvent was removed to obtain the desired ester in quantitative yield. The ester was dissolved in THF (100 mL) to which was added slowly at 0° C., 20 mL of a 1M solution of lithium aluminium hydride in tetrahydrofuran. The reaction mixture was stirred at room temperature for 8 h, then quenched with aqueous hydrochloric acid (1 M) and diluted with ethyl acetate. The organic layer was isolated, dried over magnesium sulfate and concentrated under vacuum. The residual material was purified by silica gel chromatography (hexanes/ethyl acetate 50:50) to isolate the desired 4-(hydroxymethyl)-1,7,7-trimethyl-3-oxabicyclo[2.2.1]heptan-2-one.

Step 2: Following the general procedure for the synthesis of monoprotected sulfonic acids (Example 1(d)), the alcohol from Step 1 was reacted with Compound C1(Example 13). Compound A56(sodium salt) was obtained (0.4 g) as a white powder. $^1$H NMR (D$_2$O, 500 MHz) δ in ppm 0.91 (s, 3H), 0.95 (s, 3H), 0.99 (s, 3H), 1.60-1.70 (m, 2H), 1.95-2.00 (m, 3H), 2.20 (m, 2H), 2.30 (quint, J=7.0 Hz, 2H), 2.45 (m, 1H), 4.70 (AB, J=16.5 Hz, 2H).

Example 17

Preparation of Compounds A58, A60, A61 and G4 a) Compound A58:

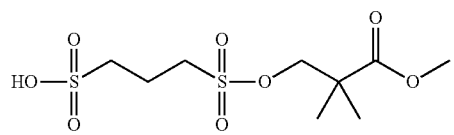 [SMILES: COC(=O)C(C)(C)COS(=O)(=O)CCCS(=O)(=O)O]

Following the general procedure for the synthesis of monoprotected sulfonic acids (Example 1(d)), methyl 3-hydroxy-2,2-dimethyl-propanoate (WO 2007/053346, incorporated herein by reference) was reacted with Compound C1(Example 13). Compound A58 was obtained (1.2 g, 48% yield) as a white solid. $^1$H NMR (D$_2$O, 500 MHz) δ in ppm 1.26 (s, 6H), 2.40 (m, 2H), 3.05 (t, J=7.5 Hz, 2H), 3.55 (t, J=7.5H, 2H), 3.74 (s, 3H), 4.35 (s, 2H).

b) Compound A60(Sodium Salt):

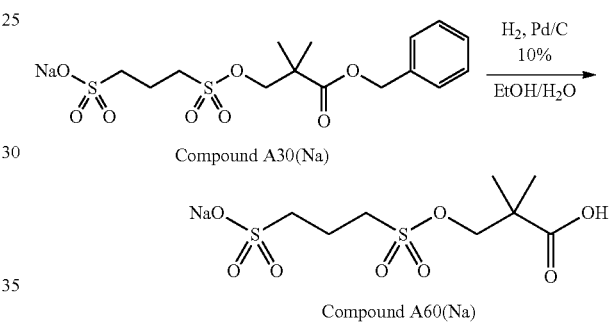

To a solution of Compound A30(sodium salt) (0.54 g, 1.3 mmol; Example 11(b)) in a 3:1 water/ethanol solution (30 mL) was added a suspension of 10% Pd/C (0.12 g) in ethanol (2 mL). The resulting solution was stirred for 30 min under hydrogen atmosphere (balloon) and filtered over a pad of Celite™. The cake was washed with methanol (15 mL) and the filtrate was evaporated to dryness to afford Compound A60(sodium salt) (0.41 g, 96% yield) as a white solid. $^1$H NMR (DMSO, 500 MHz) δ in ppm: 1.15 (s, 6H), 1.94-2.00 (m, 2H), 2.52-2.55 (t, 2H, partly masked by DMSO-d$_6$), 3.47 (t, J=7.8 Hz, 2H), 4.14 (s, 2H), 12.65 (bs, 0.75H, CO2H).

c) Compound A61:

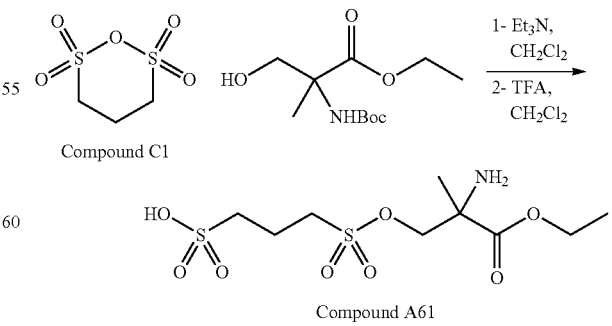

Following the general procedure for the synthesis of monoprotected sulfonic acids (Example 1(d)), ethyl 2-(tert-butoxycarbonylamino)-3-hydroxy-2-methyl-propanoate (Yu S. et al. (2005), *Angewandte Chemie, International Edition*, 44(1), 135-138, incorporated herein by reference) was reacted with Compound C1(Example 13). The resulting mixture was treated with trifluoroacetic acid in dichloromethane to afford Compound A61 (4.2 g, 52% yield) as a white solid. $^1$HNMR ($D_2O$, 500 MHz) δ in ppm 1.31 (t, J=7.1 Hz, 3H), 1.64 (s, 3H), 2.25 (quint, J=7.0 Hz, 2H), 3.05 (t, J=7.0 Hz, 2H), 3.62 (t, J=7.0 Hz, 2H), 4.36 (q, J=7.1 Hz, 2H), 4.52 & 4.84 (AB, J=11.3 Hz, 2H).

d) Compound G4:

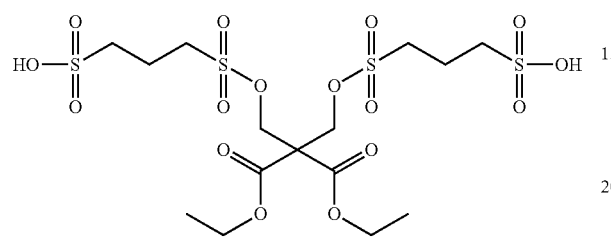

Following the general procedure for the synthesis of monoprotected sulfonic acids (Example 1(d)), commercial 2,2-bis (hydroxymethyl)propanedioate were reacted with Compound C1(Example 13). Compound G4 was obtained (0.41 g, 31% yield) as white solid. $^1$H NMR ($D_2O$, 500 MHz) δ in ppm 1.30 (t, J=7.0 Hz, 6H), 2.26 (quint, J=7.5 Hz, 4H), 3.06 (t, J=7.5 Hz, 4H), 3.62 (t, J=7.5 Hz, 4H), 4.34 (q, J=7.0 Hz, 4H), 4.86 (s, 4H).

Example 18

Preparation of Compounds B58 to B69 a) Compound B58:

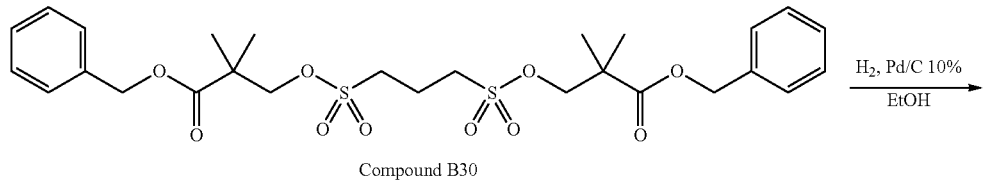

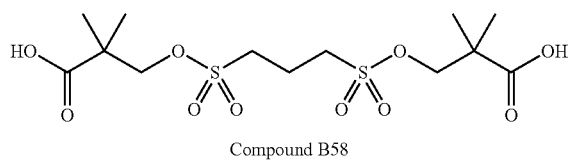

To a solution of Compound B30 (0.96 g, 1.64 mmol, Example 11 (d)) in ethanol (20 mL) was added a suspension of 10% Pd/C (0.17 g) in ethanol (2 mL). The resulting solution was stirred 2 h under hydrogen atmosphere (balloon) before being filtered over a pad of Celite™. The cake was washed with ethanol (15 mL) and the filtrate was evaporated to dryness and afforded Compound B58 (0.65 g, 98% yield) as a white solid. $^1$H NMR (DMSO, 500 MHz) δ in ppm 1.16 (s, 12H), 2.05-2.12 (m, 2H), 3.50 (t, J=7.6 Hz, 4H), 4.18 (s, 4H), 12.70 (bs, 1.5H, 2×$CO_2H$).

b) Compound B59:

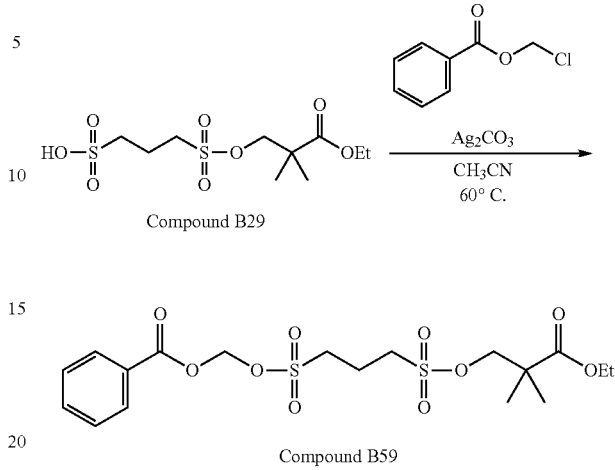

To a solution of Compound B29 (1.06 g, 3.19 mmol; Example 11 (c)) and silver carbonate (0.86 g, 3.19 mmol) in acetonitrile (25 mL) was added chloromethylbenzoate (2.73 mL, 16.0 mmol). The mixture was stirred for 4 h at 60° C. and filtered over a pad of Celite™. The cake was washed with acetonitrile (2×20 ml). The filtrate was concentrated in vacuo and the residue was purified by silica gel chromatography (hexanes/ethyl acetate 90:10 to 50:50). Compound B59 (1.30 g, 97% yield) was obtained as a colorless oil. $^1$H NMR ($CDCl_3$, 500 MHz) δ in ppm 1.24 (s, 6H), 1.26 (t, J=7.0 Hz, 3H), 2.39 (quint, J=7.5 Hz, 2H), 3.30 (t, J=7.0 Hz, 2H), 3.44 (t, J=7.5 Hz, 2H), 4.15 (q, J=7.5 Hz, 2H), 4.19 (s, 2H), 6.07 (s, 2H), 7.50 (t, J=7.5 Hz, 2H), 7.65 (t, J=7.5 Hz, 1H), 8.09 (d, J=7.0 Hz, 2H).

c) Compound B60:

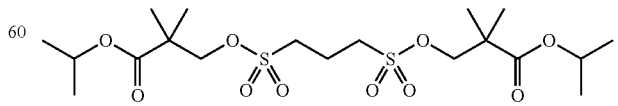

Following the general procedure for the synthesis of diprotected sulfonic acids (Example 1(e)), isopropyl 3-hydroxy-2, 2-dimethyl-propanoate (WO 2007/053346) was reacted with 1,3-propanedisulfonyl dichloride (Example 1 (a)). Compound B60 (0.47 g, 70% yield) was obtained as a colorless oil. $^1$H NMR (CDCl$_3$, 500 MHz) δ in ppm 1.24 (d, J=6.4 Hz, 12H), 1.25 (s, 6H), 2.38 (quint, J=7.0 Hz, 2H), 3.35 (t, J=7.0 Hz, 4H), 4.22 (s, 4H), 5.01 (hept, J=6.4 Hz, 2H).

d) Compound B61:

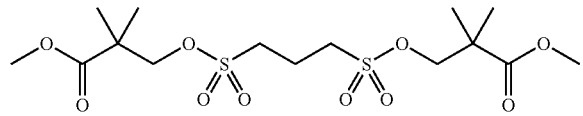

Following the general procedure for the synthesis of diprotected sulfonic acids (Example 1(e)), methyl 3-hydroxy-2,2-dimethyl-propanoate (WO 2007/053346) was reacted with 1,3-propanedisulfonyl dichloride (Example 1 (a)) to afford Compound B61 (5.3 g, 85% yield) as a white solid. $^1$H NMR (CDCl$_3$, 500 MHz) δ in ppm 4.23 (s, 4H), 3.73 (s, 6H), 3.35 (t, J=7.1 Hz, 4H), 2.37 (m, 2H), 1.27 (s, 12H).

e) Compound B62:

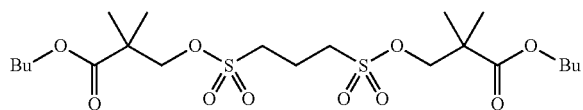

Following the general procedure for the synthesis of diprotected sulfonic acids (Example 1(e)), butyl 3-hydroxy-2,2-dimethyl-propanoate (WO 2007/053346) was reacted with 1,3-propanedisulfonyl dichloride (Example 1 (a)). Compound B62 was obtained (4.5 g, 40% yield) as a white solid. $^1$H NMR (CDCl$_3$, 500 MHz) δ in ppm 4.22 (s, 4H), 4.12 (t, J=6.5 Hz, 4H), 3.35 (t, J=7.0 Hz, 4H), 2.38 (m, 2H), 1.63 (m, 4H), 1.39 (m, 4H), 1.28 (s, 12H), 0.94 (t, J=7.3 Hz, 6H).

f) Compound B63:

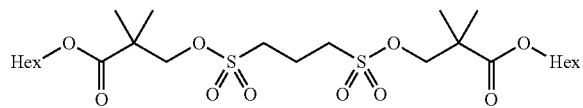

Following the general procedure for the synthesis of diprotected sulfonic acids (Example 1(e)), hexyl 3-hydroxy-2,2-dimethyl-propanoate (WO 2007/053346) was reacted with 1,3-propanedisulfonyl dichloride (Example 1 (a)). Compound B63 was obtained (2.0 g, 36% yield) as a colorless oil. $^1$H NMR (CDCl$_3$, 500 MHz) δ in ppm 0.89 (t, J=7.0 Hz, 2×3H), 1.27 (s, 2×6H), 1.30-1.35 (m, 2×6H), 1.57 (quint, J=7.5 Hz, 2×2H), 2.37 (quint, J=7.0 Hz, 2H), 3.35 (t, J=7.1 Hz, 2×2H), 4.12 (t, J=7.0 Hz, 2×2H), 4.22 (s, 2×2H).

g) Compound B64:

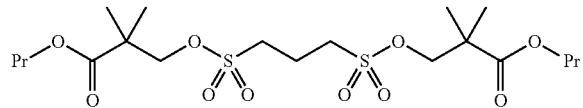

Following the general procedure for the synthesis of diprotected sulfonic acids (Example 1(e)), propyl 3-hydroxy-2,2-dimethyl-propanoate (WO 2007/053346) was reacted with 1,3-propanedisulfonyl dichloride (Example 1 (a)). Compound B64 was obtained (7.0 g, 71% yield) as a white solid. $^1$H NMR (CDCl$_3$, 500 MHz) δ in ppm: 4.23 (s, 4H), 4.08 (t, J=6.6 Hz, 4H), 3.35 (t, J=7.2 Hz, 4H), 2.38 (m, 2H), 1.67 (m, 4H), 1.27 (s, 12H), 0.9 (t, J=7.4 Hz, 6H).

h) Compound B65:

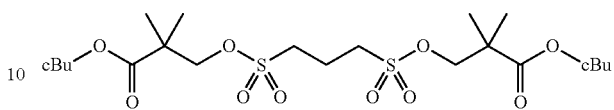

Following the general procedure for the synthesis of diprotected sulfonic acids (Example 1(e)), cyclobutyl 3-hydroxy-2,2-dimethyl-propanoate (WO 2007/053346) was reacted with 1,3-propanedisulfonyl dichloride (Example 1 (a)). Compound B65 was obtained (0.61 g, 44% yield) as a colorless oil. $^1$H NMR (CDCl$_3$, 500 MHz) δ in ppm 1.26 (s, 2×6H), 1.59-1.69 & 1.79-1.85 (m, 2×(1H & 1H), 2.02-2.10 (m, 2×2H), 2.32-2.40 (m, 2H+(2×2H)), 3.34 (t, J=7.1 Hz, 2×2H), 4.21 (s, 2×2H), 4.98 (q, J=7.6 Hz, 2×1 H).

i) Compound B66:

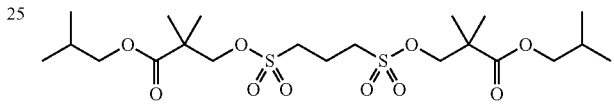

Following the general procedure for the synthesis of diprotected sulfonic acids (Example 1(e)), isobutyl 3-hydroxy-2,2-dimethyl-propanoate (WO 2007/053346) was reacted with 1,3-propanedisulfonyl dichloride (Example 1 (a)). Compound B66 was obtained (3.9 g, 32% yield) as a light yellow oil. $^1$H NMR (CDCl$_3$, 500 MHz) δ in ppm 4.23 (s, 4H), 3.90 (d, J=6.6 Hz, 4H), 3.34 (t, J=7.8 Hz, 4H), 2.37 (m, 2H), 1.95 (m, 2H), 1.28 (s, 12H), 0.94 (d, J=6.8 Hz, 12H).

j) Compound B67(bis(hydrochloride) salt):

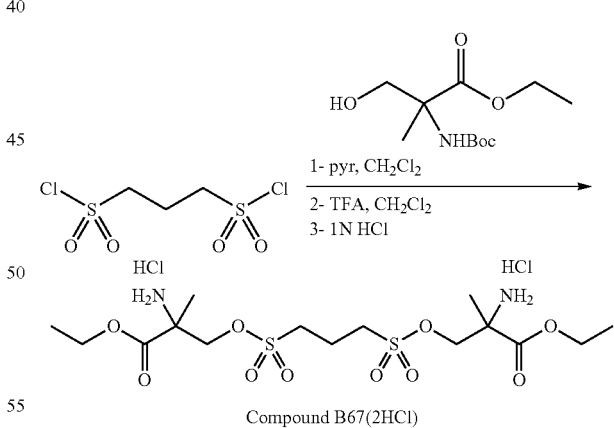

Compound B67(2HCl)

Following the general procedure for the synthesis of diprotected sulfonic acids (Example 1(e)), ethyl 2-(tert-butoxycarbonylamino)-3-hydroxy-2-methyl-propanoate (Yu S. et al. (2005), *Angewandte Chemie, International Edition*, 44(1), 135-138) was reacted with 1,3-propanedisulfonyl dichloride (Example 1 (a)). The resulting mixture was treated with trifluoroacetic acid in dichloromethane and with 1N aqueous hydrochloric acid to afford compound B67(bis(hydrochloride) salt) (0.75 g, 49% yield) as a white solid. $^1$H NMR (D$_2$O, 500 MHz) δ in ppm 1.31 (t, J=7.3 Hz, 2×3 H), 1.63 (s, 2×3 H), 2.35 (quint, J=7.0 Hz, 2H), 3.63 (t, J=7.3 Hz, 2×2 H), 4.35 (q, J=7.3 Hz, 2×2 H), 4.53 & 4.83 (AB, J=11.3 Hz, 2×2 H).

k) Compound B68:

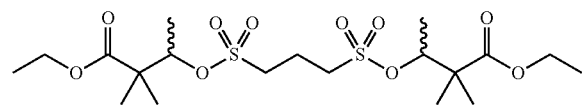

Following the general procedure for the synthesis of diprotected sulfonic acids (Example 1(e)), ethyl 3-hydroxy-2,2-dimethyl-butanoate (Boyd, V. L. et al. (1987), *J. Med. Chem.*, 30(2), 366-374, incorporated herein by reference) was reacted with 1,3-propanedisulfonyl dichloride (Example 1(a)). Compound B68 was obtained (0.65 g, 54% yield) as a colorless oil. $^1$H NMR (CDCl$_3$, 500 MHz) δ in ppm 1.17 (s, 6H); 1.25 (s, 6H); 1.28 (t, J=7.0, 6H); 1.40 (d, J=6.5 Hz, 6H); 2.35 (m, 2H); 3.30 (t, J=7.0 Hz, 4H); 4.16 (m, 4H); 5.10 (q, J=6.5 Hz, 2H).

l) Compound B69:

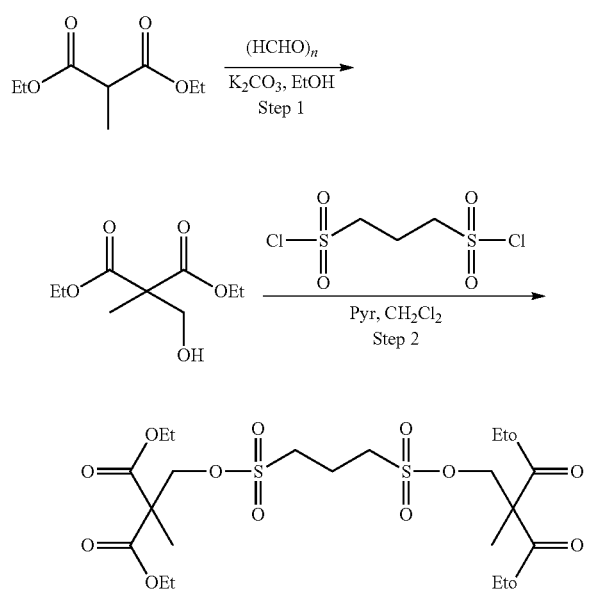

Compound B69

Step 1: To a suspension of paraformaldehyde (0.87 g, 26.4 mmol) and potassium carbonate (7.3 g, 52.8 mmol) in ethanol (100 mL) was added diethylmalonate (3 mL, 17.6 mmol). The reaction mixture was stirred at room temperature for 24 h, filtered over a pad of Celite™, and the cake obtained was washed with ethanol (2*20 mL). The filtrate was concentrated in vacuo and the residue was purified by silica gel chromatography (hexanes/ethyl acetate 90:10 to 70:30) to afford diethyl 2-(hydroxymethyl)-2-methyl-propanedioate (2.8 g, 78% yield) as a colorless oil.

Step 2: Following the general procedure for the synthesis of diprotected sulfonic acids (Example 1(a)), the alcohol from Step 1 was reacted with 1,3-propanedisulfonyl dichloride (Example 1 (a)). Compound B69 was obtained (2.64 g, 67% yield) as a colorless oil. $^1$H NMR (CDCl$_3$, 500 MHz) δ in ppm 1.28 (t, J=7.5 Hz, 12H); 1.55 (s, 6H); 2.36 (m, 2H); 3.35 (t, J=7.0 Hz, 4H); 4.23 (q, J=7.5 Hz, 8H); 4.54 (s, 4H)

Example 19

Preparation of Compounds A62(Sodium Salt) and A63(Sodium Salt)

a) Compound A62(Sodium Salt):

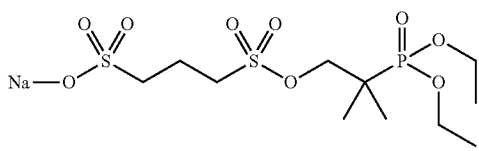

Following the general procedure for the synthesis of monoprotected sulfonic acids (Example 1(d)), diethyl ester (2-hydroxy-1,1-dimethylethyl)-phosphonic acid, (Cann P. F. et al. (1972), *J. Chem. Soc., Perkin Transactions* 2, (3), 304-311, incorporated herein by reference) was reacted with Compound C1(Example 13). Compound A62(sodium salt) was obtained (0.7 g, 84% yield) as a colorless paste. $^1$H NMR (D$_2$O, 500 MHz) δ in ppm 1.23 (s, 3H), 1.28 (s, 3H), 1.35 (t, J=7.0 Hz, 6H), 2.30 (quint, J=7.2 Hz, 2H), 3.07 (t, J=7.0 Hz, 2H), 3.58 (t, J=7.5 Hz, 2H), 4.2 (m, 4H), 4.28 (s, 1H), 4.32 (s, 1H).

b) Compound A63(sodium salt):

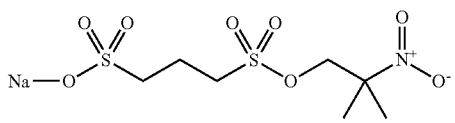

Following the general procedure for the synthesis of monoprotected sulfonic acids (Examplel (d)), 2-methyl-2-nitro-1-propanol (Janzen, E. G. et al. (1978), *J. Org. Chem.* (1978), 43(10), 1900-1903, incorporated herein by reference) was reacted with Compound C1 (Example 13). Compound A63 (sodium salt) was obtained (0.5 g, 15% yield) as a white powder. $^1$H NMR (D$_2$O, 500 MHz) δ in ppm 1.68 (s, 6H), 2.26 (quint, J=7.0 Hz, 2H), 3.05 (t, J=7.0 Hz, 2H), 3.59 (t, 7.0 Hz, 2H), 4.79 (s, 2H).

Example 20

Preparation of Compounds B56 and B70 to B72 a) Compound B56:

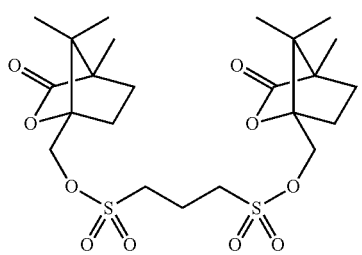 [SMILES: CC12CCC(COS(=O)(=O)CCCS(=O)(=O)OCC34CCC(C)(C(=O)O3)C4(C)C)(OC1=O)C2(C)C]

Following the general procedure for the synthesis of diprotected sulfonic acids (Example 1(e)), the alcohol from Step 1 of Example 16 was reacted with 1,3-propanedisulfonyl dichloride (Example 1 (a)). Compound B56 was obtained (0.32 g, 10% yield) as a colorless paste. $^1$H NMR (CDCl$_3$, 500

MHz) δ in ppm 0.97 (s, 2×3H), 0.98 (s, 2×3H), 1.11 (s, 2×3H), 1.67-1.73 (m, 2×1H), 1.83-1.89 (m, 2×1H), 2.00 (m, 2×1H), 2.08 (m, 1H), 2.47 (quint, J=7.0 Hz, 2H), 3.44 (m, 2×2H), 2.48 (AB, J=11.7 Hz, 2×2H).

b) Compound B70:

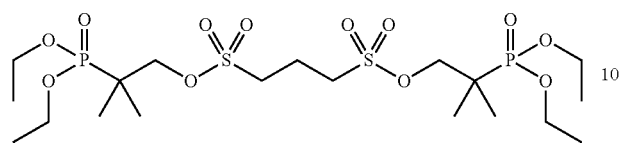

Following the general procedure for the synthesis of diprotected sulfonic acids (Example 1(e)), the diethyl ester of (2-hydroxy-1,1-dimethylethyl)-phosphonic acid (Cann P. F. et al. (1972), *J. Chem. Soc., Perkin Transactions* 2, (3), 304-311) was reacted with 1,3-propanedisulfonyl dichloride (Example 1 (a)). Compound B70 was obtained (0.70 g, 24% yield) as a yellow oil. $^1$H NMR (CDCl$_3$, 500 MHz) δ in ppm 1.24 (s, 2×3H), 1.27 (s, 2×3H), 1.34 (t, J=7.2 Hz, 2×6H), 2.44 (quint, J=7.2 Hz, 2H), 3.39 (t, J=7.0 Hz, 2×2H), 4.16 (m, 2×4H), 4.22 (s, 2×1 H), 4.25 (s, 2×1 H).

c) Compound B71:

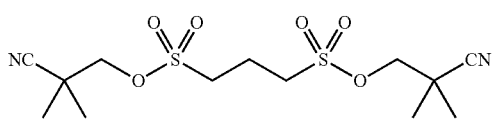 [SMILES: CC(C)(C#N)COS(=O)(=O)CCCS(=O)(=O)OCC(C)(C)C#N]

Following the general procedure for the synthesis of diprotected sulfonic acids (Example 1(e)), commercial 3-hydroxy-2,2-dimethyl-propanenitrile was reacted with 1,3-propanedisulfonyl dichloride (Example 1 (a)). Compound B71 was obtained (4.10 g, 66% yield) as a white solid. $^1$H NMR (CDCl$_3$, 500 MHz) δ in ppm 1.45 (s, 2×6H), 2.53 (quint, J=7.0 Hz, 2H), 3.47 (t, J=7.0 Hz, 2×2H), 4.15 (s, 2×2H).

d) Compound B72:

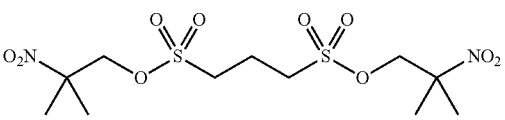 [SMILES: CC(C)(COS(=O)(=O)CCCS(=O)(=O)OCC(C)(C)[N+](=O)[O-])[N+](=O)[O-]]

Following the general procedure for the synthesis of diprotected sulfonic acids (Example 1(e)), 2-methyl-2-nitro-1-propanol (Janzen et al. (1978), *J. Org. Chem.* (1978), 43(10), 1900-1903) was reacted with 1,3-propanedisulfonyl dichloride (Example 1 (a)). Compound B72 was obtained (5.0 g, 62% yield) as a white solid. $^1$H NMR (CDCl$_3$, 500 MHz) δ in ppm 1.68 (s, 2×6H), 2.36 (quint, J=7.0 Hz, 2H), 3.36 (t, J=7.0 Hz, 2×2H), 4.52 (s, 2×2H).

Example 21

Preparation of Compound A64

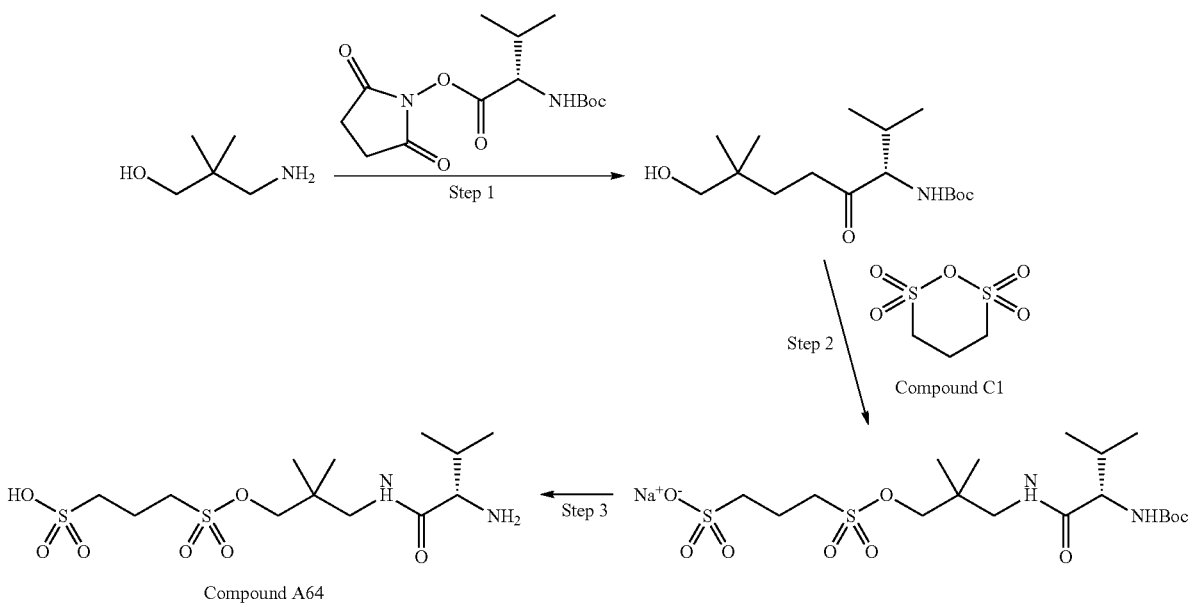

Step 1: A solution of commercial 3-amino-2,2-dimethyl-1-propanol (1.7 g, 16.5 mmol), N-[(1,1-dimethylethoxy)carbonyl]-D-Valine, 2,5-dioxo-1-pyrrolidinyl ester (Giuntini F. et al., *J. Med. Chem.* (2009), 52(13), 4026-4037, incorporated herein by reference) (4.7 g, 15.0 mmol) and 1M aqueous potassium carbonate (10 mL, 10.0 mmol) in acetonitrile (30 mL) was stirred at room temperature for 2 h. The mixture was concentrated to about one third of its volume, diluted with 1M hydrochloric acid and extracted three times with ethyl acetate. The combined organic layers were washed with water, dried over magnesium sulfate, filtered and the filtrate evaporated to a residue. The crude product was purified by silica gel chromatography using hexane/ethyl acetate (50:50) to isolate 4 g (88% yield) of tert-butyl N-[(1S)-1-[(3-hydroxy-2,2-dimethyl-propyl)carbamoyl]-2-methyl-propyl] carbamate.

Step 2: Following the general procedure for the synthesis of monoprotected sulfonic acids (Example 1(d)), the alcohol from Step 1 (1.7 g, 5.62 mmol) was reacted with Compound C1(Example 13) (1.15 g, 6.18 mmol) to give 2.6 g (89% yield) of the intermediate sodium 3-[3-[[(2S)-2-(tert-butoxycarbonylamino)-3-methyl-butanoyl]amino]-2,2-dimethyl-propoxy]sulfonylpropane-1-sulfonate.

Step 3: The intermediate from Step 2 (2.6 g, 5.0 mmol) was stirred for 3 h at room temperature in a mixture of trifluoroacetic acid (6 mL) and dichloromethane (10 mL). The mixture was evaporated to dryness to afford Compound A64 (2.3 g, 90% yield) as a white solid. $^1$H NMR (D$_2$O, 500 MHz) δ in ppm 0.99 (s, 6H), 1.02 (d, J=7.0 Hz, 3H), 1.05 (d, J=7.0 Hz, 3H), 2.22 (m, 1H), 2.28 (quint, J=7.0 Hz, 2H), 3.06 (t, J=7.0 Hz, 2H), 3.16 & 3.32 (AB, J=14.0 Hz, 2H), 3.56 (t, J=7.3 Hz, 2H), 3.82 (d, J=5.9 Hz, 1H), 4.06 (s, 2H), 8.34 (bt, CONH not completely exchanged with D$_2$O).

Example 22

Preparation of Compounds A65(Sodium Salt) to A68(Sodium Salt)

a) Compound A65(Sodium Salt):

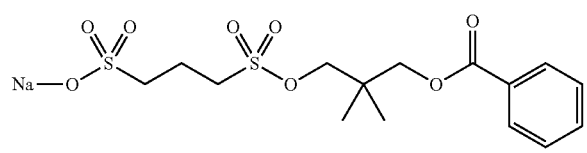

Following the general procedure for the synthesis of monoprotected sulfonic acids (Example 1(d)), commercial 1-benzoate-2,2-dimethyl-1,3-propanediol was reacted with Compound C1(Example 13). Compound A65(sodium salt) was obtained (2.3 g, 59% yield) as white solid. $^1$H NMR (D$_2$O, 500 MHz) δ in ppm 0.99 (s, 6H), 1.02 (d, J=7.0 Hz, 3H), 1.05 (d, J=7.0 Hz, 3H), 2.22 (m, 1H), 2.28 (quint, J=7.0 Hz, 2H), 3.06 (t, J=7.0 Hz, 2H), 3.16 & 3.32 (AB, J=14.0 Hz, 2H), 3.56 (t, J=7.3 Hz, 2H), 3.82 (d, J=5.9 Hz, 1H), 4.06 (s, 2H), 8.34 (bt, CONH not completely exchanged with D$_2$O).

b) Compound A66(Sodium Salt):

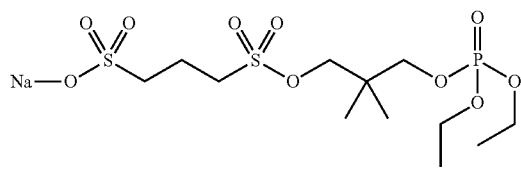

Following the general procedure for the synthesis of monoprotected sulfonic acids (Example 1(d)), phosphoric acid, diethyl 3-hydroxy-2,2-dimethylpropyl ester (Ogilvie et al., *J. Am. Chem. Soc.* (1977), 99(4), 1277-1278, incorporated herein by reference) was reacted with Compound C1(Example 13). Compound A66(sodium salt) was obtained (1.2 g, 27% yield) as a colorless waxy solid. $^1$H NMR (D$_2$O, 500 MHz) δ in ppm 1.03 (s, 6H), 1.33 (t, J=7.0 Hz, 6H), 2.28 (quint, J=7.0 Hz, 2H), 3.07 (t, J=7.0 Hz, 2H), 3.59 (t, J=7.0 Hz, 2H), 3.92 (d, J=4.6 Hz, 2H), 4.16 (s, 2H), 4.20 (m, 4H).

c) Compounds A67(Sodium Salt) and A68(Sodium Salt):

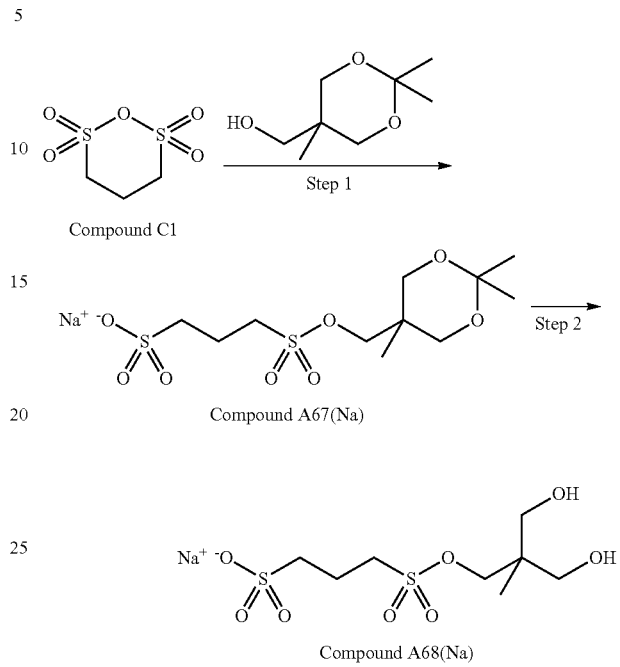

Step 1: Following the general procedure for the synthesis of monoprotected sulfonic acids (Example 1(d)), commercial 2,2,5-trimethyl-1,3-dioxane-5-methanol (1.0 g, 6.24 mmol) was reacted with Compound C1(Example 13) (1.2 g, 6.44 mmol). Compound A67(sodium salt) was obtained (0.7 g, 30% yield) as a white solid. $^1$H NMR (D$_2$O, 500 MHz) δ in ppm 0.93 (s, 3H), 1.42 (s, 3H), 1.50 (s, 3H), 2.30 (quint, J=7.2 Hz, 2H), 3.07 (t, J=7.3 Hz, 2H), 3.59 (t, J=7.6 Hz, 2H), 3.78 (AB, J=12.5 Hz, 4H), 4.39 (s, 2H).

Step 2: Compound A67(sodium salt) from Step 1 (0.70 g, 2.0 mmol) was dissolved in water (3 mL) and diluted with acetic acid (7 mL). The mixture was stirred for 10 h and the solvents were removed by evaporation to give Compound A68(sodium salt) (0.5 g, 80% yield) as a white solid. $^1$H NMR (D$_2$O, 500 MHz) δ in ppm 0.95 (s, 3H), 2.30 (quint, J=7.2 Hz, 2H), 3.07 (t, J=7.3 Hz, 2H), 3.50 (AB, J=12.5 Hz, 4H), 3.57 (t, J=7.6 Hz, 2H), 4.22 (s, 2H).

Example 23

Preparation of Compound B74

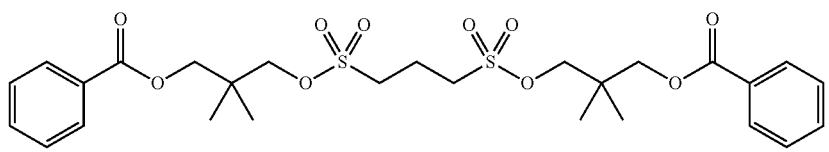 [SMILES: CC(C)(COC(=O)c1ccccc1)COS(=O)(=O)CCCS(=O)(=O)OCC(C)(C)COC(=O)c1ccccc1]

Following the general procedure for the synthesis of diprotected sulfonic acids (Example 1(e)), commercial 1-benzoate-2,2-dimethyl-1,3-propanediol was reacted with 1,3-propanedisulfonyl dichloride (Example 1 (a)). Compound B74 was obtained (0.71 g, 65% yield) as a colorless oil. $^1$H NMR (CDCl$_3$, 500 MHz) δ in ppm 1.12 (s, 2×6H), 2.40 (quint, J=7.2 Hz, 2H), 3.32 (quint, J=7.0 Hz, 2×2H), 4.13 (s, 2×2H), 4.17 (s, 2×2H), 7.46 (t, J=7.8 Hz, 2×2H), 7.58 (t, J=7.0 Hz, 2×1 H), 8.05 (d, J=8.5 Hz, 2×2H).

Example 24

Preparation of Compounds A69 and B75 a) Compound A69:

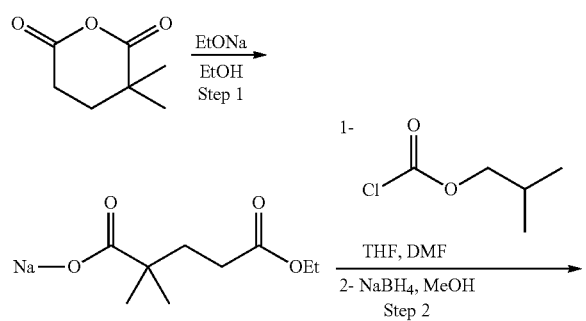

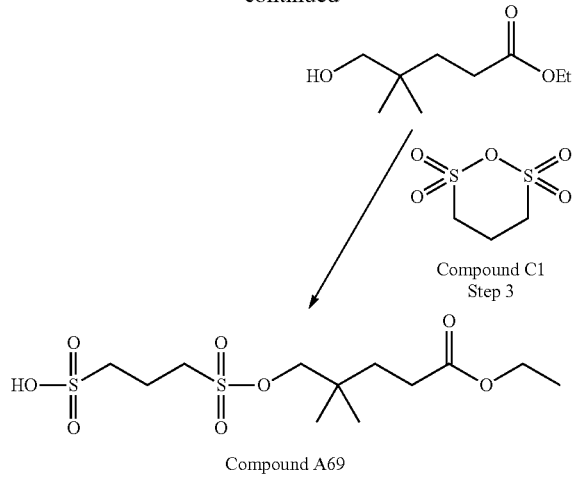

Step 1: To a solution of 3,3-dimethylglutaric anhydride (3 g, 21.1 mmol) in ethanol (30 mL) was added a 21% w/w solution of sodium ethoxide in ethanol (5.0 mL, 23.2 mmol). After 20 h of stirring, the solution was evaporated and the resulting solid was suspended in diethyl ether (50 mL). The mixture was filtered and the solid was washed with diethyl ether (2×20 mL). The solid was dried under high vacuum to afford 5-ethoxy-2,2-dimethyl-5-oxo-pentanoic acid sodium salt (2.92 g, 66% yield) as a light yellow solid.

Step 2: To a solution of acid from Step 1 (2.92 g, 13.9 mmol) in a mixture of THF/DMF (5:1, 60 mL) was added isopropylchloroformate (2.71 mL, 20.9 mmol). After 20 h of stirring at room temperature, the solution was cooled to 0° C. and NaBH$_4$ (1.06 g, 27.9 mmol) followed methanol (5 mL) was added to the solution. After 30 min of stirring, a saturated aqueous solution of ammonium chloride was added (20 mL) and followed by ethyl acetate (20 mL). The layers were separated and the aqueous layer was extracted with ethyl acetate (2×30 mL). The combined organic layers were washed with brine, dried with magnesium sulfate, filtered and the filtrate was concentrated in vacuo. The residue was purified by silica gel chromatography (hexanes/ethyl acetate 95:5 to 60:40). After evaporation at low temperature, ethyl 5-hydroxy-4,4-dimethyl-pentanoate (1.82 g, 75% yield) was obtained as a volatile colorless oil.

Step 3: Following the general procedure for the synthesis of monoprotected sulfonic acids (Example 1(d)), the alcohol from Step 2 was reacted with Compound C1(Example 13). Compound A69 was obtained (1.1 g, 56% yield) as a white solid. $^1$H NMR (D$_2$O, 500 MHz) δ in ppm 0.97 (s, 6H), 1.25 (t, J=7.0 Hz, 3H), 1.67 (t, J=8.5 Hz, 2H), 2.28 (m, 2H), 2.41 (t, J=8.0 Hz, 2H), 3.07 (t, J=7.0 Hz, 2H), 3.57 (t, J=7.5 Hz, 2H), 4.06 (s, 2H), 4.14 (q, J=7.0 Hz, 2H)

b) Compound B75:

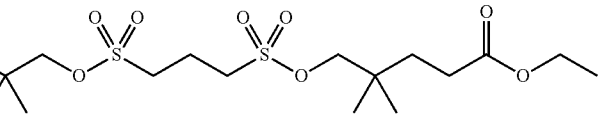

Following the general procedure for the synthesis of diprotected sulfonic acids (Example 1(e)), the alcohol from Step 2 of Example 24 (a) was reacted with 1,3-propanedisulfonyl dichloride (Example 1 (a)). Compound B75 was obtained (7.3 g, 57% yield) as a colorless oil. $^1$H NMR (CDCl$_3$, 500 MHz) δ in ppm 0.98 (s, 2×6 H), 1.26 (t, J=7.1 Hz, 2×3 H), 1.67 (t, J=7.0 Hz, 2×2 H), 2.30 (t, J=7.0 Hz, 2×2 H), 2.43 (quint, J=7.0 Hz, 2H), 3.36 (t, J=7.10 Hz, 2×2 H), 3.93 (s, 2×2 H), 4.14 (q, J=7.10 Hz, 2×2 H).

Example 25

Preparation of Compound A70(Sodium Salt)

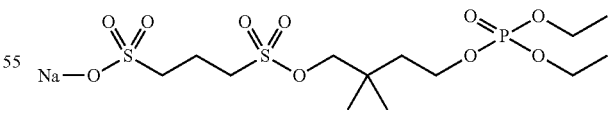

Following the general procedure for the synthesis of monoprotected sulfonic acids (Example 1(d)), diethyl (4-hydroxy-3,3-dimethyl-butyl) phosphate (WO2006/014282, incorporated herein by reference) was reacted with Compound C1(Example 13). Compound A70(sodium salt) was obtained (0.45 g, 26% yield) as a colorless paste. $^1$H NMR (D$_2$O, 500 MHz) δ in ppm 1.03 (s, 6H), 1.33 (t, J=7.0 Hz, 6H), 2.28 (quint, J=7.0 Hz, 2H), 3.07 (t, J=7.0 Hz, 2H), 3.56 (t, J=7.0 Hz, 2H), 4.09 (s, 2H), 4.15-4.25 (m, 6H).

Example 26

Preparation of Compounds A71(sodium salt) to A73(Sodium Salt)

a) Compound A71(Sodium Salt):

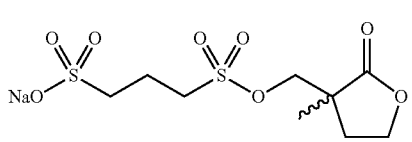

Following the general procedure for the synthesis of monoprotected sulfonic acids (Example 1(d)), dihydro-3-(hydroxymethyl)-3-methyl 2(3H)-furanone (US 2009/099253, incorporated herein by reference) was reacted with Compound C1(Example 13). Compound A71(sodium salt) was obtained (0.42 g, 26% yield) as a white powder. $^1$H NMR (D$_2$O, 500 MHz) δ in ppm 1.32 (s, 3H), 2.22-2.32 (m, 3H), 2.54 (m, 1H), 3.06 (t, J=7.3 Hz, 2H), 3.60 (dt, J=7.2 and 3.7 Hz, 2H), 4.37 & 4.46 (AB, J=10.0 Hz, 2H), 4.47 (t, J=6.0 Hz, 2H).

b) Compound A72(Sodium Salt):

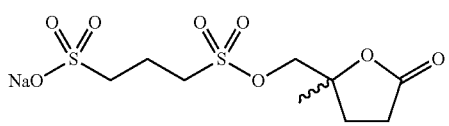

Following the general procedure for the synthesis of monoprotected sulfonic acids (Example 1(d)), dihydro-5-(hydroxymethyl)-5-methyl-2(3H)-furanone (US 2009/099253) was reacted with Compound C1(Example 13). Compound A72(sodium salt) was obtained (0.85 g, 14% yield) as a white powder. $^1$H NMR (D$_2$O, 500 MHz) δ in ppm 1.50 (s, 3H), 2.20 (m, 1H), 2.28 (quint, J=7.3 Hz, 2H), 2.38 (m, 1H), 2.77 (t, J=7.0 Hz, 2H), 3.07 (t, J=7.0 Hz, 2H), 3.60 (t, J=7.1 Hz, 2H), 4.42 (AB, J=11.3 Hz, 2H).

c) Compound A73(Sodium Salt):

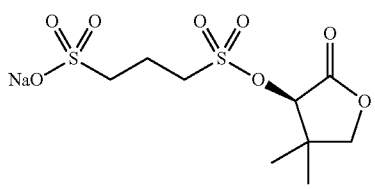

Following the general procedure for the synthesis of monoprotected sulfonic acids (Example 1(d)), commercial (3R)-dihydro-3-hydroxy-4,4-dimethyl-2(3H)-furanone was reacted with Compound C1(Example 13). Compound A73 (sodium salt) was obtained (0.47 g, 28% yield) as a waxy solid. $^1$H NMR (D$_2$O, 500 MHz) δ in ppm 1.11 (s, 3H), 1.25 (s, 3H), 2.31-2.37 (m, 2H), 3.07 (t, J=7.6 Hz, 2H), 3.70 (t, J=7.6 Hz, 2H), 4.19-4.24 (m, 2H), 5.41 (s, 1H).

Example 27

Preparation of Compounds B76 to B81 a) Compound B76:

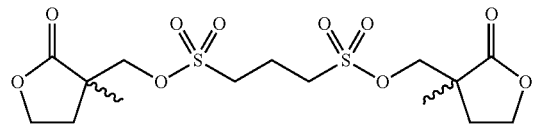

Following the general procedure for the synthesis of diprotected sulfonic acids (Example 1(e)), dihydro-3-(hydroxymethyl)-3-methyl-2(3H)-furanone (US 2009/099253) was reacted with 1,3-propanedisulfonyl dichloride (Example 1 (a)). Compound B76 was obtained (11.7 g, 79% yield) as a white solid. $^1$H NMR (CDCl$_3$, 500 MHz) δ in ppm 1.31 (s, 6H), 2.08 (ddd, J=13.2, 7.6 and 4.0 Hz, 2H), 2.30-2.40 (m, 2H), 2.60 (dt, J=13.2 and 8.5 Hz, 2H), 3.36 (t, J=7.1 Hz, 4H), 4.22 and 4.33 (AB, J=10.0 Hz, 4H), 4.30 (t, J=8.5 Hz, 2H), 4.40 (m, 2H).

b) Compound B77:

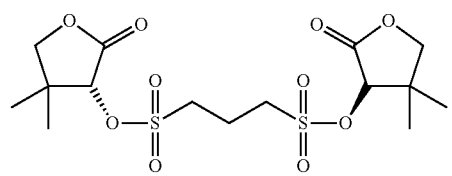

Following the general procedure for the synthesis of diprotected sulfonic acids (Example 1(e)), commercial (3R)-dihydro-3-hydroxy-4,4-dimethyl-2(3H)-furanone was reacted with 1,3-propanedisulfonyl dichloride (Example 1 (a)). Compound B77 was obtained (9.3 g, 70% yield) as a white solid. $^1$H NMR (D$_2$O, 500 MHz) δ in ppm 5.01 (s, 2H), 4.11 (d, J=9.0 Hz, 2H), 4.05 (d, J=9.0 Hz, 2H), 3.58-3.72 (10-peaks, 4H), 2.62 (pent, 2H), 1.29 (s, 6H), 1.18 (s, 6H).

c) Compound B78:

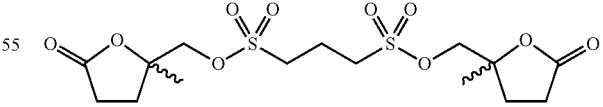

Following the general procedure for the synthesis of diprotected sulfonic acids (Example 1(e)), dihydro-5-(hydroxymethyl)-5-methyl-2(3H)-furanone (US 2009/099253) was reacted with 1,3-propanedisulfonyl dichloride (Example 1 (a)). Compound B78 was obtained (1.1 g, 57% yield) as a colorless oil. $^1$H NMR (CDCl$_3$, 500 MHz) δ in ppm 1.48 (s, 2×3H), 2.03-2.10 (m, 2H), 2.32-2.44 (m, 2×2H), 2.61-2.75 (m, 2×2H), 3.40 (m, 2×2H), 4.26 (m, 2×2H).

d) Compound B79:

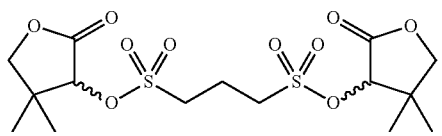 [SMILES: CC1(C)COC(=O)C1OS(=O)(=O)CCCS(=O)(=O)OC1C(=O)OCC1(C)C]

Following the general procedure for the synthesis of diprotected sulfonic acids (Example 1(e)), commercial dihydro-3-hydroxy-4,4-dimethyl-2(3H)-furanone was reacted with 1,3-propanedisulfonyl dichloride (Example 1 (a)). Compound B79 was obtained (1.34 g, 63% yield) as a white solid. $^1$H NMR (CDCl$_3$, 500 MHz) δ in ppm 1.18 (s, 6H) & 1.29 (s, 6H), 2.57-2.69 (m, 2H), 3.59-3.72 (m, 4H), 4.05 (d, J=9 Hz, 2H) & 4.11 (d, J=9 Hz, 2H), 5.00 (s, 1H) & 5.02 (s, 1H).

e) Compound B80:

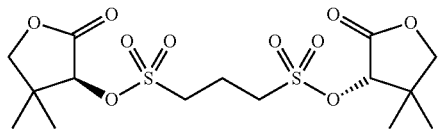

Following the general procedure for the synthesis of diprotected sulfonic acids (Example 1(e)), commercial (3S)-dihydro-3-hydroxy-4,4-dimethyl-2(3H)-furanone was reacted with 1,3-propanedisulfonyl dichloride (Example 1(a)). Compound B80 was obtained (1.70 g, 80% yield) as a white solid. $^1$H NMR (CDCl$_3$, 500 MHz) δ in ppm 1.18 (s, 6H) & 1.29 (s, 6H), 2.60-2.65 (m, 2H), 3.59-3.64 (m, 2H) & 3.66-3.72 (m, 2H), 4.05 (d, J=9 Hz, 2H) & 4.11 (d, J=9 Hz, 2H), 5.00 (s, 2H).

f) Compound B81:

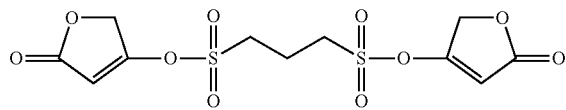 [SMILES: O=C1C=C(OS(=O)(=O)CCCS(=O)(=O)OC2=CC(=O)OC2)CO1]

Following the general procedure for the synthesis of diprotected sulfonic acids (Example 1(e)), commercial tetronic acid was reacted with 1,3-propanedisulfonyl dichloride (Example 1 (a)). Compound B81 was obtained (0.85 g, 56% yield) as a white solid. $^1$H NMR (DMSO, 500 MHz) δ in ppm 2.34 (m, 2H), 3.99 (t, J=7.5 Hz, 4H), 5.00 (s, 4H), 6.05 (t, J=1.5 Hz, 2H).

Example 28

Preparation of Compound P1 (Disodium Salt)

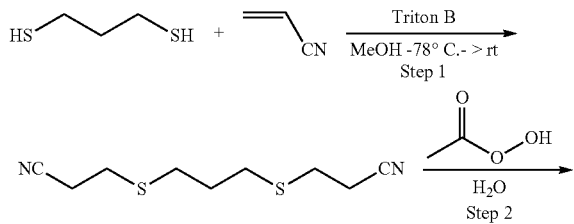

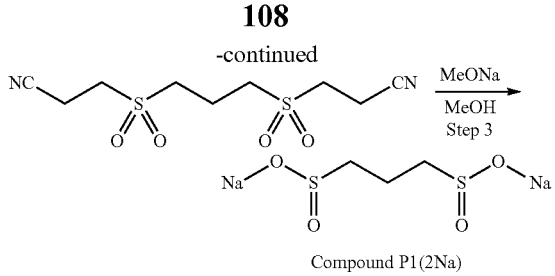

Step 1: To a solution of 1,3-propanthiol (1 mL, 10 mmol) and acrylonitrile (2 mL, 30 mmol) was added Triton B (0.1 mL). The mixture was then warmed up to rt and stirred at this temperature for 20 h. The mixture was concentrated in vacuo and the residue was purified by silica gel chromatography (hexanes/ethyl acetate 80:20 to 0:100) to afford 3-[3-(2-cyanoethylsulfanyl)propylsulfanyl]propanenitrile (2.14 g, 100% yield) as a colorless oil.

Step 2: To a solution of disulfide from Step 1 (0.5 g, 2.34 mmol) in water (10 mL) was added a 32% solution of peracetic acid in acetic acid (3.3 mL, 14.0 mmol). After 4 h at room temperature, the formed solid was filtered and washed with water (2×10 mL) and ethanol (2×10 mL). The cake was dried under high vacuum to afford 3-[3-(2-cyanoethylsulfonyl)propylsulfonyl]-propanenitrile (0.62 g, 95% yield) as a white solid.

Step 3: To a suspension of disulfone from Step 2 (0.62 g, 2.23 mmol) in methanol (15 mL) was added a 0.5M solution of sodium methoxide in methanol (8.9 mL, 4.58 mmol). After 24 h of stirring, the homogenous solution was concentrated in vacuo and the resulting solid was suspended in ethanol (20 mL) and the suspension was stirred 1 h at room temperature. The suspension was filtered and the cake washed with ethanol (2×10 mL) and diethyl ether (2×10 mL). Water (2 mL) was added to the solid and the mixture passed through a C8 pad eluting with water. The fractions containing Compound P1(disodium salt) were collected and lyophilized, affording Compound P1(disodium salt) (0.41 g, 85% yield) as a white solid. $^1$H NMR (D$_2$O, 500 MHz) δ in ppm 1.84 (quint, J=8.0 Hz, 2H), 2.44 (t, J=8.0 Hz, 4H).

Example 29

Preparation of Compounds B11 and B12 a) Compound B11:

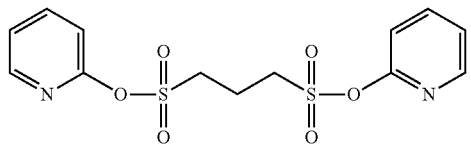 [SMILES: O=S(=O)(CCCS(=O)(=O)Oc1ccccn1)Oc1ccccn1]

Following the general procedure for the synthesis of diprotected sulfonic acids (Example 1(e)), commercial pyridin-2-ol was reacted with 1,3-propanedisulfonyl dichloride (Example 1 (a)). Compound B11 was obtained (0.59 g, 82% yield) as a colorless oil. $^1$H NMR (CDCl$_3$, 500 MHz) δ in ppm: 2.79 (q, J=7.5 Hz, 2H), 3.98 (t, J=7.5 Hz, 4H), 7.15 (c, J=8.0 Hz, 2H), 7.30 (dd, J=5.0, 7.5 Hz, 2H), 7.84 (td, J=8.0, 2.0 Hz, 2H), 8.34 (dd, J=2.0, 5.0 Hz, 2H).

b) Compound B12:

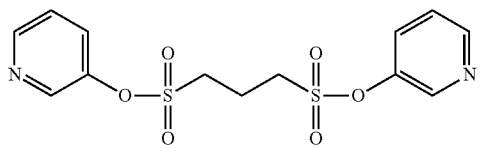 [SMILES: O=S(=O)(CCCS(=O)(=O)Oc1cccnc1)Oc1cccnc1]

Following the general procedure for the synthesis of diprotected sulfonic acids (Example 1(a)), pyridin-3-ol was reacted with 1,3-propanedisulfonyl dichloride (Example 1 (a)). Compound B12 was obtained (0.61 g, 67% yield) as a colorless oil. $^1$H NMR (DMSO, 500 MHz) δ in ppm 8.64 (d, J=2.7 Hz, 2H), 8.62 (dd, J=1.2, 4.6 Hz, 2H), 7.87 (ddd, J=1.2, 2.8, 8.5 Hz, 2H), 7.58 (dd, J=4.6, 8.5 Hz, 2H), 3.85 (t, J=7.5 Hz, 4H), 2.49-2.40 (m, 2H).

Example 30

Preparation of Compounds B82 to B87 a) Compound B82:

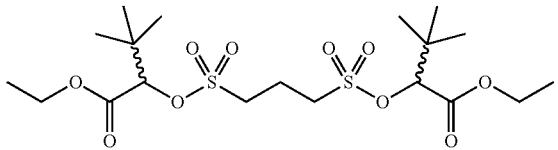 [SMILES: CCOC(=O)C(OS(=O)(=O)CCCS(=O)(=O)OC(C(=O)OCC)C(C)(C)C)C(C)(C)C]

Following the general procedure for the synthesis of diprotected sulfonic acids (Example 1(e)), ethyl 2-hydroxy-3,3-dimethyl-butanoate (Wang et al. (2006), Synlett 2006(8), 1169-1172, incorporated herein by reference) was reacted with 1,3-propanedisulfonyl dichloride (Example 1 (a)). Compound B82 was obtained (2.0 g, 82% yield) as a colorless oil. $^1$H NMR (CDCl$_3$, 500 MHz) δ in ppm 1.06 (s, 2×9H), 1.32 (t, J=7.0 Hz, 2×3H), 2.53 (quint, J=7.0 Hz, 2H), 3.44 (t, J=7.0 Hz, 2×2H), 4.27 (m, 2×2H), 4.66 (s, 2×1 H).

b) Compound B83:

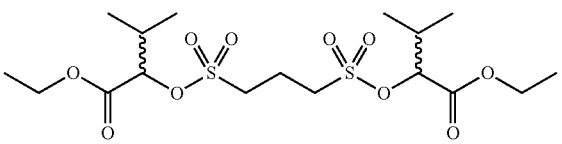 [SMILES: CCOC(=O)C(OS(=O)(=O)CCCS(=O)(=O)OC(C(=O)OCC)C(C)C)C(C)C]

Following the general procedure for the synthesis of diprotected sulfonic acids (Example 1(e)), ethyl 2-hydroxy-3-methyl-butanoate (Anand et al. (1994), *Syn. Comm.*, 24(19), 2743-2747, incorporated herein by reference) was reacted with 1,3-propanedisulfonyl dichloride (Example 1 (a)). Compound B83 was obtained (0.85 g, 73% yield) as a colorless oil. $^1$H NMR (CDCl$_3$, 500 MHz) δ in ppm 0.97 (d, J=6.8 Hz, 2×3H), 1.08 (d, J=7.0 Hz, 2×3H), 1.30 (t, J=7.0 Hz, 2×3H), 2.33 (m, 2H), 2.57 (m, 2×1H), 3.49 (m, 2×2H), 4.27 (q, J=7.0 Hz, 2×2H), 4.88 (d, J=4.0 Hz, 2×1 H).

c) Compound B84:

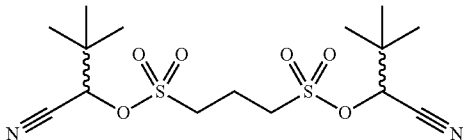 [SMILES: CC(C)(C)C(C#N)OS(=O)(=O)CCCS(=O)(=O)OC(C#N)C(C)(C)C]

Following the general procedure for the synthesis of diprotected sulfonic acids (Example 1(e)), 2-hydroxy-3,3-dimethyl-butanenitrile was reacted with 1,3-propanedisulfonyl dichloride (Example 1 (a)). Compound B84 was obtained (4.4 g, 56% yield) as a white solid. $^1$H NMR (CDCl$_3$, 500 MHz) δ in ppm 1.15 (s, 2×9H), 2.55 (quint, J=7.0 Hz, 2H), 3.52 (t, J=7.0 Hz, 2×2H), 4.86 (s, 2×1 H).

d) Compound B85:

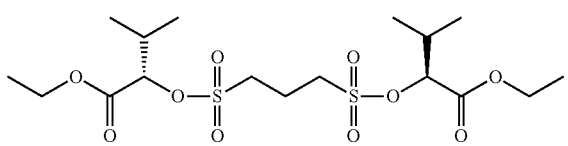 [SMILES: CCOC(=O)[C@@H](OS(=O)(=O)CCCS(=O)(=O)O[C@H](C(=O)OCC)C(C)C)C(C)C]

Following the general procedure for the synthesis of diprotected sulfonic acids (Example 1(e)), ethyl (2S)-2-hydroxy-3-methyl-butanoate (WO2008/087560, incorporated herein by reference) was reacted with 1,3-propanedisulfonyl dichloride (Example 1 (a)). Compound B85 was obtained (8.2 g, 71% yield) as a white solid. $^1$H NMR (CDCl$_3$, 500 MHz) δ in ppm: 0.97 (d, J=6.8 Hz, 2×3H) & 1.08 (d, J=6.8 Hz, 2×3H), 1.31 (t, J=7.1 Hz, 2×3H), 2.30-2.36 (m, 2H), 2.54-2.60 (m, 2×1H), 3.46-3.52 (m, 2×2H), 4.23-4.30 (m, 2×2H), 4.89 (d, J=3.9 Hz, 2×1 H).

e) Compound B86:

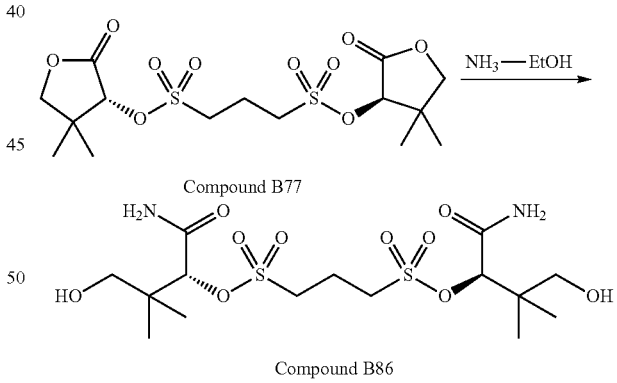

Compound B77 (8.6 g; Example 27 (b)) was dissolved in 2M ammonia in ethanol (150 mL). The solution was stirred at room temperature for 48 h. The solvent was removed under vacuum and the residual material was washed with hexanes (2×100 mL) to give the crude product (5 g) which was recrystallized from methanol. After overnight standing at room temperature, the solid was filtered and washed with cold methanol to afford Compound B86 (2.4 g, 25% yield) as a white solid. $^1$H NMR (DMSO, 500 MHz) δ in ppm 0.89 (s, 6H), 0.91 (s, 6H), 2.21 (m, 2H), 3.20 (m, 2H), 3.26 (m, 2H), 3.47 (t, J=7.5 Hz, 4H), 4.69 (s, 2H), 4.83 (t, J=4.5 Hz, 2H), 7.43 (brs, 2H), 7.58 (brs, 2H).

f) Compound B87:

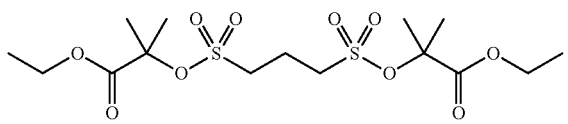 [SMILES: CCOC(=O)C(C)(C)OS(=O)(=O)CCCS(=O)(=O)OC(C)(C)C(=O)OCC]

Following the general procedure for the synthesis of diprotected sulfonic acids (Example 1(e)), ethyl 2-hydroxy-2-methyl-propanoate was reacted with 1,3-propanedisulfonyl dichloride (Example 1(a)). Compound B87 was obtained (0.85 g, 53% yield) as a colorless oil. $^1$H NMR (CDCl$_3$, 500 MHz) δ in ppm 1.32 (t, J=7.0 Hz, 2×3H), 1.73 (s, 2×6H), 2.50 (quint, J=7.0 Hz, 2H), 3.46 (t, J=7.0 Hz, 2×2H), 4.27 (q, J=7.0 Hz, 2×2H).

Example 31

General Synthetic Protocol for the Synthesis of Oxomethyl Disulfonate Esters a) 1,3-propanedisulfonic acid disilver salt

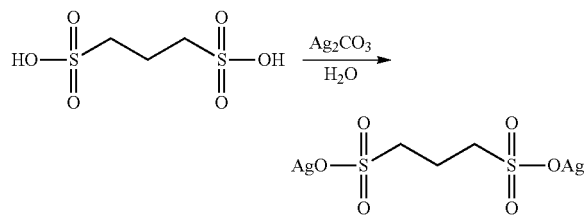

To a solution of 1,3PDS (109 g, 534 mmol) in H$_2$O (500 mL) was added silver carbonate (162 g, 587 mmol) in portion over 30 min. After 30 min at room temperature, the solution was filtered over a pad of Celite™ and the cake was washed once with water (100 mL). After evaporation of the solution on the rotavap, the solid was suspended in ethanol (500 mL) and the resulting mixture was stirred for 30 min at room temperature and filtered. The cake was washed twice with ethanol (2×150 mL) and dried under vacuum at 40° C. to afford 1,3-propanedisulfonic acid disilver salt (1,3PDS (2Ag)) (198 g, 89% yield) as a white solid.

b) 1,3-propanedisulfonic acid oxomethyl diesters

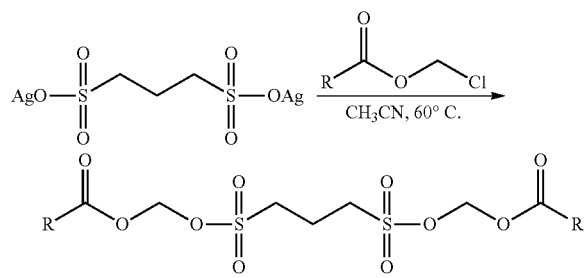

To a suspension of 1,3-propanedisulfonic acid disilver salt from Step (a) in acetonitrile is added the selected chloromethylacetate (5 eq). The mixture is heated for 24 h at 60° C. before being cooled down to room temperature and filtered over a pad of Celite™. The cake is then washed with acetonitrile and the filtrate is evaporated on the rotavap. The residue is purified by silica gel chromatography to afford the corresponding 1,3-propanedisulfonic acid oxomethyl diester.

Example 32

Preparation of Compounds D1 to D8 a) Compound D1:

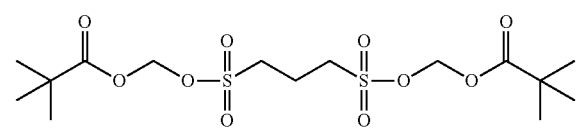 [SMILES: CC(C)(C)C(=O)OCOS(=O)(=O)CCCS(=O)(=O)OCOC(=O)C(C)(C)C]

Following the general procedure for the synthesis of oxomethyl disulfonate esters (Example 31 (b)), commercial chloromethylpivaloate was reacted with 1,3-propanedisulfonic acid disilver salt (Example 31 (a)). Compound D1 was obtained (18.3 g, 81% yield) as a white solid. $^1$H NMR (CDCl$_3$, 500 MHz) δ in ppm 1.25 (s, 18H), 2.42 (quint, 7.0 Hz, 2H), 3.41 (t, J=7.0 Hz, 4H), 5.81 (s, 4H).

b) Compound D2:

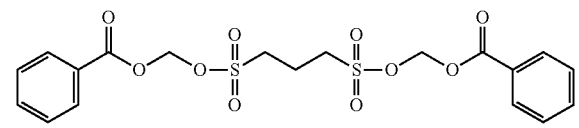 [SMILES: O=C(OCOS(=O)(=O)CCCS(=O)(=O)OCOC(=O)c1ccccc1)c1ccccc1]

Following the general procedure for the synthesis of oxomethyl disulfonate esters (Example 31 (b)), commercial chloromethylbenzoate was reacted with 1,3-propanedisulfonic acid disilver salt (Example 31 (a)). Compound D2 was obtained (0.40 g, 71% yield) as a white solid. $^1$H NMR (CDCl$_3$, 500 MHz) δ in ppm 2.40 (quint, 7.0 Hz, 2H), 3.40 (t, J=7.0 Hz, 4H), 6.02 (s, 4H), 7.49 (dt, J=8.0, 1.5 Hz, 4H), 7.64 (tt, J=9.0, 1.5 Hz, 2H), 8.08 (td, 8.5, 1.5 Hz, 4H).

c) Compound D3:

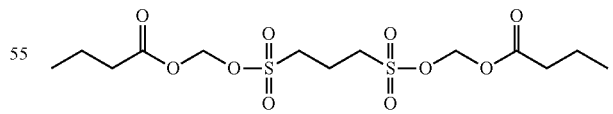

Following the general procedure for the synthesis of oxomethyl disulfonate esters (Example 31 (b)), chloromethylbutanoate (Baudy et al. (2009), *J. Med. Chem.* 52(3), 771-778, incorporated herein by reference) was reacted with 1,3-propanedisulfonic acid disilver salt (Example 31 (a)). Compound D3 was obtained (10.8 g, 76% yield) as colorless oil. $^1$H NMR (CDCl$_3$, 500 MHz) δ in ppm 0.98 (t, J=7.5 Hz, 6H), 1.70 (m, 4H), 2.42 (m, 6H), 3.41 (t, J=7.0 Hz, 4H), 5.81 (s, 4H).

d) Compound D4:

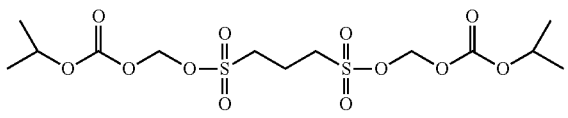 [SMILES: CC(C)OC(=O)OCOS(=O)(=O)CCCS(=O)(=O)OCOC(=O)OC(C)C]

Following the general procedure for the synthesis of oxomethyl disulfonate esters (Example 31 (b)), commercial chloromethylisopropylcarbonate was reacted with 1,3-propanedisulfonic acid disilver salt (Example 31 (a)). Compound D4 was obtained (0.98 g, 95% yield) as a colorless oil. $^1$H NMR (CDCl$_3$, 500 MHz) δ in ppm 1.35 (d, J=6.5 Hz, 12H), 2.43 (quint, J=7.0 Hz, 2H), 3.43 (t, J=7.0 Hz, 4H), 4.97 (m, 2H), 5.81 (s, 4H).

e) Compound D5:

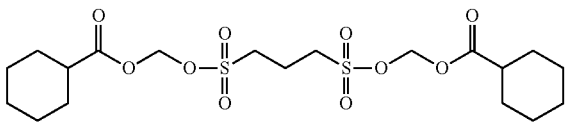 [SMILES: O=C(OCOS(=O)(=O)CCCS(=O)(=O)OCOC(=O)C1CCCCC1)C1CCCCC1]

Following the general procedure for the synthesis of oxomethyl disulfonate esters (Example 31 (b)), chloromethylcyclohexanecarboxylate (Baudy et al. (2009), *J. Med. Chem.* 52(3), 771-778) was reacted with 1,3-propanedisulfonic acid disilver salt (Example 31 (a)). Compound D5 was obtained (25.0 g, 72% yield) as a white solid. $^1$H NMR (CDCl$_3$, 500 MHz) δ in ppm 1.23-1.35 (m, 6H), 1.46 (m, 4H), 1.66 (m, 2H), 1.77 (m, 4H), 1.94 (m, 4H), 2.41 (m, 4H), 3.40 (t, J=7.5 Hz, 4H), 5.81 (s, 4H).

f) Compound D6:

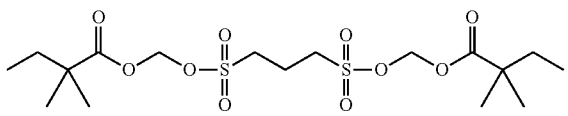 [SMILES: CCC(C)(C)C(=O)OCOS(=O)(=O)CCCS(=O)(=O)OCOC(=O)C(C)(C)CC]

Following the general procedure for the synthesis of oxomethyl disulfonate esters (Example 31 (b)), chloromethyl-2,2-dimethylbutenoate (Baudy et al. (2009), *J. Med. Chem.* 52(3), 771-778) was reacted with 1,3-propanedisulfonic acid disilver salt (Example 31 (a)). Compound D6 was obtained (2.0 g, 66% yield) as a colorless oil. $^1$H NMR (CDCl$_3$, 500 MHz) δ in ppm 0.86 (t, J=7.5 Hz, 6H); 1.21 (s, 12H); 1.61 (q, J=7.5 Hz, 4H); 2.42 (quint, J=7.0 Hz, 2H); 3.41 (t, J=7.0 Hz, 4H); 5.81 (s, 4H).

g) Compound D7:

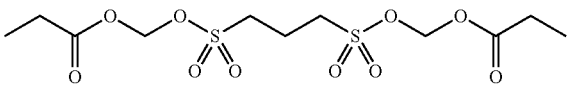 [SMILES: CCC(=O)OCOS(=O)(=O)CCCS(=O)(=O)OCOC(=O)CC]

Following the general procedure for the synthesis of oxomethyl disulfonate esters (Example 31 (b)), chloromethylpropanoate (Baudy et al. (2009), *J. Med. Chem.* 52(3), 771-778) was reacted with 1,3-propanedisulfonic acid disilver salt (Example 31 (a)). Compound D7 was obtained (13.2 g, 66% yield) as a white solid. $^1$H NMR (CDCl$_3$, 500 MHz) δ in ppm 1.91 (t, J=7.5 Hz, 6H); 2.42 (quint, J=7.0 Hz, 2H); 2.47 (q, J=7.5 Hz, 4H); 3.41 (t, J=7.0 Hz, 4H); 5.82 (s, 4H).

h) Compound D8:

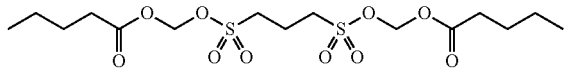 [SMILES: CCCCC(=O)OCOS(=O)(=O)CCCS(=O)(=O)OCOC(=O)CCCC]

Following the general procedure for the synthesis of oxomethyl disulfonate esters (Example 31 (b)), chloromethylpentanoate (Baudy et al. (2009), *J. Med. Chem.* 52(3), 771-778) was reacted with 1,3-propanedisulfonic acid disilver salt (Example 31 (a)). Compound D8 was obtained (1.8 g, 57% yield) as a white solid. $^1$H NMR (CDCl$_3$, 500 MHz) δ in ppm 0.93 (t, J=7.5 Hz, 6H); 1.37 (m, 4H); 1.65 (quint, J=7.0 Hz, 4H); 2.39-2.45 (m, 6H); 3.41 (t, J=7.0 Hz, 4H); 5.81 (s, 4H).

Example 33

Preparation of Compound C2

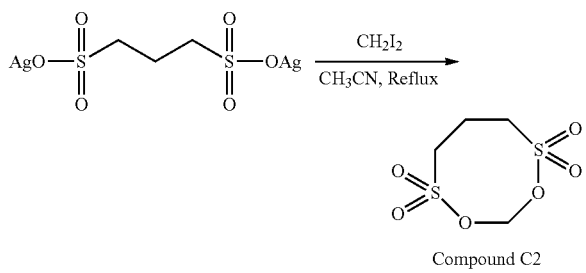

To a refluxing suspension of 1,3-propanedisulfonic acid disilver salt (Example 31 (a)) (60 g, 140 mmol) in acetonitrile (1 L) was added a solution of diiodomethane (17 mL, 210 mmol) in acetonitrile (20 mL) over 15 h (syringe pump). After the addition was completed, the mixture was refluxed for an additional 24 h, cooled down to room temperature and filtered over a pad of Celite™. The cake was washed with acetonitrile (2*100 mL) and the filtrate was concentrated in vacuo to about 150 mL. To this solution, 40 g of silica gel was added and the mixture was evaporated to dryness. The residue was loaded on a silica gel column and eluted with hexanes/ethyl acetate 80:20 to 50:50 to afford Compound C2 (22.6 g, 73% yield) as a white solid. $^1$H NMR (CDCl$_3$, 500 MHz) δ in ppm 2.54 (m, 2H), 3.60 (t, J=6.0 Hz, 4H), 5.80 (s, 2H).

Example 34

Preparation of Compound C3

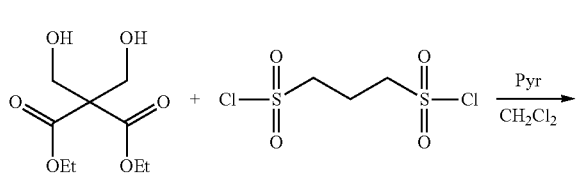

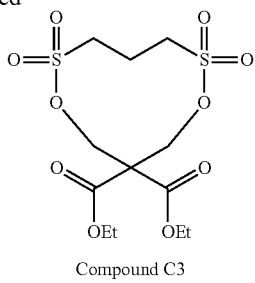

Compound C3

To a solution of commercial diethyl 2,2-bis(hydroxymethyl)propanedioate (0.91 g, 4.15 mmol) and pyridine (1.7 mL, 20.7 mmol) in dichloromethane (200 mL) was added 1,3-propanedisulfonyl dichloride (Example 1 (a)) (1 g, 4.15 mmol). The solution was refluxed for 3 days and concentrated in vacuo. The residue was purified by silica gel chromatography (hexanes/ethyl acetate 90:010 to 50:50) to afford Compound C3 (0.32 g, 20% yield) as a white solid. $^1$H NMR (CDCl$_3$, 500 MHz) δ in ppm 1.31 (t, J=7.0 Hz, 6H), 2.46 (m, 2H), 3.45 (m, 4H), 4.30 (q, J=7.0 Hz, 4H), 4.66 (s, 4H).

Example 35

General Synthetic Protocol for the Synthesis of Disulfonamides

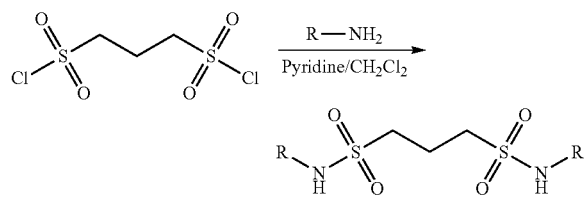

1,3-Propanedisulfonyl dichloride (Example 1(a)) (20 mmol) is added to a stirred solution of selected amine (40 mmol)) in a mixture of pyridine (10 mL) and dichloromethane (50 mL). The reaction mixture is stirred at room temperature for 15 h and then concentrated in vacuo. The residual material is purified by silica gel chromatography using a mixture of dichloromethane/methanol as eluant to yield the corresponding disulfonamide.

Example 36

Preparation of Compounds N12 and N14 a) Compound N12:

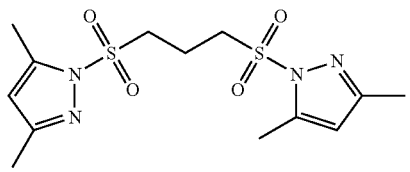 [SMILES: Cc1cc(C)n(S(=O)(=O)CCCS(=O)(=O)n2nc(C)cc2C)n1]

Following the general procedure for the synthesis of disulfonamides (Example 35), commercial 3,5-dimethylpyrazole was reacted with 1,3-propanedisulfonyl dichloride (Example 1 (a)). Compound N12 was obtained (0.73 g, 68% yield) as a white solid. $^1$H NMR (CDCl$_3$, 500 MHz) δ ppm 5.98 (s, 2H), 3.54 (t, J=7.0 Hz, 4H), 2.47 (s, 6H), 2.25 (s, 6H), 2.15 (q, J=7.0 Hz, 2H).

b) Compound N14:

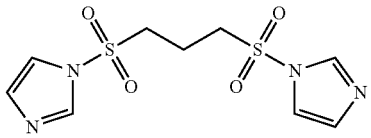 [SMILES: O=S(=O)(CCCS(=O)(=O)n1ccnc1)n1ccnc1]

Following the general procedure for the synthesis of disulfonamides (Example 35), commercial imidazole was reacted with 1,3-propanedisulfonyl dichloride (Example 1 (a)). Compound N14 was obtained (0.45 g, 53% yield) as a beige solid. $^1$H NMR (DMSO, 500 MHz) δ ppm 8.18 (s, 2H), 7.64 (s, 2H), 7.16 (s, 2H), 3.83 (t, J=7.5 Hz, 4H), 1.78 (q, J=7.5 Hz, 2H).

Example 37

Preparation of Compounds N15 and N16

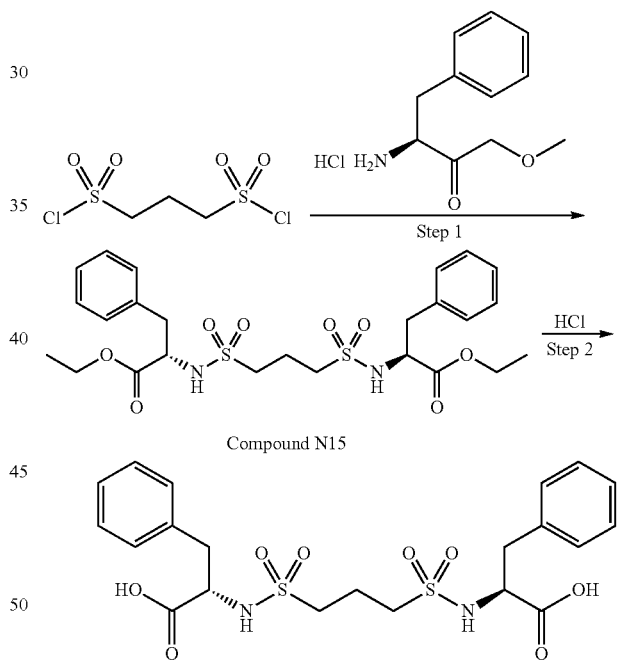

Compound N15

Compound N16

Step 1: Following the general procedure for the synthesis of disulfonamides (Example 35), commercial ethyl ester L-phenylalanine hydrochloride (1.8 g, 8.0 mmol) was reacted with 1,3-propanedisulfonyl dichloride (Example 1 (a)) (0.964 g, 4.0 mmol). Compound N15 was obtained (0.6 g, 28% yield) as an oil. $^1$H NMR (CDCl$_3$, 500 MHz) δ in ppm 1.25 (t, J=7.0 Hz, 6H), 2.04 (m, 2H), 2.73 (m, 2H), 2.91 (m, 2H), 3.04 & 3.14 (ABX, J=14.0 & 5.7 Hz, 4H), 4.18 (m, 4H), 4.34 (m, 2H), 5.07 (d, J=9.3 Hz, 2H), 7.17-7.32 (m, 10H).

Step 2: To a solution of Compound N15 from Step 1 (0.60 g, 1.1 mmol) in ethanol (10 mL) was added 6N aqueous hydrochloric acid (20 mL) and the mixture was stirred under reflux for 4 h. The mixture was cooled, evaporated to dryness and diluted in a 95:5 mixture of dichloromethane/methanol for purification by silica gel chromatography. Elution with a mixture of ethyl acetate/acetic acid (97:3) permitted to isolate Compound N16 (0.31 g, 57% yield) as a white solid. $^{1}$H NMR (DMSO, 500 MHz) δ in ppm 1.64 (quint, J=7.0 Hz, 2H), 2.47 (m, 2H), 2.60 (m, 2H), 2.78 (dd, J=13.5 & 9.5 Hz, 2H), 3.05 (dd, 13.5 & 5.5 Hz, 2H), 3.98 (m, 2H), 7.20-7.32 (m, 10H), 7.80 (d, J=9.0 Hz, 2H), 13.00 (bs, 2H).

Example 38

Preparation of Compounds N17 and N18(bis(trifluoroacetate)salt)

late the desired tert-butyl N-[1-benzyl-2-[3-[[2-(tert-butoxy-carbonylamino)-3-phenyl-propanoyl]sulfamoyl]propylsul-fonylamino]-2-oxo-ethyl]carbamate (0.9 g, 87% yield).

Step 3: To a solution of intermediate from Step 2 (0.90 g, 1.3 mmol) in dichloromethane (10 mL) was added trifluoroacetic acid (5 mL). The mixture was stirred at room temperature for 5 h and concentrated to dryness. Trituration using an ether/hexanes mixture allowed to isolate Compound N18(bis(trifluoroacetate)salt) (0.68, 72% yield) as a white solid. $^{1}$H NMR (D$_2$O, 500 MHz) δ in ppm 2.01 (quint, J=7.0 Hz, 2H), 3.06 & 3.15 (ABX, J=14.0 & 7.0 Hz, 4H), 3.29-3.42 (m, 4H), 4.07 (t, J=7.0 Hz, 2H), 7.15-7.30 (m, 10H).

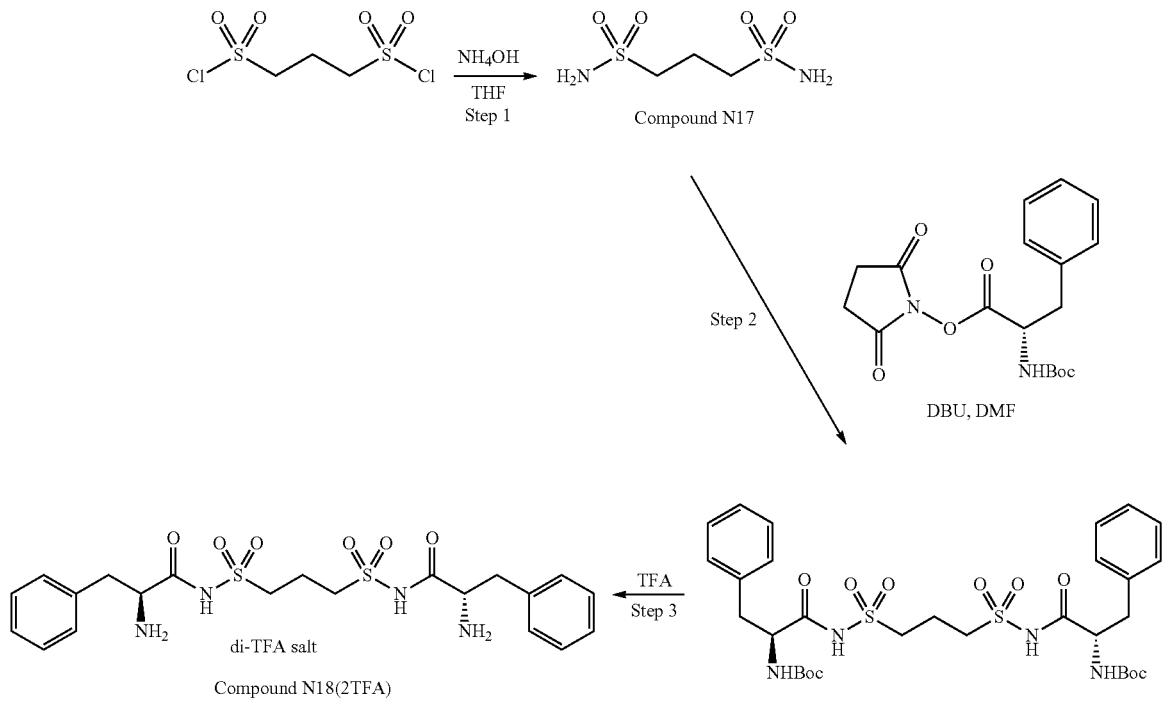

Step 1: To a stirred solution of 1,3-propanedisulfonyl dichloride (Example 1 (a)) (1.5 g, 6.2 mmol) in tetrahydrofuran (30 mL) was added 28% ammonium hydroxide (6 mL). The reaction was exothermic and was stirred for an additional hour at room temperature. The mixture was concentrated under vacuum, dissolved in a minimum amount of water/methanol, mixed with silica gel and evaporated to dryness. The silica gel support was applied on top of column for silica gel chromatography using as eluent a mixture of dichloromethane/methanol (70:30) to afford Compound N17 (0.30 g, 24% yield) as a white powder. $^{1}$H NMR (D$_2$O, 500 MHz) δ in ppm 2.19 (quint, J=7.0 Hz, 2H), 3.28 (t, J=7.0 Hz, 4H).

Step 2: To a solution of Compound N17 from Step 1 (0.303 g, 1.5 mmol) in DMF (20 mL) were added commercial N-[(1,1-dimethylethoxy)carbonyl]-L-phenylalanine, 2,5-dioxo-1-pyrrolidinyl ester (1.2 g, 3.3 mmol) and DBU (0.49 mL, 3.3 mmol). The mixture was stirred for 15 h, diluted with ethyl acetate and 1N HCl, and extracted three times with ethyl acetate. The combined organic layers were washed with water, dried over magnesium sulfate, filtered and filtrate concentrated in vacuo. The residue was purified by silica gel chromatography using hexanes/ethyl acetate (50:50) to iso- Example 39

In Vitro Stability of the Compounds of the Invention a) Water and Simulated Gastric Fluid Stability The objective of this test was to determine the stability of the prodrugs in simulated gastric fluid (SGF) and water at 37° C. up to 2 hours and in water at room temperature up to 24 hours. The stability was performed as indicated in Table 1.

TABLE 1

Temperatures and Sampling Summary

| Time-Points (hours) | SGF at 37° C. | dH$_2$O at 37° C. | dH$_2$O at room temperature |
|---|---|---|---|
| 0 | Yes | No | Yes |
| 1 | Yes | Yes | No |
| 2 | Yes | Yes | No |
| 24 | No | No | Yes |

Simulated gastric fluid and water samples were incubated in a shaking water bath at 37° C. for up to 2 hours. The compound (prodrug) was added at Time-point 0. At each selected time point (refer to table), sample aliquots were withdrawn and analyzed to determine the concentration of 1,3-propanedisulfonic acid (1,3PDS). The concentrations of 1,3PDS were calculated based on their respective peak area. The % appearance of 1,3PDS was determined by the amounts of compound determined at each time point compared to nominal concentration (100%) of 1,3PDS generated by 100% of the prodrug (equivalent concentration).

i) Simulated Gastric Fluid Preparation:

Amounts of 0.2 g of sodium chloride and 0.32 g of pepsin were weighted and transferred into a 100-mL volumetric flask. Approximately 50 mL of deionized water was added and the mixture well mixed. A volume of 700 µL of hydrochloric acid was added, and the volume completed to 100 mL with deionized water. The resulting mixture was transferred in a polypropylene bottle and pH measured (pH=1.5).

ii) Sample Preparation:

A fresh stock solution at approximately 2 mg/mL of the compound was prepared. One stability solution at 200 µg/mL in the SGF was prepared (sample referred to as Tube A). A stability solution at 200 µg/mL in deionized water was prepared (sample referred to as Tube B). Immediately after preparation, each 200 µg/mL solution was diluted in triplicates to 20 µg/mL in deionized water and analyzed using LC-MS/MS method (Time-point 0). Thereafter, the incubation of tubes A and B was continued in the shaking water bath at 37° C. for 1 and 2 hours while one aliquot of tube B was kept at room temperature for 24 hours. At each specific time point of incubation, 3 aliquots (triplicate) of 50 µL were removed, diluted in 450 µL of water and analyzed using LC-MS/MS method. In parallel, 3 reference samples of 1,3PDS at 100, 10 and 1 µg/mL were prepared, diluted in triplicate in water and injected at the beginning and at the end of the batch. These samples were considered as reference samples.

iii) Evaluation:

The concentrations of 1,3PDS were calculated based on response of the reference samples and their respective peak area response. The % appearance of 1,3PDS was determined by the amounts of compound determined at each time point compared to expected nominal concentration (100%) of 1,3PDS generated by 100% of the prodrug (equivalent concentration). The results of water stability are presented in Table 2 and simulated gastric fluid are presented in Table 3.

TABLE 2

Water Stability Results

| ID No | Conversion to 1,3PDS (%) | | | |
|---|---|---|---|---|
| | 0 h | 1 h | 2 h | 24 h |
| A6(Na) | 0.4 | 1.0 | 1.6 | 1.4 |
| A13 | 0.0 | 0.0 | 0.0 | 0.0 |
| A14 | 0.2 | 0.4 | 1.4 | — |
| A18(Na) | 12.8 | 23.0 | 28.4 | 15.8 |
| A26(Na) | 3.1 | 5.9 | 8.6 | 10.0 |
| A32(Na) | 0.0 | 0.1 | 0.1 | 0.0 |
| A51 | 13 | 14 | 18 | — |
| A52(K) | 7.0 | 14.6 | 18.8 | 21.3 |
| B13 | 0.3 | 0.4 | 0.4 | — |
| B14 | 0.0 | 0.0 | 0.0 | — |
| B23 | 0.0 | 0.0 | 0.0 | 0.0 |
| B30 | 0.0 | 0.0 | 0.0 | 0.0 |
| C1 | 50.3 | 57.3 | 63.1 | 61.2 |

TABLE 3

Simulated Gastric Fluid Stability Results

| ID No | Conversion to 1,3PDS (%) | | |
|---|---|---|---|
| | 0 h | 1 h | 2 h |
| A6(Na) | 0.3 | 1.0 | 1.6 |
| A13 | 0.0 | 0.0 | 0.0 |
| A14 | 0.2 | 0.3 | 0.4 |
| A18(Na) | 2.2 | 3.8 | 4.8 |
| A26(Na) | 2.7 | 5.8 | 8.4 |
| A32(Na) | 0.0 | 0.0 | 0.0 |
| A51 | 11 | 11 | 13 |
| A52(K) | 6.2 | 13.1 | 15.9 |
| B13 | 0.1 | 0.2 | 0.2 |
| B14 | 0.0 | 0.0 | 0.0 |
| B23 | 0.0 | 0.0 | 0.0 |
| B30 | 0.0 | 0.0 | 0.0 |
| C1 | 51.2 | 59.8 | 65.9 | b) Whole Blood Stability:

The objective of this test was to determine the stability of the prodrugs in fresh human whole blood at different timepoints (0, 0.5, 1, 4, 24 hours). Blood samples were incubated in a shaking water bath at 37° C. for up to 24 hours. The compound (prodrug) was added at Time-point 0, and sample aliquots were withdrawn and analyzed at each time point to determine the concentration of 1,3PDS. If possible, the loss of compound was determined by the amounts of compound determined at each time point compared to the amount determined at Time-point 0. To eliminate the conversion due to the matrix, a special Time-point 0 was prepared in pre-extracted blood sample.

i) Sample Preparation:

Approximately 2.5 mL of whole blood was incubated in a gently shaking water bath at 37° C. for 15 minutes. Two (2) mL of the pre-incubated whole blood were aliquoted in an eppendorf tube. A 100 µL aliquot of blood was removed and 100 µL of the compound Stock Solution was added. The solution was mixed by inversion. This sample was referred to as Tube A. The final concentration of the compound in tube A was approximately at 100 µg/mL. Immediately after mixing, 100 µL of Tube A was aliquotted into 3 different eppendorf tubes. These samples were extracted as described in the "Extraction Procedure" Section. These samples were referred to Time-point 0. Thereafter, the incubation of Tube A was continued in the shaking water bath at 37° C. for 0.5, 1, 4 and 24 hours. At each specific time point of incubation, aliquots (triplicate) of 100 µL were removed and extracted as described in the "Extraction Procedure" Section. To avoid potential further degradation of compound and/or possible degradation products, the aliquot extracts were kept on ice until analysis. After extraction, samples were analyzed using LC-MS/MS method.

ii) Extraction Procedure:

A volume of 300 µL of cold-ice acetonitrile was added to a 1.5 mL eppendorf tube and kept on ice until utilization. 100 µL of the sample to be extracted was added and the mix was vortexed (acetonitrile and blood). The sample was centrifuged at 16250×g (13200 rpm on IEC centrifuge with eppendorf rotor) for 5 minutes. A volume of 250 µL of the supernatant was transferred to another tube and evaporated to dryness under a nitrogen stream. The residue was reconstituted with the mobile phase. This sample was then analyzed according to 1,3PDS specific methods.

iii) Evaluation:

The concentrations of 1,3PDS were calculated based on the nominal concentration of the calibration standards and their respective peak area ratio. A linear regression using a weight of $1/x^2$ is used to derive the concentration of 1,3PDS. The % appearance of 1,3PDS was determined by the amounts of compound determined at each time point compared to nominal concentration (100%) of 1,3PDS generated by 100% of the prodrug (equivalent concentration). The results obtained are summarized in Table 4 below.

TABLE 4

Human Whole Blood Stability Results

| ID No | Conversion to 1,3PDS (% by molar ratio) | | | | |
|---|---|---|---|---|---|
| | 0 h | 0.5 h | 1 h | 4 h | 24 h |
| A6(Na) | 0.5 | 0.7 | 0.8 | 1.2 | 4.7 |
| A13 | 12.8 | 44.0 | 47.8 | 61.7 | 62.3 |
| A14 | 1.6 | 2.5 | 3.0 | 5.8 | 23.3 |
| A18(Na) | 9.5 | 16.4 | 18.3 | 39.8 | 71.9 |
| A26(Na) | 11.1 | 12.2 | 14.5 | 14.5 | 31.6 |
| A32(Na) | 0.1 | 0.1 | 0.2 | 0.4 | 2.0 |
| A51 | 23.7 | 21.8 | 26.5 | 34.4 | 63.6 |
| A52(K) | 21.7 | 24.4 | 29.0 | 32.8 | 55.6 |
| B13 | 5.5 | 106.1 | 91.1 | 67.0 | 73.2 |
| B14 | 0.1 | 5.0 | 17.0 | 44.9 | 55.1 |
| B23 | 1.2 | 103.4 | 98.5 | 59.0 | 66.5 |
| B30 | BLLQ | 0.1 | 0.2 | 2.0 | 15.0 |
| C1 | AULQ | AULQ | AULQ | AULQ | AULQ |

BLLQ: Below lower limit of quantitation
AULQ: Above upper limit of quantitation

In summary, the stability results showed that the compounds act as prodrugs and liberate 1,3PDS either in gastric fluid or in whole blood. In fact most of them were found to be cleaved in whole blood to a greater extent than in gastric fluid or water, even some released 1,3PDS only in whole blood while being relatively stable in water and simulated gastric fluids.

Example 40

Preparation of Dosing Formulation a) Dosing Vehicle for Formulation:

Double processed tissue culture water (Sigma, W3500) was used for all the formulation prepared in water. The vehicle 0.5% Methocel™ (Methocel™ K4M, Dow Chemical, #002891) in water (double processed tissue culture water) used for preparation of all Methocel™ formulations was prepared according to literature procedures. The 2% benzyl alcohol in corn oil was prepared by adding benzyl alcohol to corn oil according to proportions, which was used for the preparation of oil formulation of prodrugs.

b) Dosing Formulation Concentration:

For 1,3PDS(2Na), the concentration in the dosing formulation was standardized to such a level that the dose would be 100 mg/kg (or 0.4 mmol/kg) for in vivo protocol specified dosing volume in a particular animal species. For a prodrug, the weight of sample in the dosing formulation varied based on molecular weight in such a way that equimolar dose (0.4 mmol/kg) for all the prodrugs would be administered when given same volume of dosing formulation to the animals. The dosing volume used for was 10 mL/kg for rats and monkeys, and 5 mL/kg for ferrets; or the concentration of dosing formulation was 0.04 mmol/mL for rats and monkeys, and 0.08 mmole/mL for ferrets. The vehicles used can either be water, 0.5% Methocel™ in water or 2% benzyl alcohol in corn oil.

The dosing solution can either be a solution, a suspension or an emulsion. For different levels of doses, the amounts of the compounds used in the dosing formulation preparation were adjusted accordingly.

c) Dosing Formulation Preparation:

For compounds soluble in the selected vehicle, the appropriate amount was added to a stirring solution of vehicle. The mixture was prepared 30 min prior dosing.

For compound insoluble in the selected vehicle, suspension (for solid) or emulsion (for oil) was prepared using a planetary micro mill (Pulverisette 7, Fritsch). The vehicles used are either 0.5% Methocel™ in water or 2% benzyl alcohol in corn oil. The appropriate amount of compound was added, in portion, to the selected vehicle and the mixture was processed using the planetary micro mill for 10 min at 800 rpm. The obtained suspension or emulsion was kept under stirring using a stirring bar until dosing. The mixture could be prepared 30 min to 18 h prior dosing.

Example 41

In Vivo Protocols a) PK Study in Rats

One group of four male Sprague-Dawley rats of age 7-9 weeks (body weight of 200-300 g) were fasted for 15 to 17 h before being dosed through oral gavage administration with the dosing solution/suspension prepared from test compounds according to Example 40 at a dose specified in Table 5 in a concentration adjusted to a dosing volume of 10 ml/kg-body weight. Food was supplied two hours post dose. Blood samples (200 μL blood) were collected into Sarstedt micro tubes (EDTA $K_3E$/0.5 mL) from the jugular vein of each animal (4 animals/group) at pre-dose and at the following time-points of post-dose: 15 min., 30 min., 1 h, 2 h, 4 h, 6 h, 8 h, 12 h, and 24 h. The collected blood samples were kept on ice and then centrifuged at 4° C. at a minimum speed of 3000 rpm (1620G) for 10 min to prepare the plasma samples. The plasma samples were stored at −80° C. until analysis. An aliquot of dosing formulation was also taken prior to the dosing and stored at −20° C. for analysis.

TABLE 5

1,3PDS AUC Results in Rats after Oral Administration of Prodrugs

| ID No[1] | Vehicle[2] | Dose[3] (mg/kg) | 1,3PDS $AUC_{0-Tlast}$ (ng·h/mL)[7] |
|---|---|---|---|
| 1,3PDS(2Na) | 1 | 100 | 40374 |
| 1,3PDS(2Na) | 2 | 100 | 32104 |
| A4 | 2 | 116 | 14855 |
| A6(Na) | 1 | 119 | 650 |
| A13 | 1 | 185 | 25817 |
| A14 | 1 | 161 | 25972 |
| A16(Na) | 2 | 188 | 30000 |
| A18(Na) | 1 | 189 | 26146 |
| A20(Na) | 1 | 195 | 19225 |
| A23(Na) | 2 | 163 | 19387 |
| A26(Na) | 1 | 154 | 5456 |
| A29(Na) | 1 | 142 | 3088 |
| A30(Na) | 1 | 167 | 14040 |
| A32(Na) | 1 | 144 | 1097 |
| A51 | 1 | 175 | 29713 |
| A51 | 2 | 175 | 23270 |
| A52(K) | 1 | 230 | 18109 |
| A53(Na) | 1 | 159 | 5778 |
| A58 | 1 | 127 | 4734 |
| A60(Na) | 2 | 131 | 45530 |
| A61 | 2 | 133 | 49388 |
| A62(Na) | 2 | 167 | 741 |

TABLE 5-continued 1,3PDS AUC Results in Rats after Oral Administration of Prodrugs

| ID No[1] | Vehicle[2] | Dose[3] (mg/kg) | 1,3PDS AUC$_{0-Tlast}$ (ng·h/mL)[7] |
|---|---|---|---|
| A63(Na) | 2 | 131 | 2013 |
| A64 | 2 | 155 | 13501 |
| A65(Na) | 2 | 167 | 595 |
| A66(Na) | 2 | 179 | BLLQ |
| A68(Na) | 2 | 131 | BLLQ |
| A69 | 1 | 144 | 23423 |
| A69 | 2 | 144 | 9567 |
| A70(Na) | 2 | 185 | 98.0 |
| A71(Na) | 2 | 135 | 2022 |
| A72(Na) | 2 | 135 | 2602 |
| A73(Na) | 2 | 135 | 5582 |
| B11 | 2 | 143 | 5682 |
| B13 | 3 | 288 | 11770 |
| B14 | 3 | 240 | 15084 |
| B23 | 2 | 245 | 6033 |
| B29 | 2 | 92[4] | 20670 |
| B29 | 2 | 184 | 37717, 47664 |
| B29 | 2 | 461[5] | 65070 |
| B29 | 2 | 921[6] | 98321 |
| B29 | 3 | 184 | 45585 |
| B30 | 3 | 234 | 36903 |
| B51(2TFA) | 1 | 359 | 10756 |
| B58 | 2 | 81[4] | 31865 |
| B58 | 2 | 162 | 52982, 53724 |
| B58 | 2 | 809[6] | 188592 |
| B59 | 2 | 187 | 5060 |
| B60 | 2 | 195 | 24258 |
| B61 | 2 | 173 | 33340, 43365 |
| B62 | 2 | 207 | 10566 |
| B63 | 2 | 229 | 4028 |
| B64 | 2 | 195 | 20687 |
| B65 | 2 | 205 | 14372 |
| B66 | 2 | 207 | 10802 |
| B67(2HCl) | 2 | 214 | 44526, 46223 |
| B68 | 2 | 195 | 14178 |
| B70 | 2 | 235 | 128 |
| B71 | 2 | 147 | BLLQ |
| B72 | 2 | 163 | BLLQ |
| B73 | 2 | 207 | 1472 |
| B74 | 2 | 234 | 753 |
| B75 | 2 | 207 | 31039, 29201 |
| B76 | 2 | 86[4] | 22150 |
| B76 | 2 | 171 | 36025, 36606 |
| B76 | 2 | 857[6] | 131932 |
| B77 | 2 | 86[4] | 19175 |
| B77 | 2 | 171 | 57973, 38230 |
| B77 | 2 | 429[5] | 30726 |
| B78 | 2 | 171 | 36767 |
| B80 | 2 | 171 | 44258 |
| B81 | 2 | 147 | 9572 |
| B82 | 2 | 195 | 13535 |
| B83 | 2 | 184 | 499297 |
| B83 | 2 | 184 | 522308 |
| B84 | 2 | 158 | 2953 |
| B85 | 2 | 184 | 222417 |
| B87 | 2 | 173 | 37909 |
| C1 | 1 | 74 | 41103 |
| C1 | 2 | 74 | 34219 |
| C1 | 3 | 74 | 45637 |
| C2 | 2 | 43[4] | 29800 |
| C2 | 2 | 86 | 66542, 58313 |
| C2 | 2 | 216[5] | 142985 |
| C3 | 2 | 155 | 10049 |
| D1 | 2 | 173 | 46036, 44860 |
| D1 | 2 | 865[6] | 249360 |
| D1 | 3 | 173 | 54987 |
| D2 | 2 | 189 | 38053 |
| D3 | 2 | 81[4] | 26199 |
| D3 | 2 | 162 | 51842, 61390 |
| D3 | 2 | 809[6] | 223842 |
| D4 | 2 | 175 | 47144 |
| D5 | 2 | 194 | 57353 |
| D6 | 2 | 184 | 37036 |
| D7 | 2 | 151 | 59543, 57502 |
| D7 | 2 | 753[6] | 270641 |
| D8 | 2 | 173 | 51253 |
| G4 | 1 | 119 | 1457 |
| P1(2Na) | 2 | 86 | BLLQ |

[1] A compound can be tested as the parent or a salt form. When the compound is in a salt form, the specific salt form is indicated in the bracket following the code number: Na, sodium salt; 2Na, disodium salt; K potassium salt; 2HCl, dichloride salt; 2TFA, bis(trifluoroacetate) salt.
[2] Dosing vehicle used: 1, water; 2, 0.5% Methocel™ in water; 3, 2% benzyl alcohol in corn oil
[3] Dose of 1,3PDS prodrugs is molar equivalent to 100 mg/kg 1,3PDS(2Na) except when specified otherwise
[4] Dose is equimolar to 50 mg/kg 1,3PDS(2Na)
[5] Dose is equimolar to 250 mg/kg of 1,3PDS(2Na)
[6] Dose is equimolar to 500 mg/kg of 1,3PDS(2Na)
[7] Two values indicate results from two independent experiments.
BLLQ = below low limit of quantification.

b) PK Study in Monkeys

One group of four non-naïve cynomolgus monkeys (2 males and 2 females) received a single dose of a compound by oral gavage administration with at least a 7-day washout period between each experiment. The dosing formulation was prepared according to Example 40. A representative dosing formulation (5 mL) was taken prior dosing for analysis. The dosing formulation was administered using a gavage tube attached to a plastic syringe. The dosing volume was 10 mL/kg for all animals; and the actual dosing volume was calculated and adjusted according the most recent body weight of each animal. The animals were housed individually in stainless steel monkey cages at a conventional animal facility, maintained under 12-h light/dark cycle at 24±3° C. and 50±20% relative humidity. All animals had access to 5 cookies (Harlan 25% Protein Primate Diet #2055) in the morning (at about 07:45) and 5 cookies in the afternoon (at about 16:30) except on the morning of dosing where the morning cookies were given at least 4 hours after the dose. Maximum allowable concentrations of contaminants in the diet (e.g. heavy metals, alfatoxin, organophosphate, chlorinated hydrocarbons and PCB's) were controlled and routinely analyzed by the manufacturer. Reverse osmosis water was available ad libitum at all times. In addition, all animals had access to a daily enrichment diet (e.g. Prima treats, ice with fruits, popcorn, fruits, vegetables, peanuts, pasta, fruit crunchies or fruity gems). However, no treats were given to any animals within 4 hours of dosing. The animals were acclimated to the gavage procedure for 3 days during the 7-day pretreatment period. Thereafter, the animals were acclimated to the oral gavage procedure only if they are more than 7 days between administrations of 2 compounds. Prior to the first dosing, four (4) animals (2 males and 2 females) were assigned to the study. Any animal with unacceptable pretreatment data (i.e. clinical signs, body weight) would not be included in the study. All animals were subjected to a detailed physical examination once during the 7-day pretreatment period and weekly thereafter. Cage-side clinical signs (ill, health, behavioral changes, etc.) were recorded once daily during the treatment period. Body weights were recorded for all animals once during the 7-day pretreatment period and weekly thereafter. All animals were restrained using a sling apparatus from the completion of the oral gavage until a maximum of 1 hour post-dose to facilitate blood collection. All animals were then returned to their respective housing cage for the remaining blood collection period.

Blood samples (approximately 1.0 mL each) were collected via the femoral vein from each animal at the following time-points: Pre-dose, 15, 30 min., 1, 2, 4, 6, 8, 12 and 24 h post-dose. Any deviations in blood sampling times were documented in the report. For each time-point, blood samples were collected and split into two tubes containing $K_3$-EDTA. One series of tubes (for plasma samples) were kept on wet ice pending centrifugation (maximum 30 minutes). Samples were centrifuged under refrigeration (4° C.) at a minimum speed of 3000 rpm for 10 minutes. Plasma were harvested into polypropylene tubes, immediately placed on dry ice and stored frozen (at approximately –80° C.) until shipment. The second series of tubes (whole blood) were immediately placed on dry ice and stored frozen until shipment and analysis.

TABLE 6

PK Parameters for 1,3PDS after Oral Administration of Prodrugs to Monkeys[1]

| ID No[2] | Dose[3] (mg/kg) | $C_{max}$ (ng/mL) | $T_{max}$ (h) | $AUC_{0-Tlast}$ (ng·h/mL) |
|---|---|---|---|---|
| 1,3PDS(2Na) | 100 | 1933 | 1.0 | 19573 |
| A23(Na) | 172 | 7818 | 4.0 | 51197 |
| A51 | 175 | 10308 | 2.0 | 26480 |
| B75 | 207 | 9180 | 1.5 | 37280 |
| B76 | 171 | 21846 | 2.0 | 98971 |
| B77 | 171 | 7440 | 2.0 | 57079 |
| D5 | 194 | 3933 | 4.0 | 26369 |

[1]Pharmacokinetic parameter values are mean except for Tmax for which the median is presented
[2]See the footnote 1 under Table 5.
[3]Dose of prodrugs is molar equivalent to 100 mg/kg 1,3PDS.

c) In Vivo Study in Ferrets

One group of three male non-naïve ferrets (domestic strain, >16 weeks, >1.2 Kg) were starved for approximately 1.5 h prior to administration of a dosing formulation. Food was given 2 hours post dose. All animals were dosed with the dosing formulation of a compound by oral gavage administration at dose level of 0.4 mmole/kg either in 0.5 Methocel™ or in water. The dosing volume was adjusted to 5 mL/kg. Clinical signs were recorded throughout the study period. Blood samples (200 μl of blood) were collected, from the jugular vein from each animal (3 animals/group) at time-point of 15 min, 30 min, 1, 2, 4, 6, 8 and 12 h post dose, into Sarstedt micro tubes (EDTA $K_3E/0.5$ ml), kept on ice until centrifugation at 4° C. at a minimum speed of 3000 rpm (1620G) for 10 min, to prepare plasma samples. Plasma samples were stored frozen at –80° C. pending transfer to analysis. An aliquot of dosing solution (0.5 mL) was taken prior to dosing and stored frozen at –20° C. pending transfer to analysis. Animals used for multiple studies after a wash out of a minimum twelve day period.

Prodrugs evaluated in ferrets were Compounds A23(Na), A51, A61, B29, B58, B75, B76, B77, B82, B83, C2, D1, D3, D5, and D7. Compounds A23(Na), A51, A61, B29, B76, B77, B82, and B83 were all safe prodrugs and showed no clinical signs at standard dose (0.04 mmol/kg) after oral administration. After administration of Compound B75, 2 out of 3 animals showed abdomen scratching but recovered after 1 h. Administration of B58 caused animal vomiting. Compound C2 showed severe toxicity and all the three animals became sick and had to be killed 4 days after compound administration. Administration of Compounds D1, D3, D5, and D7 caused different side effects, ranging from green face (D1) to abdominal contracting and/or vomiting (D3, D5, and D7).

d) Rat Urine Collection Experiment

Animals (one group of four), dose, and the compound administration were the same as described in Example 41 (a). Food was given 2 h post dose. Following prodrug administration, animals were housed individually in metabolic cage; and urine samples were collected from each animal, one pre-dose and one during the period of the first 24 h post-dose. Urine sample was collected in pre-weighed polypropylene tube over dry-ice, and then stored at –80° C. immediately following collection pending transfer to analysis. An aliquot of dosing solution (0.5 mL) was taken prior to dosing and stored frozen at –20° C. pending transfer to analysis.

TABLE 7

1,3PDS Urinary Excretion after Oral Administration of Prodrugs

| ID No[1] | Dose (mg/kg)[2] | $F_e$ (% dose)[3] |
|---|---|---|
| 1,3PDS(2Na) | 100 | 54.2, 49.1 |
| A23(Na) | 163 | 44.9 |
| A29(Na) | 142 | 7.8 |
| B29 | 183 | 69.0 |
| B58 | 162 | 87.5 |
| B61 | 173 | 72.1 |
| B68 | 195 | 32.7 |
| B76 | 171 | 22.4, 23.4 |
| B77 | 171 | 7.4, 6.7 |
| B83 | 184 | 45.5 |
| C2 | 86 | 80.4 |
| D1 | 173 | 71.1 |
| D3 | 162 | 79.8 |
| D7 | 151 | 85.2 |

[1]See footnote 1 under Table 5.
[2]All the compounds were administrated orally at 0.4 mmole/kg (equivalent to 100 mg/kg dose of 1,3PDS(2Na)). All the compounds were dosed in 0.5% Methocel™.
[3]$F_e$ is calculated from the molar amount of 1,3PDS excreted in urine divided by the molar amount of prodrug administrated, expressed in percentage. Two values indicate two independent experiments.

Example 42

Plasma and Urine Sample Analysis a) Plasma Sample Analysis 1,3PDS was extracted from an aliquot of rat, mouse, ferret or monkey plasma using protein precipitation and then injected into a liquid chromatograph equipped with a tandem mass spectrometry detector. Quantification was done by peak area ratio method. A weighted ($1/X^2$) linear regression was performed to back calculate the concentration of the analyte. On the day of analysis, 1 standard curve, a minimum of 2 replicates of each QC level and the appropriate study plasma samples were analyzed using the following step:
  Vortex the samples.
  Aliquot 25 μL of each sample into separate 1.5-mL polypropylene tubes.
  Add 100 μL of ISWS in appropriate samples.
  Add 150 μL of chilled acetonitrile and vortex for a few seconds.
  Centrifuge at 13200 rpm at room temperature for 5 minutes.
  Transfer the supernatant into a 96-well polypropylene collection plate and evaporate to dryness (approximately 20 minutes).
  Reconstitute the residue with 400 μL of $dH_2O$ and vortex the plate.
  Centrifuge the plate at 2000 rpm for 2 minutes at room temperature.
  Inject samples onto the LC-MS/MS.

b) Urine Sample Analysis 1,3PDS was extracted from an aliquot of urine sample using sample dilution. The diluted sample was then injected into a liquid chromatograph equipped with a tandem mass spectrometry detector. Quantitation was done by peak area ratio method. A weighted (1/X²) Quadratic regression was performed to back calculate the concentration of the analyte. On the day of analysis, 1 standard curve, a minimum of 2 replicates of each QC level and the appropriate study plasma samples were analyzed using the following step:
- Vortex the samples.
- Aliquot 25 µL of each sample into separate 50-mL polypropylene tubes.
- Add 100 µL of ISWS in appropriate samples.
- Add 50 mL of water and vortex adequately.
- Transfer 400 µL of the solution into a 96-well polypropylene collection plate.
- Centrifuge the plate at 2000 rpm for 2 minutes at room temperature.
- Inject samples onto the LC-MS/MS.

Example 43

PK Data Analysis

For the various pharmacokinetic studies conducted in rats, ferrets and monkeys, plasma (and blood) concentration-time data for the prodrug and 1,3PDS were analyzed by non-compartmental analysis (NCA) using the software program WinNonlin® Professional Version 5.2.1. In order to conduct the NCA, at least 3 measurable concentrations had to be available in a concentration-time profile. The following pharmacokinetic parameters were determined for plasma (or blood) data: $C_{max}$, $T_{max}$, $AUC_{0-Tlast}$, $AUC_{0-\infty}$, $\lambda_z$, and $T_{1/2}$. Since the prodrugs and 1,3PDS were administered at equimolar doses, the effect of the prodrugs on the bioavailability of 1,3PDS was assessed by comparing the $C_{max}$ and AUC of 1,3PDS after administering a prodrug with that after administering 1,3PDS.

Example 44

Bacterial Mutation Tests (Ames Test)

Bacterial mutation tests were performed at Charles River Laboratories to evaluate the mutagenic potential of various prodrugs. *Salmonella typhimurium* strains (TA1535, TA1537, TA98, TA100) and *Escherichia coli* strain WP2 uvrA were treated with prodrugs at concentrations ranging from 1.58 to 5000 µg/plate in the presence and absence of a supplemented liver fraction (S9 mix) using the pre-incubation version of the bacterial mutation test. All concentrations of each compound were evaluated in triplicate. Bacteria were incubated with standard positive control agents, and the response of the various bacterial strains to these agents confirmed the sensitivity of the test system and the activity of the S9 mix.

TABLE 8

Results of Bacterial Mutation Tests

| ID No[1] | Vehicle | Result In presence of S9 | Result In absence of S9 |
|---|---|---|---|
| A23(Na) | DMSO | Negative | Negative |
| A29(Na) | Water | Positive | Negative |
| A51 | Water | Negative | Negative |
| A61 | Water | Positive | Positive |
| B29 | DMSO | Positive | Negative |
| B58 | DMSO | Positive | Positive |
| B68 | DMSO | Negative | Negative |

TABLE 8-continued

Results of Bacterial Mutation Tests

| ID No[1] | Vehicle | Result In presence of S9 | Result In absence of S9 |
|---|---|---|---|
| B75 | DMSO | Negative | Negative |
| B76 | DMSO | Negative | Negative |
| B77 | DMSO | Negative | Negative |
| B78 | DMSO | Negative | Negative |
| B83 | DMSO | Negative | Negative |

[1]See footnote 1 below Table 5.

It is understood that the examples and embodiments described herein are for illustrative purposes only and that various modifications or changes in light thereof will be suggested to persons skilled in the art and are to be included within the spirit and purview of this application and scope of the appended claims. Any publication, document, patent, patent application or publication referred to herein should be construed as incorporated by reference each in their entirety for all purposes.

The invention claimed is:

1. A compound of Formula II:

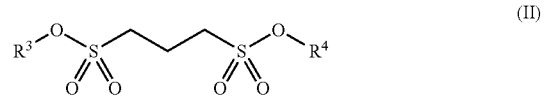

(II)

wherein, $R^3$ is selected from hydrogen and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

$R^4$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl;

wherein at least one of $R^3$ and $R^4$ is a group selected from Formula B, E and F:

(B)

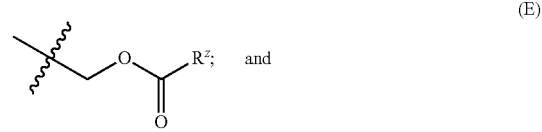

(E)

(F)

wherein, $R^6$, $R^7$ and $R^8$ are each independently a substituted or unsubstituted group selected from $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, $C_6$-$C_{10}$aryl, $C_5$-$C_{10}$heteroaryl, $NH_2$, and $NHC(O)OC_1$-$C_6$alkyl; or $R^7$ and $R^8$ are taken together with their adjacent carbon atom to form a group selected from $C_3$-$C_8$cycloalkyl and $C_3$-$C_8$heterocycloalkyl; or $R^6$, $R^7$ and $R^8$ are taken together with their adjacent carbon atom to form a $C_4$-$C_{10}$cycloalkyl fused ring, a $C_4$-$C_{10}$heterocycloalkyl fused ring, or a $C_5$-$C_{10}$heteroaryl;

$R^{22}$ is a hydrogen atom or a group selected from $C_1$-$C_6$alkyl, $C(O)OH$, or $C(O)OC_1$-$C_6$alkyl;

W—Y—Z is selected from $C(O)OCH_2$, $OC(O)CH_2$, $CH_2C(O)O$, and $CH_2OC(O)$;

$R^w$, $R^x$, and $R^y$ are each independently selected from a hydrogen atom or a substituted or unsubstituted $C_1$-$C_3$alkyl group, or $R^w$ and $R^x$ are taken together with their adjacent carbon atoms to form a double bond;

$R^z$ is a substituted or unsubstituted group selected from $C_1$-$C_{12}$alkyl, $C_2$-$C_{12}$alkenyl, $C_2$-$C_{12}$alkynyl, $C_3$-$C_{15}$ cyclo alkyl, $C_3$-$C_{15}$heterocycloalkyl, $C_6$-$C_{15}$aryl, $C_5$-$C_{15}$heteroaryl, $OC_1$-$C_{12}$alkyl, $OC_2$-$C_{12}$alkenyl, $OC_2$-$C_{12}$ alkynyl, $OC_3$-$C_{15}$ cycloalkyl, $OC_3$—$OC_{15}$heterocycloalkyl, $OC_6$-$C_{15}$aryl, and $OC_5$-$C_{15}$heteroaryl; and k is an integer selected from 0, 1 and 2;

or a pharmaceutically acceptable salt or solvate thereof.

2. The compound of claim 1, wherein $R^3$ is a substituted or unsubstituted group selected from $C_1$-$C_{12}$ alkyl, $C_2$-$C_{12}$ alkenyl, $C_2$-$C_{12}$alkynyl, $C_3$-$C_{15}$ cycloalkyl, $C_3$-$C_{15}$heterocycloalkyl, $C_6$-$C_{15}$ aryl, and $C_5$-$C_{15}$heteroaryl.

3. The compound of claim 1, wherein at least one of $R^3$ and $R^4$ is a group of Formula B.

4. The compound of claim 3, wherein said $R^{22}$ is $C_2$-$C_6$alkyl, or wherein said $R^{22}$ is $C_3$-$C_5$alkyl, or wherein said $R^{22}$ is a $C_3$-$C_4$alkyl.

5. The compound of claim 3, wherein $R^6$, $R^7$ and $R^8$ are each independently a substituted or unsubstituted group selected from $C_1$-$C_6$alkyl, $C_2$-$C_6$alkenyl, $C_2$-$C_6$alkynyl, $C_3$-$C_6$cycloalkyl, $C_3$-$C_6$heterocycloalkyl, $C_6$-$C_{10}$aryl, and $C_5$-$C_{10}$heteroaryl; or $R^7$ and $R^8$ are taken together with their adjacent carbon atom to form a group selected from $C_3$-$C_8$cycloalkyl and $C_3$-$C_8$heterocycloalkyl; or $R^6$, $R^7$ and $R^8$ are taken together with their adjacent carbon atom to form a $C_4$-$C_{10}$cycloalkyl fused ring group, a $C_4$-$C_{10}$heterocycloalkyl fused ring group, or a $C_5$-$C_{10}$heteroaryl.

6. The compound of claim 3, wherein $R^6$ is a group of Formula C:

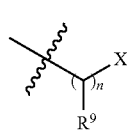

(C)

wherein, $R^9$ is, separately in each occurrence, selected from hydrogen, hydroxyl, $NH_2$, $NHR^{11}$, $N(R^{11})_2$, $NHC(O)R^{11}$, halogen, cyano, $C(O)OH$, $C(O)OR^{11}$, $OR^{11}$, $OC(O)R^{11}$, $OC(O)OR^{11}$, trifluoromethyl, nitro, and a substituted or unsubstituted group selected from $C_1$-$C_6$alkyl, $C_3$-$C_6$cycloalkyl, $C_3$-$C_6$heterocycloalkyl, $C_6$aryl, and $C_5$-$C_6$heteroaryl;

X is selected from the group consisting of OH, $NH_2$, $NO_2$, CN, SH, $C(O)OH$, $C(O)OR^{12}$, $OC(O)OR^{12}$, $NHC(O)OR^{12}$, $SC(O)OR^{12}$, $P(O)(OH)_2$, $P(O)(OR^{12})_2$, $P(O)(OR^{12})(OH)$, $OC(O)R^{13}$, $OC(O)NHR^{13}$, $SC(O)R^{13}$, $C(O)R^{14}$, and $NHR^{15}$;

n is an integer selected from 1, 2 and 3;

$R^{11}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl and benzyl;

$R^{12}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl, benzyl, $CH_2R^{16}$, and $CH(C_1$-$C_6$alkyl$)R^{16}$;

$R^{13}$ is a substituted or unsubstituted group selected from $C_1$-$C_6$alkyl, $C_3$-$C_6$cycloalkyl, $C_3$-$C_6$heterocycloalkyl, $C_6$aryl, $C_5$-$C_6$heteroaryl, and benzyl;

$R^{14}$ is the residue of a natural or unnatural N-coupled amino acid having a protected or unprotected carboxyl end;

$R^{15}$ is the residue of a natural or unnatural C-coupled amino acid having a protected or unprotected amino end; and $R^{16}$ is selected from the group consisting of $OC(O)C_1$-$C_6$alkyl and $OC(O)OC_1$-$C_6$alkyl.

7. The compound of claim 6, wherein X is selected from the group consisting of OH, $NH_2$, SH, $C(O)OH$, $C(O)OR^{12}$, $OC(O)OR^{12}$, $NHC(O)OR^{12}$, $SC(O)OR^{12}$, $OC(O)R^{13}$, $OC(O)NHR^{13}$, $SC(O)R^{13}$, $C(O)R^{14}$, and $NHR^{15}$.

8. The compound of claim 1, wherein at least one of $R^3$ and $R^4$ is a group of Formula E or Formula F.

9. The compound of claim 1, wherein said compound is selected from:

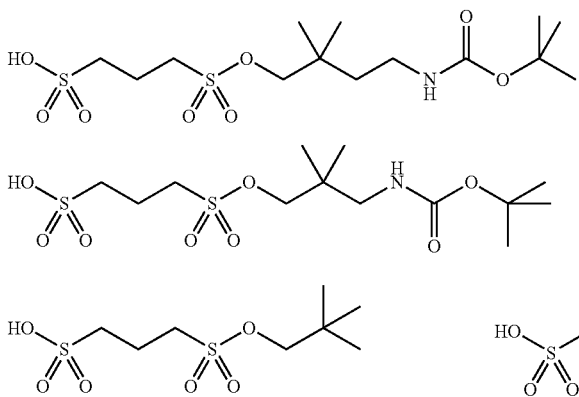

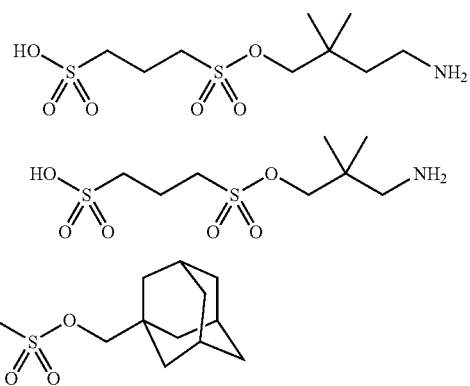

131
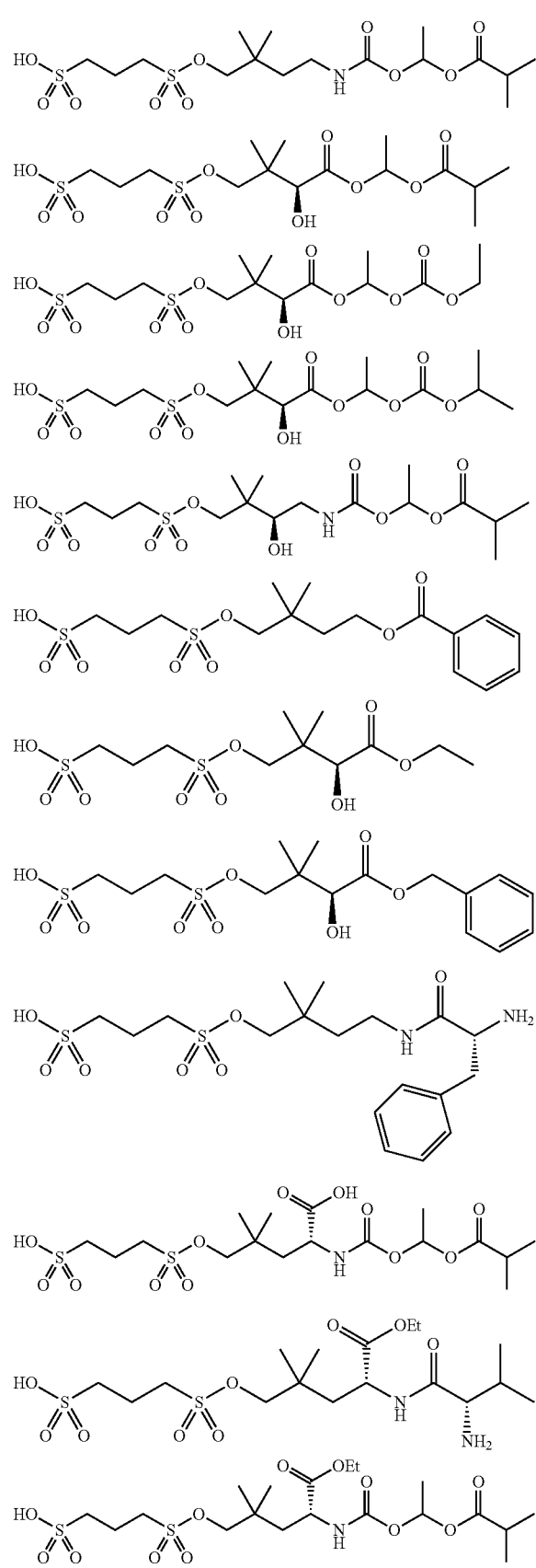
132
-continued
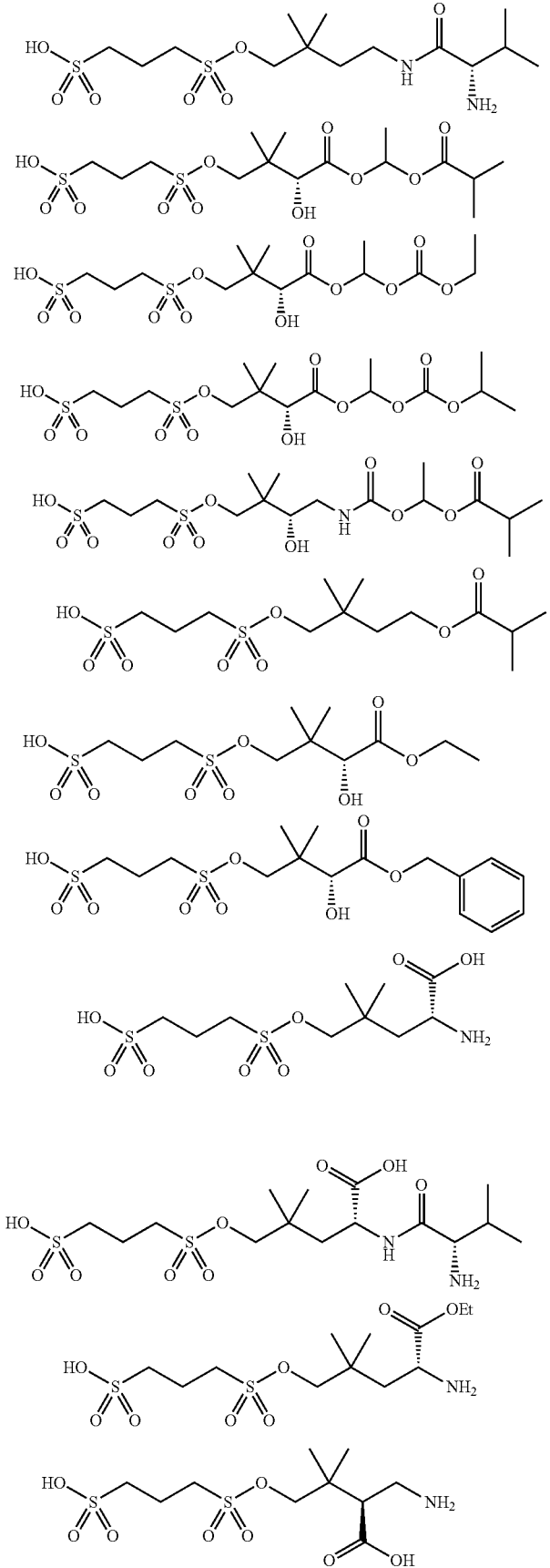

133 134
-continued
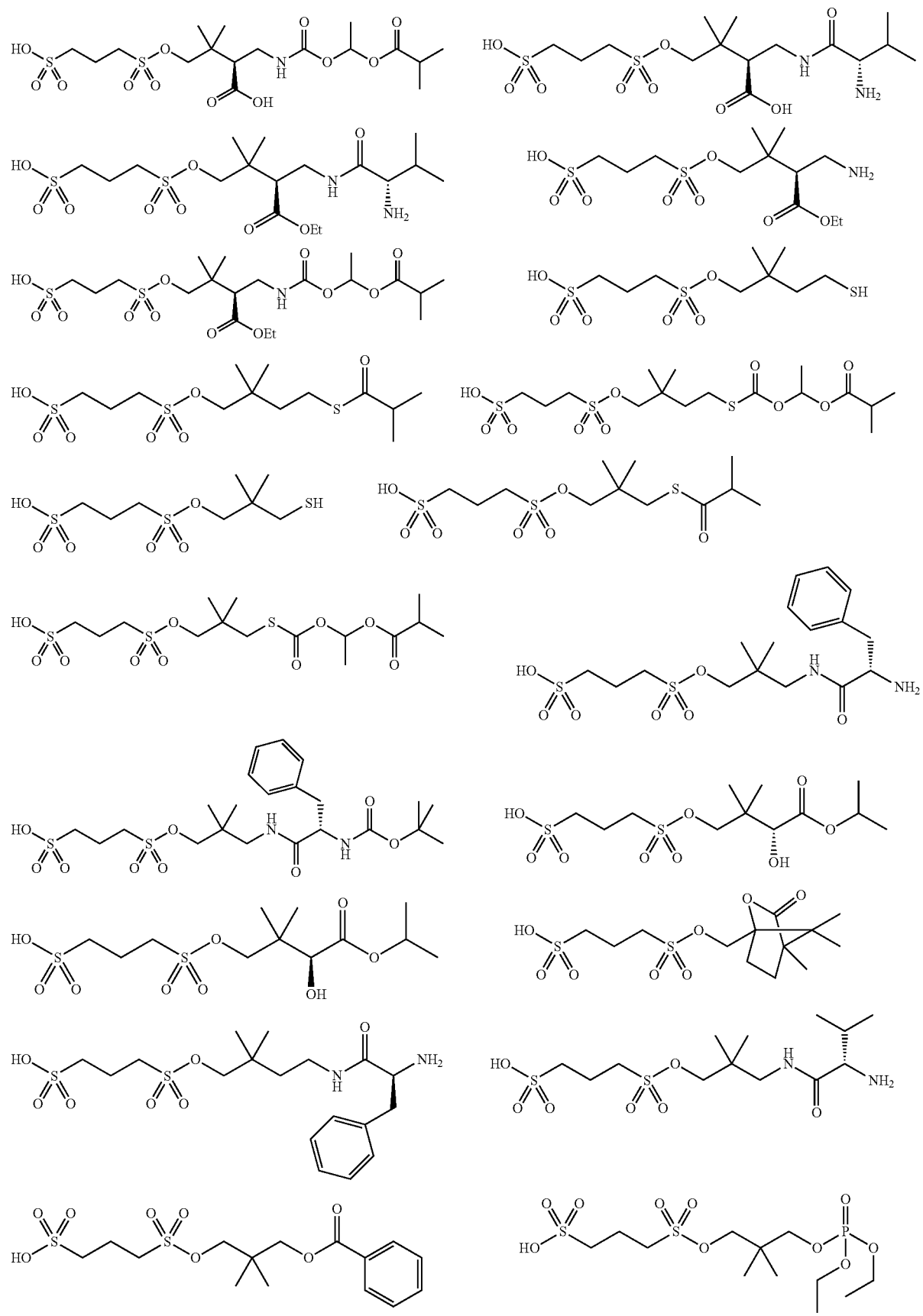

135 136
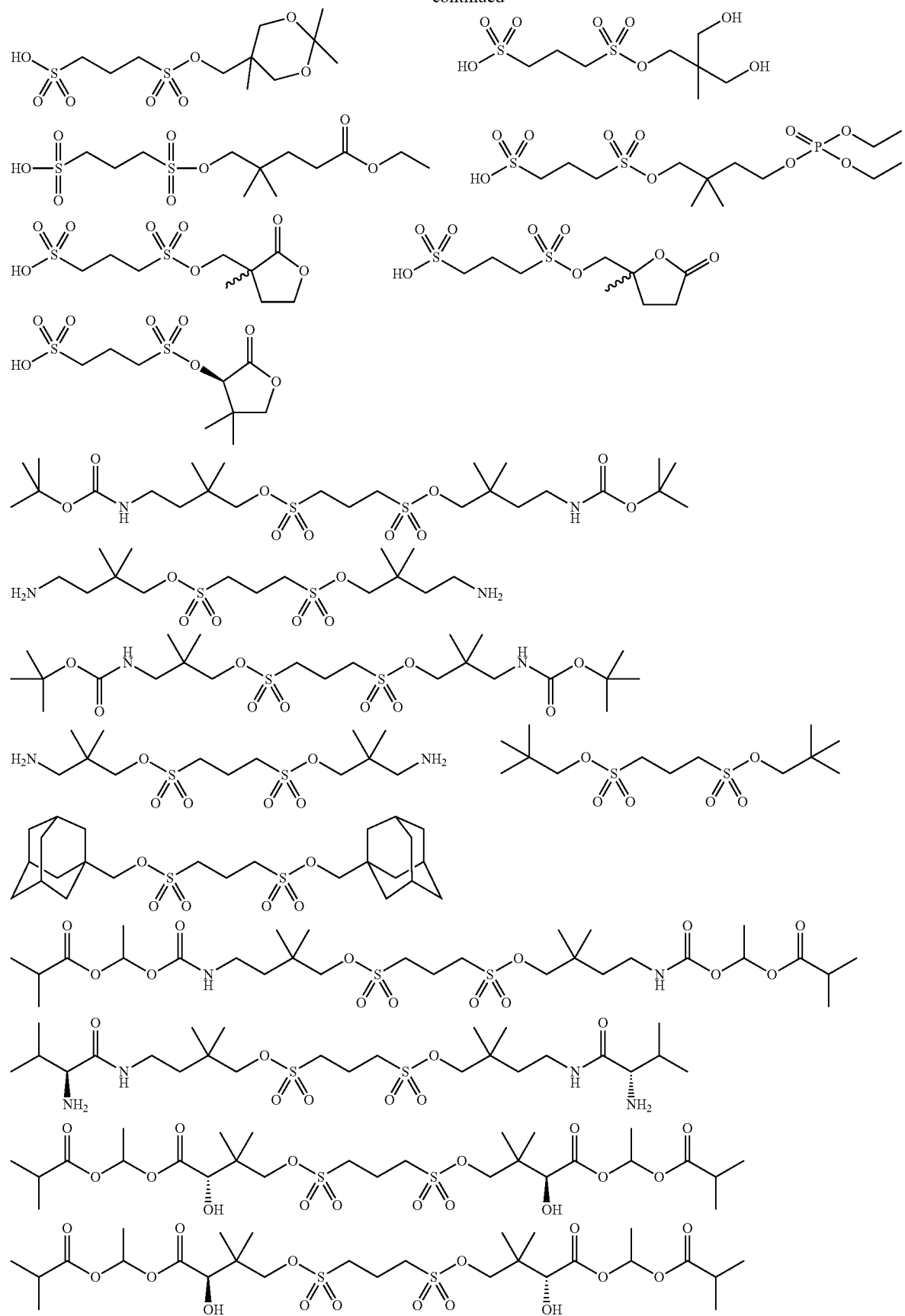

-continued
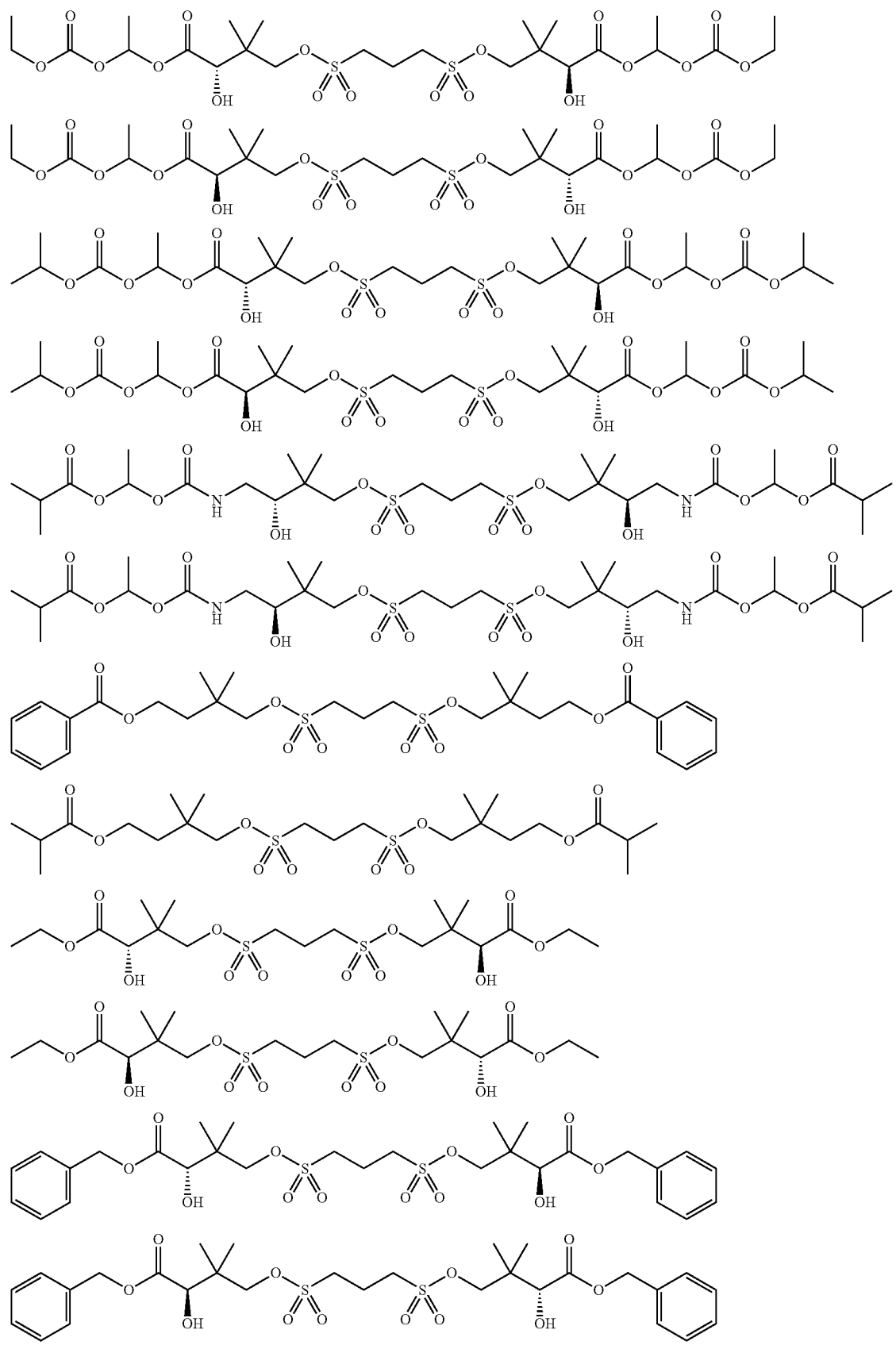

-continued
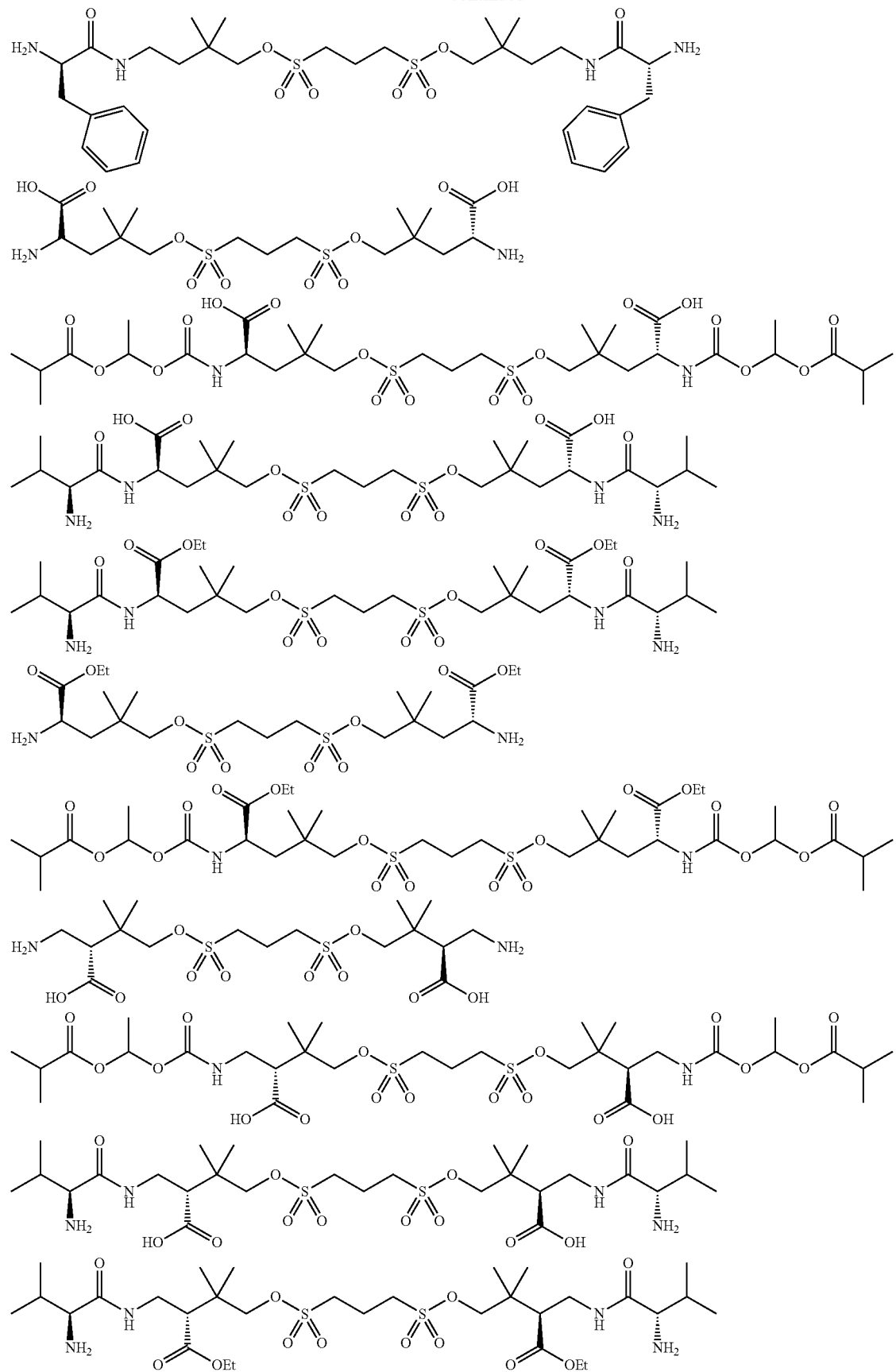

141
-continued
142
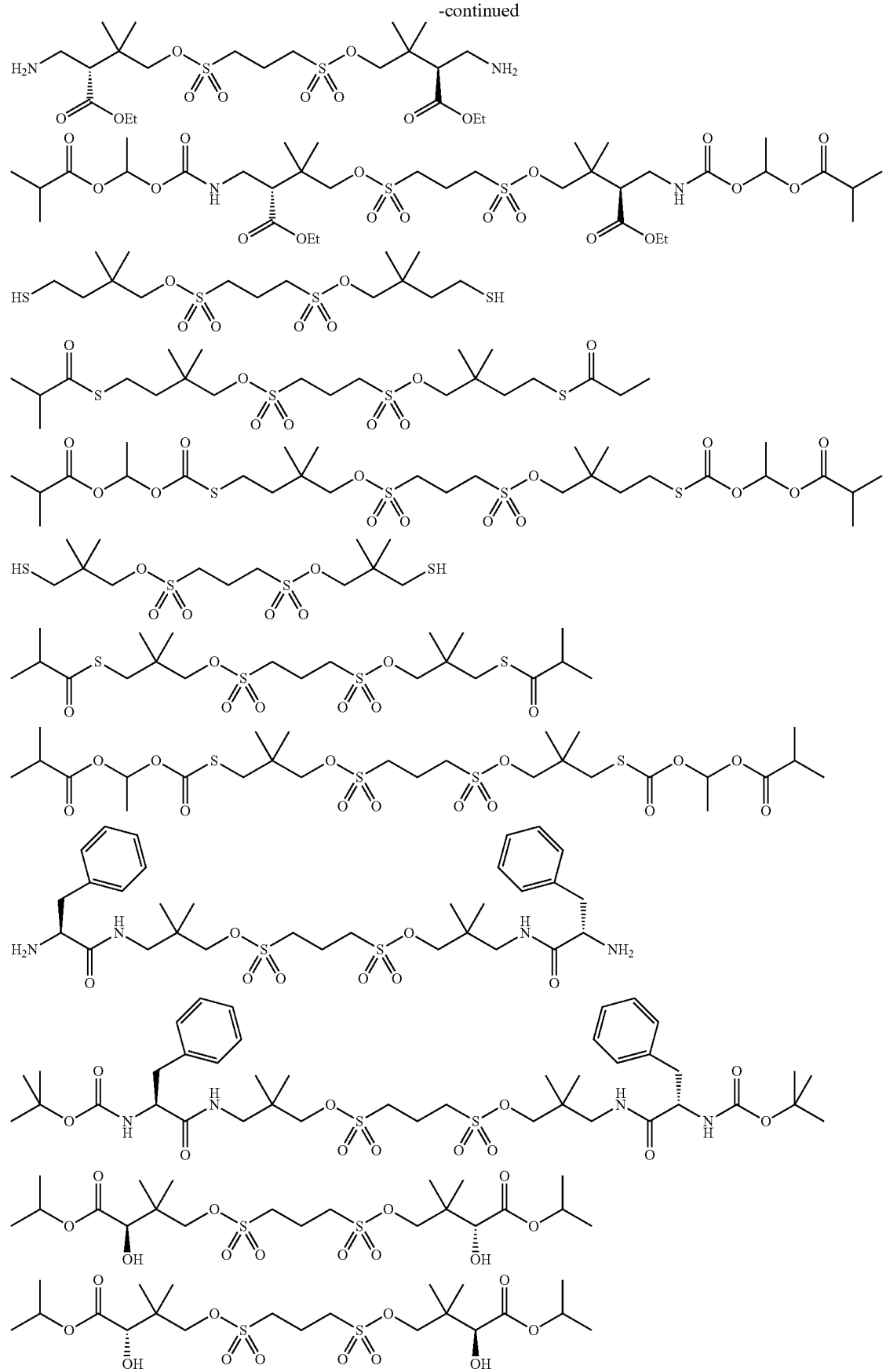

-continued
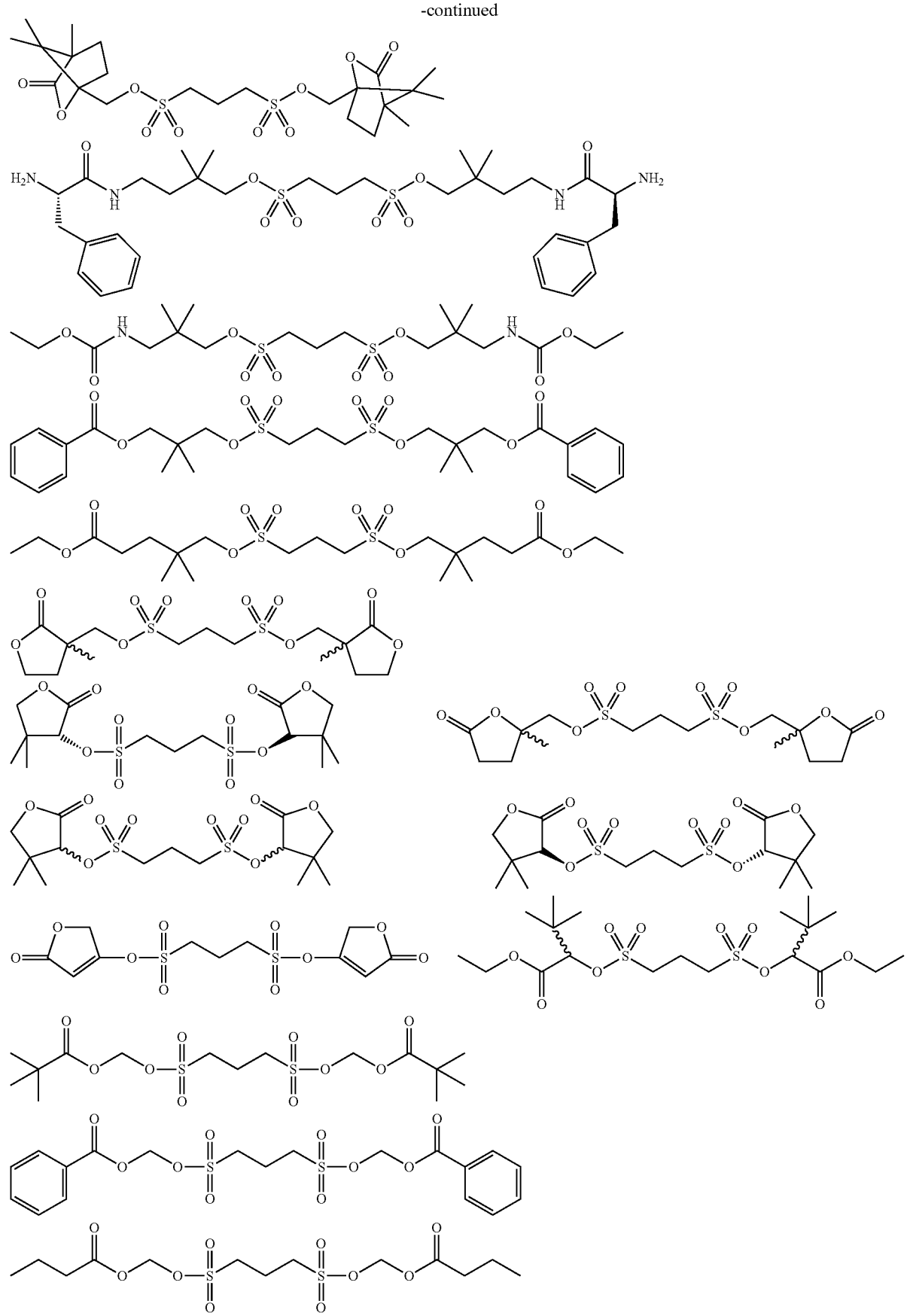

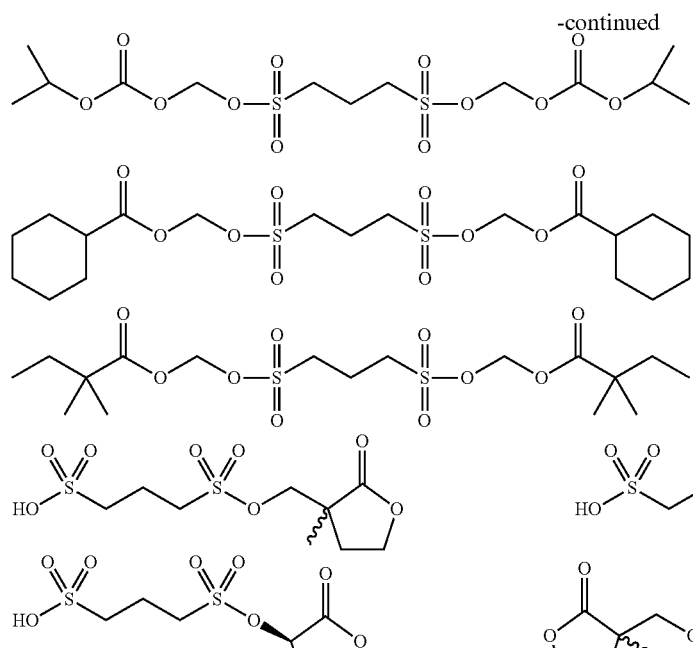
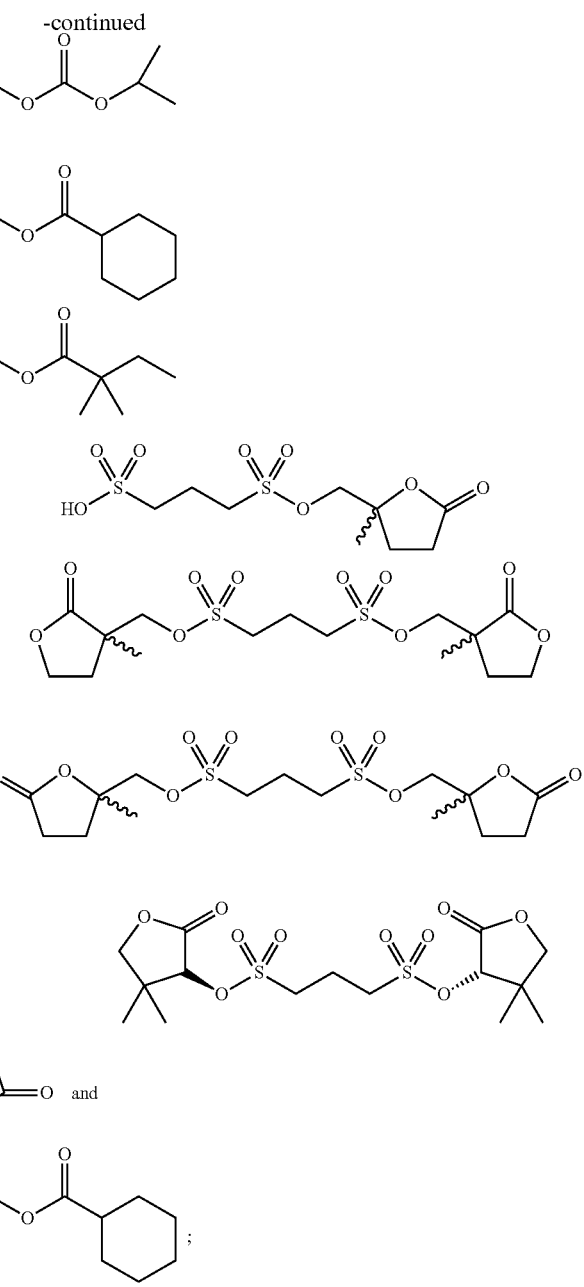
or a pharmaceutically acceptable salt or solvate thereof.
10. The compound of claim 1, wherein said compound is selected from:
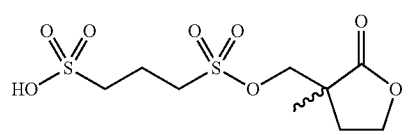
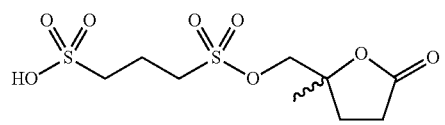
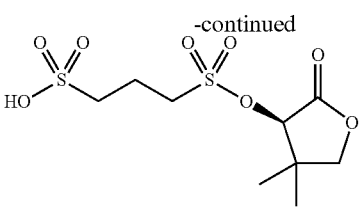
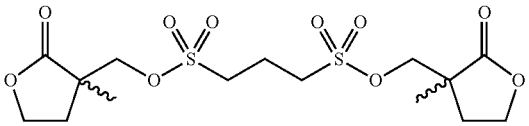

-continued

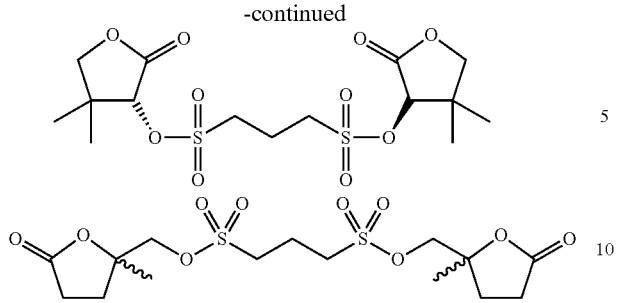

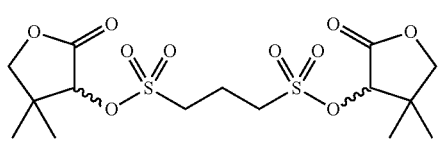

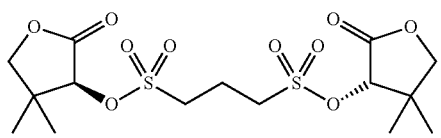

11. The compound of claim 10, wherein said compound is selected from:

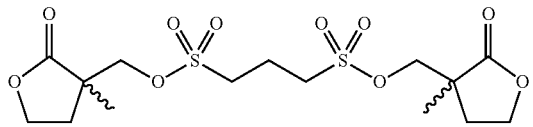

and

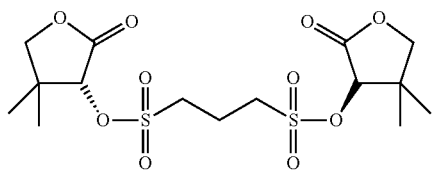

or a pharmaceutically acceptable solvate thereof.

12. A compound selected from:

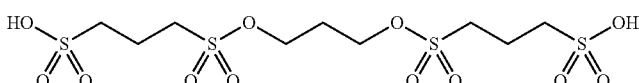

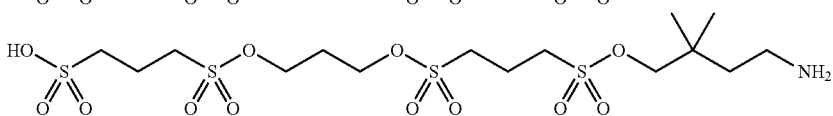

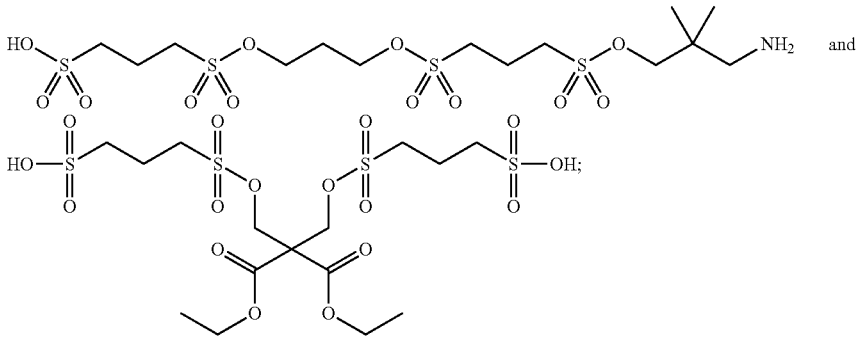

or a pharmaceutically acceptable salt or solvate thereof.

-continued

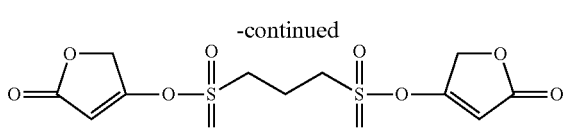

and

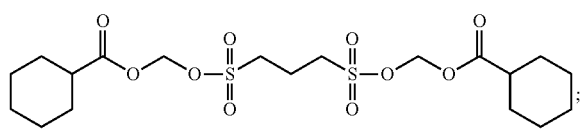

or a pharmaceutically acceptable salt or solvate thereof.

13. A pharmaceutical composition comprising a compound according to claim 1 together with a pharmaceutically acceptable carrier.

14. A method for treating AA amyloidosis or diabetic nephropathy comprising the step of administering to a subject in need thereof, a therapeutically effective amount of a compound of claim 1 such that said AA amyloidosis or diabetic nephropathy is treated.

15. The method of claim 14, wherein diabetic nephropathy is treated.

16. A method for the treatment of metabolic syndrome, hyperglycemia, or diabetes mellitus, comprising the step of administering a therapeutically effective amount of a compound of claim 1 to a subject in need thereof, such that said metabolic syndrome, hyperglycemia, or diabetes mellitus is treated.

17. The method of claim 16, wherein said diabetes mellitus is type 1 diabetes.

18. The method of claim 16, wherein said diabetes mellitus is type 2 diabetes.

19. The method of claim 16, wherein said diabetes mellitus is type 2 diabetes with features of metabolic syndrome.

20. A method for increasing insulin levels circulating in blood in response to food, decreasing resistance to insulin and/or increasing insulin sensitivity in selected tissues, increasing insulin secretion by pancreatic cells, increasing beta-cells and/or islets of Langerhans neogenesis and/or regeneration of islets of Langerhans or preventing their destruction by apoptosis, preventing apoptosis in beta-cells, stabilizing, restoring, and/or improving beta-cells size, growth and/or function, or delaying the requirement for treating a diabetic patient with exogenous insulin, comprising administering a therapeutically effective amount of a compound of claim 1 to a subject in need thereof.

21. The method of claim 14, wherein AA amyloidosis is treated.

\* \* \* \* \*

UNITED STATES PATENT AND TRADEMARK OFFICE
CERTIFICATE OF CORRECTION

PATENT NO.         : 9,051,248 B2                                        Page 1 of 2
APPLICATION NO.    : 13/389606
DATED              : June 9, 2015
INVENTOR(S)        : Kong et al.

It is certified that error appears in the above-identified patent and that said Letters Patent is hereby corrected as shown below:

In The Claims

Column 141-142, Line 4    replace the structure

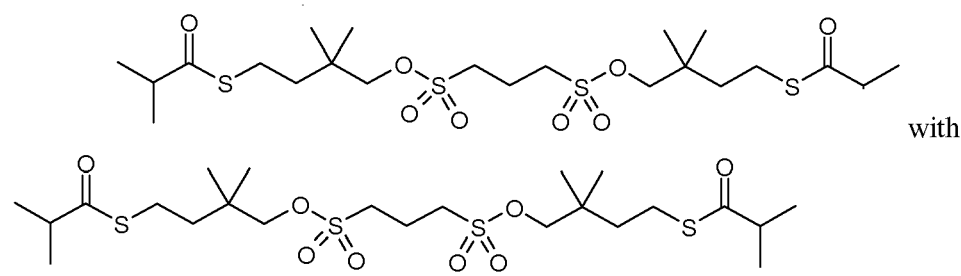

with

Column 145-146, Lines 3-8    replace the structures

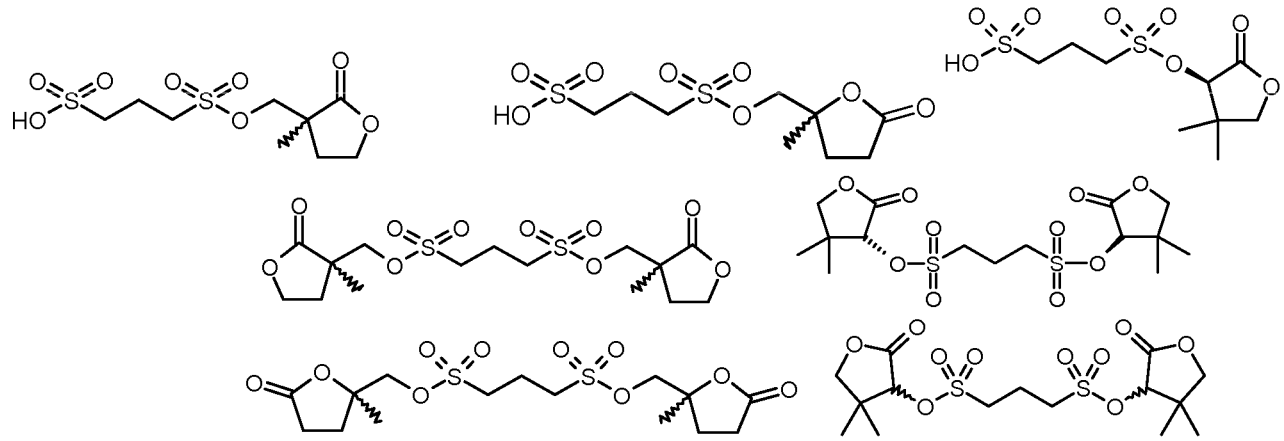

Signed and Sealed this
Fifth Day of January, 2016

Michelle K. Lee
*Director of the United States Patent and Trademark Office*

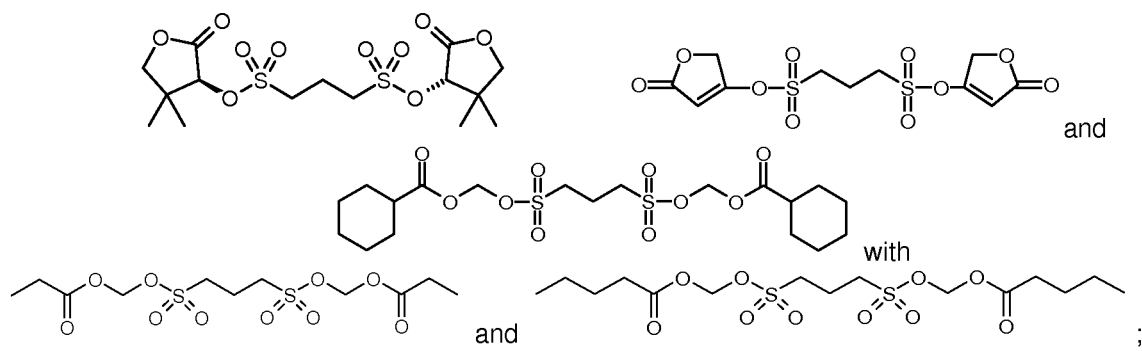
and with and ;